US012779038B2

(12) United States Patent
McMinn et al.

(10) Patent No.: US 12,779,038 B2
(45) Date of Patent: *Nov. 3, 2026

(54) ISOMERICALLY PURE BETA-CYCLODEXTRIN DERIVATIVES AND USES THEREOF

(71) Applicant: Beren Therapeutics P.B.C., Thousand Oaks, CA (US)

(72) Inventors: Dustin McMinn, Thousand Oaks, CA (US); Brad Herberich, Thousand Oaks, CA (US)

(73) Assignee: Beren Therapeutics P.B.C., Thousand Oaks, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 19/539,178

(22) Filed: Feb. 13, 2026

(65) Prior Publication Data

US 2026/0174863 A1 Jun. 25, 2026

Related U.S. Application Data

(63) Continuation of application No. PCT/IB2024/057921, filed on Aug. 15, 2024.

(60) Provisional application No. 63/519,905, filed on Aug. 16, 2023.

(51) Int. Cl.
*A61K 45/06* (2006.01)
*A61K 31/485* (2006.01)
*A61K 31/505* (2006.01)

(52) U.S. Cl.
CPC ............ *A61K 45/06* (2013.01); *A61K 31/485* (2013.01); *A61K 31/505* (2013.01); *A61K 2300/00* (2013.01)

(58) Field of Classification Search
None
See application file for complete search history.

(56) References Cited

FOREIGN PATENT DOCUMENTS

| | | | |
|---|---|---|---|
| CN | 109675054 | A | 4/2019 |
| WO | 2025037263 | A1 | 2/2025 |

OTHER PUBLICATIONS

Irie, T., & Uekama, K. (1997). Pharmaceutical applications of cyclodextrins. III. Toxicological issues and safety evaluation. Journal of pharmaceutical sciences, 86(2), 147-162. (Year: 1997).*

Torque, C., Bricout, H., Hapiot, F., & Monflier, E. (2004). Substrate-selective aqueous organometallic catalysis. How size and chemical modification of cyclodextrin influence the substrate selectivity. Tetrahedron, 60(31), 6487-6493. (Year: 2004).*

Al-Kassou et al. (2022) "Novel Assay for Quantifying the Cholesterol Crystal Dissolution Capacity of Serum Predicts Outcomes in Patients with Severe Aortic Stenosis Undergoing TAVR", European Heart Journal, 43(Supplement_2):ehac544-1623.

Cross L.C (1976) "Rules for Nomenclature of Organic-Chemistry E. Stereochemistry (Recommendations 1974)", Pure Appl Chem., 45:13-30.

Davidson et al. (Sep. 2009) "Chronic Cyclodextrin Treatment of Murine Niemann-Pick C Disease Ameliorates Neuronal Cholesterol and Glycosphingolipid Storage and Disease Progression", Plos one, 4(9):e6951 (15 Pages).

Dzeletovic et al. (1995) "Determination of Cholesterol Oxidation Products in Human Plasma by Isotope Dilution-Mass Spectrometry", Analytical biochemistry, 225(1):73-80.

Gu et al. (2014) "Controlled Acid-Mediated Regioselective O-Desilylations for Multifunctionalization of Cyclodextrins", European Journal of Organic Chemistry, 26:5793-5805.

Gubica et al. (Feb. 17, 2009) "The Influence of Selected O-Alkyl Derivatives of Cyclodextrins on the Enzymatic Decomposition of L-Tryptophan by L-Tryptophan Indole-Lyase", Carbohydrate Research, 344(3):304-310.

Guo et al. (2000) "Quantification In Situ of Crystalline Cholesterol and Calcium Phosphate Hydroxyapatite in Human Atherosclerotic Plaques by Solid-State Magic Angle Spinning NMR", Arteriosclerosis, thrombosis, and vascular biology, 20(6):1630-1636.

Idriss et al. (2013) "Effect of the Second Coordination Sphere on New Contrast Agents Based on Cyclodextrin Scaffolds for MRI Signals", RSC advances, 3(14):4531-4534.

Jindrich et al. (1995) "Separation of Cyclodextrins and their Derivatives by Thin-Layer and Preparative Column Chromatography", Carbohydrate Research, 275(1):1-7.

Lopez-Melgar et al. (2016) "Accurate Quantification of Atherosclerotic Plaque Volume by 3D Vascular Ultrasound Using the Volumetric Linear Array Method", Atherosclerosis, 248:230-237.

Mischnick Petra (1989) "Determination of the Patterns of Substitution of Hydroxyethyl- and Hydroxypropyl-Cyclomaltoheptaoses", Carbohydrate Research, 192:233-241.

Pitha et al. (1990) "Distribution of Substituents in 2-Hydroxypropyl Ethers of Cyclomaltoheptaose", Carbohydrate Research, 200:429-435.

Pitha et al. (Mar. 1, 1986) "Hydroxypropyl-β-Cyclodextrin: Preparation and Characterization; Effects on Solubility of Drugs", International Journal of Pharmaceutics, 29(1):73-82.

Quintao et al. (1971) "An Evaluation of our Methods for Measuring Cholesterol Absorption by the Intestine in Man", Journal of lipid research, 12(2):221-232.

Rao et al. (Jun. 1990) "Pharmaceutical Usefulness of Hydroxypropylcyclodextrins: "E Pluribus Unum" Is an Essential Feature", Pharmaceutical research, 7(6):612-615.

Schött et al. (2015) "Validation of an Isotope Dilution Gas Chromatography-Mass Spectrometry Method for Combined Analysis of Oxysterols and Oxyphytosterols in Serum Samples", Steroids, 99:139-150.

(Continued)

*Primary Examiner* — Dale R Miller
(74) *Attorney, Agent, or Firm* — Mintz, Levin, Cohn, Ferris, Glovsky and Popeo

(57) ABSTRACT

Disclosed herein are novel compounds of Formula I, Ia, Ib, Ic, Id, Ie, or If, useful in treating diseases in which cholesterol is implicated, including cardiovascular diseases.

20 Claims, 5 Drawing Sheets

(56) References Cited

OTHER PUBLICATIONS

Stiles et al. (2014) "Genetic, Anatomic, and Clinical Determinants of Human Serum Sterol and Vitamin D Levels", Proceedings of the National Academy of Sciences, 111(38):E4006-4014.
Weert et al. (2008) "Assessment of Atherosclerotic Carotid Plaque Volume with Multidetector Computed Tomography Angiography", The international journal of cardiovascular imaging, 24(7):751-759.

* cited by examiner

ISOMERICALLY PURE BETA-CYCLODEXTRIN DERIVATIVES AND USES THEREOF

RELATED APPLICATIONS

This application is a bypass continuation and claims priority to PCT/IB2024/057921, filed on Aug. 15, 2024, which claims priority to, and the benefit of, U.S. provisional application No. 63/519,905, filed Aug. 16, 2023, the entire content of which is incorporated herein by reference in its entirety.

BACKGROUND

High intracellular cholesterol levels can lead to changes in fundamental cell processes (e.g., organelle dysfunction, disruption of signaling events and induction of apoptosis) leading to a number of diseases (e.g., neurodegenerative diseases, cancers and arterial diseases). Thus, new treatments are needed to reduce intracellular cholesterol. Cholesterol can be removed from the body by reverse cholesterol transport (RCT), which begins with cholesterol efflux from the cell. Once cholesterol is removed from the cell via transporters (e.g., ABCA1 and ABCG1) it is bound by plasma borne entities (e.g., APOA1, HDL, and LDL), transported to the liver for processing, and then excreted. Cholesterol efflux from the cell is typically the rate limiting step of RCT. Thus, treatments to accelerate cholesterol efflux from cells are needed.

Hydroxypropyl beta-cyclodextrin (2-HPBCD) was first discovered in the mid-1980s, as a promising excipient to solubilize poorly soluble drugs. See Pitha J. et al., International Journal of Pharmaceutics, 29 (1986), pp. 73-82 ("Pitha 1986"), incorporated herein by reference in its entirety.

Commercially available and traditionally synthesized 2-HPBCD formulations are known to be complex mixtures of molecules, each of which has a differing degree of hydroxypropylation on the cyclodextrin ring. These complex mixtures typically also comprise different regioisomers of 2-HPBCD due to hydroxypropylation at different positions of the sugar monomers. This is because 2-HPBCD is generally still made today in the same way it was first synthesized by Pitha et al: via a condensation reaction between beta-cyclodextrin and propylene oxide. See Pitha 1986. Adjusting synthesis conditions, such as the amount of propylene oxide or the amount of base used in facilitating the condensation reaction, can offer some control of the average degree of hydroxypropylation (i.e., the number of hydroxypropyl moieties per cyclodextrin molecule) (Pitha 1986). However, the reaction still results in complex, heterogeneous mixtures of 2-HPBCD molecules with varying degrees and locations of hydroxypropylation. A number of attempts have been made to elucidate the exact composition of 2-HPBCD made by traditional methods, as well as to obtain 2-HPBCD with specific desired specifications (e.g., a specific average degree of substitution or a narrower distribution of the degrees of substitution). See Mischnick et al., Carbohydrate Research 192 (1989) pp. 233-241 ("Mischnick"); and J. Pitha et al., Carbohydr. Res. 200, (1990), pp 429-435 ("Pitha 1990"); each of which are incorporated herein by reference in their entireties.

The complexity of commercially available or traditionally synthesized 2-HPBCD products could be problematic when 2-HPBCD is intended to be used in a desired therapeutic setting, where consistent clinical safety and efficacy responses are required. Hence, it is of importance to selectively and consistently produce 2-HPBCD species that have the desired therapeutic activity.

Methods and products described herein address this need. For example, protecting group chemistry can be used to obtain single isomers of 2-HPBCD molecules or close analogs thereof with groups exclusively at the 3-0 position (e.g., Compound 4 or Compound 6), or exclusively at the 2-0 position (e.g., Compound 1, Compound 2, Compound 3, Compound 5, or Compound 7), and with a controlled degree of substitution.

The inventors have also found that 2-HPBCD compounds characterized by different positions of substitution may also differ in their physicochemical properties and biological effects. Thus, isomerically pure forms of 2-HPBCD or close analogs thereof, and synthetic processes for the production of said isomerically pure forms, are required. The provision of isomerically pure forms of 2-HPBCD or close analogs thereof enables the final properties of the product to be tailored to the specific use required. For example, the inventors have found that isomerically pure forms of 2-HPBCD or close analogs thereof with groups substituted exclusively at the 2-0 position, e.g., Compound 1, Compound 2, Compound 3, Compound 5, or Compound 7 herein, may be advantageous. For example, isomerically pure forms of 2-HPBCD or close analogs thereof, e.g., isomerically pure forms of 2-HPBCD or close analogs thereof with groups substituted exclusively at the 2-0 position, e.g., Compound 1, Compound 2, Compound 3, Compound 5, or Compound 7, may have a particularly low propensity towards forming aggregates or self-inclusion complexes.

SUMMARY OF THE DISCLOSURE

In one aspect, disclosed herein are compounds of Formula I:

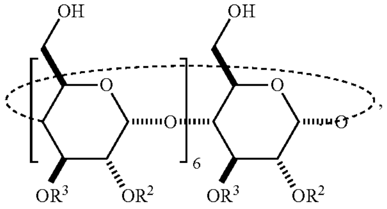

(I)

wherein:

each $R^2$ and $R^3$ independently, at each occurrence for each of the seven independent monomers, is H or $C_2$-$C_4$ alkyl substituted with one or more groups selected from —O($C_1$-$C_4$ alkyl) and —OH, wherein at least one $R^2$ or at least one $R^3$ is $C_2$-$C_4$ alkyl substituted with one or more groups selected from —O($C_1$-$C_4$ alkyl) and —OH.

In another aspect, disclosed herein are compounds of Formula II:

(II)

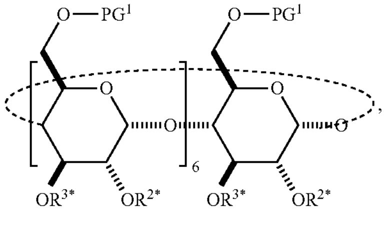

wherein:

$PG^1$ is a first alcohol protecting group; and each $R^{2*}$ and $R^{3*}$ independently, at each occurrence for each of the seven independent monomers, is $PG^1$, $—CH_2C(O)CH_3$, or $C_2$-$C_6$ alkenyl optionally substituted with one or more —OH or $—OPG^2$, wherein $PG^2$ is a second alcohol protecting group, and wherein at least one $R^{2*}$ or at least one $R^{3*}$ is $—CH_2C(O)CH_3$ or $C_2$-$C_6$ alkenyl optionally substituted with one or more —OH or $—OPG^2$.

In another aspect, disclosed herein are compounds of Formula IIa:

(IIa)

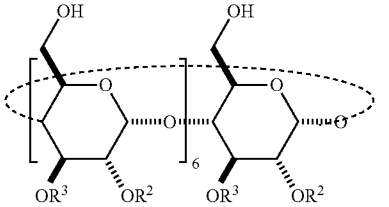

wherein:

each $R^2$ and $R^3$ independently, at each occurrence for each of the seven independent monomers, is H or $C_2$-$C_4$ alkenyl, wherein at least one $R^2$ or at least one $R^3$ is $C_2$-$C_4$ alkenyl.

In another aspect, the present disclosure provides a pharmaceutical composition comprising a compound described herein (e.g., a compound of Formula I, Ia, Ib, Ic, Id, Ie, or If) or a pharmaceutically active substance described herein and a pharmaceutically acceptable carrier.

In another aspect, the present disclosure provides methods of treatment comprising administration of a compound described herein (e.g., a compound of Formula I, Ia, Ib, Ic, Id, Ie, or If) or a pharmaceutically active substance, or pharmaceutical composition described herein.

In another aspect, the present disclosure provides a compound described herein (e.g., a compound of Formula I, Ia, Ib, Ic, Id, Ie, or If) or a pharmaceutically active substance, or pharmaceutical composition described herein for use in methods of treatment as described herein.

DETAILED DESCRIPTION OF THE DISCLOSURE

Definitions

Figure 1:
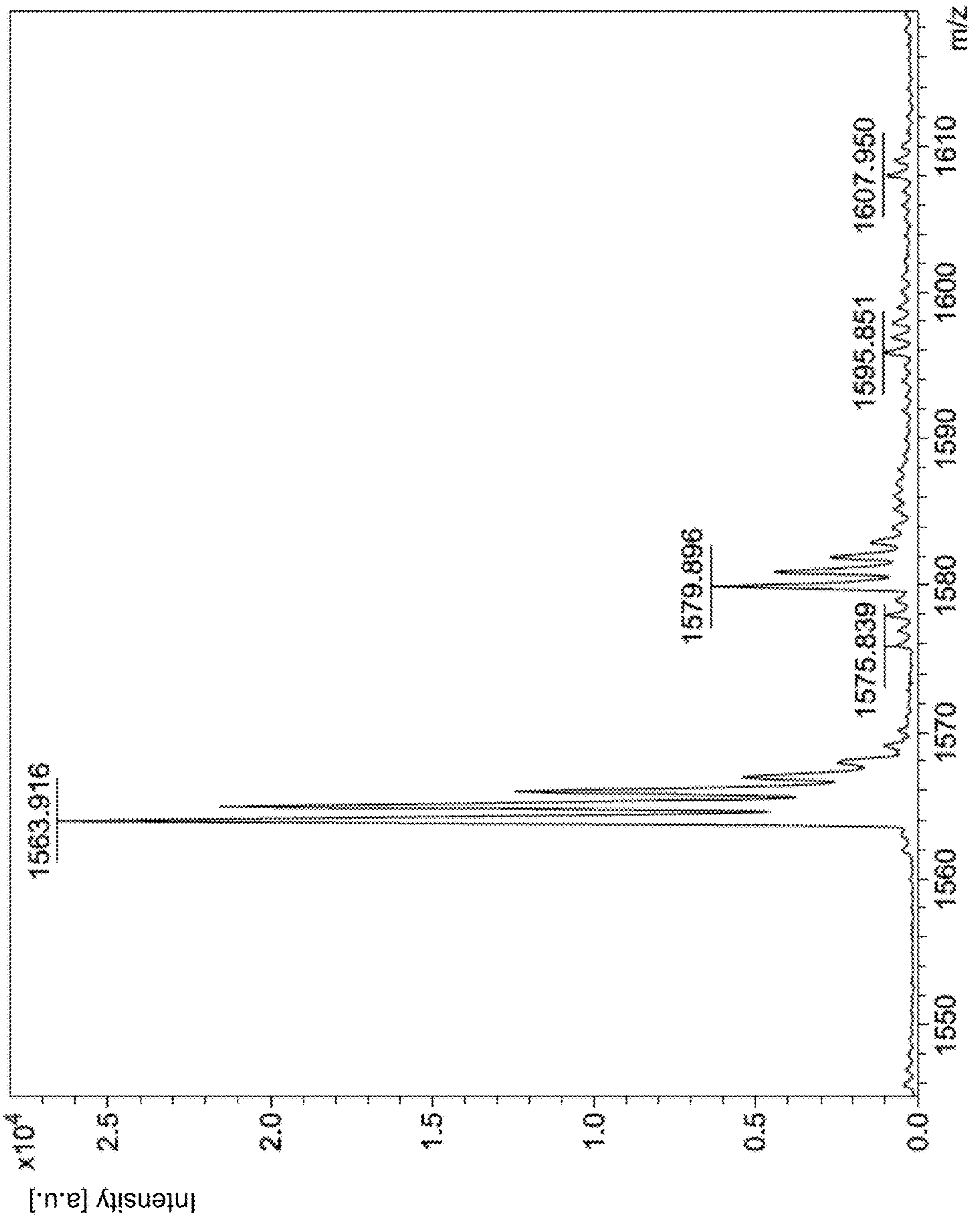
FIG. 1 is a matrix assisted laser desorption/ionization (MALDI) mass spectrum of Compound 5, synthesized according to the method described in Example 1.

The below terms are discussed to illustrate meanings of the terms as used in this specification, in addition to the understanding of these terms by those of skill in the art. As used herein and in the appended claims, the singular forms "a," "an," and, "the" include plural referents unless the context clearly dictates otherwise. It is further noted that the claims can be drafted to exclude any optional element. As such, this statement is intended to serve as antecedent basis for use of such exclusive terminology as "solely," "only," and the like in connection with the recitation of claim elements, or use of a "negative" limitation.

As used herein, the term "about" when used in the context of describing a number refers to that number plus or minus 10% of that number. The term "about" in a range refers to that range minus 10% of its lowest value and plus 10% of its greatest value.

As used herein, the term "active pharmaceutical ingredient" or "pharmaceutically active substance" refers to a compound or substance that, when administered to a subject, brings about a desired result. For example, in some embodiments, an active pharmaceutical ingredient or a pharmaceutically active substance refers to a compound or substance that, when administered to a subject in need of treatment of a disease or condition, relieves, to some extent, one or more of the symptoms of the disease or condition, or reduces the underlying cause of the disease or condition. In some embodiments, the result is a reduction and/or alleviation of the signs, symptoms, or causes of a disease, or any other desired alteration of a biological system. For example, in some embodiments, an active pharmaceutical ingredient or a pharmaceutically active substance refers to a compound that when administered to a subject accelerates cholesterol efflux from a cell of the subject. An active pharmaceutical ingredient or a pharmaceutically active substance may also refer to a compound that when contacted with a cell in vitro, accelerates cholesterol efflux from said cell.

"Cholesterol efflux capacity (CEC)" generally refers to the ability of cells to remove cholesterol from their membranes so that it can be transported it to the liver for excretion. "Cholesterol efflux capacity" also refers to an in-vitro assay that measures the ability of a compound (e.g., HDL or a compound of the disclosure) to promote cholesterol efflux from cholesterol donor cells such as macrophages. "Cholesterol efflux" is a mechanism in which accumulated cholesterol is removed from macrophages, e.g, by ATP-binding membrane cassette transporter A1 (ABCA1) or by other mechanisms, including but not limited to passive diffusion, scavenger receptor B1 (SR-B1), caveolins and sterol 27-hydroxylase, and collected by HDL and apoA-I.

Chemical moieties referred to as univalent chemical moieties (e.g., alkyl, aryl, etc.) also encompass structurally permissible multivalent moieties, as understood by those skilled in the art. For example, while an "alkyl" moiety generally refers to a monovalent radical (e.g., $CH_3CH_2$—), in appropriate circumstances an "alkyl" moiety can also refer to a divalent radical (e.g., —$CH_2CH_2$—, which is equivalent to an "alkylene" group). Similarly, under circumstances where a divalent moiety is required, those skilled in the art will understand that the term "aryl" refers to the corresponding divalent arylene group.

All atoms are understood to have their normal number of valences for bond formation (e.g., 4 for carbon, 3 for N, 2 for O, and 2, 4, or 6 for S, depending on the atom's oxidation state). On occasion a moiety can be defined, for example, as $(A)_aB$, wherein a is 0 or 1. In such instances, when a is 0 the moiety is B and when a is 1 the moiety is AB.

Where a substituent can vary in the number of atoms or groups of the same kind (e.g., alkyl groups can be $C_1$, $C_2$, $C_3$, etc.), the number of repeated atoms or groups can be represented by a range (e.g., $C_1$-$C_6$ alkyl) which includes each and every number in the range and any and all sub ranges. For example, $C_1$-$C_3$ alkyl includes $C_1$, $C_2$, $C_3$, $C_{1-2}$, $C_{1-3}$, and $C_{2-3}$ alkyl.

"Alkanoyl" refers to a carbonyl group with a lower alkyl group as a substituent.

"Alkylamino" refers to an amino group substituted by an alkyl group.

"Alkoxy" refers to an O-atom substituted by an alkyl group as defined herein, for example, methoxy [—$OCH_3$, a $C_1$alkoxy]. The term "$C_{1-6}$ alkoxy" encompasses $C_1$ alkoxy, $C_2$ alkoxy, $C_3$ alkoxy, $C_4$ alkoxy, $C_5$ alkoxy, $C_6$ alkoxy, and any sub-range thereof.

"Alkoxycarbonyl" refers to a carbonyl group with an alkoxy group as a substituent.

As used herein, "Alkyl" refers to optionally substituted, straight and branched chain aliphatic groups having from 1 to 30 carbon atoms. "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl, or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms. The term "heteroalkyl" as used herein contemplates an alkyl with one or more heteroatoms.

As used herein, the term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ and $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

As used herein, the term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Alkylene" refers to an optionally substituted divalent radical which is a branched or unbranched hydrocarbon fragment containing the specified number of carbon atoms, and having two points of attachment. An example is propylene [—$CH_2CH_2CH_2$—, a $C_3$alkylene].

"Amino" refers to the group —$NH_2$.

The term "Aryl" refers to cyclic, aromatic hydrocarbon groups that have 1 to 3 aromatic rings, including monocyclic or bicyclic groups such as phenyl, biphenyl, or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen. —O—($C_1$-$C_6$) alkyl, ($C_1$-$C_6$) alkyl, —O—($C_2$-$C_6$) alkenyl, —O—($C_2$-$C_6$) alkynyl, ($C_2$-$C_6$) alkenyl, ($C_2$-$C_6$) alkynyl, OH, $OP(O)(OH)_2$, OC(O)($C_1$-$C_6$) alkyl, C(O)($C_1$-$C_6$) alkyl, OC(O)O($C_1$-$C_6$) alkyl, $NH_2$, NH(($C_1$-$C_6$) alkyl), $N((C_1\text{-}C_6)\ alkyl)_2$, $S(O)_2$ ($C_1$-$C_6$) alkyl, S(O)NH($C_1$-$C_6$) alkyl, and $S(O)N((C_1\text{-}C_6)alkyl)_2$. The substituents can themselves be optionally substituted. Furthermore, when containing two or more fused rings, the aryl groups herein defined may have a saturated or partially unsaturated ring fused with a fully unsaturated aromatic ring Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, 10,11-dihydro-5H-dibenzo[a,d][7]annulenyl, and the like.

"Carbonyl" refers to a group of the Formula

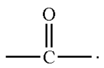

"Cycloalkyl" refers to a non-aromatic single saturated or partially unsaturated all carbon ring having 3 to 20 annular carbon atoms (i.e., $C_{3-20}$ cycloalkyl), for example from 3 to 12 annular atoms, for example from 3 to 10 annular atoms, or 3 to 8 annular atoms, or 3 to 6 annular atoms, or 3 to 5 annular atoms, or 3 to 4 annular atoms. The term "cycloalkyl" also includes multiple condensed, saturated and partially unsaturated non-aromatic all carbon ring systems (e.g., ring systems comprising 2, 3 or 4 carbocyclic rings). Accordingly, cycloalkyl includes multicyclic carbocycles such as a bicyclic carbocycles (e.g., bicyclic carbocycles having about 6 to 12 annular carbon atoms such as bicyclo[3.1.0]hexane and bicyclo[2.1.1]hexane), and polycyclic carbocycles (e.g. tricyclic and tetracyclic carbocycles with up to about 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

"Heterocycle" refers to a saturated or partially unsaturated 3-8 membered monocyclic or bicyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofurran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, 5,6-dihydro-4H-cyclopenta[b]thiophenyl, and the like. In the case of multicyclic heterocycloalkyl, only one of the rings in the heterocycloalkyl needs to be non-aromatic (e.g., 4,5,6,7-tetrahydrobenzo[c]isoxazolyl).

"Halogen" refers to a chloro, bromo, fluoro or iodo atom radical. The term "halogen" also contemplates terms "halo" or "halide."

"Heteroatom" refers to a non-carbon atom, where boron, nitrogen, oxygen, sulfur and phosphorus are preferred heteroatoms, with nitrogen, oxygen and sulfur being particularly preferred heteroatoms in the compounds of the present disclosure.

"Heteroaryl" means a monovalent monocyclic or polycyclic aromatic radical of 5 to 24 ring atoms, containing one or more ring heteroatoms selected from N, O, S, P, Se, or B, the remaining ring atoms being C. Heteroaryl as herein defined also means a bicyclic heteroaromatic group wherein the heteroatom is selected from N, O, S, P, Se, or B. Heteroaryl as herein defined also means a tricyclic heteroaromatic group containing one or more ring heteroatoms selected from N, O, S, P, Se, or B. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolinyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3, 4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1λ2-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzoxazolyl, benzisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore, when containing two or more fused rings, the heteroaryl groups defined herein may have one or more saturated or partially unsaturated ring fused with a fully unsaturated aromatic ring, e.g., a 5-membered heteroaromatic ring containing 1 to 3 heteroatoms selected from N, O, S, P, Se, or B, or a 6-membered heteroaromatic ring containing 1 to 3 nitrogens, wherein the saturated or partially unsaturated ring includes 0 to 4 heteroatoms selected from N, O, S, P, Se, or B, and is optionally substituted with one or more oxo. In heteroaryl ring systems containing more than two fused rings, a saturated or partially unsaturated ring may further be fused with a saturated or partially unsaturated ring described herein. Exemplary ring systems of these heteroaryl groups include, for example, indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuranyl, benzofuranonyl, indolinyl, oxindolyl, indolyl, 1,6-dihydro-7H-pyrazolo[3,4-c]pyridin-7-onyl, 7,8-dihydro-6H-pyrido[3,2-b]pyrrolizinyl, 8H-pyrido[3,2-b]pyrrolizinyl, 1,5,6,7-tetrahydrocyclopenta[b]pyrazolo[4,3-e]pyridinyl, 7,8-dihydro-6H-pyrido[3,2-b]pyrrolizine, pyrazolo[1,5-a]pyrimidin-7(4H)-only, 3,4-dihydropyrazino[1,2-a]indol-1(2H)-onyl, or benzo[c][1,2]oxaborol-1(3H)-olyl.

An "optionally substituted" moiety can be substituted with from one to four, or preferably from one to three, or more preferably one or two non-hydrogen substituents. Unless otherwise specified, when the substituent is on a carbon, it is selected from the group consisting of —OH, —CN, —$NO_2$, halogen, alkyl, heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, none of which are further substituted. Unless otherwise specified, when the substituent is on a nitrogen, it is selected from the group consisting of alkyl, heteroalkyl, cycloalkyl, heterocycle, aryl, heteroaryl, aralkyl, alkoxy, alkoxycarbonyl, alkanoyl, carbamoyl, sulfonyl, sulfonate and sulfonamide none of which are further substituted.

Compounds of the present disclosure can exist as stereoisomers, wherein asymmetric or chiral centers are present. Stereoisomers are designated (R) or (S) depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13-30, hereby incorporated by reference. The present disclosure contemplates various stereoisomers and mixtures thereof and are specifically included within the scope of the present disclosure. Stereoisomers include enantiomers, diastereomers, and mixtures of enantiomers or diastereomers.

Also, moieties disclosed herein which exist in multiple tautomeric forms include all such forms encompassed by a given tautomeric Formula.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of keto-enol equilibria is between pyridin-2(1H)-ones and the corresponding pyridin-2-ols, as shown below.

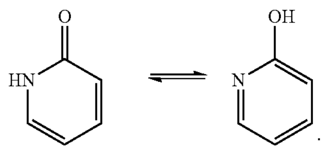

pyridin-2(1H)-one pyridin-2-ol

Individual atoms in the disclosed compounds may be any isotope of that element. For example hydrogen may be in the form of deuterium. For example, any atom of the compounds disclosed herein, e.g. compounds of Formula I, Ia, Ib, Ic, Id, Ie, or If described herein may be substituted with any suitable isotope. In some embodiments, any one or more hydrogen atoms of the compound of Formula I, Ia, Ib, Ic, Id, Ie, or If of the methods, pharmaceutical compositions, and pharmaceutical formulations is substituted or replaced with deuterium atoms. Deuterium is a safe, stable, non-radioactive isotope of hydrogen. Compared to hydrogen, deuterium forms stronger bonds with carbon. In some instances, the increased bond strength imparted by deuterium positively impacts properties of the compound of Formula I, Ia, Ib, Ic, Id, Ie, or If, creating the potential for improved drug efficacy, safety, and/or tolerability. In addition, deuteration may cause decreased metabolic clearance in vivo, thereby increasing the half-life and circulation of the compound. At the same time, because the size and shape of deuterium are essentially identical to those of hydrogen, replacement of hydrogen by deuterium would not be expected to affect the biochemical potency and selectivity of the compound as compared to the original chemical entity that contains only hydrogen.

The term "pharmaceutically acceptable" denotes an attribute of a material which is useful in preparing a pharmaceutical composition or pharmaceutical formulation that is generally safe, non-toxic, and neither biologically nor otherwise undesirable and is acceptable for veterinary as well as human pharmaceutical use. "Pharmaceutically acceptable" can refer to a material, such as a carrier, or diluent, which does not abrogate the biological activity or properties of the compound, and is relatively nontoxic, e.g., the material may be administered to an individual without causing undesirable biological effects or interacting in a deleterious manner with any of the components of the composition in which it is contained.

As used herein, the terms "subject," "individual", and "patient" are used interchangeably. None of the terms are to be interpreted as requiring the supervision of a medical professional (e.g., a doctor, nurse, physician's assistant, orderly, hospice worker). As used herein, the subject may be any animal, including mammals (e.g., a human or non-human animal) and non-mammals. In some embodiments, the subject is a human. As used herein, the terms "treat," "treating", or "treatment," and other grammatical equivalents, include ameliorating the underlying causes of one or more symptoms of a disease or condition; alleviating, abating, or ameliorating one or more symptoms of a disease or condition; ameliorating or reducing the appearance, severity, or frequency of one or more symptoms of a disease or condition; inhibiting the disease or condition, such as, for example, arresting the development of the disease or condition, relieving the disease or condition, causing regression of the disease or condition, relieving a condition caused by the disease or condition, or inhibiting the symptoms of the disease or condition either prophylactically and/or therapeutically. Methods of treatment as disclosed herein include disclosures of the use of the compounds, pharmaceutical compositions, or pharmaceutical formulations provided herein for the treatment of any indication described herein, and include disclosures of the compounds, pharmaceutical compositions, or pharmaceutical formulations provided herein for the use in treating any indication described herein.

"Pharmaceutically acceptable excipient" as used herein, refers to any pharmaceutically acceptable ingredient in a pharmaceutical composition or pharmaceutical formulation having no therapeutic activity and being non-toxic to the subject administered, such as disintegrators, binders, fillers, solvents, buffers, tonicity agents, stabilizers, antioxidants, surfactants, carriers, diluents, excipients, preservatives or lubricants used in formulating pharmaceutical products.

The term "effective amount," as used herein, refers to a sufficient amount of a compound or pharmaceutical composition being administered which relieves, to some extent, one or more of the symptoms of the disease or condition being treated, or reduces the underlying cause of the disease or condition being treated. In some embodiments, the result is a reduction and/or alleviation of the signs, symptoms, or causes of a disease, or any other desired alteration of a biological system. For example, an "effective amount" for therapeutic uses is the amount of a compound or pharmaceutical composition disclosed herein required to provide a clinically significant decrease in disease symptoms or underlying cause of the disease (e.g., without undue adverse side effects). In some embodiments, an "effective amount" refers to a pharmaceutically effective amount of a compound or pharmaceutical composition disclosed herein required to provide a pharmaceutical effect to prevent, reduce, ameliorate, or inhibit progression of at least one symptom of a disease, disorder or condition in the subject in need of the administration of such amount of the composition. In some embodiments, an appropriate "effective amount" in any individual case is determined using techniques, such as a dose escalation study. An "effective amount" of a compound, pharmaceutical composition, or pharmaceutical formulation disclosed herein may be an amount effective to achieve a desired effect or therapeutic improvement (e.g., without undue adverse side effects). An "effective amount" of a compound, pharmaceutical composition, or pharmaceutical formulation disclosed herein may be an amount effective to achieve one or more desired outcomes.

Compounds of the Disclosure

In one aspect, disclosed herein are compounds of Formula I:

(I)

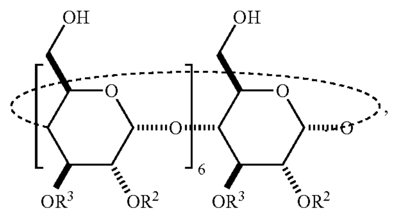

wherein:

each $R^2$ and $R^3$ independently, at each occurrence for each of the seven independent monomers, is H or $C_2$-$C_4$ alkyl substituted with one or more groups selected from —O($C_1$-$C_4$ alkyl) and —OH, wherein at least one $R^2$ or at least one $R^3$ is $C_2$-$C_4$ alkyl substituted with one or more groups selected from —O($C_1$-$C_4$ alkyl) and —OH.

In another aspect, provided herein are methods of using compounds of Formula I.

In some embodiments, the compound of Formula (I) is a compound of Formula Ia:

(Ia)

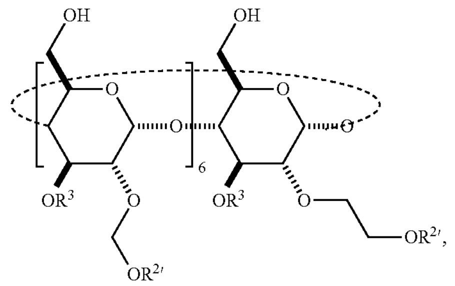

wherein each $R^{2'}$ independently is $C_1$-$C_4$ alkyl. In some embodiments, each $R^{2'}$ independently is —$CH_3$ or —$CH_2CH_3$. In some embodiments, each $R^{2'}$ is —$CH_3$. In some embodiments, each $R^{2'}$ is —$CH_2CH_3$.

In some embodiments, the compound of Formula (I) is a compound of Formula Ib:

(Ib)

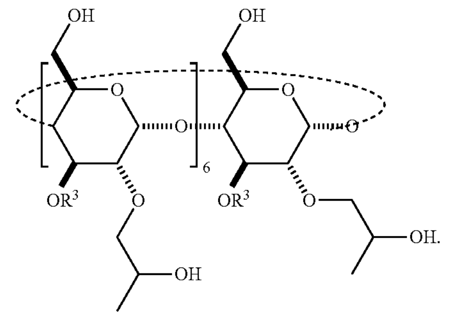

In some embodiments, the compound of Formula (I) is a compound of Formula Ic:

(Ic)

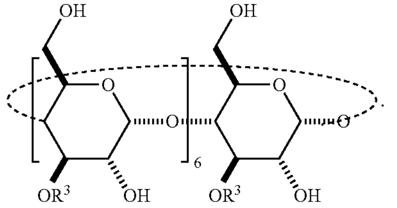

In some embodiments, the compound of Formula (I) is a compound of Formula Id:

(Id)

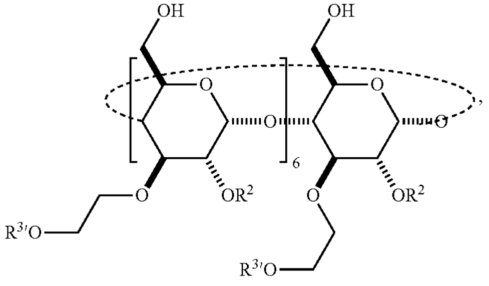

wherein each $R^{3'}$ independently is $C_1$-$C_4$ alkyl. In some embodiments, each $R^{3'}$ independently is —$CH_3$ or —$CH_2CH_3$. In some embodiments, each $R^{3'}$ is —$CH_3$. In some embodiments, each $R^{3'}$ is —$CH_2CH_3$.

In some embodiments, the compound of Formula (I) is a compound of Formula Ie:

(Ie)

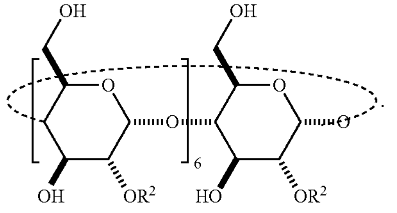

In some embodiments, the compound of Formula (I) is a compound of Formula If:

(If)

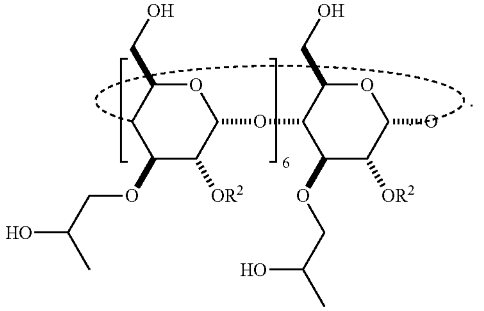

In a first aspect, the present disclosure relates to a compound of Formula I, Ia, Ib, Ic, Id, Ie, or If. In some embodiments of the compounds of Formula I or Ia, each $R^2$ and $R^3$ independently, at each occurrence for each of the seven independent monomers, is H or $C_2$-$C_4$ alkyl substituted with one or more groups selected from —O($C_1$-$C_4$ alkyl) and —OH, wherein at least one $R^2$ or at least one $R^3$ is $C_2$-$C_4$ alkyl substituted with one or more groups selected from —O($C_1$-$C_4$ alkyl) and —OH.

In some embodiments of the compounds of Formula I, Id, Ie, or If, each $R^2$ is H.

In some embodiments of the compounds of Formula I, Id, Ie, or If, $R^2$ for each of the seven independent monomers is $C_2$-$C_4$ alkyl substituted with one or more groups selected from —O($C_1$-$C_4$ alkyl) and —OH. In some embodiments, each $R^2$ independently is a $C_2$-$C_4$ alkyl substituted with one or two OH. In some embodiments, each $R^2$ is 2-hydroxypropyl. In some embodiments, each $R^2$ is 2-hydroxybutyl (e.g., 2-hydroxyisobutyl). In some embodiments, each $R^2$ independently is $C_2$-$C_4$ alkyl substituted with one or two —$OCH_3$ or —$OCH_2CH_3$. In some embodiments, each $R^2$ independently is $C_2$-$C_4$ alkyl substituted with one —$OCH_3$ or —$OCH_2CH_3$.

In some embodiments of the compounds of Formula I, Id, Ie, or If, $R^2$ for each of the seven independent monomers is ethyl substituted with one or more groups selected from —O($C_1$-$C_4$ alkyl) and —OH. In some embodiments, each $R^2$ independently is an ethyl substituted with one or two OH. In some embodiments, each $R^2$ independently is ethyl substituted with one or two —$OCH_3$ or —$OCH_2CH_3$. In some embodiments, each $R^2$ independently is ethyl substituted with one —$OCH_3$ or —$OCH_2CH_3$.

In some embodiments of the compounds of Formula I, Id, Ie, or If, $R^2$ for each of the seven independent monomers is $C_2$-$C_4$ alkyl substituted with one or more groups selected from —O($C_1$-$C_4$ alkyl) and —OH; and each $R^3$ is H. In some embodiments, each $R^2$ independently is a $C_2$-$C_4$ alkyl substituted with one or two OH; and each $R^3$ is H. In some embodiments, each $R^2$ is 2-hydroxypropyl; and each $R^3$ is H. In some embodiments, each $R^2$ is 2-hydroxybutyl (e.g., 2-hydroxyisobutyl); and each $R^3$ is H. In some embodiments, each $R^2$ independently is $C_2$-$C_4$ alkyl substituted with one or two —$OCH_3$ or —$OCH_2CH_3$; and each $R^3$ is H. In some embodiments, each $R^2$ independently is $C_2$-$C_4$ alkyl substituted with one —$OCH_3$ or —$OCH_2CH_3$; and each $R^3$ is H.

In some embodiments of the compounds of Formula I, Id, Ie, or If, $R^2$ for each of the seven independent monomers is ethyl substituted with one or more groups selected from —O($C_1$-$C_4$ alkyl) and —OH; and each $R^3$ is H. In some embodiments, each $R^2$ independently is an ethyl substituted with one or two OH; and each $R^3$ is H. In some embodiments, each $R^2$ independently is ethyl substituted with one or two —$OCH_3$ or —$OCH_2CH_3$; and each $R^3$ is H. In some embodiments, each $R^2$ independently is ethyl substituted with one —$OCH_3$ or —$OCH_2CH_3$; and each $R^3$ is H.

In some embodiments of the compounds of Formula I, Ia, Ib, or Ic, each $R^3$ is H.

In some embodiments of the compounds of Formula I, Ia, Ib, or Ic, $R^3$ for each of the seven independent monomers is $C_2$-$C_4$ alkyl substituted with one or more groups selected from —O($C_1$-$C_4$ alkyl) and —OH. In some embodiments, each $R^3$ independently is $C_2$-$C_4$ alkyl substituted with one or two OH. In some embodiments, each $R^3$ is 2-hydroxypropyl. In some embodiments, each $R^3$ is 2-hydroxyisobutyl. In some embodiments, each $R^3$ independently is $C_2$-$C_4$ alkyl substituted with one or two —O($C_1$-$C_4$ alkyl). In some embodiments, each $R^3$ independently is $C_2$-$C_4$ alkyl substituted with one or two —$OCH_3$ or —$OCH_2CH_3$. In some embodiments, each $R^3$ independently is $C_2$-$C_4$ alkyl substituted with one —$OCH_3$ or —$OCH_2CH_3$.

In some embodiments of the compounds of Formula I, Ia, Ib, or Ic, $R^3$ for each of the seven independent monomers is ethyl substituted with one or more groups selected from —O($C_1$-$C_4$ alkyl) and —OH. In some embodiments, each $R^3$ independently is ethyl substituted with one or two OH. In some embodiments, each $R^3$ independently is ethyl substituted with one or two —O($C_1$-$C_4$ alkyl). In some embodiments, each $R^3$ independently is ethyl substituted with one or two —$OCH_3$ or —$OCH_2CH_3$. In some embodiments, each $R^3$ independently is ethyl substituted with one —$OCH_3$ or —$OCH_2CH_3$.

In some embodiments of the compounds of the disclosure, each $R^2$ is the same.

In some embodiments of the compounds of the disclosure, each $R^3$ is the same.

In some embodiments, the compound of Formula I (e.g., a compound of formula, Ia, Ib, Ic, Id, Ie, or If) is selected from Table C-1:

TABLE C-1

| Compounds of Formula I | |
|---|---|
| Cmpd. No. | Structure |
| 1 | 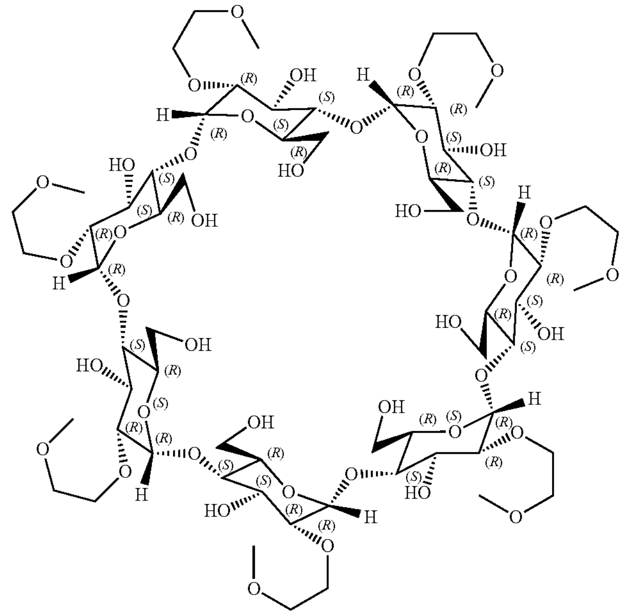 [SMILES: COCCO[C@H]1[C@H]2O[C@H]3[C@H](O)[C@@H](OCCOC)[C@@H](O[C@H]4[C@H](O)[C@@H](OCCOC)[C@@H](O[C@H]5[C@H](O)[C@@H](OCCOC)[C@@H](O[C@H]6[C@H](O)[C@@H](OCCOC)[C@@H](O[C@H]7[C@H](O)[C@@H](OCCOC)[C@@H](O[C@H]8[C@H](O)[C@@H](OCCOC)[C@@H](O[C@@H]([C@@H]1O)[C@@H](CO)O2)O[C@@H]8CO)O[C@@H]7CO)O[C@@H]6CO)O[C@@H]5CO)O[C@@H]4CO)O[C@@H]3CO] |
| 2 | 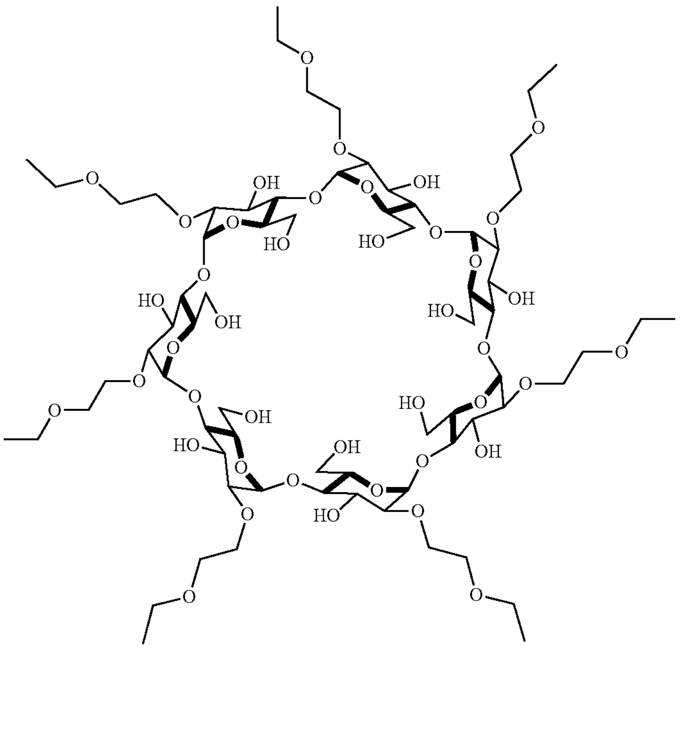 |

TABLE C-1-continued
| Compounds of Formula I | |
|---|---|
| Cmpd. No. | Structure |
| 3 | 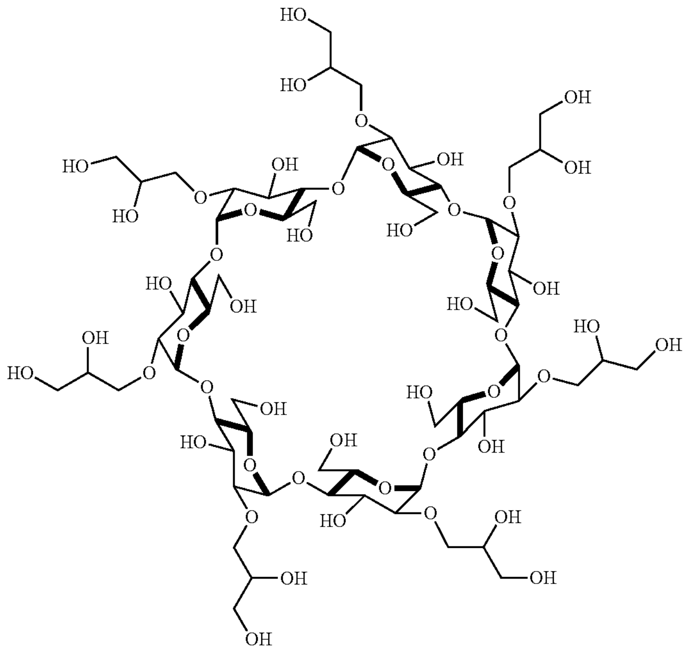 |
| 4 | 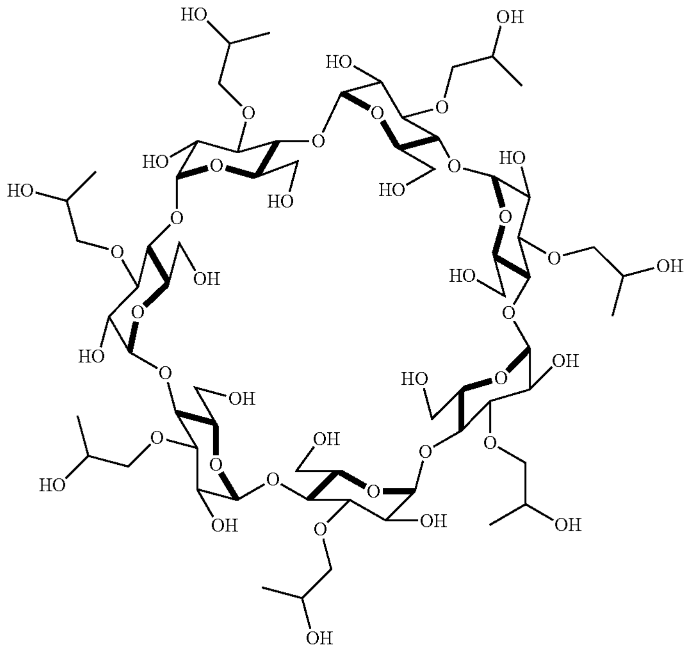 |

TABLE C-1-continued
| Compounds of Formula I | |
|---|---|
| Cmpd. No. | Structure |
| 5 | 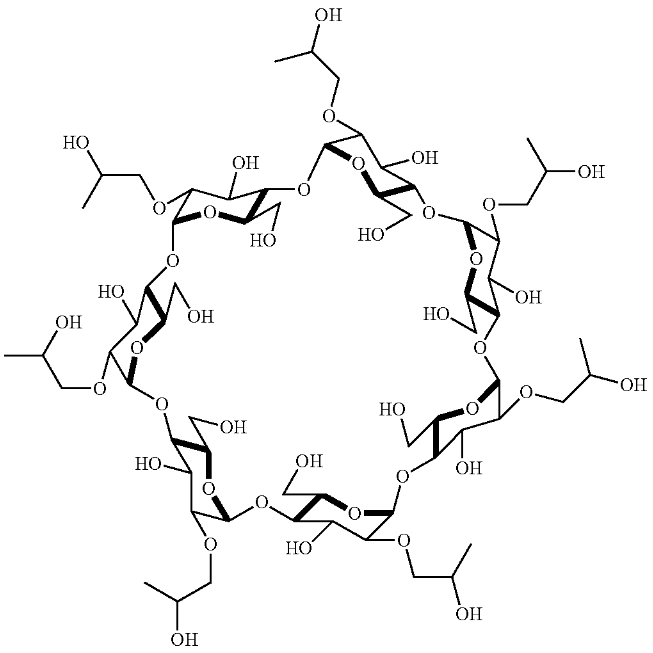 |
| 6 | 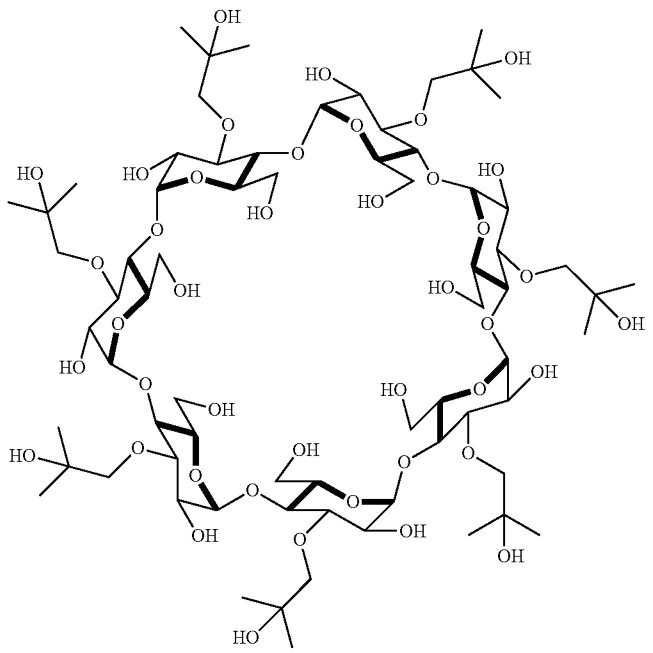 |

TABLE C-1-continued
| Compounds of Formula I | |
|---|---|
| Cmpd. No. | Structure |
| 7 | 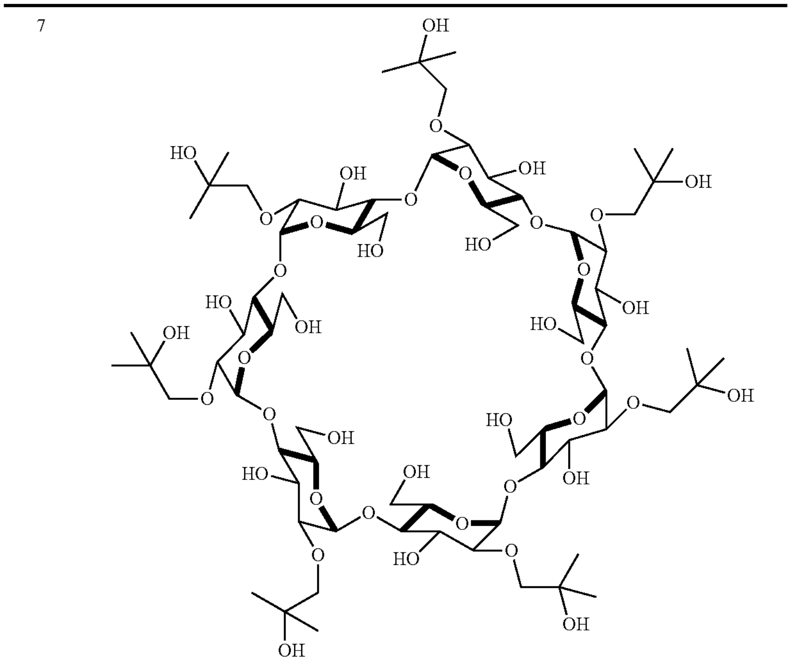 |
In some embodiments, the compound of Formula I is selected from the group consisting of
| Cmpd. No. | Structure |
|---|---|
| 3 | 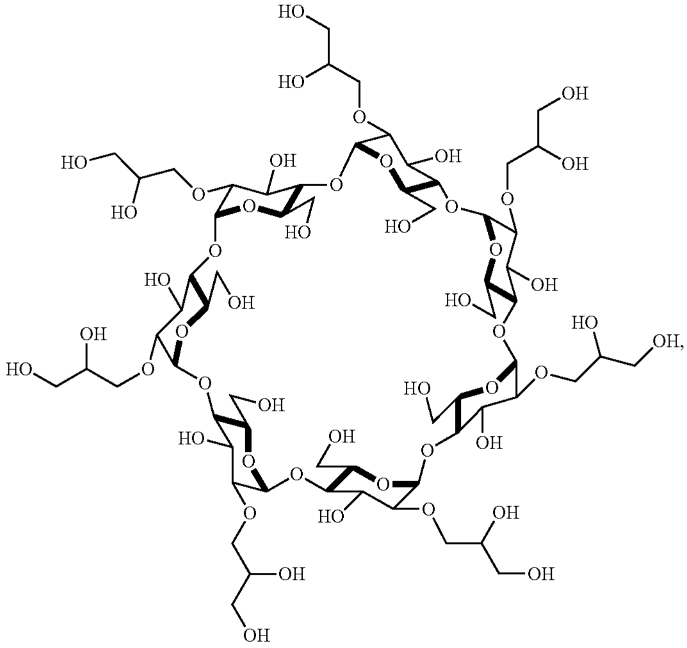 |

-continued
| Cmpd. No. | Structure |
| --- | --- |
| 5 | 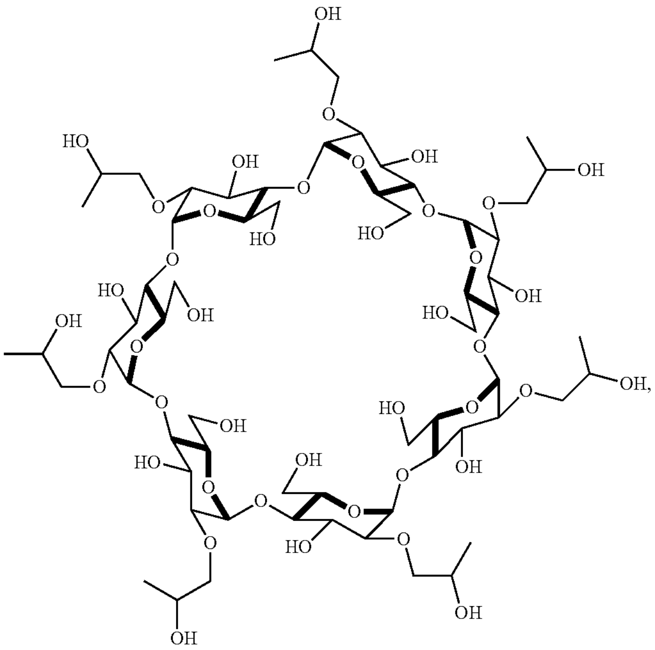 |
| | and |
| 7 | 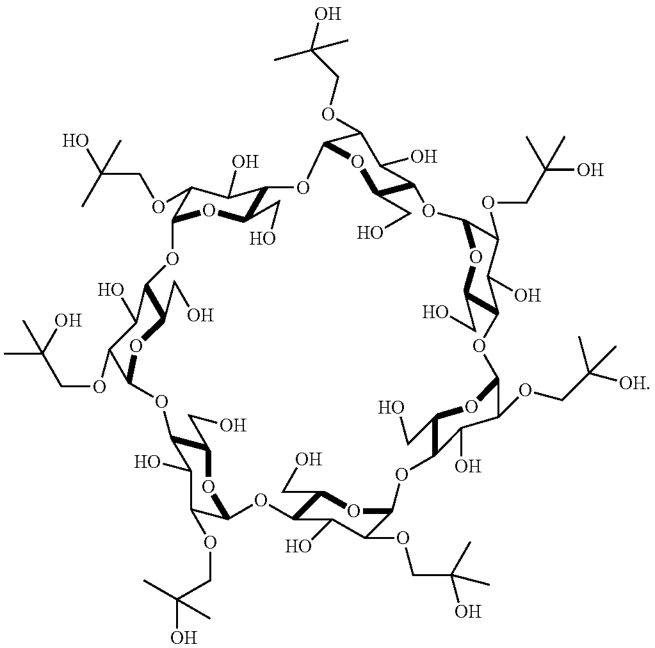 |

In some embodiments, the compound of Formula I is selected from the group consisting of:
| Cmpd. No. | Structure |
|---|---|
| 4 | 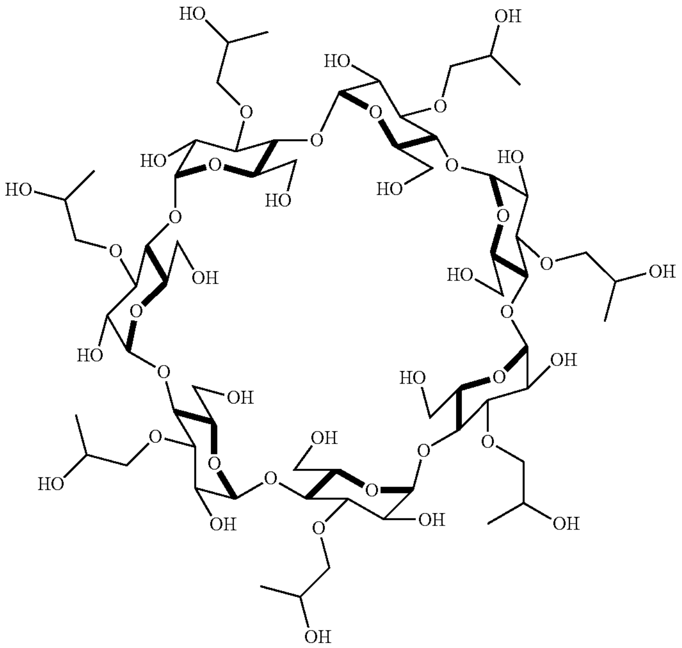 and |
| 6 | 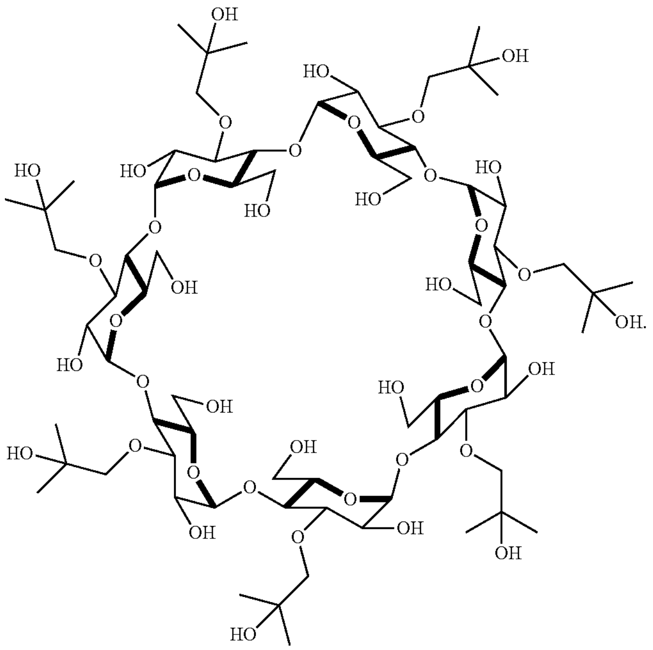 |

In some embodiments, the compound of Formula I is selected from the group consisting of:
| Cmpd. No. | Structure |
|---|---|
| 1 | 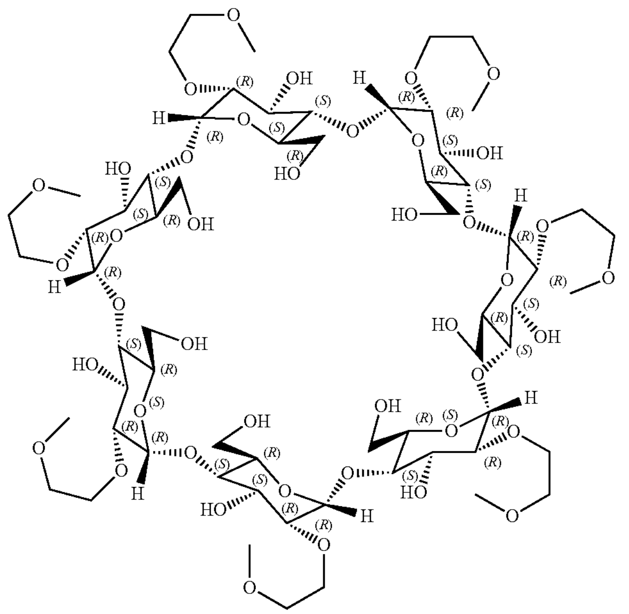 [SMILES: COCCO[C@H]1[C@H]2O[C@H]3[C@H](O)[C@@H](OCCOC)[C@@H](O[C@H]4[C@H](O)[C@@H](OCCOC)[C@@H](O[C@H]5[C@H](O)[C@@H](OCCOC)[C@@H](O[C@H]6[C@H](O)[C@@H](OCCOC)[C@@H](O[C@H]7[C@H](O)[C@@H](OCCOC)[C@@H](O[C@H]8[C@H](O)[C@@H](OCCOC)[C@@H](O[C@@H]([C@@H]1O)[C@@H](CO)O2)O[C@@H]8CO)O[C@@H]7CO)O[C@@H]6CO)O[C@@H]5CO)O[C@@H]4CO)O[C@@H]3CO] |
| | and |
| 2 | 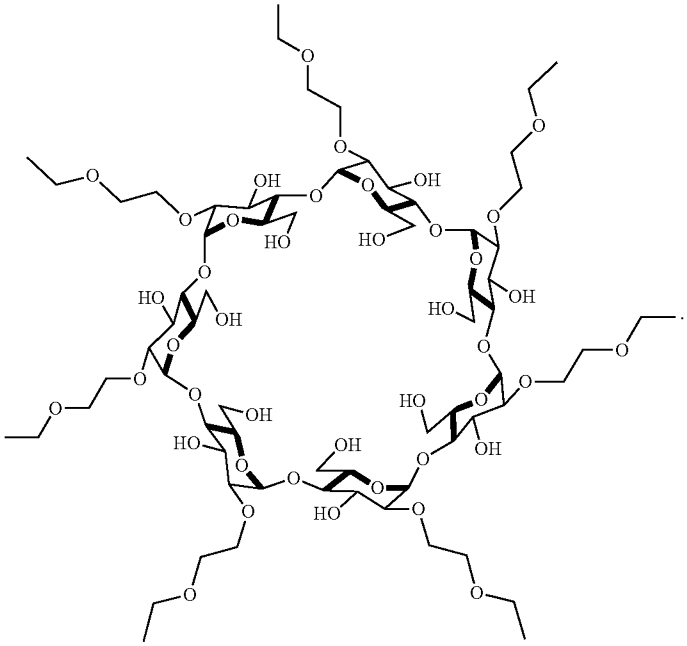 |

In some embodiments, the compound of Formula I is selected from the group consisting of:

| Cmpd. No. | Structure |
|---|---|
| 2 | 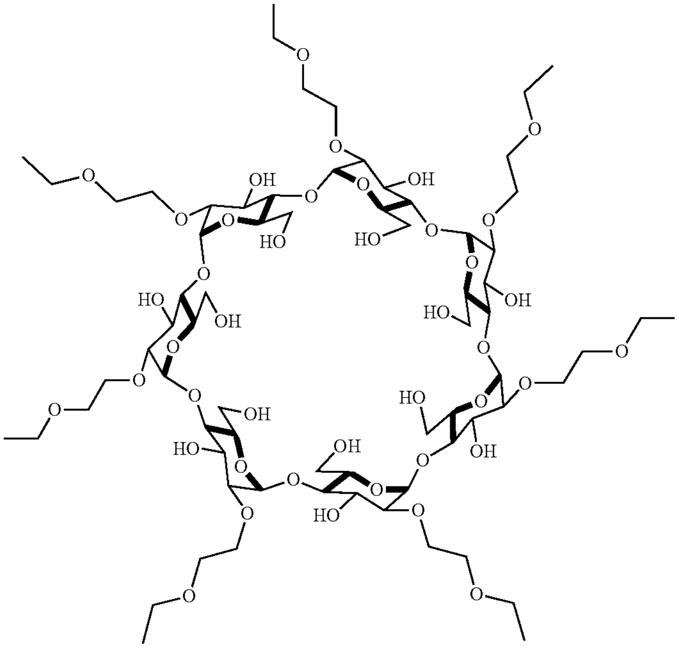 |
| | and |
| 7 | 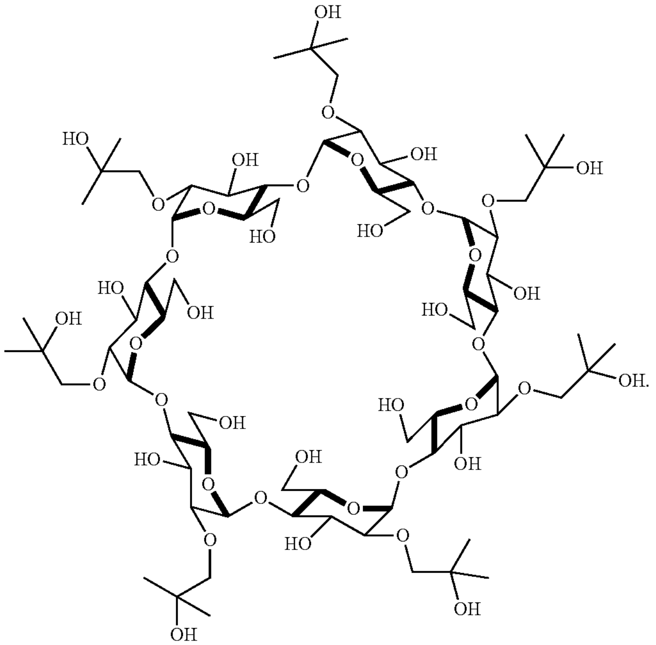 |

Figure 2:
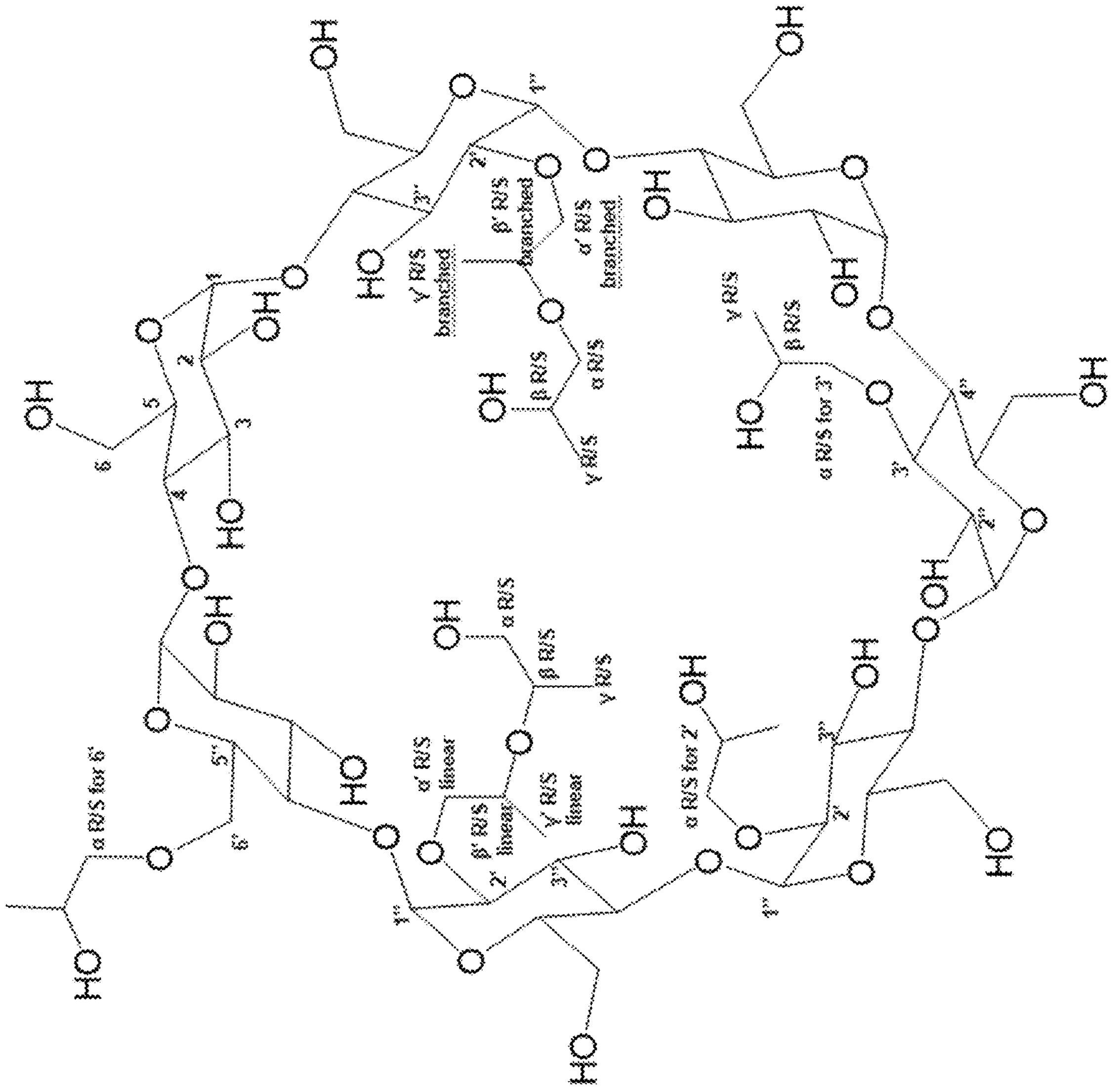
FIG. 2 illustrates the nomenclature and atom numbering used to assign $^1$H-NMR spectra peaks in substituted 2-HPBCDs. The numbers 1, 2, 3, 4, 5, and 6 identify the position of the glucose protons, the letters a, 3, and y identify side chain protons, the symbol ' (e.g., 2', and 3') identifies a position carrying a substituent, the symbol " (e.g., 2", and 3") identifies a position neighboring a position carrying a substituent, R and S identify splitting caused by a chiral center, and the terms "branched" and "linear" refer to the isomerism of an oligomerized side chain (if present).

In some embodiments, a compound of Formula I (e.g., Compound 1, Compound 2, Compound 3, Compound 5, or Compound 7) is characterized by a 1D H-NMR spectrum having only a single peak attributable to the hydrogen at the anomeric center (which is the position 1 or 1" in the exemplary 2-HPBCD of FIG. 2). In some embodiments, a compound of Formula (I) (e.g., Compound 1, Compound 2, Compound 3, Compound 5, or Compound 7) is characterized by a 1D H-NMR spectrum collected in $D_2O$ having only a single peak in the anomeric region. In some embodiments, a compound of Formula (I) (e.g., Compound 1, Compound 2, Compound 3, Compound 5, or Compound 7) is characterized by a 1D H-NMR spectrum collected in $D_2O$ having only a single peak attributable to the compound in the region located between 4.4 ppm and 5.6 ppm, including the endpoints (e.g., in the region between 5.2 ppm and 5.6 ppm, including the endpoints). In some embodiments, the single peak occurs at a chemical shift of 5.0 ppm or higher (e.g., at a chemical shift of 5.2 ppm or higher). In some embodiments, the single peak occurs at a chemical shift of between about 5.0 ppm and about 5.5 ppm, including the endpoints (e.g., between about 5.2 ppm and about 5.5 ppm, including the endpoints). In some embodiments, the single peak occurs at a chemical shift of about 5.3 ppm. In some embodiments, a compound of Formula I (e.g., Compound 5) is characterized by a 1D H-NMR spectrum collected in $D_2O$ that is substantially the same as the spectrum of FIG. 3. In some embodiments, a compound of Formula I (e.g., Compound 5) is characterized by a 1D H-NMR spectrum collected in $D_2O$ that is substantially the same as the spectrum of FIG. 3 in the region located between 3.0 ppm and 4.0 ppm, including the endpoints.

In some embodiments, as demonstrated in Biological Example 1 herein, a compound of Formula I, Ia, Ib, Ic, Id, Ie, or If is capable of increasing or accelerating cholesterol efflux from a cell. In some embodiments, the cell is in vitro. In some embodiments, the cell is in a subject. In some embodiments, a compound of Formula I, Ia, Ib, Ic, Id, Ie, or If, (e.g., an isomerically pure compound or single isomer of the structure of Formula I, Ia, Ib, Ic, Id, Ie, or If) is capable of increasing or accelerating cholesterol efflux from a cell more efficaciously or at a higher rate than a reference standard (e.g., a non-isomerically pure hydroxypropyl beta-cyclodextrin).

In some embodiments, as demonstrated in Examples 1 and 2, a compound of Formula I, Ia, Ib, Ic, Id, Ie, or If, (e.g., an isomerically pure compound or a single isomer of the structure of Formula I, Ia, Ib, Ic, Id, Ie, or If) is capable of increasing or accelerating cholesterol efflux from a cell more efficaciously or at a higher rate than a reference standard (e.g., a non-isomerically pure hydroxypropyl beta-cyclodextrin) while causing less or comparable cytotoxic effects.

Benefits of Compounds of Formula I

Commercially available or traditionally synthesized 2-HPBCD products (which are complex mixtures of molecules, each of which has a differing degree of hydroxypropylation on the cyclodextrin ring and wherein the complex mixture typically also comprises different regioisomers of 2-HPBCD) can contain compounds that form aggregates in certain solvents or biological environments (e.g., aqueous solutions). Without wishing to be bound by any particular theory, oligomerized side chains can occur in such compounds and aggregation may be particularly prevalent in compounds comprising oligomerized side chains in certain positions on the glucose subunit. Aggregation could result in reduced workability or difficulties in formulating commercially available or traditionally synthesized 2-HPBCD products for medical uses. Moreover, aggregation of these compounds in vivo (e.g., in the bloodstream) could result in unwanted effects such as reduction of efficacy or even toxicity. Compounds of the disclosure address this problem. Without wishing to be bound by any particular theory, certain compounds of the disclosure, e.g., isomerically pure forms of 2-HPBCD with hydroxypropyl groups substituted exclusively at the 2-0 position (e.g., Compound 5) or analogs thereof (e.g., Compound 1, Compound 2, Compound 3, or Compound 7), may be less likely than compounds comprised in commercially available or traditionally synthesized 2-HPBCD products to form aggregates, or may not form aggregates at all. The formation of aggregates by compounds of the disclosure can be measured by dissolving a compound of the disclosure (e.g., Compound 1, Compound 2, Compound 3, Compound 5, or Compound 7) in water and measuring average particle sizes in the resulting solution using dynamic light scattering. Larger average particle sizes (for example, in some instances, average particle diameters of >10 nm) indicate the formation of aggregates.

Similarly, some compounds comprised in commercially available or traditionally synthesized 2-HPBCD products can form self-inclusion complexes, i.e., compounds in which a hydroxypropyl substituent is included in the cavity of the cyclodextrin scaffold bearing it. This could diminish the therapeutic efficacy of these compounds because their cavity would no longer be available for guest inclusion. Without wishing to be bound by any particular theory, some compounds of the disclosure, e.g., isomerically pure forms of 2-HPBCD with hydroxypropyl groups substituted exclusively at the 2-0 position, (e.g., Compound 5) or analogs thereof (e.g., Compound 1, Compound 2, Compound 3, or Compound 7), may have a lower likelihood of forming self-inclusion complexes than compounds comprised in commercially available or traditionally synthesized 2-HPBCD products or may not form self-inclusion complexes at all. Self-inclusion complexes can be identified via 2D-NMR analytical methods (e.g., Rotating-Frame Overhauser Enhancement Spectroscopy (ROESY), Diffusion-Ordered Spectroscopy (DOSY) or combinations of both methods), by observing the nature of cross-correlations between the substituent on the cyclodextrin scaffold (e.g., hydroxypropyl) and the hydrogen atoms of the cyclodextrin scaffold.

Lastly, certain compounds of the disclosure, e.g., isomerically pure forms of 2-HPBCD with hydroxypropyl groups substituted exclusively at the 2-0 position, (e.g., Compound 5) or analogs thereof (e.g., Compound 1, Compound 2, Compound 3, or Compound 7), may have the ability to separate enantiomers comprised in a chiral analyte. For example, compounds of the disclosure (e.g., isomerically pure forms of 2-HPBCD with hydroxypropyl groups substituted exclusively at the 2-0 position (e.g., Compound 5) or analogs thereof (e.g., Compound 1, Compound 2, Compound 3, or Compound 7), may be particularly suitable for use in chromatographic separation of enantiomers comprised in a chiral analyte. The ability of a compound of the disclosure, e.g., a isomerically pure form of 2-HPBCD with hydroxypropyl groups substituted exclusively at the 2-0 position (e.g., Compound 5) or analogs thereof (e.g., Compound 1, Compound 2, Compound 3, or Compound 7), to separate enantiomers comprised in a chiral analyte can be evaluated as follows: First a solution of the compound of the disclosure (e.g., Compound 1, Compound 2, Compound 3, Compound 5, or Compound 7) in an appropriate solvent system (e.g., a biphasic solvent system for enantioseparation of the particular analyte) is loaded onto a silica column via chemical immobilization, or into a countercurrent chromatographic separation column, where a compound of the disclosure, e.g., a isomerically pure form of 2-HPBCD with hydroxypropyl groups substituted exclusively at the 2-0 position, (e.g., Compound 5) or an analog thereof (e.g., Compound 1, Compound 2, Compound 3, or Compound 7), is applied to the mobile phase prior to introducing the chiral analyte. Subsequently, the chiral analyte is introduced into the same column. Lastly, the effluent from the column is analyzed, e.g., via UV-VIS, to determine separation of the enantiomers of the chiral analyte. Alternatively, the enantioseparation potency of a compound of the disclosure, e.g., Compound 1, Compound 2, Compound 3, Compound 5, or Compound 7, can be tested using capillary electrophoresis (with the compound of the disclosure, e.g., Compound 1, Compound 2, Compound 3, Compound 5, or Compound 7 as the chiral selector) combined with NMR measurements.

In another aspect, disclosed herein are compounds of Formula II:

(II)

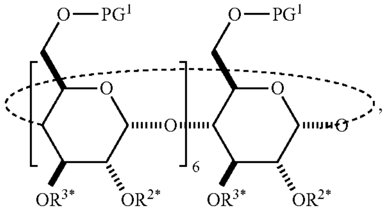

wherein:

$PG^1$ is a first alcohol protecting group; and each $R^{2*}$ and $R^{3*}$ independently, at each occurrence for each of the seven independent monomers, is $PG^1$, $—CH_2C(O)CH_3$, or $C_2$-$C_6$ alkenyl optionally substituted with one or more —OH or $—OPG^2$, wherein $PG^2$ is a second alcohol protecting group, and wherein at least one $R^{2*}$ or at least one $R^{3*}$ is $—CH_2C(O)CH_3$ or $C_2$-$C_6$ alkenyl optionally substituted with one or more —OH or $—OPG^2$.

In some embodiments of the compounds of Formula (II), each $R^{2*}$ and $R^{3*}$ independently, at each occurrence for each of the seven independent monomers, is $PG^1$ or $—CH_2C(O)CH_3$.

In some embodiments of the compounds of Formula (II), each $R^{2*}$ and $R^{3*}$ independently, at each occurrence for each of the seven independent monomers, is $PG^1$ or unsubstituted $C_2$-$C_6$ alkenyl.

In some embodiments of the compounds of Formula (II), each $R^{2*}$ and $R^{3*}$ independently, at each occurrence for each of the seven independent monomers, is $PG^1$ or $C_2$-$C_6$ alkenyl substituted with one or more $—OPG^2$.

In some embodiments of the compounds of Formula (II), $PG^1$ is selected from tert-butyldimethylsilyl, trimethylsilyl, triisopropylsilyloxymethyl, and triisopropylsilyl.

In some embodiments, $PG^1$ is benzyl, p-methoxybenzyl, dimethoxybenzyl, or p-methoxyphenyl.

In some embodiments of the compounds of Formula (II), $PG^2$ is ethoxymethyl or methoxymethyl.

In some embodiments of the compound of Formula (II), the compound is selected from the group consisting of:

| Cmpd. No. | Structure |
| --- | --- |
| II-1 | 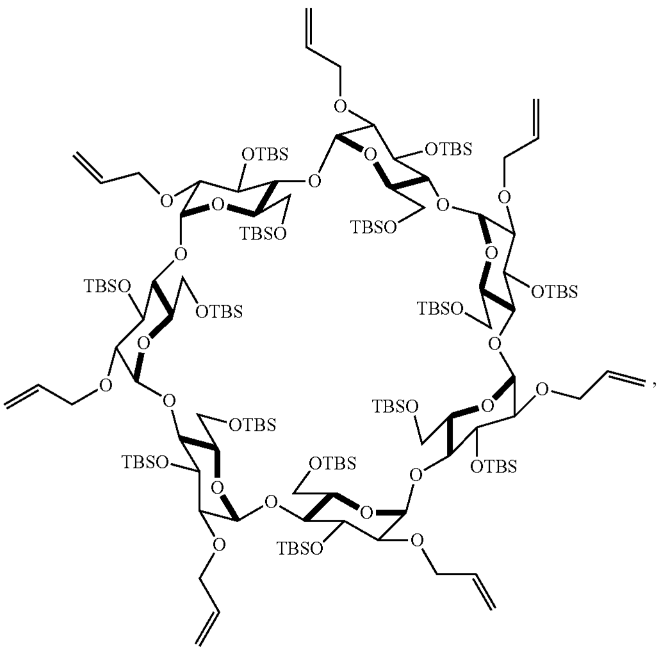 |

-continued
| Cmpd. No. | Structure |
| --- | --- |
| II-2 | 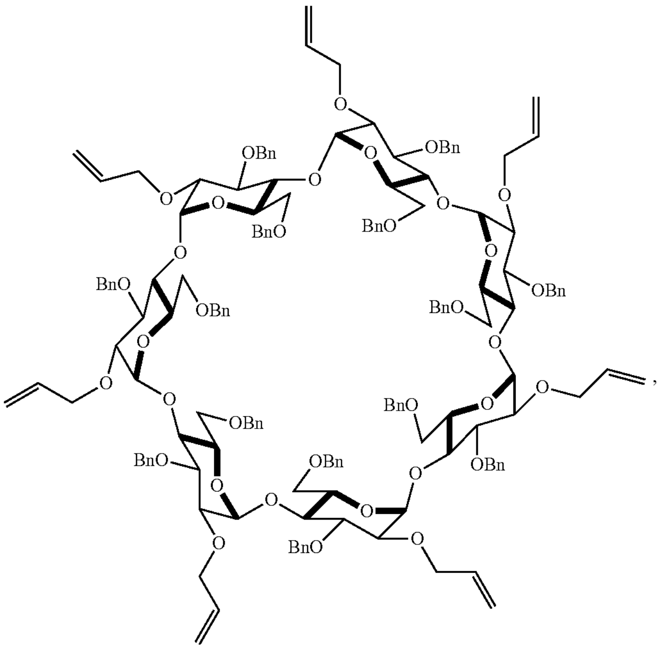 |
| II-3 | 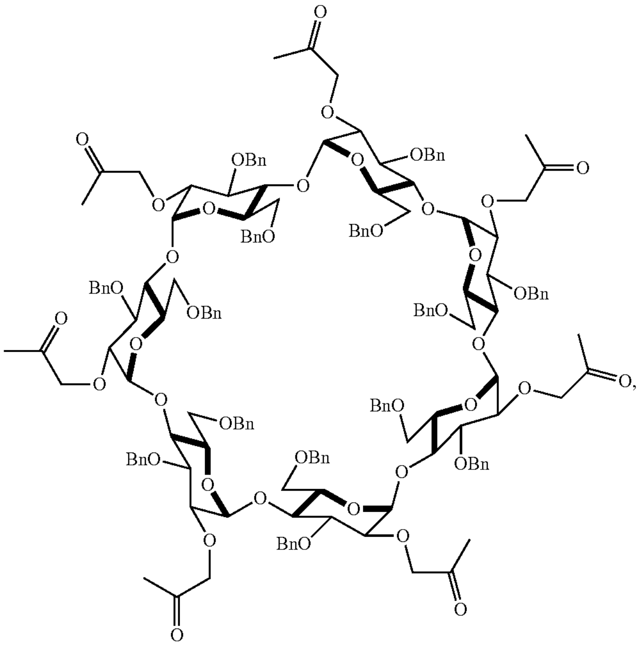 |

-continued
| Cmpd. No. | Structure |
| --- | --- |
| II-4 | 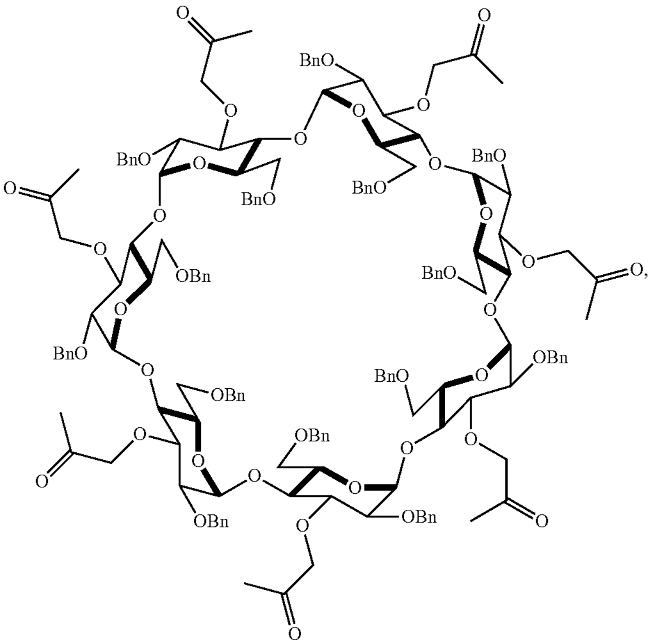 |
| II-5 | 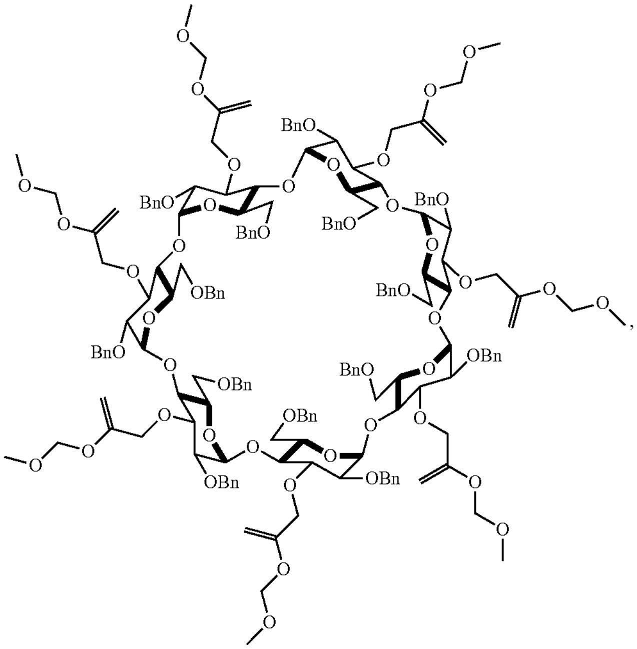 |

-continued
| Cmpd. No. | Structure |
|---|---|
| II-6 | 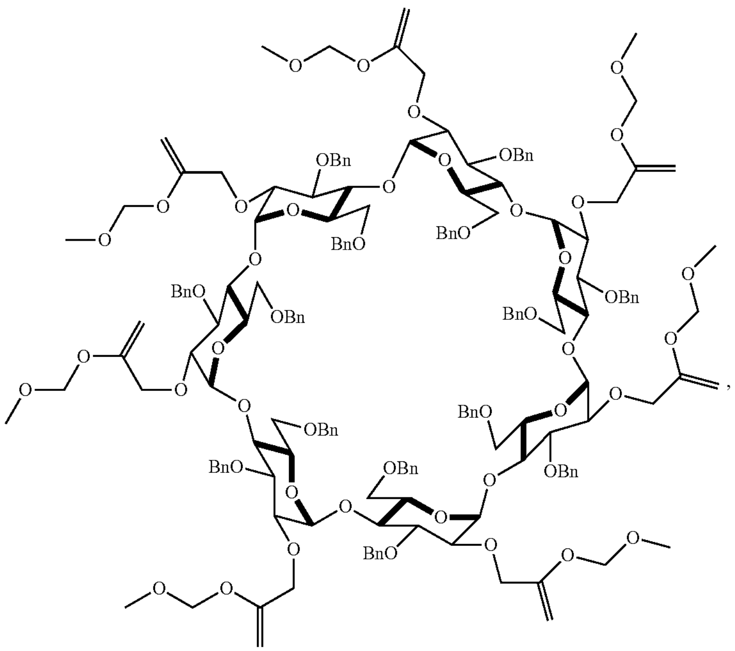 and |
| II-7 | 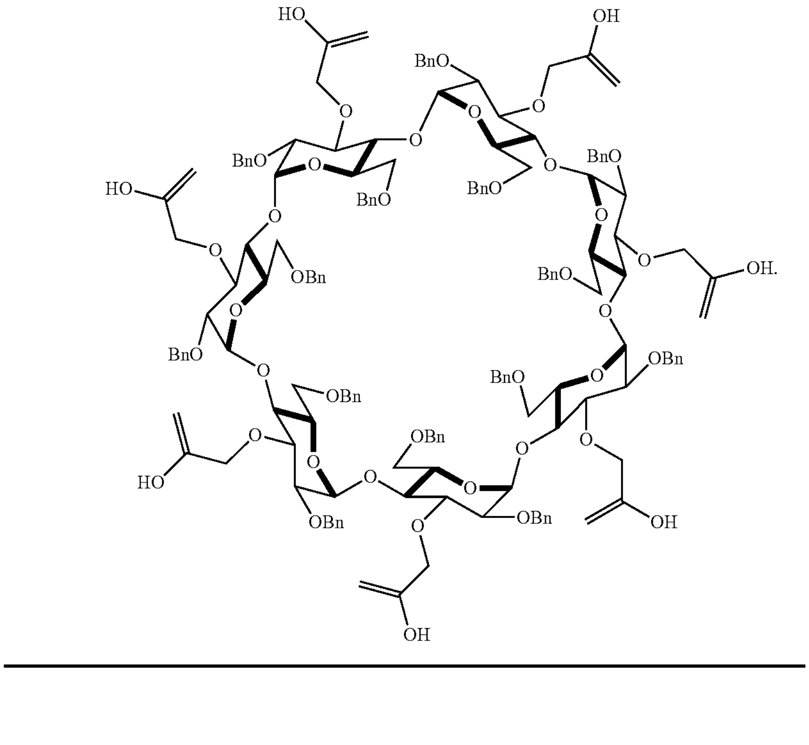 |

In another aspect, disclosed herein are compounds of Formula IIa:

(IIa)

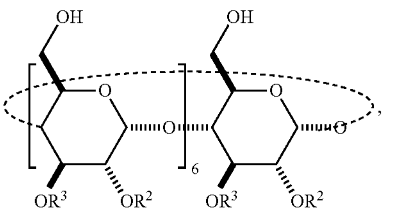

wherein:

each $R^2$ and $R^3$ independently, at each occurrence for each of the seven independent monomers, is H or $C_2$-$C_4$ alkenyl, wherein at least one $R^2$ or at least one $R^3$ is $C_2$-$C_4$ alkenyl.

In one embodiment of the compounds of Formula IIa, the compound is

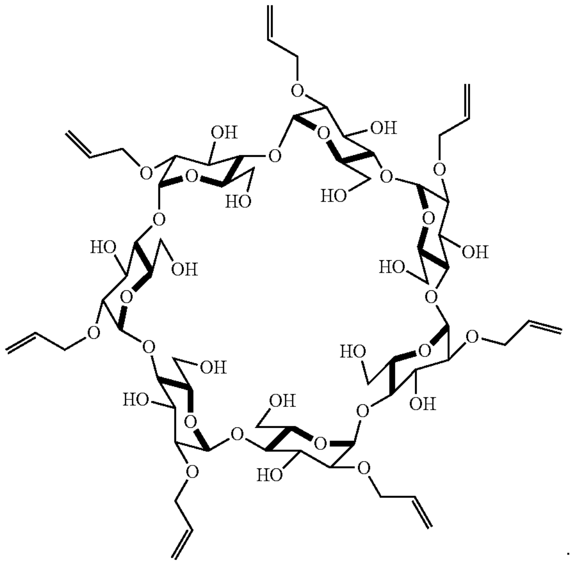

.

In some embodiments, the compound of Formula I, Ia, Ib, Ic, Id, Ie, If, II, or IIa has a purity of at least 95%. For example, in some embodiments, the compound of Formula I, Ia, Ib, Ic, Id, Ie, If, II, or IIa has a purity of 95%, 96%, 97%, 98%, 99%, or 100%. In some embodiments, the purity is the purity as determined by HPLC.

In some embodiments, the compound of Formula I, Ia, Ib, Ic, Id, Ie, If, II, or IIa is isomerically pure. For example, in some embodiments, the compound of Formula I, Ia, Ib, Ic, Id, Ie, If, II, or IIa has an isomeric purity of at least 95%. For example, in some embodiments, the compound of Formula I, Ia, Ib, Ic, Id, Ie, If, II, or IIa has an isomeric purity of 95%, 96%, 97%, 98%, 99%, or 100%. In some embodiments, the regioisomeric purity of the compounds is determined via $^1$HNMR.

In some embodiments, the compound of Formula I, Ia, Ib, Ic, Id, Ie, If, II, or IIa is regisomerically pure. For example, in some embodiments, the compound of Formula I, Ia, Ib, Ic, Id, Ie, If, II, or IIa has an regioisomeric purity of at least 95%. For example, in some embodiments, the compound of Formula I, Ia, Ib, Ic, Id, Ie, If, II, or IIa has an regioisomeric purity of 95%, 96%, 97%, 98%, 99%, or 100%. In some embodiments, the regioisomeric purity of the compounds is determined via $^1$HNMR. $^1$HNMR data of non-limiting examples of compounds of the disclosure, e.g., compounds of Formula I, Ia, Ib, Ic, Id, Ie, If, II, or IIa, are presented in Example 1.

Methods of Treating Diseases

Biological Example 1 herein depicts the results of a cholesterol efflux capacity (CEC) assay for representative compounds of Formula I, Ia, Ib, Ic, Id, Ie, or If. The data demonstrates increased cholesterol efflux from a cell after contacting a cell with a compound of Formula I, Ia, Ib, Ic, Id, Ie, or If.

Biological Example 2 depicts the results of a lactate dehydrogenase (LDH) cytotoxicity assay for representative compounds of Formula I, Ia, Ib, Ic, Id, Ie, or If. It is shown that in some embodiments, a compound of Formula I, Ia, Ib, Ic, Id, Ie, or If increases or accelerates cholesterol efflux more efficaciously or at a higher rate than a reference, but has a cytotoxicity that is comparable or lower than the cytotoxicity of a reference standard.

In some embodiments, administration of a compound of the disclosure (e.g., a compound of Formula I, Ia, Ib, Ic, Id, Ie, or If) increases cholesterol efflux capacity in a cell. For example, in some embodiments, administration of a compound of the disclosure (e.g., a compound of Formula I, Ia, Ib, Ic, Id, Ie, or If) results in an increase in cholesterol efflux from a cell after administration of the compound of the disclosure as compared to the cholesterol efflux measured before administration of the compound of the disclosure, as shown in Biological Example 1. The increase in cholesterol efflux may be up to about 1%, up to about 2%, up to about 4%, up to about 6%, up to about 8%, up to about 10%, about 2% to about 10%, about 4% to about 10%, about 6% to about 10%, about 8% to about 10%, up to about 5%, about 5% to about 10%, or at least about 10% (e.g., 15%, 20%, 25%, 30%, 35%, 40%, 45%, 50%, or more), measured in a certain time frame after administration of a compound of Formula I, Ia, Ib, Ic, Id, Ie, or If.

In some embodiments, administration of a compound of the disclosure (e.g., a compound of Formula I, Ia, Ib, Ic, Id, Ie, or If) to a subject results in an increase or acceleration in cholesterol efflux from a cell of the subject after administration of the compound of the disclosure as compared to the cholesterol efflux measured after administration of a reference standard to the subject. In some embodiments, the cholesterol efflux is from about 106% to about 125% (e.g., about 110%, about 115%, about 120%, or about 125%) of the cholesterol efflux measured after administration of a reference standard. In some embodiments, the cholesterol efflux is about 126% or more (e.g., about 130%, about 135%, about 140%, or about 145%) of the cholesterol efflux measured after administration of a reference standard. In some embodiments, the reference standard is a non-isomerically pure hydroxypropyl beta-cyclodextrin.

In some embodiments, contacting a cell with a compound of the disclosure (e.g., a compound of Formula I, Ia, Ib, Ic, Id, Ie, or If) results in an increase or acceleration of cholesterol efflux from the cell after contacting the cell with the compound of the disclosure as compared to the cholesterol efflux measured after contacting the cell with a reference standard, as shown in Biological Example 1. In some embodiments, the cholesterol efflux is from about 106% to about 125% (e.g., about 110%, about 115%, about 120%, or about 125%) of the cholesterol efflux measured after administration of a reference standard. In some embodiments, the cholesterol efflux is about 126% or more (e.g., about 130%, about 135%, about 140%, or about 145%) of the cholesterol efflux measured after administration of a reference standard.

In some embodiments, the reference standard is a non-isomerically pure hydroxypropyl beta-cyclodextrin.

In some embodiments, contacting a cell with a compound of the disclosure (e.g., a compound of Formula I, Ia, Ib, Ic, Id, Ie, or If) results in lower or similar cytotoxicity as contacting the cell with a reference standard, as shown in Biological Example 2. In some embodiments, the cytotoxicity of a compound of the disclosure or a reference standard is determined by measuring the release of lactate dehydrogenase (LDH) from a cell after contacting the cell with the reference standard or the compound of the disclosure. In some embodiments, the release of LDH from a cell contacted with a compound of the disclosure is 70% or less of the release of LDH from a cell contacted with a reference standard. In some embodiments, the release of LDH from a cell contacted with a compound of the disclosure is from about 71% to about 95% of the release of LDH from a cell contacted with a reference standard. In some embodiments, the release of LDH from a cell contacted with a compound of the disclosure is from about 96% to about 105% of the release of LDH from a cell contacted with a reference standard. In some embodiments, the release of LDH from a cell contacted with a compound of the disclosure is within 120% of the release of LDH from a cell contacted with a reference standard. In some embodiments, the reference standard is a non-isomerically pure hydroxypropyl beta-cyclodextrin.

In additional embodiments, the cholesterol efflux is sustained or even increased relative to the pre-dose levels, even after the compounds of Formula I, Ia, Ib, Ic, Id, Ie, or If, pharmaceutical compositions, and pharmaceutical formulations described herein have cleared from the subject, or after the circulating and/or systemic levels of the compound of Formula I, Ia, Ib, Ic, Id, Ie, or If is reduced (e.g., during an interval of administration dosages, or after the last dosage for administration). Without wishing to be bound by any particular theory, the compound of Formula I, Ia, Ib, Ic, Id, Ie, or If may facilitate cholesterol migration via various endogenous vehicles (e.g., ApoA1-containing HDL particles) that continues once the compound of Formula I, Ia, Ib, Ic, Id, Ie, or If has cleared the subject.

In some embodiments, compounds of Formula I, Ia, Ib, Ic, Id, Ie, or If are useful in the treatment of certain diseases associated with intracellular cholesterol or high levels of cholesterol in the body.

For example, in some embodiments, the disclosure provides a method of treating cardiovascular disease (such as atherosclerosis and diseases or disorders correlated to atherosclerosis) in a human in need thereof, comprising administering a compound of Formula I, Ia, Ib, Ic, Id, Ie, or If; inducing cholesterol efflux out of atheromas of the human subject; and, inducing reverse cholesterol transport from macrophages to the feces or urine of the human subject. In some embodiments, the disclosure also provides a method of treating cardiovascular disease in a human in need thereof, comprising administering a compound of Formula I, Ia, Ib, Ic, Id, Ie, or If; inducing cholesterol efflux out of atheromas of the human subject; and inducing reverse cholesterol transport from macrophages to the feces or urine of the human subject; wherein the amount of cholesterol efflux induced by the compound of Formula I, Ia, Ib, Ic, Id, Ie, or If is greater than the cholesterol efflux induced by a HDL mimetic.

In another aspect, the present disclosure provides a method of increasing cholesterol efflux from a tissue or a cell in a subject, comprising administering to the subject a therapeutically effective amount of a compound described herein (e.g., a compound of Formula I, Ia, Ib, Ic, Id, Ie, or If), or a pharmaceutical composition described herein.

In another aspect, the present disclosure provides a method of sequestering cholesterol in the blood of a subject, comprising administering to the subject a therapeutically effective amount of a compound described herein (e.g., a compound of Formula I, Ia, Ib, Ic, Id, Ie, or If), or a pharmaceutical composition described herein.

In another aspect, the present disclosure provides a method of reducing intracellular cholesterol in a tissue or cell of a subject in need thereof, the method comprising administering to the subject a compound described herein (e.g., a compound of Formula I, Ia, Ib, Ic, Id, Ie, or If), or a pharmaceutical composition described herein.

In another aspect, the present disclosure provides a method of reducing inflammation and/or oxidative stress induced by oxidized LDL in a subject in need thereof, the method comprising administering to the subject a compound described herein (e.g., a compound of Formula I, Ia, Ib, Ic, Id, Ie, or If), or a pharmaceutical composition described herein.

In another aspect, the present disclosure provides a method of improving the renal and/or hepatogenic clearance of cholesterol in a subject in need thereof, the method comprising administering to the subject a compound described herein (e.g., a compound of Formula I, Ia, Ib, Ic, Id, Ie, or If), or a pharmaceutical composition described herein.

In another aspect, the present disclosure provides a method of increasing circulating and/or systemic levels of one or more oxysterol in a subject in need thereof, the method comprising administering to the subject a compound s described herein (e.g., a compound of Formula I, Ia, Ib, Ic, Id, Ie, or If), or a pharmaceutical composition described herein. In some embodiments, the circulating and/or systemic level of the one or more oxysterol in the human individual is increased by at least about 15%, at least about 20%, at least about 30%, at least about 40%, or at least about 50% after the administering as compared to prior to the administering. In some embodiments, the one or more oxysterols are selected from the group consisting of: 27-hydroxycholesterol and 24-hydroxycholesterol.

In another aspect, the present disclosure provides a method of increasing plasma cholesterol crystal dissolution capacity (CCDC) in a subject in need thereof, the method comprising administering to the subject a compound described herein (e.g., a compound of Formula I, Ia, Ib, Ic, Id, Ie, or If), or a pharmaceutical composition described herein.

In another aspect, the present disclosure provides a method of increasing levels of ABCA1 and/or ABCG1 in a subject in need thereof, the method comprising administering to the subject a compound described herein (e.g., a compound of Formula I, Ia, Ib, Ic, Id, Ie, or If), or a pharmaceutical composition described herein.

In another aspect, the present disclosure provides a method of reducing the risk of or preventing cholesterol crystal embolization (CCE) or a symptom thereof in a subject in need thereof, the method comprising administering to the subject a compound described herein (e.g., a compound of Formula I, Ia, Ib, Ic, Id, Ie, or If), or a pharmaceutical composition described herein.

In another aspect, the present disclosure provides a method of treating a disorder of cholesterol metabolism in a subject in need thereof, comprising administering to the subject a therapeutically effective amount of a compound described herein (e.g., a compound of Formula I, Ia, Ib, Ic, Id, Ie, or If), or a pharmaceutical composition described herein.

Evaluation of Efficacy of Compounds of the Disclosure

Plaque volumes may be measured by various methods, such as imaging technology [e.g., coronary computed tomography angiography (CCTA) and multidetector computed tomography angiography (MDCTA; see de Weert et al., *Int J Cardiovasc Imaging.* 2008; 24(7):751-9)], 3D vascular ultrasound technology (see López-Melgar et al., *Atherosclerosis.* 2016; 248:230-7), etc.

Cholesterol crystal dissolution capacity (CCDC) may be measured and quantified by various methods, such as flow cytometry and NMR. An illustrative assay for enumerating crystals is given in Al-Kassou et al., *European Heart Journal,* 2022; 43:Suppl 2, ehac544.1623. An alternative NMR method is shown in Guo et al., *Arterioscler Thromb Vasc Biol,* 2000, 20(6): 1630-1636.

Cholesterol levels and excretion (e.g., in urine and/or stool) may be measured by multiple methods. At least four illustrative methods for measuring cholesterol absorption by the intestine (through measuring excretion of radiolabeled cholesterol) are introduced in Quintao et al., *J Lipid Res.* 1971; 12(2):221-232.

Cholesterol metabolites may be measured by multiple methods. For example, oxysterols are usually measured by gas chromatography-mass spectrometry (GC-MS) methods incorporating selected-ion monitoring (see Dzeletovic et al., *Anal. Biochem.* 1995; 225: 73-80 and Schott et al., Steroids 2015; 99: 139-150) or liquid chromatography tandem-mass spectrometry (LC-MS/MS) methods exploiting multiple reaction monitoring (Stiles et al., *Proc. Natl Acad. Sci. U.S.A.* 2014; 111: E4006-E4014).

Without wishing to be bound by any particular theory, measuring cholesterol efflux can be used to determine efficacy of treatment with a compound of Formula I, Ia, Ib, Ic, Id, Ie, or If. Cholesterol efflux capacity generally refers to the ability of a cell (e.g., macrophages) to remove cholesterol from the cell membrane. The removal from the cell membrane makes the cholesterol available for transport to the liver for excretion.

The measurement of the efficacy of a therapeutic intervention using CEC may demonstrate the effect that such therapy has on the expression of endogenous cholesterol-carrying vehicles such as apoA-1, HDL and other factors that facilitate the shuttling of cholesterol out of cells. One way to measure the effect of a therapeutic intervention on cholesterol efflux is to measure cholesterol efflux capacity before and after the introduction of a therapeutic intervention. Note that the CEC assay described below does not measure the presence of a therapeutic intervention per se, but rather the effect that therapeutic intervention had on the expression of cholesterol-carrying endogenous vehicles such as apoA-1, HDL, etc.

The methods used for measuring CEC generally comprise incubating macrophage cells with a labeled cholesterol source, such as radiolabeled cholesterol (e.g., cholesterol labeled with tritium ($^3H$)), or a fluorescent labeled cholesterol, contacting the cells with serum samples which have been taken from a subject administered a compound of Formula I, Ia, Ib, Ic, Id, Ie, or If, and measuring the amount of cholesterol that is effluxed from the cells over time. For instance, J774, Raw264, or differentiated THP-1 cells may be labeled with [$^3H$]cholesterol ([$^3H$]C) and then incubated with serum samples (e.g., from a subject administered IV of a compound of Formula I, Ia, Ib, Ic, Id, Ie, or If intravenously), and the amount of [$^3H$]C released by cells into the medium is measured. CEC is typically measured using radioisotope-labeled cholesterol, but any isotopes that are safe and effective may be utilized by one of skill in the art. The labelling step may be performed by incubating the cells in a growth medium that includes the radiolabeled cholesterol and ACAT inhibitor. Commercially available cell-based cholesterol efflux assay kits, such as e.g., ab196985, may be used.

To provide more detail, the method used for measuring CEC may comprise the following steps. Step 1: labelling cellular cholesterol by adding labelled cholesterol to cells, and then introducing serum-containing medium (which contains, e.g., a serum or plasma sample from a subject administered with a compound of Formula I, Ia, Ib, Ic, Id, Ie, or If) and incubating with cells for 24-48 h. This step may be combined with loading of cells with cholesterol. Step 2: incubation of cells in serum-free medium to equilibrate labelled cholesterol among all intracellular cholesterol pools. This stage may be combined with activation of cellular cholesterol transporters. Step 3: incubation of cells with extracellular acceptor and quantitation of movement of labelled cholesterol from cells. If cholesterol precursors were used to label newly synthesized cholesterol, a fourth step, purification of cholesterol, may be required. The CEC testing generally delivers the following information: (i) how a particular treatment affects the capacity of cells to efflux cholesterol and (ii) how the capacity of plasma acceptors to accept cholesterol is affected by a treatment. The CEC testing method is highly reproducible, allowing for the comparison of CEC between different treatments.

In some embodiments of the invention, CEC is measured using tritium (3H) labeled cholesterol cells (e.g., J774 cells) in order to physiologically generate serum HDL with radiolabeled cholesterol. After efflux, radiolabeled HDL media may be used to measure cholesterol esterification by chromatography (e.g., TLC or HPLC). Optionally, a second aliquot may be cultured with Fu5AH rat hepatoma cells to assess hepatic cell uptake. Further optionally, sera may be analyzed by gel electrophoresis (e.g., SPIFE) to measure cholesterol distribution across lipoprotein classes.

The amount of effluxed cholesterol may be measured using various methods, such as scintillation counting, fluorescence imaging, or mass spectrometry. In an exemplary embodiment, the amount of effluxed cholesterol is measured by liquid scintillation counting.

The method of the present invention is simple, inexpensive, and may be performed in a laboratory setting with commonly available equipment and reagents. The method is also highly reproducible, allowing for the comparison of efflux capacity between different cells or treatments.

Pharmaceutical Compositions and Pharmaceutical Formulations

Disclosed herein, in certain embodiments, are pharmaceutical compositions or pharmaceutical formulations comprising an effective amount of compound of Formula I, Ia, Ib, Ic, Id, Ie, or If; and a pharmaceutically acceptable excipient.

A pharmaceutical composition of the invention is formulated to be compatible with its intended route of administration. Examples of routes of administration include parenteral, e.g., intrathecal, intravenous, intradermal, subcutaneous, oral (e.g., inhalation), transdermal (topical), and transmucosal administration, e.g., intravenous, intradermal, subcutaneous, oral (e.g., inhalation), transdermal (topical), and transmucosal administration. Solutions or suspensions used for parenteral, intradermal, or subcutaneous application can include one or more of the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In some embodiments, the pharmaceutical formulation is formulated for single dose administration.

In some embodiments, the pharmaceutical formulation is formulated for repeated administration.

Kits

Further provided herein are kits. In some embodiments, the kits include one or more container (e.g., a vial, a flask, a jar, a tube, an ampoule, etc.) containing one or more pharmaceutical compositions or pharmaceutical formulations provided herein (e.g., a compound of Formula I, Ia, Ib, Ic, Id, Ie, or If and a pharmaceutically acceptable excipient). In some embodiments, the kit comprises more than one container (e.g., two, three, four, five, six, seven, eight, nine, ten, or more containers). The one or more container may include a single dosage of the pharmaceutical composition, or multiple dosages (e.g., two, three, four, five, six, seven, eight, nine, ten, or more) of the pharmaceutical composition. The kit may further comprise instructions, e.g., for administering the pharmaceutical composition to a subject for the use of treating any indication described herein. The kit may be provided in a box, a bag, or any other suitable container.

General Synthetic Schemes

Compounds of the present disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds first aspect (or an embodiment thereof) can be synthesized, and various modifications to these schemes can be made and will be suggested to one skilled in the art reading this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over suitable temperature ranges including from about −78° C. to about 150° C., from about 0° C. to about 125° C., and/or about room (or ambient) temperature, e.g., about 20° C.

Compounds of the disclosure can be prepared as illustrated and described in Schemes 1-6 below.

General Synthetic Scheme 1

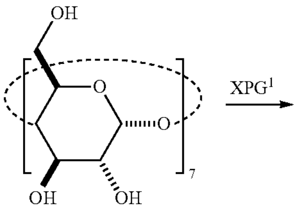

i1

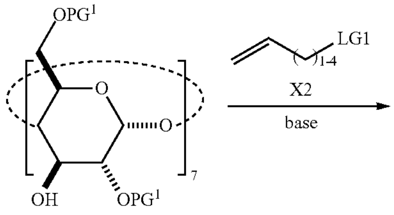

i1a'

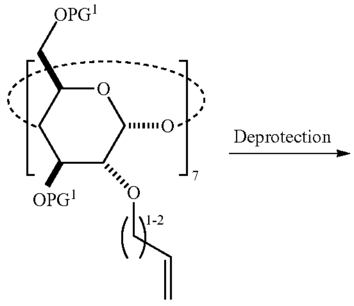

i1b

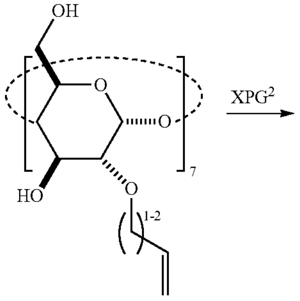

i1c

-continued

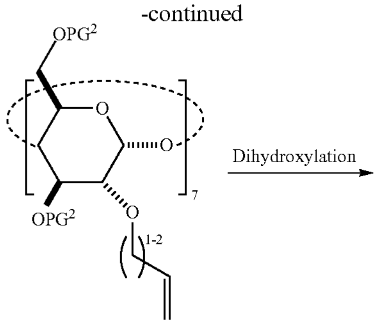

i1d

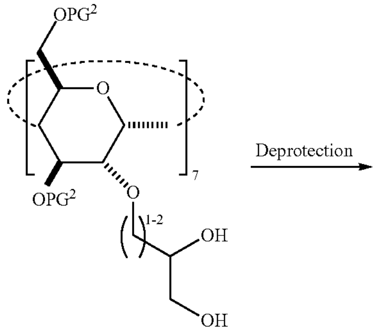

i4-1

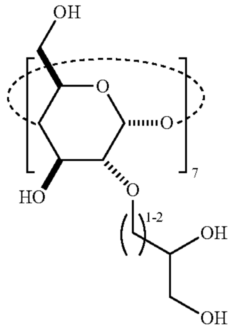

Compound of Formula (I)

Protection of compound i1 by reacting compound i1 with a protecting group reagent of formula XPG$^1$, wherein PG$^1$ is an alcohol protecting group (e.g., tert-butyldimethylsilyl, trimethylsilyl, tri-iso-propylsilyloxymethyl, or triisopropylsilyl) and XPG$^1$ is a compound comprising PG$^1$, where X is e.g., a halogen (e.g., chloride, bromide, or iodide) results in compound i1a'. Compound i1a' is reacted with a compound X2, where LG1 is a leaving group (e.g., a halogen, e.g., chloride, bromide, or iodide), in the presence of a strong base (e.g., NaH) to yield compound i1b. Compound i1b is deprotected e.g., using fluoride ion promoted deprotection (e.g., TBAF, HF, or $NH_4F$) to yield the compound i1c. Compound i1c is reacted with a protecting group reagent of formula XPG$^2$, wherein PG$^2$ is an alcohol protecting group (e.g., benzyl, p-methoxybenzyl, dimethoxybenzyl) and XPG$^2$ is a compound comprising PG$^2$ where X is e.g., a halogen (e.g., chloride or bromide), in the presence of a strong base (e.g., NaH) to yield compound i1d. Compound i1d is dihydroxylated with an appropriate reagent, (e.g., osmium tetroxide or catalytic amounts of osmium tetroxide with an oxidant, e.g., N-methylmorpholine N-oxide or $H_2O_2$). This results in compound i4-1 which is deprotected using e.g., palladium catalyzed hydrogenation, to yield the compound of Formula (I).

General Synthetic Scheme 2

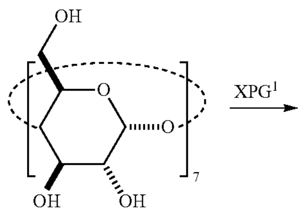

i1

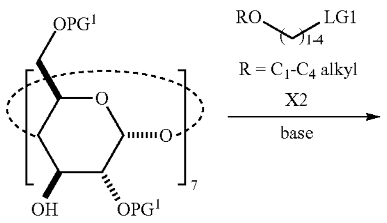

i1a'

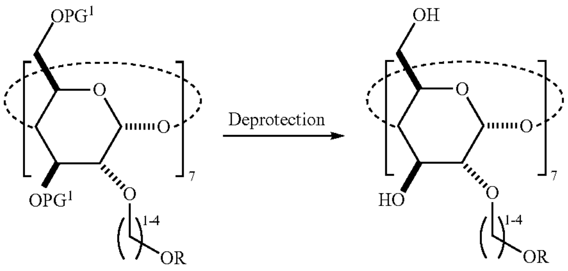

i4-2

Compound of Formula (I)

Compound i1a' is made according to General Synthetic Scheme 1 and reacted with a compound λ2, where LG1 is a leaving group (e.g., a halogen, e.g., chloride, bromide, or iodide), in the presence of a strong base (e.g., NaH) to yield compound i4-2. Compound i4-2 is deprotected e.g., using fluoride ion promoted deprotection (e.g., TBAF, HF, or $NH_4F$) to yield the compound of Formula (I).

General Synthetic Scheme 3

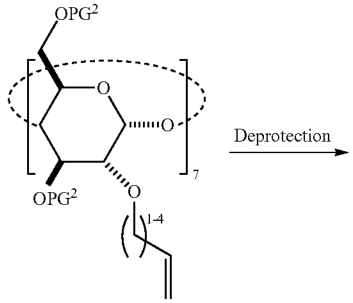

i1d

-continued

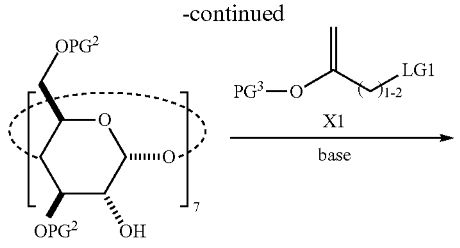

i2

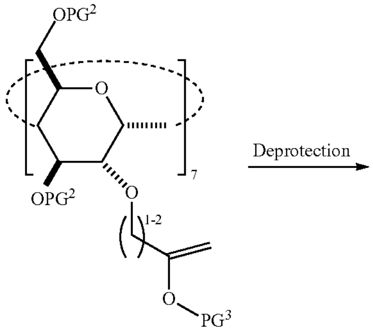

i3-1a

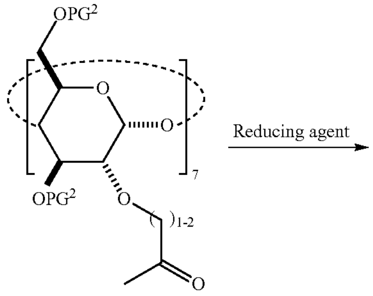

i3-1b

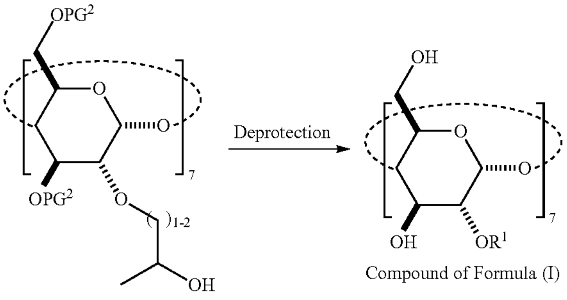

i4-3

Compound of Formula (I)

Compound i1d is prepared as in General Synthetic Scheme 1 and deprotected (using e.g., palladium catalyzed hydrogenation) to yield compound i2. Compound i2 is reacted with a compound of formula X1, where LG1 is a leaving group (e.g., a halogen, e.g., chloride, bromide, or iodide) and $PG^3$ is an alcohol protecting group (e.g., methoxymethyl or ethoxymethyl), in the presence of a strong base (e.g., NaH) to yield compound i3-1a. Compound i3-1a is deprotected under acidic conditions (e.g., TFA or HCl) to yield compound i3-1b, which is treated with a reducing agent (e.g., $NaBH_4$) to yield compound i4-3. Final deprotection using e.g., palladium catalyzed hydrogenation of compound i4-3 yields the compound of Formula (I).

General Synthetic Scheme 4
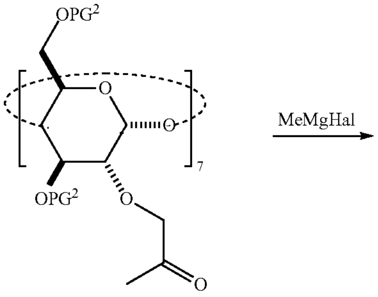
i3-1b
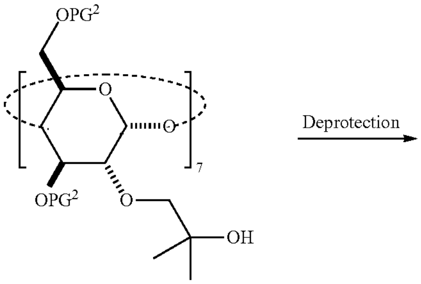
i4-4
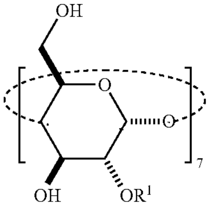
Compound of Formula (I)
Compound i3-1b is prepared as in General Synthetic Scheme 3 and reacted to compound i4-4 under Grignard conditions. Final deprotection (e.g., palladium catalyzed hydrogenation) of compound i4-4 yields the compound of Formula (I).
General Synthetic Scheme 5
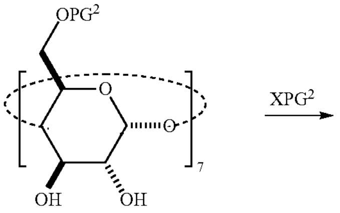
i1
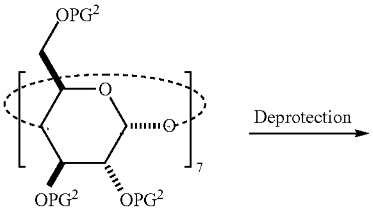
i2'
-continued
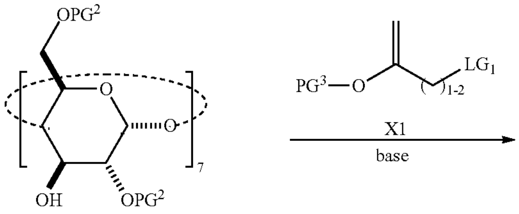
i3
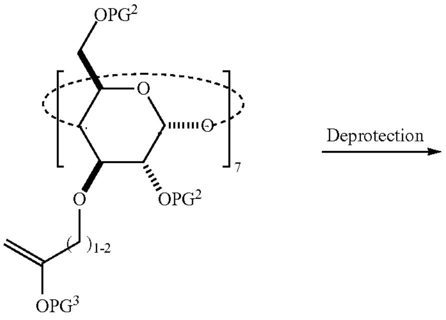
i3-1
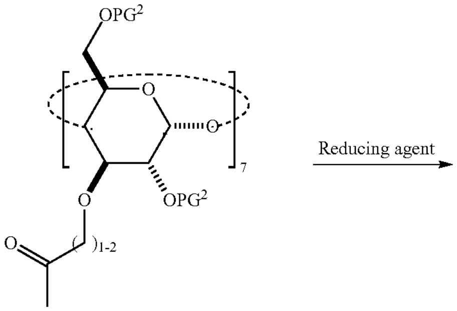
i3-2
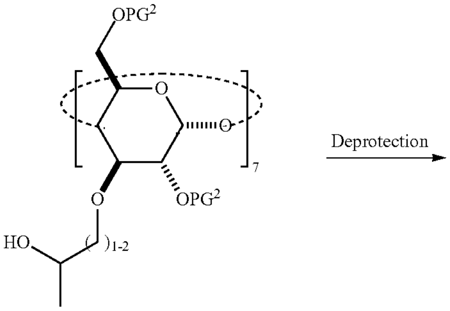
i4-5
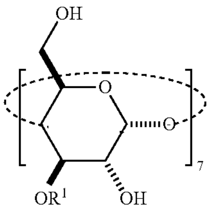
Compound of Formula (I)

Compound i1 is reacted with a protecting group reagent of formula $XPG^2$, wherein $PG^2$ is an alcohol protecting group (e.g., benzyl, p-methoxybenzyl, dimethoxybenzyl) and $XPG^2$ is a compound comprising $PG^2$, where X is e.g., a halogen (e.g., chloride or bromide), in the presence of a strong base (e.g., NaH). This results in a compound of formula i2'. The 3 position of compound i2' is selectively deprotected using e.g., triethylsilane to yield compound i3. Compound i3 is reacted with a compound of formula X1, where LG1 is a leaving group and $PG^3$ is an alcohol protecting group (e.g., methoxymethyl or ethoxymethyl), in the presence of a strong base (e.g., NaH) to yield compound i3-1. Compound i3-1 is deprotected under acidic conditions (e.g., TFA or HCl) to yield compound i3-2, which is treated with a reducing agent (e.g., $NaBH_4$) to yield compound i4-5. Final deprotection using e.g., palladium catalyzed hydrogenation, of compound i4-5 yields the compound of Formula (I).

General Synthetic Scheme 6

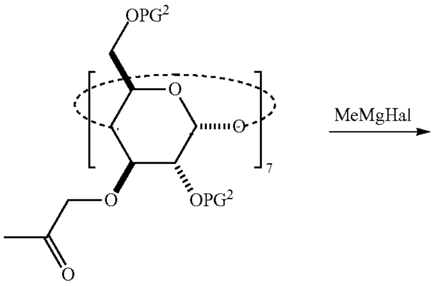

i3-2

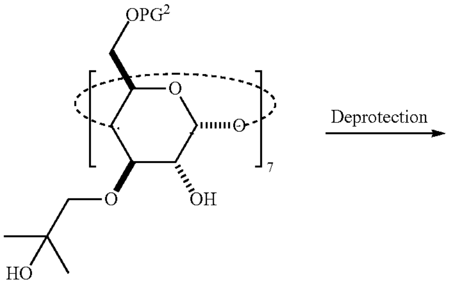

i4-6

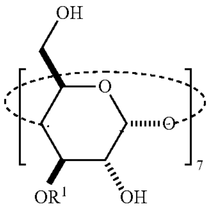

Compound of Formula (I)

Compound i3-2 is prepared as in General Synthetic Scheme 5 and reacted to compound i4-6 under Grignard conditions. Final deprotection (e.g., palladium catalyzed hydrogenation) of compound i4-6 yields the compound of Formula (I).

EXAMPLES

Example 1—Syntheses of Compounds and Synthetic Intermediates

Preparation of Compound 1 (1S,3R,5R,6S,8R,10R,11S,13R,15R,16S,18R,20R,21S,23R,25R,26S,28R,30R,31S,33R,35R,36S,37R,38S,39R,40S,41R,42S,43R,44S,45R,46S,47R,48S,49R)-5,10,15,20,25,30,35-heptakis(hydroxymethyl)-37,39,41,43,45,47,49-heptakis(2-methoxyethoxy)-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontane-36,38,40,42,44,46,48-heptol Step 1:

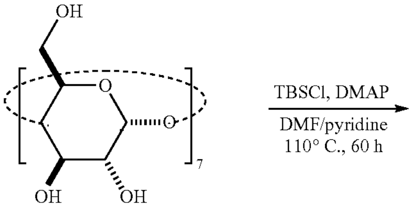

beta-CD

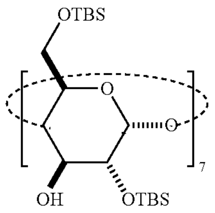

1.1

To a stirred solution of (1S,3R,5R,6S,8R,10R,11S,13R,15R,16S,18R,20R,21S,23R,25R,26S,28R,30R,31S,33R,35R,36R,37R,38R,39R,40R,41R,42R,43R,44R,45R,46R,47R,48R,49R)-5,10,15,20,25,30,35-heptakis(hydroxymethyl)-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontane-36,37,38,39,40,41,42,43,44,45,46,47,48,49-tetradecol beta-CD (20 g, 17.6 mmol, 1 equiv) and DMAP (107 mg, 0.88 mmol, 0.05 equiv) in DMF (200 mL) was added TBSCl (112 g, 741 mmol, 42.0 equiv) in pyridine (120 mL). The resulting mixture was stirred for 60 h at 110° C. and upon cooling to room temperature was then concentrated under reduced pressure. The residue was dissolved in DCM (500 mL), washed with $KHSO_4$ (0.5 M) (3×150 mL), dried over anhydrous $Na_2SO_4$ and filtered. The filtrate was then concentrated under reduced pressure and the residue was purified by silica gel column chromatography, eluting with EtOAc/PE (0%~10%) to afford (1S,3R,5R,6S,8R,10R,11S,13R,15R,16S,18R,20R,21S,23R,25R,26S,28R,30R,31S,33R,35R,36S,37R,38S,39R,40S,41R,42S,43R,44S,45R,46S,47R,48S,49R)-37,39,41,43,45,47,49-heptakis[(tert-butyldimethylsilyl)oxy]-5,10,15,20,25,30,35-heptakis({[(tert-butyldimethylsilyl)oxy]methyl})-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontane-36,38,40,42,44,46,48-heptol (Compound 1.1) (33 g, 72%) as a white solid.

$^1$H NMR (400 MHz, Chloroform-d) δ 4.81 (d, J=3.3 Hz, 7H), 4.41 (s, 7H), 3.95-3.78 (m, 14H), 3.65-3.40 (m, 28H), 0.86 (d, J=18.3 Hz, 126H), 0.13 (d, J=4.2 Hz, 42H).

Step 2:

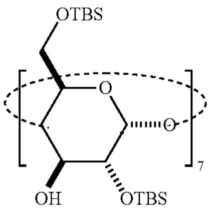

1.1

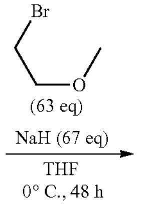

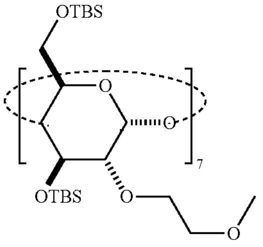

1.2

To a stirred solution of (1S,3R,5R,6S,8R,10R,11S,13R,15R,16S,18R,20R,21S,23R,25R,26S,28R,30R,31S,33R,35R,36S,37R,38S,39R,40S,41R,42S,43R,44S,45R,46S,47R,48S,49R)-37,39,41,43,45,47,49-heptakis[(tert-butyldimethylsilyl)oxy]-5,10,15,20,25,30,35-heptakis({[(tert-butyldimethylsilyl)oxy]methyl})-2,4,7,9,12,14,17,19,22,24,27,29,32,34-tetradecaoxaoctacyclo[31.2.2.$2^{3,6}$ $2^{8,11}$.$2^{13,16}$.$2^{18,21}$.$2^{23,26}$.$2^{28,31}$]nonatetracontane-36,38,40,42,44,46,48-heptol (Compound 1.1) (5 g, 1.82 mmol) in dry THF (150 ml, 30 vol) was added NaH (2.94 g, 122 mmol) at 0° C. The reaction mixture for was stirred for 1 h at 0° C., and 2-bromoethyl methyl ether (15.93 g, 114 mmol) was then added dropwise. The reaction mixture was stirred for another 1 h at 0° C. The suspension was allowed to warm to room temperature and stirred for an additional 48 h. The reaction mixture was cooled with an ice bath and methanol was added (20 ml, 4 vol). The reaction mixture was concentrated under reduced pressure and the residue was suspended in DCM (400 ml, 80 vol). The organic mixture was washed with water (2×200 ml), followed by saturated brine (200 ml), and then concentrated to obtain 3.2 g of crude product. The crude mixture was purified by column chromatography using silica gel (2-4% EtOAc/Hexane) to obtain tert-butyl({[(1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-36,38,40,42,44,46,48-heptakis[(tert-butyldimethylsilyl)oxy]-10,15,20,25,30,35-hexakis({[(tert-butyldimethylsilyl)oxy]methyl})-37,39,41,43,45,47,49-heptakis(2-methoxyethoxy)-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontan-5-yl]methoxy})dimethylsilane (Compound 1.2)(1.2 g, 21% yield).

Step 3:

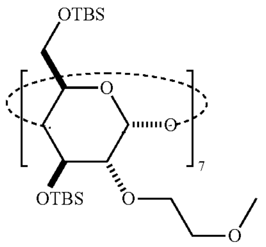

1.2

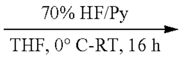

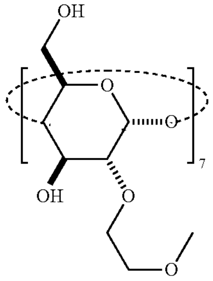

Compound 1

To a stirred solution of tert-butyl({[(1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-36,38,40,42,44,46,48-heptakis[(tert-butyldimethylsilyl)oxy]-10,15,20,25,30,35-hexakis({[(tert-butyldimethylsilyl)oxy]methyl})-37,39,41,43,45,47,49-heptakis(2-methoxyethoxy)-2,4,7,9,12,14,17,19,22,24,27,29,32,34-tetradecaoxaoctacyclo[31.2.2.$2^{3,6}$$2^{8,11}$.$2^{13,16}$.$2^{18,21}$.$2^{23,26}$.$2^{28,31}$]nonatetracontan-5-yl]methoxy})dimethylsilane (Compound 1.2) (1.5 g, 0.478 mmol) in dry THF (30 ml, 20 vol) was added 70% HF/pyridine (6 ml, 4 vol) at 0° C. The reaction mixture was stirred for 18 h at room temperature. $NaHCO_3$ solution (1.2 M, 180 ml) was then added, and the mixture was concentrated under reduced pressure. The residue was slurried in methanol (15 ml, 10 vol) and filtered to obtain 0.6 g of crude product. The crude product was recrystallized with DCM/Hexane (1:2, 30 ml), and the crystals were washed with n-pentane (3 ml) to obtain 300 mg of (1S,3R,5R,6S,8R,10R,11S,13R,15R,16S,18R,20R,21S,23R,25R,26S,28R,30R,31S,33R,35R,36S,37R,38S,39R,40S,41R,42S,43R,44S,45R,46S,47R,48S,49R)-5,10,15,20,25,30,35-heptakis(hydroxymethyl)-37,39,41,43,45,47,49-heptakis(2-methoxyethoxy)-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontane-36,38,40,42,44,46,48-heptol (Compound 1) (300 mg, 41%).

$^1$HNMR (400 MHz, $D_2O$): δ 5.22 (d, J=3.6 Hz, 7H), 4.05-4.00 (t, J=9.2, 18.8 Hz, 7H), 3.98-3.82 (m, 36H), 3.65-3.58 (m, 21H), 3.51-3.48 (dd, J=3.2, 9.6 Hz, 7H), 3.39 (s, 21H).

-continued

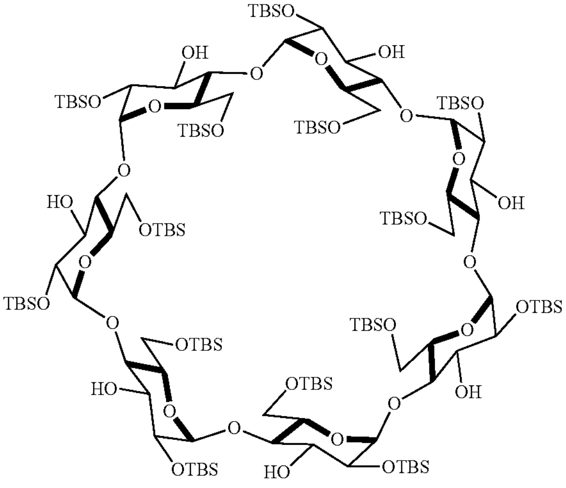

2.1

Preparation of Compound 2 (1S,3R,5R,6R,8R,10R,11S,13R,15R,16S,18R,20R,21S,23R,25R,26S,28R,30R,31S,33R,35R,36S,37R,38S,39R,40S,41R,42S,43R,44S,45R,46S,47R,48R,49R)-37,39,41,43,45,47,48-heptakis(2-ethoxyethoxy)-5,10,15,20,25,30,35-heptakis(hydroxymethyl)-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontane-36,38,40,42,44,46,49-heptol Step 1:

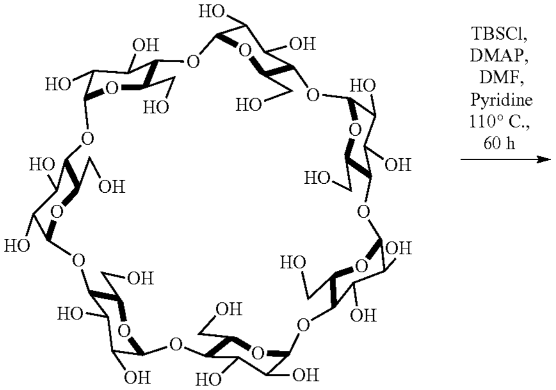

beta-CD

To a stirred solution of (1S,3R,5R,6S,8R,10R,11S,13R,15R,16S,18R,20R,21S,23R,25R,26S,28R,30R,31S,33R,35R,36R,37R,38R,39R,40R,41R,42R,43R,44R,45R,46R,47R,48R,49R)-5,10,15,20,25,30,35-heptakis(hydroxymethyl)-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontane-36,37,38,39,40,41,42,43,44,45,46,47,48,49-tetradecol beta-CD (20 g, 17.6 mmol, 1 equiv) and DMAP (107 mg, 0.88 mmol, 0.05 equiv) in DMF (200 mL) was added TBSCl (112 g, 741 mmol, 42.0 equiv) in pyridine (120 mL). The resulting mixture was stirred for 60 h at 110° C. and upon cooling to room temperature was then concentrated under reduced pressure. The residue was dissolved in DCM (500 mL), washed with $KHSO_4$ (0.5 M) (3×150 mL), dried over anhydrous $Na_2SO_4$ and filtered. The filtrate was then concentrated under reduced pressure and the residue was purified by silica gel column chromatography, eluting with EAtOAc/PE (0%~10%) to afford (1S,3R,5R,6S,8R,10R,11 S,13R,15R,16S,18R,20R,21S,23R,25R,26S,28R,30R,31S,33R,35R,36S,37R,38S,39R,40S,41R,42S,43R,44S,45R,46S,47R,48S,49R)-37,39,41,43,45,47,49-heptakis[(tert-butyldimethylsilyl)oxy]-5,10,15,20,25,30,35-heptakis({[(tert-butyldimethylsilyl)oxy]methyl})-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontane-36,38,40,42,44,46,48-heptol (Compound 2.1) (33 g, 72%) as a white solid.

$^1$H NMR (400 MHz, Chloroform-d) δ 4.81 (d, J=3.3 Hz, 7H), 4.41 (s, 7H), 3.95-3.78 (m, 14H), 3.65-3.40 (m, 28H), 0.86 (d, J=18.3 Hz, 126H), 0.13 (d, J=4.2 Hz, 42H).

Step 2:

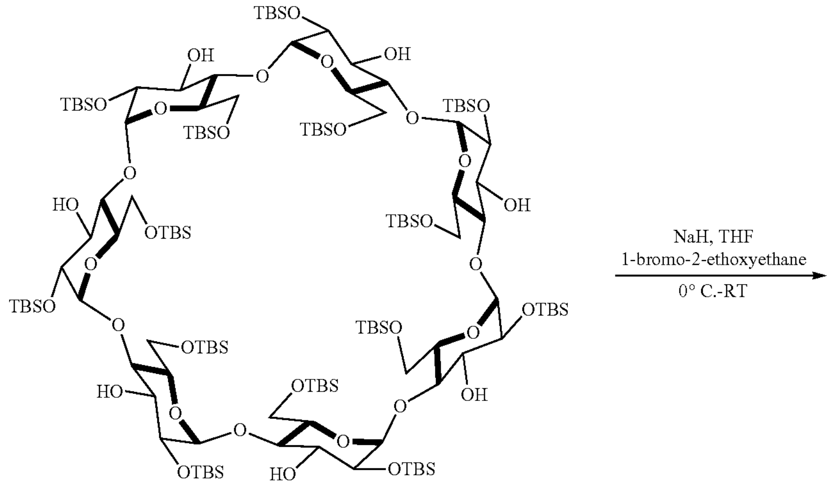

2.1

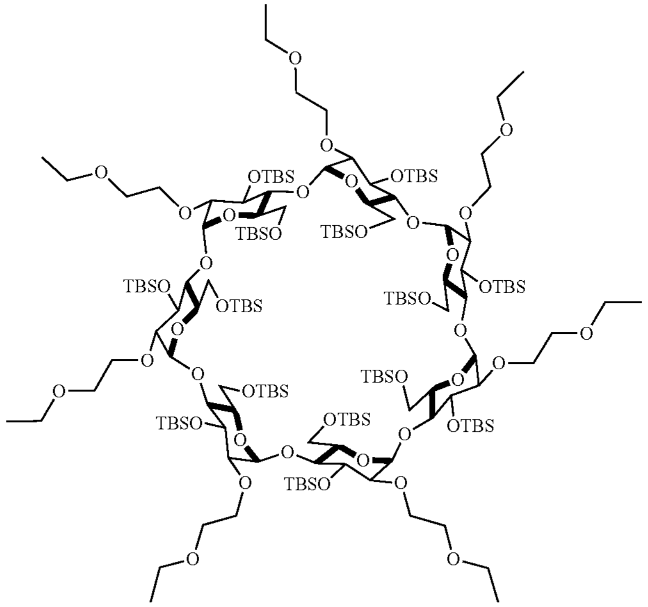

2.2

To a stirred solution of (1S,3R,5R,6S,8R,10R,11S,13R,15R,16S,18R,20R,21S,23R,25R,26S,28R,30R,31S,33R,35R,36S,37R,38S,39R,40S,41R,42S,43R,44S,45R,46S,47R,48S,49R)-37,39,41,43,45,47,49-heptakis[(tert-butyldimethylsilyl)oxy]-5,10,15,20,25,30,35-heptakis({[(tert-butyldimethylsilyl)oxy]methyl})-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontane-36,38,40,42,44,46,48-heptol (Compound 2.1) (5 g, 1.83 mmol) in dry THF (130 mL) under nitrogen at 0-10° C., was added NaH (4.9 g, 122.5 mmol, 67 equiv) portion wise and the reaction mixture was allowed to stir for 30 min at 0-10° C. Then 1-bromo-2-ethoxyethane (13 mL, 115.2 mmol, 63 equiv) was added to the mixture at 0-10° C. and reaction mixture was stirred at 0-10° C. for 1 h and then allowed to slowly warm to RT and stirred for 48 h. The reaction mixture was cooled to 0-10° C. and cold $H_2O$ (50 mL) was added. The mixture was extracted with EtOAc (2×100 mL) and the combined organic layers was washed with saturated aqueous sodium chloride solution (20 mL), dried over $Na_2SO_4$, filtered and concentrated under reduced pressure. The residue was purified by silica gel column chromatography (1-2% EtOAc/hexane) to afford tert-butyl({[(1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-36,38,40,42,44,46,49-heptakis[(tert-butyldimethylsilyl)oxy]-10,15,20,25,30,35-hexakis({[(tert-butyldimethylsilyl)oxy]methyl})-37,39,41,43,45,47,48-heptakis(2-ethoxyethoxy)-2,4,7,9,12,14,17,19,22,24,27,29,32,34-tetradecaoxaoctacyclo[31.2.2.$2^{3,6}$ $2^{8,11}$.$2^{13,16}$.$2^{18,21}$.$2^{23,26}$.$2^{28,31}$]nonatetracontan-5-yl]methoxy})dimethylsilane (Compound 2.2) (3 g, 0.93 mmol, 51% yield) as a colorless liquid.

$^1$HNMR (400 MHz, $CDCl_3$): δ 5.18 (brs, 7H), 4.20-4.05 (m, 14H), 3.84-3.79 (m, 7H), 3.78-3.60 (m, 21H), 3.59-3.40 (m, 35H), 3.28-3.18 (m, 7H), 1.16 (t, J=7.2 Hz, 21H), 0.89 (s, 126H), 0.11 (d, J=4.8 Hz, 42H), 0.03 (s, 42H).

Step 3:

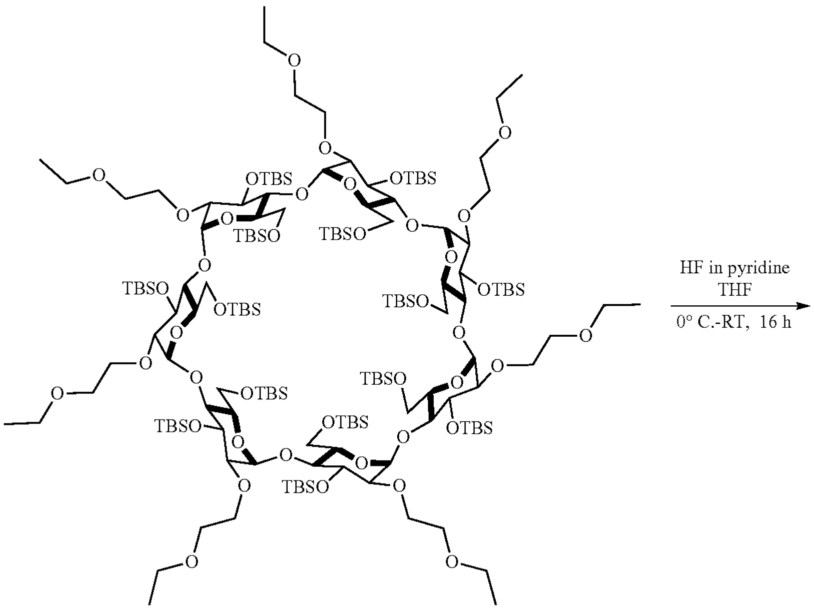

2.2

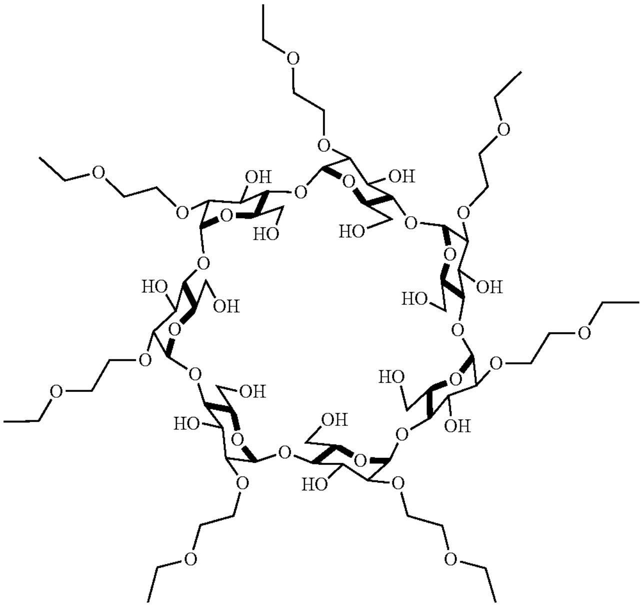

Compound 2

To a stirred solution of tert-butyl({[(1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-36,38,40,42,44,46,49-heptakis[(tert-butyldimethylsilyl)oxy]-10,15,20,25,30,35-hexakis({[(tert-butyldimethylsilyl)oxy]methyl})-37,39,41,43,45,47,48-heptakis(2-ethoxyethoxy)-2,4,7,9,12,14,17,19,22,24,27,29,32,34-tetradecaoxaoctacyclo$[31.2.2.2^{3,6}.2^{8,11}.2^{13,16}.2^{18,21}.2^{23,26}.2^{28,31}]$nonatetracontan-5-yl]methoxy})dimethylsilane (Compound 2.2) (2.5 g, 0.77 mmol) in THF (50 mL) at 0-10° C. was added HF in pyridine (10 mL). The reaction mixture was allowed to warm up to RT and was stirred for 16 h. The reaction mixture was cooled to 0-10° C. and saturated $NaHCO_3$ (aq., 300 mL) was added. The mixture was extracted with DCM (2×100 mL) and the combined organic layers was dried over $Na_2SO_4$, filtered and concentrated under reduced pressure and then lyophilized to afford (1S,3R,5R,6R,8R,10R,11S,13R,15R,16S,18R,20R,21S,23R,25R,26S,28R,30R,31S,33R,35R,36S,37R,38S,39R,40S,41R,42S,43R,44S,45R,46S,47R,48R,49R)-37,39,41,43,45,47,48-heptakis(2-ethoxyethoxy)-5,10,15,20,25,30,35-heptakis(hydroxymethyl)-2,4,7,9,12,14,17,19,22,24,27,29,32,34-tetradecaoxaoctacyclo$[31.2.2.2^{3,6}.2^{8,11}.2^{13,16}.2^{18,21}.2^{23,26}.2^{28,31}]$nonatetracontane-36,38,40,42,44,46,49-heptol (Compound 2) (1 g, 0.61 mmol, 79% yield) as an off white solid. MALDI (ES): $[M+Na]^+$=1662.02.

$^1H$ NMR (400 MHz, $D_2O$): δ 5.22 (d, J=3.6 Hz, 7H), 4.02 (t, J=9.2 Hz, 7H), 4.00-3.80 (m, 35H), 3.68-3.57 (m, 35H), 3.49 (dd, J=3.6 Hz, 9.6 Hz, 7H), 1.21 (t, J=7.2 Hz, 21H), —OH peaks not observed.
Preparation of Compound 3 (1S,3R,5R,6R,8R,10R,11S,13R,15R,16S,18R,20R,21S,23R,25R,26S,28R,30R,31S,33R,35R,36S,37R,38S,39R,40S,41R,42S,43R,44S,45R,46S,47R,48R,49R)-37,39,41,43,45,47,48-heptakis(2,3-dihydroxypropoxy)-5,10,15,20,25,30,35-heptakis(hydroxymethyl)-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontane-36,38,40,42,44,46,49-heptol
Compound 3
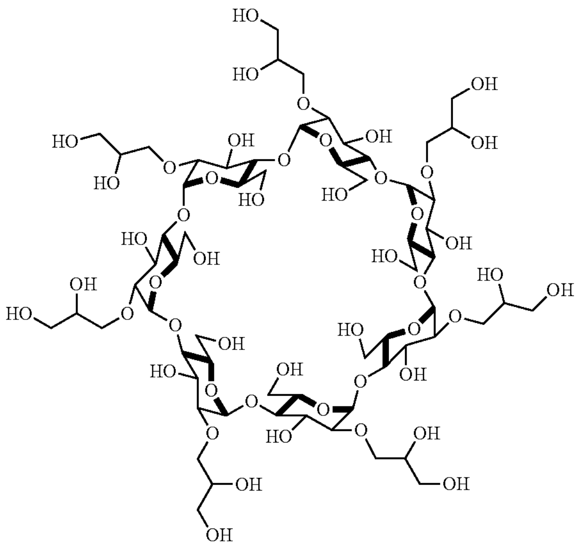
Step 1:
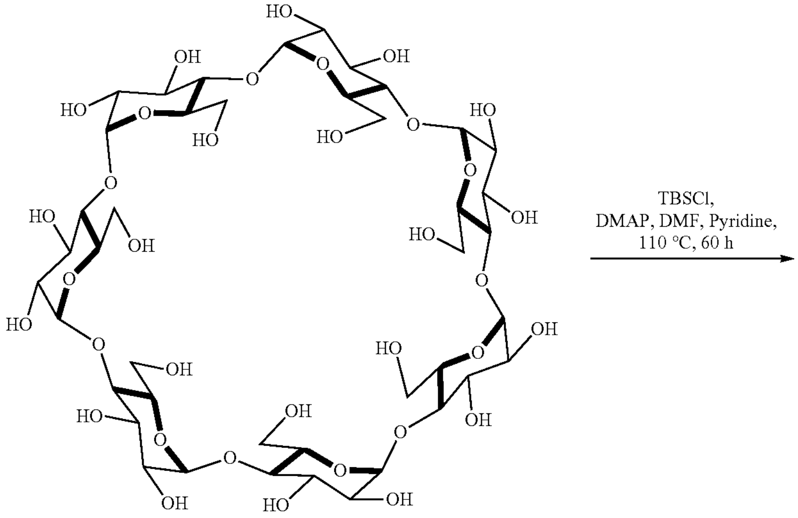
beta-CD -continued

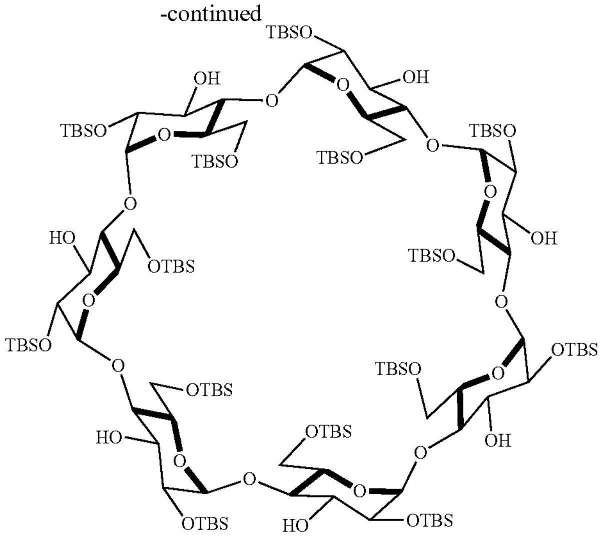

3.1

To a stirred solution of (1S,3R,5R,6S,8R,10R,11S,13R,15R,16S,18R,20R,21S,23R,25R,26S,28R,30R,31S,33R,35R,36R,37R,38R,39R,40R,41R,42R,43R,44R,45R,46R,47R,48R,49R)-5,10,15,20,25,30,35-heptakis (hydroxymethyl)-2,4,7,9,12,14,17,19,22,24,27,29,32,34-tetradecaoxaoctacyclo[31.2.2.2$^{3,6}$2$^{8,11}$.2$^{13,16}$.2$^{18,21}$.2$^{23,26}$.2$^{28,31}$]nonatetracontane-36,37,38,39,40,41,42,43,44,45,46,47,48,49-tetradecol beta-CD (20 g, 17.64 mmol, 1 equiv) and DMAP (107 mg, 0.88 mmol, 0.05 equiv) in DMF (200 mL) was added TBSCl (112 g, 741 mmol, 42.0 equiv) in pyridine (120 mL). The resulting mixture was stirred for 60 h at 110° C. and upon cooling to room temperature was then concentrated under reduced pressure. The residue was dissolved in DCM (500 mL), washed with $KHSO_4$ (0.5 M) (3×150 mL), dried over anhydrous $Na_2SO_4$ and filtered. The filtrate was then concentrated under reduced pressure and the residue was purified by silica gel column chromatography, eluting with EAtOAc/PE (0%~10%) to afford (1S,3R,5R,6S,8R,10R,11 S,13R,15R,16S,18R,20R,21S,23R,25R,26S,28R,30R,31S,33R,35R,36S,37R,38S,39R,40S,41R,42S,43R,44S,45R,46S,47R,48S,49R)-37,39,41,43,45,47,49-heptakis[(tert-butyldimethylsilyl)oxy]-5,10,15,20,25,30,35-heptakis({[(tert-butyldimethylsilyl)oxy]methyl})-2,4,7,9,12,14,17,19,22,24,27,29,32,34-tetradecaoxaoctacyclo [31.2.2.2$^{3,6}$.2$^{8,11}$.2$^{13,16}$.2$^{18,21}$.2$^{23,26}$.2$^{28,31}$] nonatetracontane-36,38,40,42,44,46,48-heptol (Compound 3.1) (33 g, 72%) as a white solid. [0159]$^{1}$H NMR (400 MHz, Chloroform-d) δ 4.81 (d, J=3.3 Hz, 7H), 4.41 (s, 7H), 3.95-3.78 (m, 14H), 3.65-3.40 (m, 28H), 0.86 (d, J=18.3 Hz, 126H), 0.13 (d, J=4.2 Hz, 42H).

Step 2:

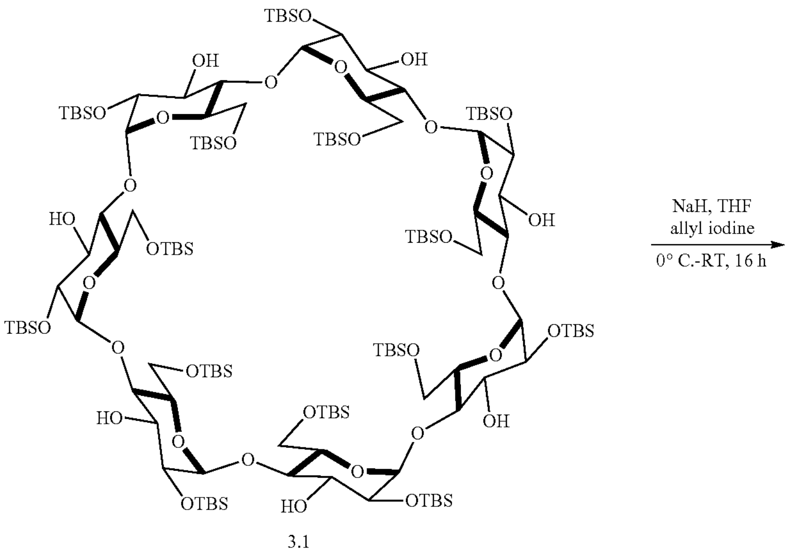

3.1

-continued

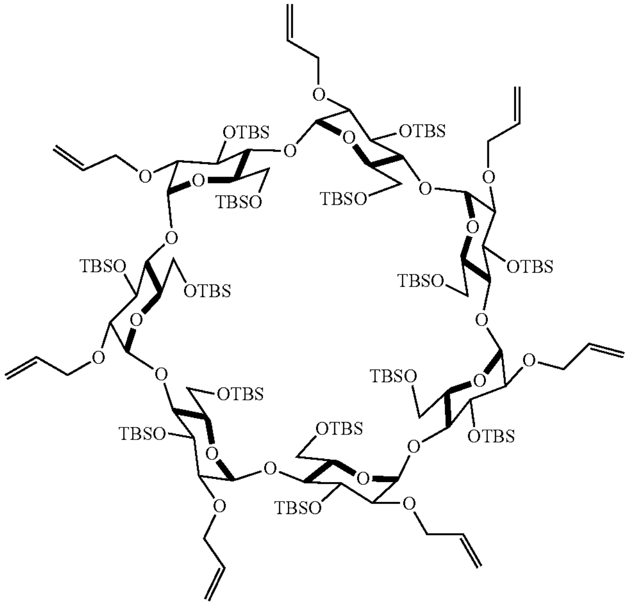

3.2

To a stirred solution of (1S,3R,5R,6S,8R,10R,11S,13R,15R,16S,18R,20R,21S,23R,25R,26S,28R,30R,31S,33R,35R,36S,37R,38S,39R,40S,41R,42S,43R,44S,45R,46S,47R,48S,49R)-37,39,41,43,45,47,49-heptakis[(tert-butyldimethylsilyl)oxy]-5,10,15,20,25,30,35-heptakis({[(tert-butyldimethylsilyl)oxy]methyl})-2,4,7,9,12,14,17,19,22,24,27,29,32,34-tetradecaoxaoctacyclo[31.2.2.2$^{3,6}$.2$^{8,11}$.2$^{13,16}$.2$^{18,21}$2$^{23,26}$.2$^{28,31}$]nonatetracontane-36,38,40,42,44,46,48-heptol (Compound 3.1) (20 g, 7.31 mmol) in dry THF (200 mL) under nitrogen at 0-10° C., was added NaH (6.14 g, 153.6 mmol, 21 equiv) portion wise and the mixture was allowed to stir for 30 min at 0-10° C. Allyl iodide (12 mL, 131.6 mmol, 18 equiv) was added to the mixture at 0-10° C. under dark and the mixture was stirred at 0-10° C. for 1 h and then was allowed to warm up to RT and stirred for 16 h. The reaction mixture was cooled to 0-10° C. and cold $H_2O$ (100 mL) was added. The mixture was extracted with EtOAc (2×200 mL) and the combined organic layers were washed with saturated aqueous sodium chloride solution (20 mL), dried over $Na_2SO_4$, filtered and concentrated under reduced pressure. The residue was purified by silica gel column chromatography (1-2% EtOAc/hexane) to afford tert-butyl({[(1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-36,38,40,42,44,46,49-heptakis[(tert-butyldimethylsilyl)oxy]-10,15,20,25,30,35-hexakis({[(tert-butyldimethylsilyl)oxy]methyl})-37,39,41,43,45,47,48-heptakis(prop-2-en-1-yloxy)-2,4,7,9,12,14,17,19,22,24,27,29,32,34-tetradecaoxaoctacyclo[31.2.2.2$^{3,6}$.2$^{8,11}$.2$^{13,16}$.2$^{18,21}$.2$^{23,26}$.2$^{28,31}$]nonatetracontan-5-yl]methoxy})dimethylsilane (Compound 3.2) (16 g, 5.3 mmol, 72% yield) as a white solid.

$^1$HNMR (400 MHz, $CDCl_3$): δ 5.93-5.86 (m, 7H), 5.21 (dd, J=1.6 Hz, 17.2 Hz, 7H), 5.15-5.07 (m, 14H), 4.10-3.97 (m, 28H), 3.87-3.68 (m, 21H), 3.21 (br s, 7H), 0.09 (s, 126H), 0.09 (s, 42H), 0.02 (s, 42H).

Step 3:

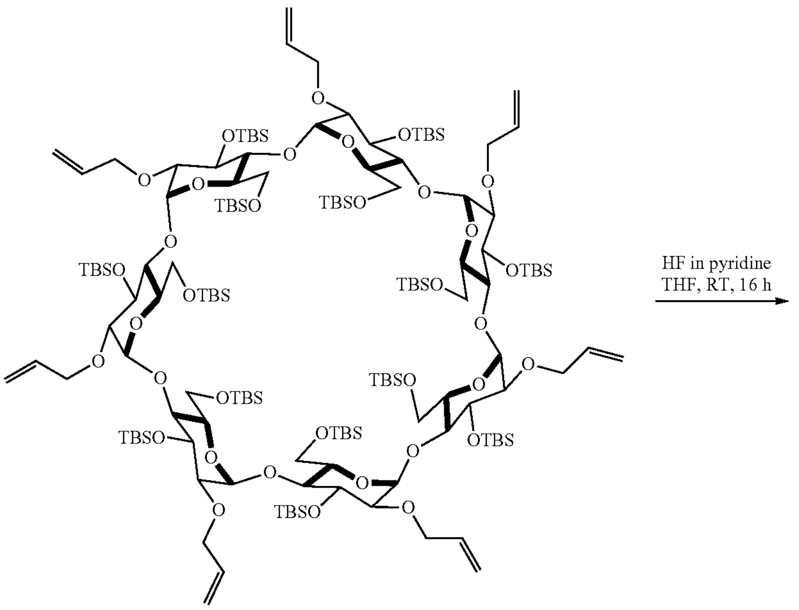

3.2

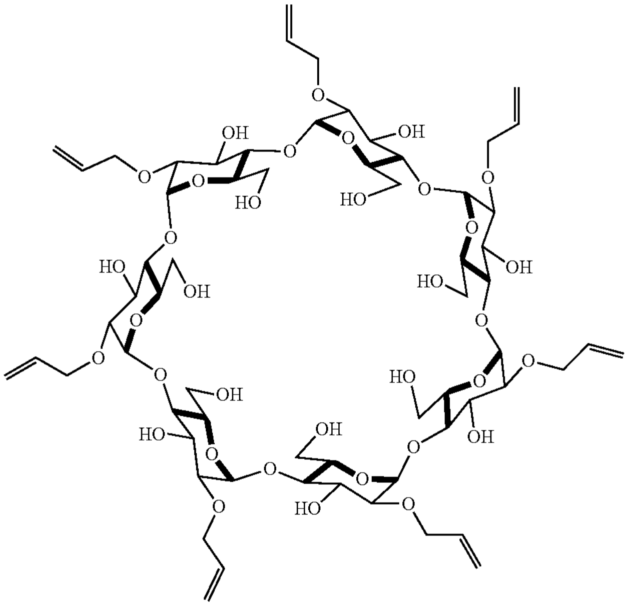

3.3

To a stirred solution of tert-butyl({[(1R,3R,5R,6R,8R, 10R,11R,13R,15R,16R,18R,20R,21R,23R,25R,26R,28R, 30R,31R,33R,35R,36S,37R,38S,39R,40S,41R,42S,43R, 44S,45R,46S,47R,48S,49R)-36,38,40,42,44,46,49-heptakis [(tert-butyldimethylsilyl)oxy]-10,15,20,25,30,35-hexakis ({[(tert-butyldimethylsilyl)oxy]methyl})-37,39,41,43,45, 47,48-heptakis(prop-2-en-1-yloxy)-2,4,7,9,12,14,17,19,22, 24,27,29,32,34-tetradecaoxaoctacyclo[31.2.2.$2^{3,6}2^{8,11}$. $2^{13,16}$.$2^{18,21}$.$2^{23,26}$.$2^{28,31}$]nonatetracontan-5-yl]methoxy}) dimethylsilane (Compound 3.2), 16 g, 5.3 mmol) in THF (320 mL) at 0-10° C. was added HF in pyridine (64 mL). The reaction mixture was allowed to warm up to RT and stirred for 16 h. The mixture was cooled to 0-10° C. and saturated $NaHCO_3$ solution (aq., 2 L) was added. The mixture was extracted with DCM (2×1 L) and the combined organic layers were dried over $Na_2SO_4$, filtered, and concentrated under reduced pressure and lyophilized to afford (1S,3R,5R, 6R,8R,10R,11S,13R,15R,16S,18R,20R,21S,23R,25R,26S, 28R,30R,31S,33R,35R,36S,37R,38S,39R,40S,41R,42S, 43R,44S,45R,46S,47R,48R,49R)-5,10,15,20,25,30,35-heptakis(hydroxymethyl)-37,39,41,43,45,47,48-heptakis (prop-2-en-1-yloxy)-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontane-36,38,40,42,44,46,49-heptol (Compound 3.3) (8 g, 5.65 mmol) as an off white solid.

$^1$HNMR (400 MHz, DMSO-d6): δ 5.94-5.84 (m, 7H), 5.33-5.28 (m, 7H), 5.20 (d, J=1.6 Hz, 7H), 4.90-4.95 (m, 7H), 4.75 (s, 7H), 4.70 (t, J=5.6 Hz, 7H), 4.33 (dd, J=5.6 Hz, 9.2 Hz, 7H), 4.20 (dd, J=6.0 Hz, 12.8 Hz, 7H), 3.77 (t, J=9.2 Hz, 7H), 3.69-3.54 (m, 21H), 3.43-3.31 (m, 7H), 3.30-3.28 (m, 7H).

Step 4:

30 min at 0-10° C. To the reaction mixture, BnBr (23.3 mL, 195.04 mmol) was added dropwise at 0-10° C. The reaction mixture was allowed to warm up to RT and stirred for 24 h. The mixture was cooled to 0-10° C. and $H_2O$ (100 mL) was

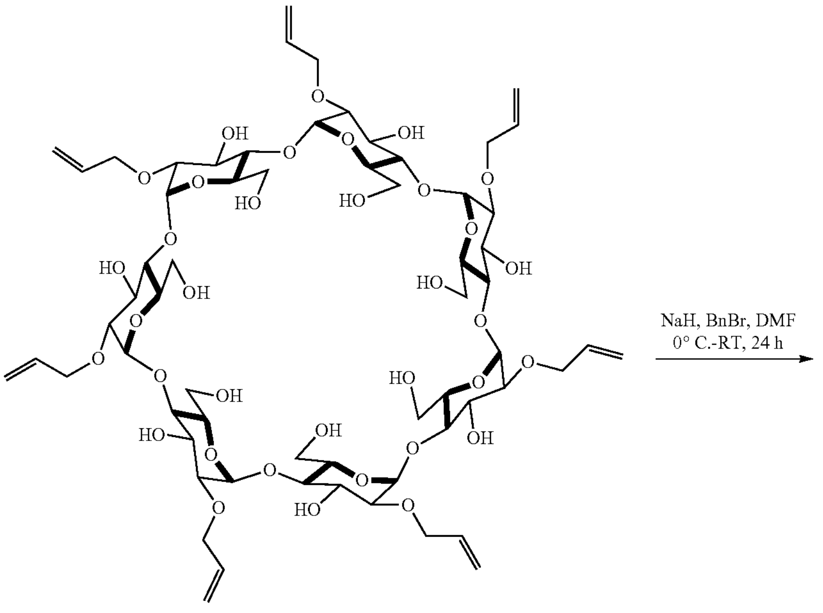

3.3

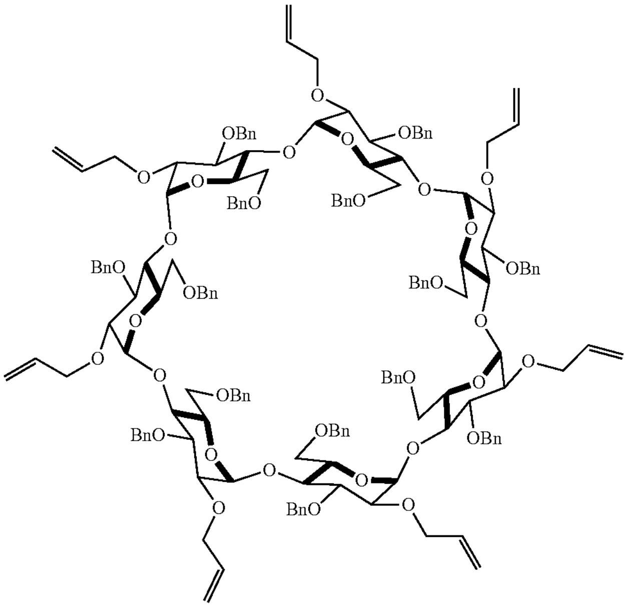

3.4

To a stirred solution of (1S,3R,5R,6R,8R,10R,11S,13R,15R,16S,18R,20R,21S,23R,25R,26S,28R,30R,31S,33R,35R,36S,37R,38S,39R,40S,41R,42S,43R,44S,45R,46S,47R,48R,49R)-5,10,15,20,25,30,35-heptakis(hydroxymethyl)-37,39,41,43,45,47,48-heptakis(prop-2-en-1-yloxy)-2,4,7,9,12,14,17,19,22,24,27,29,32,34-tetradecaoxaoctacyclo[31.2.2.$2^{3,6}2^{8,11}.2^{13,16}.2^{18,21}.2^{23,26}.2^{28,31}$]nonatetracontane-36,38,40,42,44,46,49-heptol (Compound 3.3) (6 g, 4.24 mmol) in DMF (420 mL) at 0-10° C. was added NaH (6.5 g, 161.1 mmol) and stirred for added. The mixture was extracted with EtOAc (2×150 mL). The organic layer was dried over $Na_2SO_4$, filtered, and concentrated under reduced pressure. The residue was purified by silica gel column chromatography (20-25% EtOAc/hexane) to afford (1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-36,38,40,42,44,46,49-heptakis(benzyloxy)-5,10,15,20,25,30,35-heptakis[(benzyloxy)methyl]-37,39,41,43,45, 47,48-heptakis(prop-2-en-1-yloxy)-2,4,7,9,12,14,17,19,22,24,27,29,32,34-tetradecaoxaoctacyclo[31.2.2.2$^{3,6}$.2$^{8,11}$.2$^{13,16}$.2$^{18,21}$.2$^{23,26}$.2$^{28,31}$]nonatetracontane (Compound 3.4) (8 g, 2.99 mmol, 70% yield) as a colorless gummy compound.

$^1$HNMR (400 MHz, $CDCl_3$): δ 7.38-7.18 (m, 70H), 5.72-5.61 (m, 7H), 5.25-5.20 (m, 7H), 5.05 (dd, J=1.2 Hz, 17.2 Hz, 14H), 4.92 (d, J=10.4 Hz, 7H), 4.78 (d, J=10.8 Hz, 7H), 4.46-4.38 (m, 14H), 4.04 (d, J=9.2 Hz, 7H), 3.98-3.86 (m, 35H), 3.56 (d, J=10.4 Hz, 7H), 3.40-3.35 (m, 7H).

Step 5:

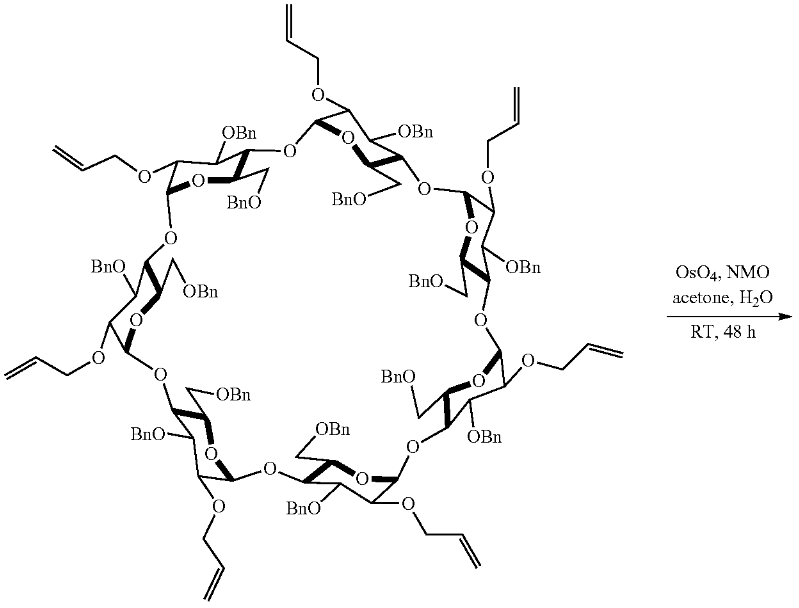

3.4

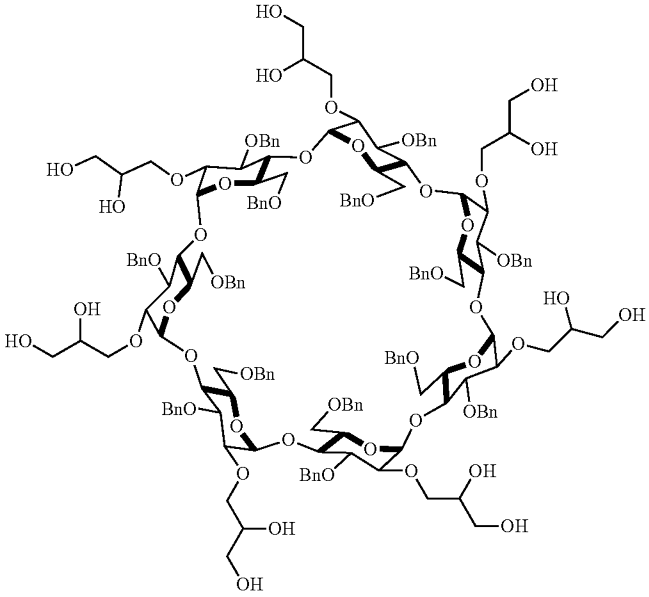

3.5

To a solution of (1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-36,38,40,42,44,46,49-heptakis(benzyloxy)-5,10,15,20,25,30,35-heptakis[(benzyloxy)methyl]-37,39,41,43,45,47,48-heptakis(prop-2-en-1-yloxy)-2,4,7,9,12,14,17,19,22,24,27,29,32,34-tetradecaoxaoctacyclo[31.2.2.2$^{3,6}$.2$^{8,11}$.2$^{13,16}$.2$^{18,21}$.2$^{23,26}$.2$^{28,31}$]nonatetracontane (Compound 3.4, 7 g, 2.61 mmol) in acetone (168 mL) was added 4-methylmorpholine N-oxide monohydrate (10.6 g, 78.5 mmol). To the reaction mixture was added water (133 mL) followed by osmium tetraoxide (67 μL of a 4 wt % solution in water, 0.26 mmol). The cloudy mixture was stirred at RT and after 1 h, 133 mL of water was added. The reaction mixture was stirred for 48 h at RT and then a thiosulphate solution (100 mL) was added. The mixture was extracted with EtOAc (2×200 mL). The combined organic layers were dried over $Na_2SO_4$, filtered and concentrated under reduced pressure. The residue was purified by reverse-phase chromatography (80% ACN:$H_2O$) and the fractions were lyophilized to afford 3-{[(1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-37,38,40,42,44,46,48-heptakis(benzyloxy)-5,10,15,20,25,30,35-heptakis[(benzyloxy)methyl]-39,41,43,45,47,49-hexakis(2,3-dihydroxypropoxy)-2,4,7,9,12,14,17,19,22,24,27,29,32,34-tetradecaoxaoctacyclo[31.2.2.2$^{3,6}$.2$^{8,11}$.2$^{13,16}$.2$^{18,21}$.2$^{23,26}$.2$^{28,31}$]nonatetracontan-36-yl]oxy}propane-1,2-diol (Compound 3.5) (3 g, 1.03 mmol, 39% yield) as a grey color solid.

$^1$HNMR (400 MHz, DMSO-d6): δ 7.43-7.18 (m, 70H), 5.27 (brs, 7H), 5.02-4.94 (m, 7H), 4.80-4.68 (m, 7H), 4.34 (brs, 14H), 4.02-3.92 (m, 7H), 3.90-3.81 (m, 28H), 3.53-3.33 (m, 42H), 3.28-3.14 (m, 14H).

Step 6:

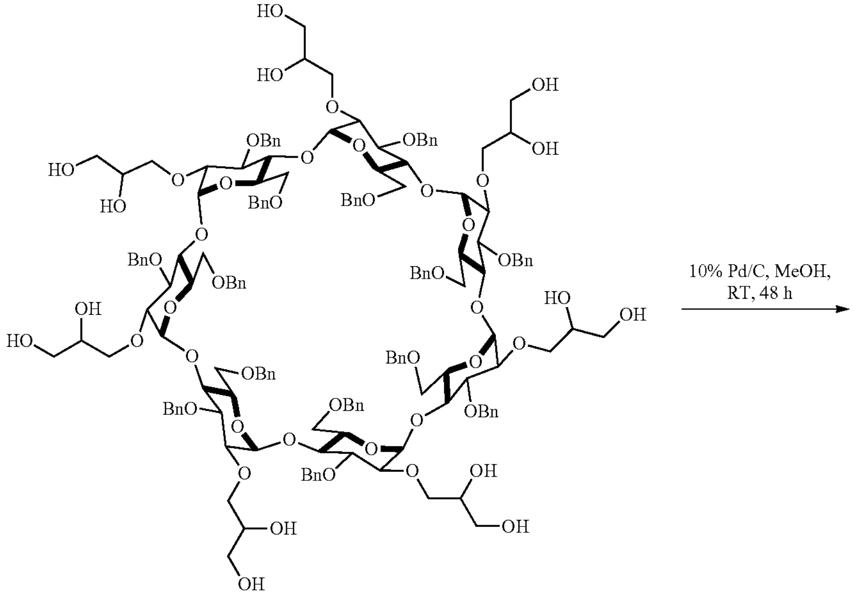

3.5

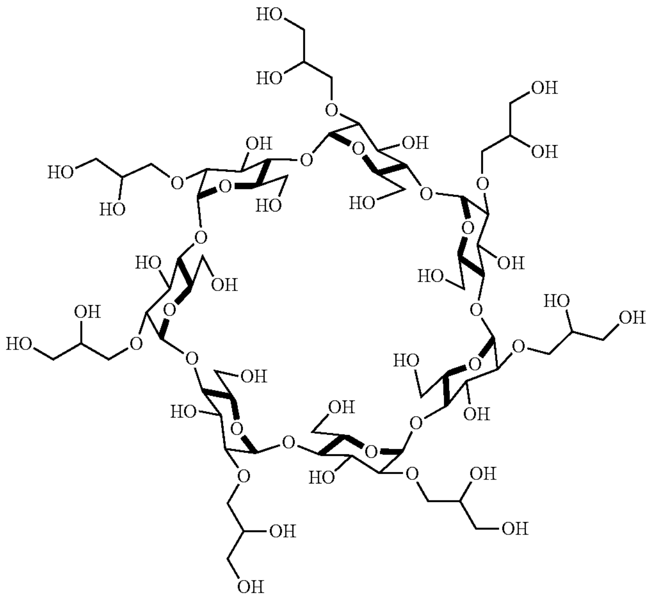

Compound 3

To a stirred solution of 3-{[(1R,3R,5R,6R,8R,10R,11R,13R,15R,16R,18R,20R,21R,23R,25R,26R,28R,30R,31R,33R,35R, 36S,37R,38S,39R,40S,41R,42S,43R,44S,45R,46S,47R,48S,49R)-37,38,40,42,44,46,48-heptakis(benzyloxy)-5,10,15,20,25,30,35-heptakis[(benzyloxy)methyl]-39,41,43,45,47,49-hexakis(2,3-dihydroxypropoxy)-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontan-36-yl]oxy}propane-1,2-diol (Compound 3.5) (1 g, 0.34 mmol) in MeOH (10 mL) under a nitrogen atmosphere at RT was added 10% Pd/C (300 mg). The reaction mixture was kept under a hydrogen atmosphere and stirred for 48 h. The mixture was filtered through a celite pad and the pad was washed with MeOH (50 mL). The filtrate was concentrated under reduced pressure and lyophilized to afford (1S,3R,5R,6R,8R,10R,11S,13R,15R,16S,18R,20R,21S,23R,25R,26S,28R,30R,31S,33R,35R,36S,37R,38S,39R,40S,41R,42S,43R,44S,45R,46S,47R,48R,49R)-37,39,41,43,45,47,48-heptakis(2,3-dihydroxypropoxy)-5,10,15,20,25,30,35-heptakis(hydroxymethyl)-2,4,7,9,12,14,17,19,22,24,27,29,32,34-tetradecaoxaoctacyclo[31.2.2.$2^{3,6}2^{8,11}$.$2^{13,16}$.$2^{18,21}$.$2^{23,26}$.$2^{28,31}$]nonatetracontane-36,38,40,42,44,46,49-heptol (Compound 3) (490 mg, 0.29 mmol, 87% yield) as a off white solid. MALDI (ES): $[M+Na]^+$=1675.61.

$^1$HNMR (400 MHz, $D_2O$): δ 5.28 (brs, 7H), 4.08-3.95 (m, 7H), 3.95-3.75 (m, 35H), 3.73-3.54 (m, 28H), 3.53-3.49 (m, 7H), —OH peaks not observed.

Preparation of Compound 4 (1R,3R,5R,6R,8R,10R,11R,13R,15R,16R,18R,20R,21R,23R,25R,26R,28R,30R,31R,33R,35R,36R,37R,38R,39R,40R,41R,42R,43R,44R,45R,46R,47R,48R,49R)-5,10,15,20,25,30,35-heptakis(hydroxymethyl)-36,38,40,42,44,46,48-heptakis(2-hydroxypropoxy)-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontane-37,39,41,43,45,47,49-heptol Compound 4

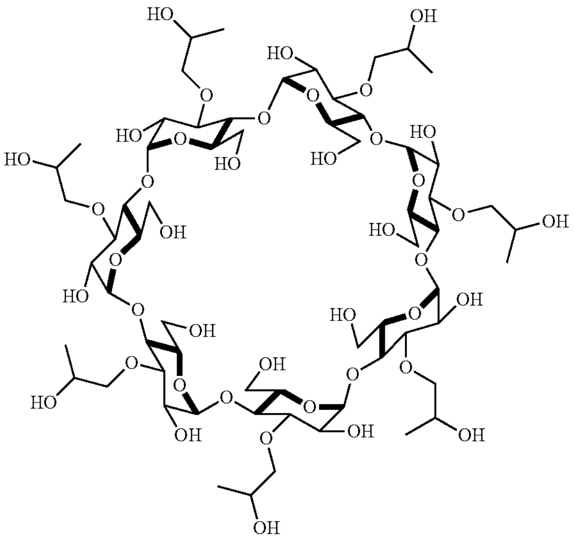

Step 1:

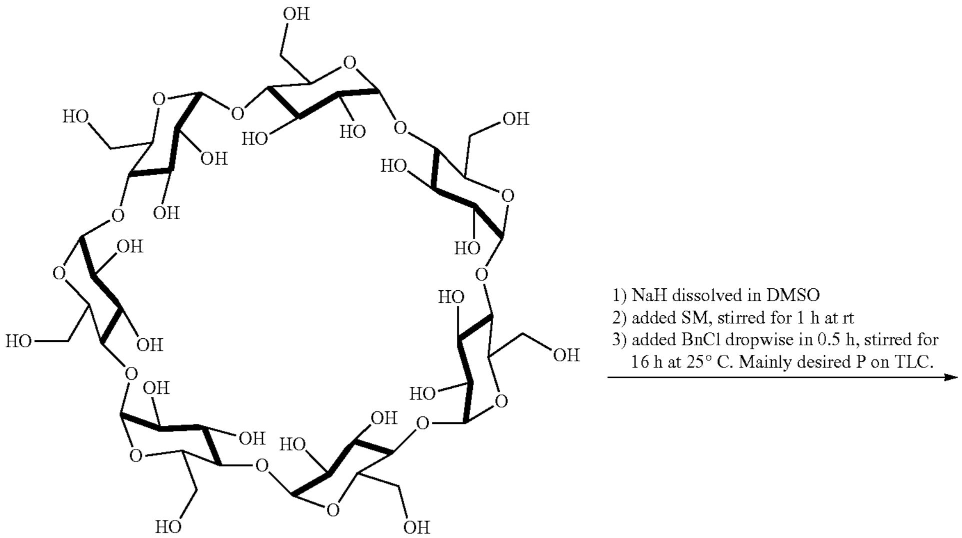

beta-CD

-continued

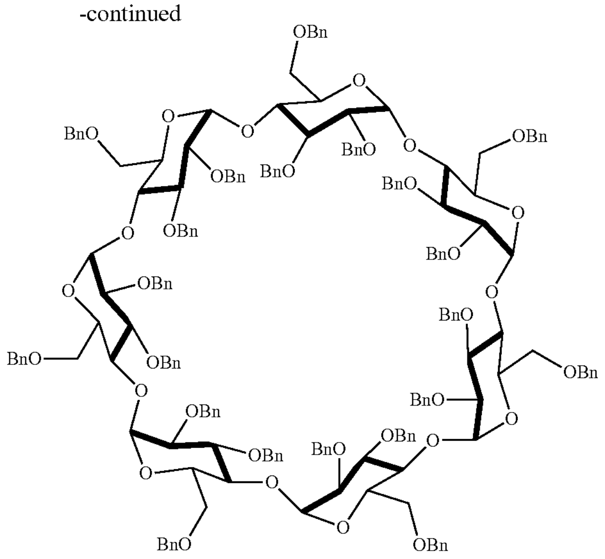

4.1

To a mixture of 60% NaH (44.4 g, 1111.1 mmol, 63 equiv) in DMSO (100 mL) was added (1S,3R,5R,6S,8R,10R,11S,13R,15R,16S,18R,20R,21S,23R,25R,26S,28R,30R,31S,33R,35R,36R,37R,38R,39R,40R,41R,42R,43R,44R,45R,46R,47R,48R,49R)-5,10,15,20,25,30,35-heptakis(hydroxymethyl)-2,4,7,9,12,14,17,19,22,24,27,29,32,34-tetradecaoxaoctacyclo[31.2.2.2$^{3,6}$.2$^{8,11}$.2$^{13,16}$.2$^{18,21}$.2$^{23,26}$.2$^{28,31}$]nonatetracontane-36,37,38,39,40,41,42,43,44,45,46,47,48,49-tetradecol (20 g, 17.6 mmol, 1 equiv) in batches and stirred for 1 h at RT under a nitrogen atmosphere. Then (chloromethyl)benzene (188.2 g, 1481.5 mmol, 84 equiv) was added dropwise over 30 minutes at RT. The mixture was stirred for 16 h at RT and then 800 mL of sat. $NH_4Cl$ (aq.) was added. The resulting mixture was extracted with EtOAc (3×800 mL). The combined organic layers were washed with brine (3×500 mL), dried over anhydrous $Na_2SO_4$, filtered, and concentrated under reduced pressure. MeOH was added and the precipitate was collected by filtration and washed with MeOH (3×500 mL). This material was purified by silica gel column chromatography, eluting with 3/1 PE/EA to afford (1R,3R,5R,6R,8R,10R,11R,13R,15R,16R,18R,20R,21R,23R,25R,26R,28R,30R,31R,33R, 35R,36S,37R,38S,39R,40S,41R,42S,43R,44S,45R,46S,47R,48S,49R)-36,37,38,39,40,41,42,43,44,45,46,47,48,49-tetradecakis(benzyloxy)-5,10,15,20,25,30,35-heptakis[(benzyloxy)methyl]-2,4,7,9,12,14,17,19,22,24,27,29,32,34-tetradecaoxaoctacyclo[31.2.2.2$^{3,6}$2$^{8,11}$.2$^{13,16}$.2$^{18,21}$.2$^{23,26}$.2$^{28,31}$]nonatetracontane (Compound 4.1) (40.25 g, 75%) as a white oil. MALDI-TOF (ES): [M+$Na^+$]$^+$=3050.98.

Example 4, Step 2

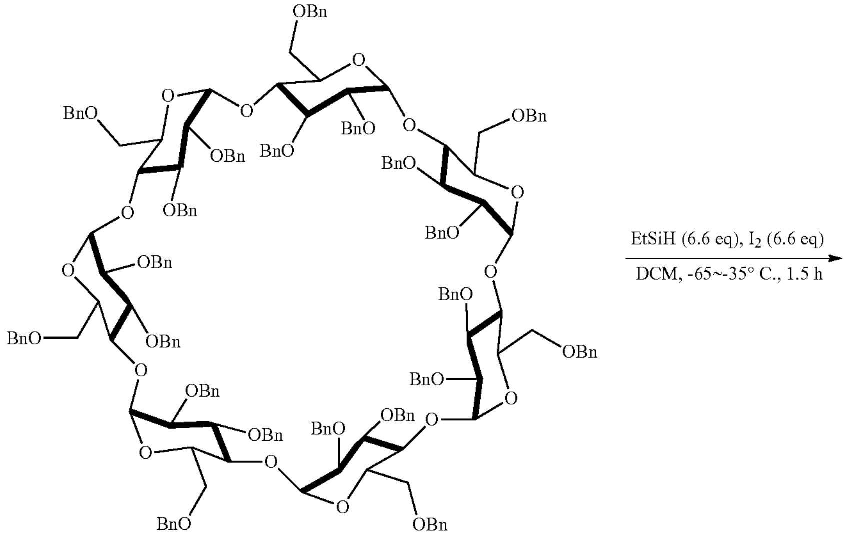

4.1

-continued

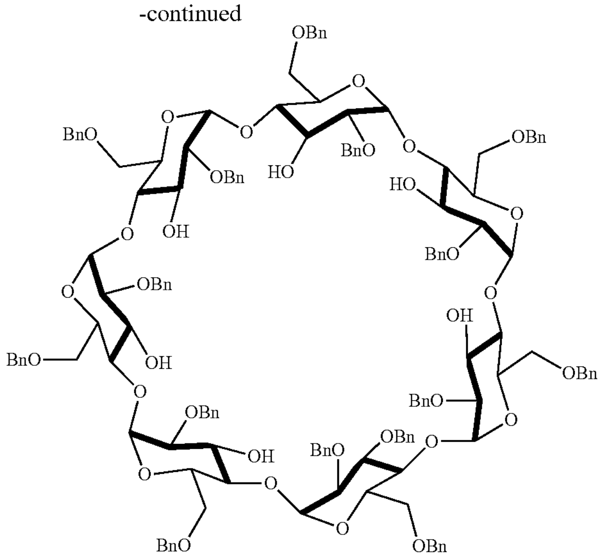

4.2

A solution of (1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-36,37,38,39,40,41,42,43,44,45,46,47,48,49-tetradecakis(benzyloxy)-5,10,15,20,25,30,35-heptakis[(benzyloxy)methyl]-2,4,7,9,12,14,17,19,22,24,27,29,32,34-tetradecaoxaoctacyclo[31.2.2.$2^{3,6}2^{8,11}.2^{13,16}.2^{18,21}.2^{23,26}.2^{28,31}$]nonatetracontane (Compound 4.1) (10 g, 3.3 mmol, 1 equiv) and $I_2$ (5.6 g, 21.8 mmol, 6.6 equiv) in DCM (100 mL) was stirred for 5 min at RT under a nitrogen atmosphere. To the mixture was added triethylsilane (2.56 g, 21.8 mmol, 6.6 equiv) in portions over 5 min at −65° C. The mixture was stirred for 1.5 h at −35° C.~-40° C. and then a 1/1 mixture of sat. $Na_2S_2O_3$ (aq.)/sat. $NaHCO_3$ (aq.) was added and the mixture was allowed to warm up to room temperature. The mixture was extracted with DCM (3×500 mL) and the combined organic layers were washed with brine (2×300 mL), dried over anhydrous $Na_2SO_4$, filtered and concentrated under reduced pressure. The residue was purified by silica gel column chromatography, eluting with 2/3 PE/EtOAc to afford (1S,3R,5R,6S,8R,10R,11S,13R,15R,16S,18R,20R,21S,23R,25R,26S,28R,30R,31S,33R,35R,36S,37R,38S,39R,40S,41R,42S,43R,44S,45R,46S,47R,48S,49R)-37,39,41,43,45,47,49-heptakis(benzyloxy)-5,10,15,20,25,30,35-heptakis[(benzyloxy)methyl]-2,4,7,9,12,14,17,19,22,24,27,29,32,34-tetradecaoxaoctacyclo[31.2.2.$2^{3,6}2^{8,11}.2^{13,16}.2^{18,21}.2^{23,26}.2^{28,31}$]nonatetracontane-36,38,40,42,44,46,48-heptol (Compound 4.2) (4.2 g, 52%) as a white solid. QTOF (ES): $[M+Na^+]^+$=2418.0090.

Step 3:

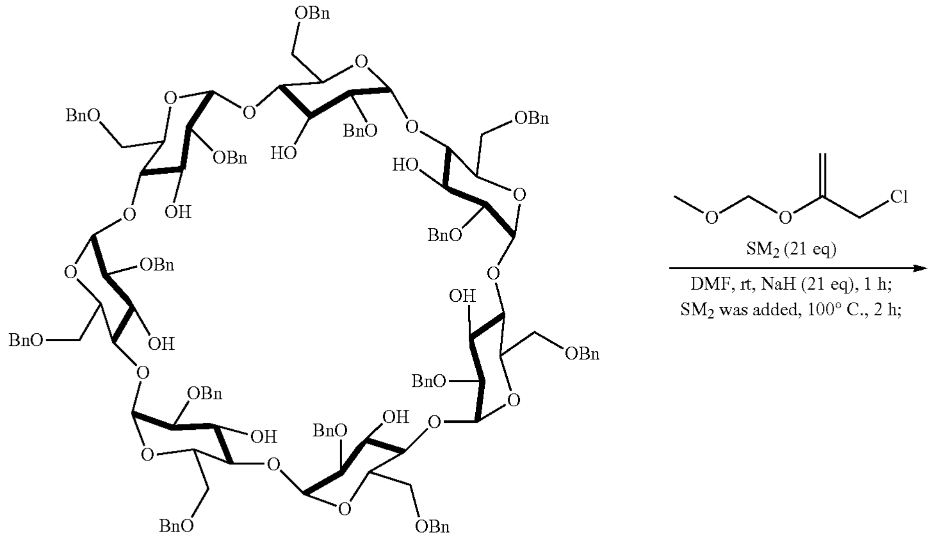

4.2

-continued

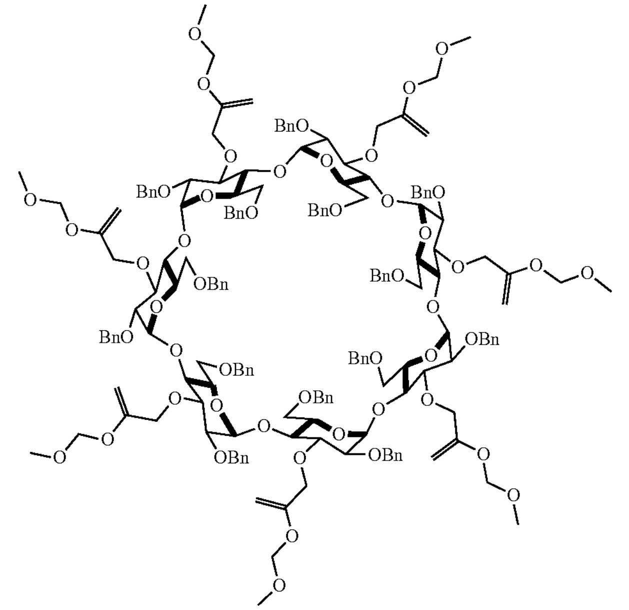

4.3

A solution of (1S,3R,5R,6S,8R,10R,11S,13R,15R,16S,18R,20R,21S,23R,25R,26S,28R,30R,31S,33R,35R,36S,37R,38S,39R,40S,41R,42S,43R,44S,45R,46S,47R,48S,49R)-37,39,41,43,45,47,49-heptakis(benzyloxy)-5,10,15,20,25,30,35-heptakis[(benzyloxy)methyl]-2,4,7,9,12,14,17,19,22,24,27,29,32,34-tetradecaoxaoctacyclo[31.2.2.2$^{3,6}$2$^{8,11}$.2$^{13,16}$.2$^{18,21}$.2$^{23,26}$.2$^{28,31}$]nonatetracontane-36,38,40,42,44,46,48-heptol (Compound 4.2) (4.2 g, 1.75 mmol, 1 equiv) and 60% NaH (1.47 g, 36.83 mmol, 21 equiv) in DMF (45 mL) was stirred for 1 h at RT under a nitrogen atmosphere. To the mixture was added 3-chloro-2-(methoxymethoxy)prop-1-ene (4.67 g, 34.18 mmol, 21 equiv) and stirred for 2 h at 100° C. The reaction was cooled to RT and 150 mL of sat. $NH_4Cl$ was added. The mixture was extracted with EtOAc (2×300 mL) and the combined organic layers were washed with brine (2×200 mL), dried over anhydrous $Na_2SO_4$, filtered and concentrated under reduced pressure. The residue was purified by silica gel column chromatography, eluting with 3/2 PE/EtOAc to afford (1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-37,39,41,43,45,47,49-heptakis(benzyloxy)-5,10,15,20,25,30,35-heptakis[(benzyloxy)methyl]-36,38,40,42,44,46,48-heptakis({[2-(methoxymethoxy)prop-2-en-1-yl]oxy})-2,4,7,9,12,14,17,19,22,24,27,29,32,34-tetradecaoxaoctacyclo[31.2.2.2$^{3,6}$2$^{8,11}$.2$^{13,16}$.2$^{18,21}$.2$^{23,26}$.2$^{28,31}$]nonatetracontane (Compound 4.3) (3 g, 55%) as a light yellow oil. QTOF (ES): $[M+Na^+]^+$=3118.3817.

Step 4:

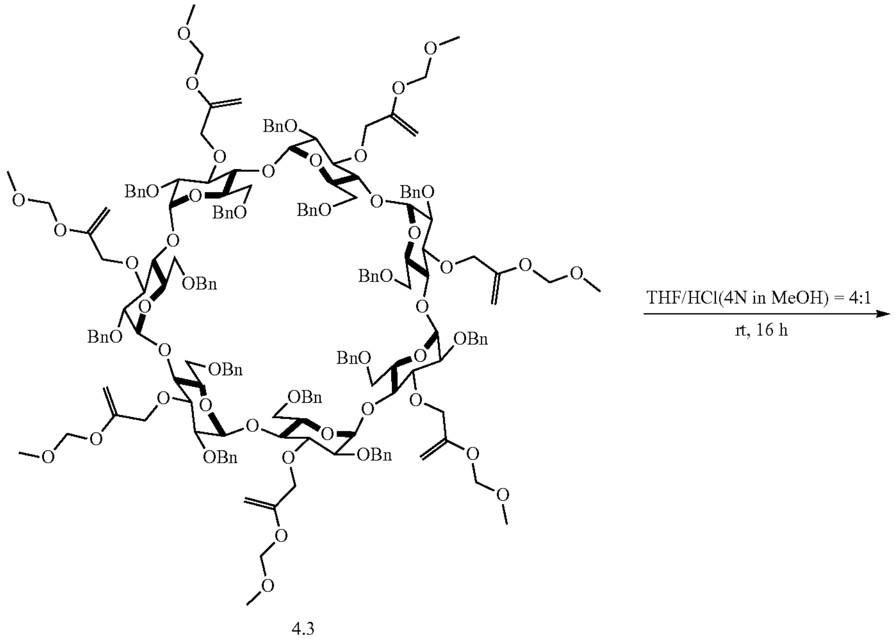

4.3

-continued

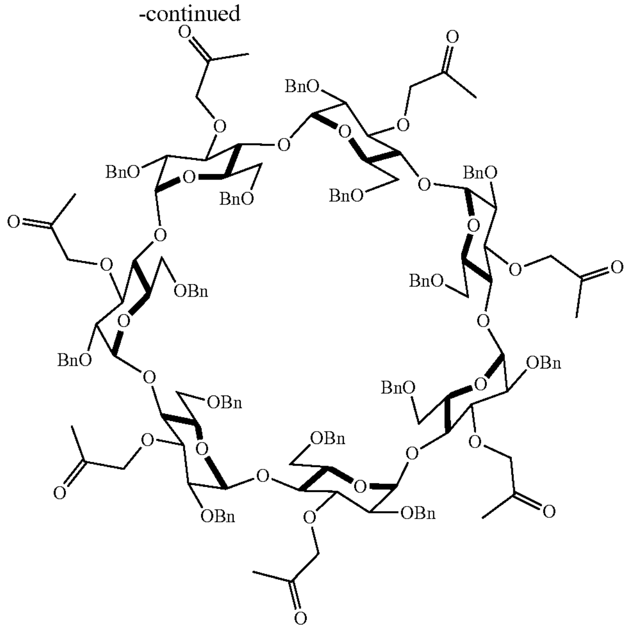

4.4

A solution of (1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-37,39,41,43,45,47,49-heptakis(benzyloxy)-5,10,15,20,25,30,35-heptakis[(benzyloxy)methyl]-36,38,40,42,44,46,48-heptakis({[2-(methoxymethoxy)prop-2-en-1-yl]oxy})-2,4,7,9,12,14,17,19,22,24,27,29,32,34-tetradecaoxaoctacyclo[31.2.2.2$^{3,6}$.2$^{8,11}$.2$^{13,16}$.2$^{18,21}$.2$^{23,26}$.2$^{28,31}$]nonatetracontane (Compound 4.3) (3 g, 0.97 mmol, 1 equiv) and HCl (6 mL, 4 N in MeOH) in THF (24 mL) was stirred for 16 h at RT and then 150 mL of sat. $NaHCO_3$ (aq.) was added. The mixture was extracted with EtOAc (3×200 mL) and the combined organic layers were washed with brine (2×200 mL), dried over anhydrous $Na_2SO_4$, filtered and concentrated under reduced pressure. The residue was purified by silica gel column chromatography, eluting with 3/2 PE/EtOAc to afford 1-{[(1R,3R,5R,6R,8R,10R,11R,13R,15R,16R,18R,20R,21R,23R,25R,26R,28R,30R,31R,33R,35R, 36S,37R,38S,39R,40S,41R,42S,43R,44S,45R,46S,47R,48S,49R)-37,39,41,43,45,47,49-heptakis(benzyloxy)-5,10,15,20,25,30,35-heptakis[(benzyloxy)methyl]-38,40,42,44,46,48-hexakis(2-oxopropoxy)-2,4,7,9,12,14,17,19,22,24,27,29,32,34-tetradecaoxaoctacyclo[31.2.2.2$^{3,6}$.2$^{8,11}$.2$^{13,16}$.2$^{18,21}$.2$^{23,26}$.2$^{28,31}$]nonatetracontan-36-yl]oxy}propan-2-one (Compound 4.4) (1.97 g, 73%) as a light yellow oil. QTOF (ES): [M+Na$^+$]$^+$=2810.2005.

Step 5:

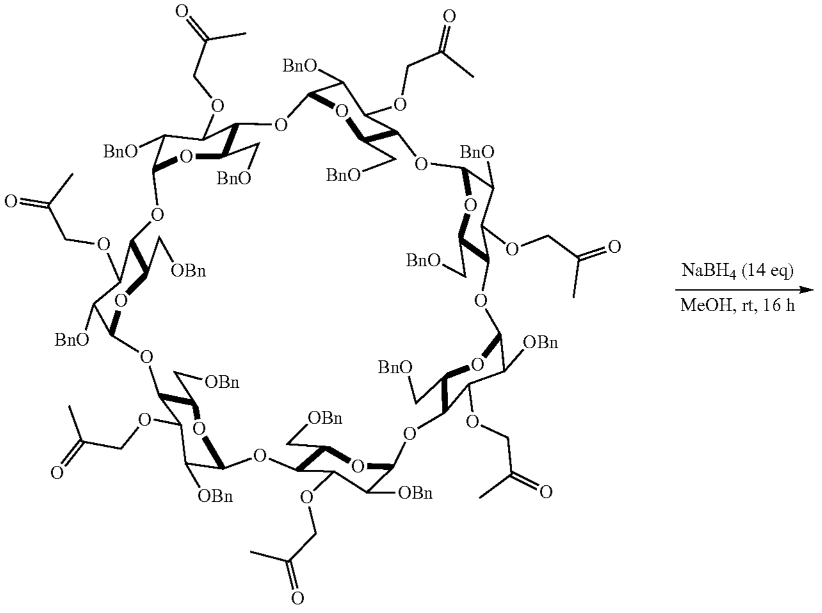

4.4

-continued

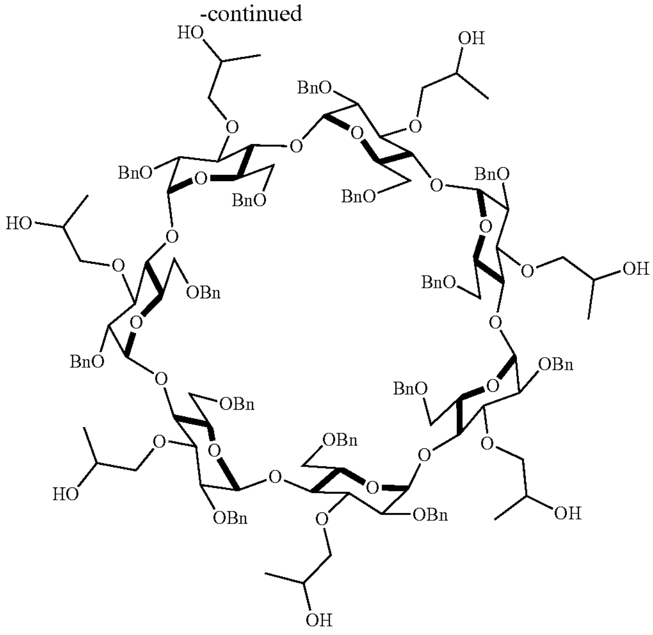

4.5

To a stirred solution of 1-{[(1R,3R,5R,6R,8R,10R,11R,13R,15R,16R,18R,20R,21R,23R,25R,26R,28R,30R,31R,33R,35R, 36S,37R,38S,39R,40S,41R,42S,43R,44S,45R,46S,47R,48S,49R)-37,39,41,43,45,47,49-heptakis(benzyloxy)-5,10,15,20,25,30,35-heptakis[(benzyloxy)methyl]-38,40,42,44,46,48-hexakis(2-oxopropoxy)-2,4,7,9,12,14,17,19,22,24,27,29,32,34-tetradecaoxaoctacyclo[31.2.2.2$^{3,6}$.2$^{8,11}$.2$^{13,16}$.2$^{18,21}$.2$^{23,26}$.2$^{28,31}$]nonatetracontan-36-yl]oxy}propan-2-one (Compound 4.4) (1.97 g, 0.71 mmol, 1 equiv) in MeOH (20 mL) was added $NaBH_4$ (378 mg, 9.94 mmol, 14 equiv) in portions at RT and the mixture was stirred for 16 h at RT. Then 100 mL of water was added and the mixture was extracted with DCM (3×200 mL). The combined organic layers were washed with brine (2×200 mL), dried over anhydrous $Na_2SO_4$, filtered and concentrated under reduced pressure. The residue was purified by silica gel column chromatography, eluting with 1/1 PE/EtOAc to afford {[(1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-37,39,41,43,45,47,49-heptakis(benzyloxy)-5,10,15,20,25,30,35-heptakis[(benzyloxy)methyl]-38,40,42,44,46,48-hexakis(2-hydroxypropoxy)-2,4,7,9,12,14,17,19,22,24,27,29,32,34-tetradecaoxaoctacyclo[31.2.2.2$^{3,6}$2$^{8,11}$.2$^{13,16}$.2$^{18,21}$.2$^{23,26}$.2$^{28,31}$]nonatetracontan-36-yl]oxy}propan-2-ol (Compound 4.5) (1.2 g, 61%) as a yellow oil. QTOF (ES): $[M+Na^+]^+$=2825.3072.

Step 6:

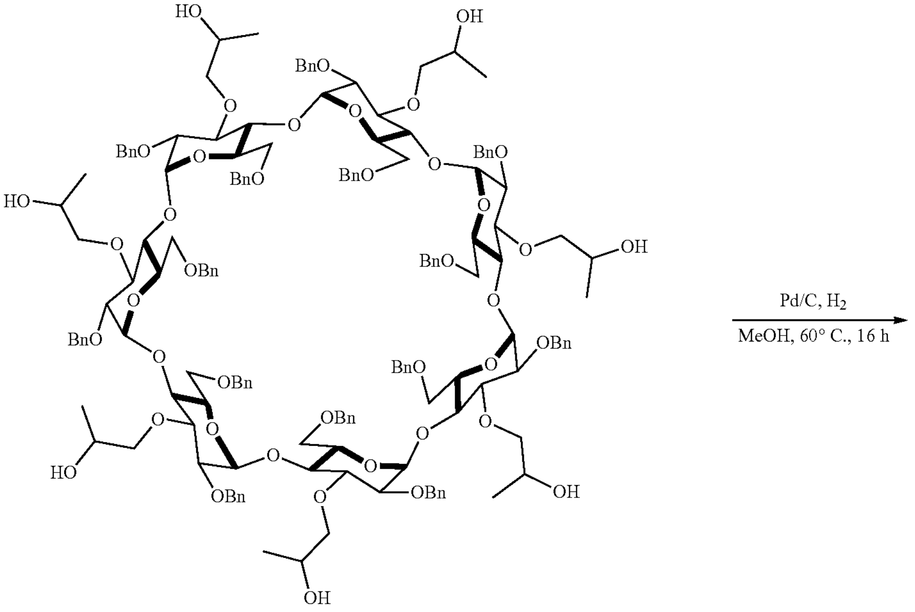

4.5

-continued

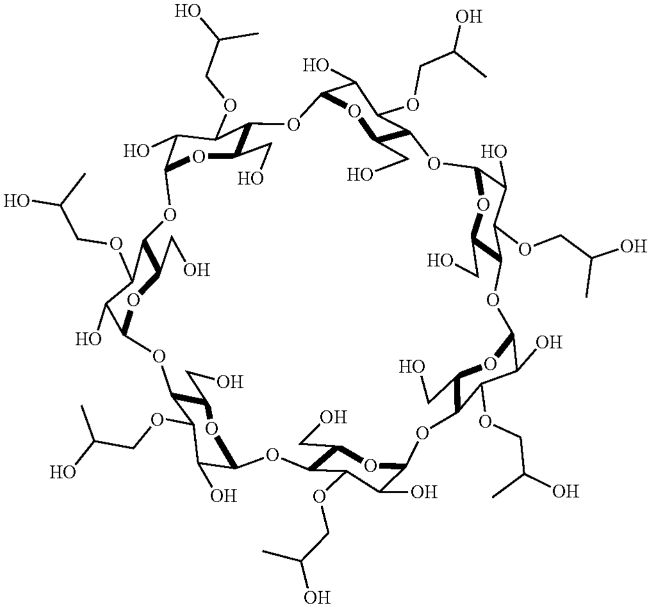

Compound 4

A mixture of 1-{[(1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-37,39,41,43,45,47,49-heptakis(benzyloxy)-5,10,15,20,25,30,35-heptakis[(benzyloxy)methyl]-38,40,42,44,46,48-hexakis(2-hydroxypropoxy)-2,4,7,9,12,14,17,19,22,24,27,29,32,34-tetradecaoxaoctacyclo[31.2.2.2$^{3,6}$2$^{8,11}$.2$^{13,16}$.2$^{18,21}$.2$^{23,26}$.2$^{28,31}$]nonatetracontan-36-yl]oxy}propan-2-ol (Compound 4.5) (1.2 g, 0.43 mmol, 1 equiv) and 10% Pd/C (0.6 g) in MeOH (20 mL) was stirred for 16 h at 60° C. under a hydrogen atmosphere. The mixture was filtered through a Celite pad and concentrated under reduced pressure. The crude product was purified by prep-HPLC with the following conditions (Column: XBridge Prep OBD C18 Column, 19*250 mm, 5 m; Mobile Phase A: MeCN, Mobile Phase B: MeCN (0.1% isoproylamine); Flow rate: 20 mL/min; Gradient: 5% B to 35% B in 14 min; RT1(min): 7.0) to afford (1R,3R,5R,6R,8R,10R,11R,13R,15R,16R,18R,20R,21R,23R,25R,26R,28R,30R,31R,33R,35R,36R,37R,38R,39R,40R,41R,42R,43R,44R,45R,46R,47R,48R,49R)-5,10,15,20,25,30,35-heptakis(hydroxymethyl)-36,38,40,42,44,46,48-heptakis(2-hydroxypropoxy)-2,4,7,9,12,14,17,19,22,24,27,29,32,34-tetradecaoxaoctacyclo[31.2.2.2$^{3,6}$.2$^{8,11}$.2$^{13,16}$.2$^{18,21}$.2$^{23,26}$.2$^{28,31}$]nonatetracontane-37,39,41,43,45,47,49-heptol (Compound 4) (225 mg, 32%) as a white solid. LC-MS (ES): $[M+H]^+$=1541.80.

$^1$H NMR (400 MHz, DMSO-d6) δ 5.15-4.78 (m, 21H), 4.60 (s, 7H), 3.94-3.71 (m, 21H), 3.56 (dt, J=33.0, 8.7 Hz, 35H), 3.39-3.28 (m, 7H), 1.01 (dd, J=6.5, 3.0 Hz, 21H).

Preparation of Compound 5 (1S,3R,5R,6S,8R,10R,11S,13R,15R,16S,18R,20R,21S,23R,25R,26S,28R,30R,31S,33R,35R,36S,37R,38S,39R,40S,41R,42S,43R,44S,45R,46S,47R,48S,49R)-5,10,15,20,25,30,35-heptakis(hydroxymethyl)-37,39,41,43,45,47,49-heptakis(2-hydroxypropoxy)-2,4,7,9,12,14,17,19,22,24,27,29,32,34-tetradecaoxaoctacyclo[31.2.2.2$^{3,6}$.2$^{8,11}$.2$^{13,16}$.2$^{18,21}$.2$^{23,26}$.2$^{28,31}$]nonatetracontane-36,38,40,42,44,46,48-heptol Compound 5

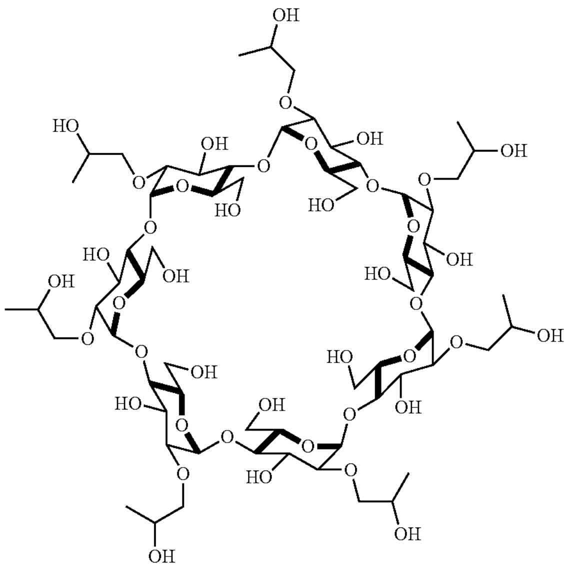

Step 1:

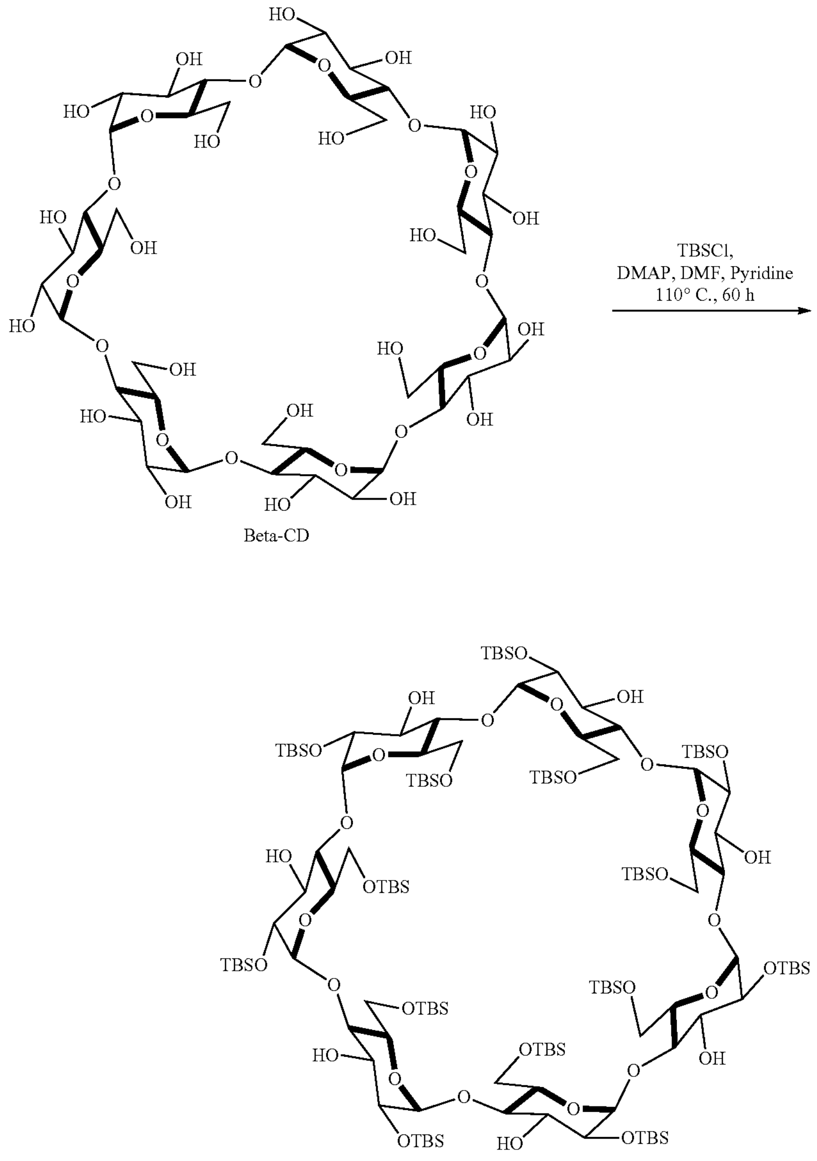

Beta-CD 5.1

To a stirred solution of (1S,3R,5R,6S,8R,10R,11S,13R,15R,16S,18R,20R,21S,23R,25R,26S,28R,30R,31S,33R,35R,36R,37R,38R,39R,40R,41R,42R,43R,44R,45R,46R,47R,48R,49R)-5,10,15,20,25,30,35-heptakis(hydroxymethyl)-2,4,7,9,12,14,17,19,22,24,27,29,32,34-tetradecaoxaoctacyclo[31.2.2.$2^{3,6}2^{8,11}.2^{13,16}.2^{18,21}.2^{23,26}.2^{28,31}$]nonatetracontane-36,37,38,39,40,41,42,43,44,45,46,47,48,49-tetradecol beta-CD (20 g, 17.6 mmol, 1 equiv) and DMAP (107 mg, 0.88 mmol, 0.05 equiv) in DMF (200 mL) was added TBSCl (112 g, 741 mmol, 42.0 equiv) in pyridine (120 mL). The resulting mixture was stirred for 60 h at 110° C. and upon cooling to room temperature was then concentrated under reduced pressure. The residue was dissolved in DCM (500 mL), washed with $KHSO_4$ (0.5 M) (3×150 mL), dried over anhydrous $Na_2SO_4$ and filtered. The filtrate was then concentrated under reduced pressure and the residue was purified by silica gel column chromatography, eluting with 0 to 10% EtOAc in PE to afford (1S,3R,5R,6S,8R,10R,11S,13R,15R,16S,18R,20R,21S,23R,25R,26S,28R,30R,31S,33R,35R,36S,37R,38S,39R,40S,41R,42S,43R,44S,45R,46S,47R,48S,49R)-37,39,41,43,45,47,49-heptakis[(tert-butyldimethylsilyl)oxy]-5,10,15,20,25,30,35-heptakis({[(tert-butyldimethylsilyl)oxy]methyl})-2,4,7,9,12,14,17,19,22,24,27,29,32,34-tetradecaoxaoctacyclo[31.2.2.$2^{3,6}.2^{8,11}.2^{13,16}.2^{18,21}.2^{23,26}.2^{28,31}$]nonatetracontane-36,38,40,42,44,46,48-heptol (Compound 5.1) (33 g, 72%) as a white solid.

$^1$H NMR (400 MHz, Chloroform-d) δ 4.81 (d, J=3.3 Hz, 7H), 4.41 (s, 7H), 3.95-3.78 (m, 14H), 3.65-3.40 (m, 28H), 0.86 (d, J=18.3 Hz, 126H), 0.13 (d, J=4.2 Hz, 42H).

Step 2:

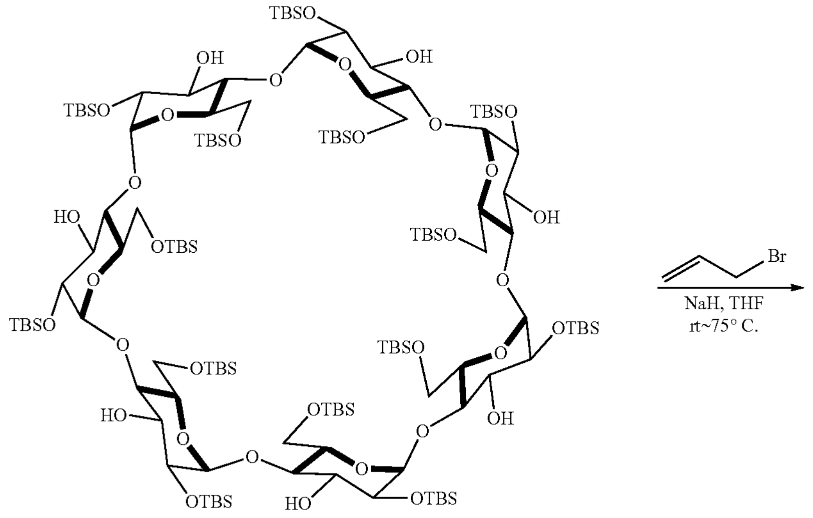

5.1

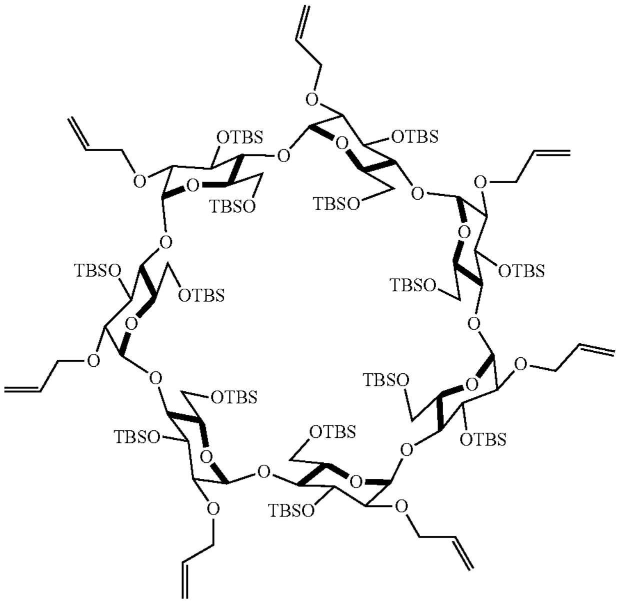

5.2

To a solution of (1S,3R,5R,6S,8R,10R,11S,13R,15R,16S,18R,20R,21S,23R,25R,26S,28R,30R,31S,33R,35R,36S,37R,38S,39R,40S,41R,42S,43R,44S,45R,46S,47R,48S,49R)-37,39,41,43,45,47,49-heptakis[(tert-butyldimethylsilyl)oxy]-5,10,15,20,25,30,35-heptakis({[(tert-butyldimethylsilyl)oxy]methyl})-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontane-36,38,40,42,44,46,48-heptol (Compound 5.1) (20 g, 7.31 mmol, 1 equiv) in 250 mL of THF was added NaH (60% in mineral oil, 6.14 g, 153.57 mmol, 21 equiv) and the mixture was allowed to stir for 1 h at room temperature. Allyl bromide (18.58 g, 153.57 mmol, 21 equiv) was added dropwise over 30 min at RT. The mixture was stirred and heated to 70° C. for 16 h. The reaction mixture was cooled to room temperature and saturated $NH_4Cl$ (aq, 150 mL) was added. The mixture was extracted with EtOAc (3×500 mL) and the combined organic layers were washed with saturated aqueous sodium chloride solution (3×500 mL), dried over $Na_2SO_4$, filtered and concentrated under reduced pressure. The crude product was re-crystallized from 12/1 MeOH/DCM (700 mL) and was then purified by silica gel column chromatography, eluting with 10/1 PE/EtOAc to afford tert butyl({[(1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-36,38,40,42,44,46,48-heptakis[(tert-butyldimethylsilyl)oxy]-10,15,20,25,30,35-hexakis({[(tert-butyldimethylsilyl)oxy]methyl})-37,39,41,43,45,47,49-heptakis(prop-2-en-1-yloxy)-2,4,7,9,12,14,17,19,22,24,27,29,32,34-tetradecaoxaoctacyclo[31.2.2.$2^{3,6}2^{8,11}$.$2^{13,16}$.$2^{18,21}$.$2^{23,26}$.$2^{28,31}$]nonatetracontan-5-yl]methoxy})dimethylsilane (Compound 5.2) (12.4 g, 4.11 mmol, 56% yield) as a white solid.

Step 3:

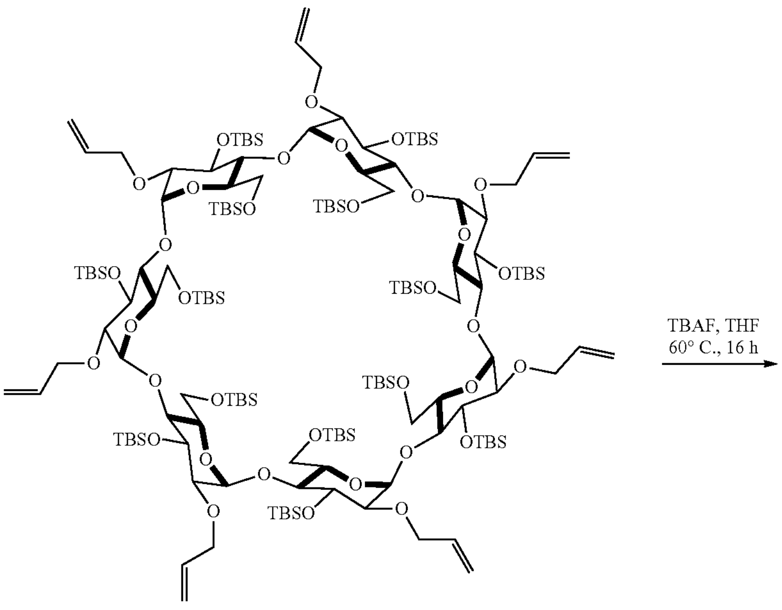

5.2

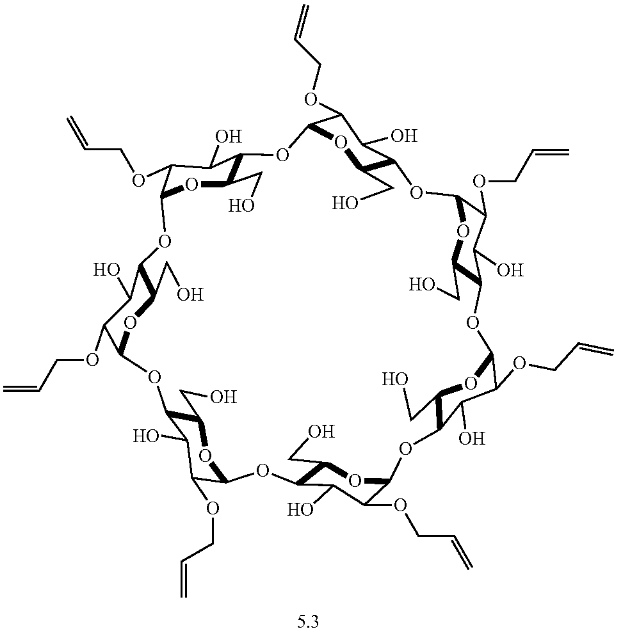

5.3

To a solution of tert-butyl({[(1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-36,38,40,42,44,46,48-heptakis[(tert-butyldimethylsilyl)oxy]-10,15,20,25,30,35-hexakis({[(tert-butyldimethylsilyl)oxy]methyl})-37,39,41,43,45,47,49-heptakis(prop-2-en-1-yloxy)-2,4,7,9,12,14,17,19,22,24,27,29,32,34-tetradecaoxaoctacyclo[31.2.2.$2^{3,6}2^{8,11}.2^{13,16}.2^{18,21}.2^{23,26}.2^{28,31}$]nonatetracontan-5-yl]methoxy})dimethylsilane (Compound 5.2) (12.4 g, 4.11 mmol, 1 equiv) in 60 mL of THF was added tetrabutylammonium fluoride (1 M in THF, 115 mL, 115 mmol, 28 equiv) and stirred for 16 h at 60° C. The mixture was allowed to cool down to RT and concentrated under reduced pressure. The mixture was extracted with EtOAc (3×100 mL) and the combined organic layers were washed with water (5×50 mL), dried over anhydrous $Na_2SO_4$, filtered and concentrated under reduced pressure. The residue was purified by silica gel column chromatography, eluting with 2/1 $CH_2Cl_2$/MeOH to afford (1S,3R,5R,6S,8R,10R,11S,13R,15R,16S,18R,20R,21S,23R,25R,26S,28R,30R,31S,33R,35R,36S,37R,38S,39R,40S,41R,42S,43R,44S,45R,46S,47R,48S,49R)-5,10,15,20,25,30,35-heptakis(hydroxymethyl)-37,39,41,43,45,47,49-heptakis(prop-2-en-1-yloxy)-2,4,7,9,12,14,17,19,22,24,27,29,32,34-tetradecaoxaoctacyclo[31.2.2.$2^{3,6}2^{8,11}.2^{13,16}.2^{18,21}.2^{23,26}.2^{28,31}$]nonatetracontane-36,38,40,42,44,46,48-heptol (Compound 5.3) (3 g, 52%) as a light-yellow solid. QTOF (ES): $[M-H^+]^-$=1413.85.

Step 4:

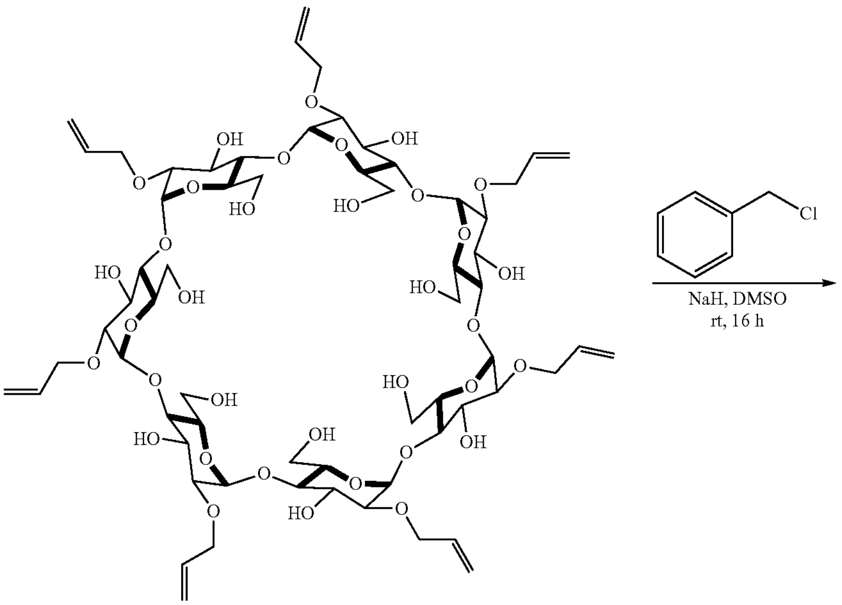

5.3

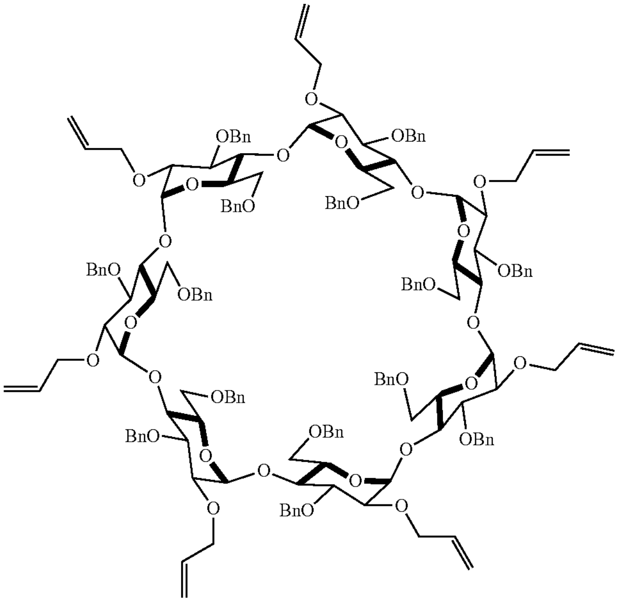

5.4

To a solution of (1S,3R,5R,6S,8R,10R,11S,13R,15R,16S,18R,20R,21S,23R,25R,26S,28R,30R,31S,33R,35R,36S,37R,38S,39R,40S,41R,42S,43R,44S,45R,46S,47R,48S,49R)-5,10,15,20,25,30,35-heptakis(hydroxymethyl)-37,39,41,43,45,47,49-heptakis(prop-2-en-1-yloxy)-2,4,7,9,12,14,17,19,22,24,27,29,32,34-tetradecaoxaoctacyclo[31.2.2.$2^{3,6}2^{8,11}.2^{13,16}.2^{18,21}.2^{23,26}.2^{28,31}$]nonatetracontane-36,38,40,42,44,46,48-heptol (Compound 5.3) (3 g, 2.12 mmol, 1 equiv) in 20 mL of DMSO was added 60% NaH (3.56 g, 89.0 mmol, 42 equiv) in portions over 15 min at 0° C. The mixture was stirred for 1 h at RT and then benzyl chloride (11.27 g, 89.0 mmol, 42 equiv) was added dropwise over 10 min at RT. The mixture was stirred for 16 h at RT and then 200 mL of sat. $NH_4Cl$ (aq.) was added. The mixture was extracted with EtOAc (3×100 mL) and the combined organic layers were washed with brine (3×30 mL), dried over anhydrous $Na_2SO_4$, filtered and concentrated under reduced pressure. The crude product was re-crystallized from MeOH to afford (1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-36,38,40,42,44,46,48-heptakis(benzyloxy)-5,10,15,20,25,30,35-heptakis[(benzyloxy)methyl]-37,39,41,43,45,47,49-heptakis(prop-2-en-1-yloxy)-2,4,7,9,12,14,17,19,22,24,27,29,32,34-tetradecaoxaoctacyclo[31.2.2.$2^{3,6}$.$2^{8,11}.2^{13,16}.2^{18,21}.2^{23,26}.2^{28,31}$]nonatetracontane (Compound 5.4) (2.4 g, 42%) as a light-yellow solid.

Step 5:

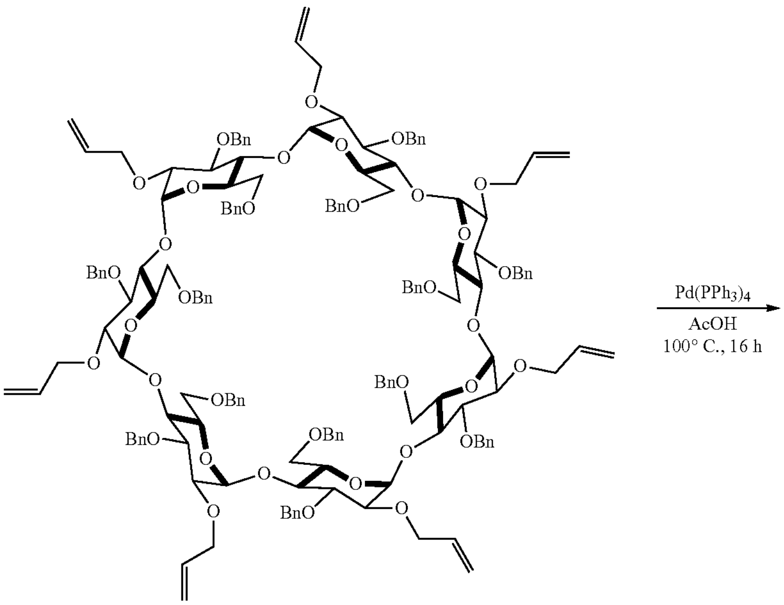

5.4

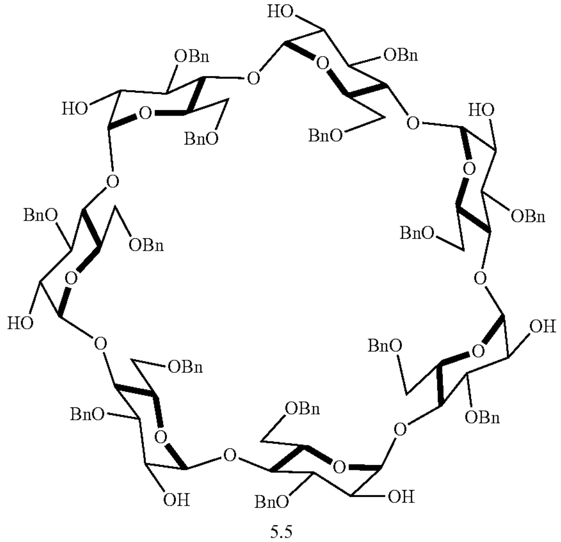

5.5

A solution of (1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-36,38,40,42,44,46,48-heptakis(benzyloxy)-5,10,15,20,25,30,35-heptakis[(benzyloxy)methyl]-37,39,41,43,45,47,49-heptakis(prop-2-en-1-yloxy)-2,4,7,9,12,14,17,19,22,24,27,29,32,34-tetradecaoxaoctacyclo[31.2.2.2$^{3,6}$2$^{8,11}$2$^{13,16}$.2$^{18,21}$.2$^{23,26}$.2$^{28,31}$]nonatetracontane (Compound 5.4) (2.4 g, 0.90 mmol, 1 equiv) and tetrakis(triphenylphosphine) palladium(0) (3.63 g, 3.14 mmol, 3.5 equiv) in 30 mL of AcOH was stirred for 16 h at 100° C. under a nitrogen atmosphere. The mixture was allowed to cool down to RT and concentrated under reduced pressure. The residue was dissolved in EtOAc (30 mL) and the organic layer was washed with sat. $NaHCO_3$ (aq.) (3×10 mL), dried over anhydrous $Na_2SO_4$, filtered, and concentrated under reduced pressure. The residue was purified by silica gel column chromatography, eluting with 1/1 PE/EtOAc (1:1) and then purified by prep-TLC 4/3 PE/EA to afford (1R,3R,5R,6R,8R,10R,11R,13R,15R,16R,18R,20R,21R,23R,25R,26R,28R,30R,31R,33R,35R,36R,37R,38R,39R,40R,41R,42R,43R,44R,45R,46R,47R,48R,49R)-36,38,40,42,44,46,48-heptakis(benzyloxy)-5,10,15,20,25,30,35-heptakis[(benzyloxy)methyl]-2,4,7,9,12,14,17,19,22,24,27,29,32,34-tetradecaoxaoctacyclo[31.2.2.2$^{3,6}$2$^{8,11}$.2$^{13,16}$.2$^{18,21}$.2$^{23,26}$.2$^{28,31}$]nonatetracontane-37,39,41,43,45,47,49-heptol (Compound 5.5) (1.05 g, 49%) as a light yellow oil.

Step 6:

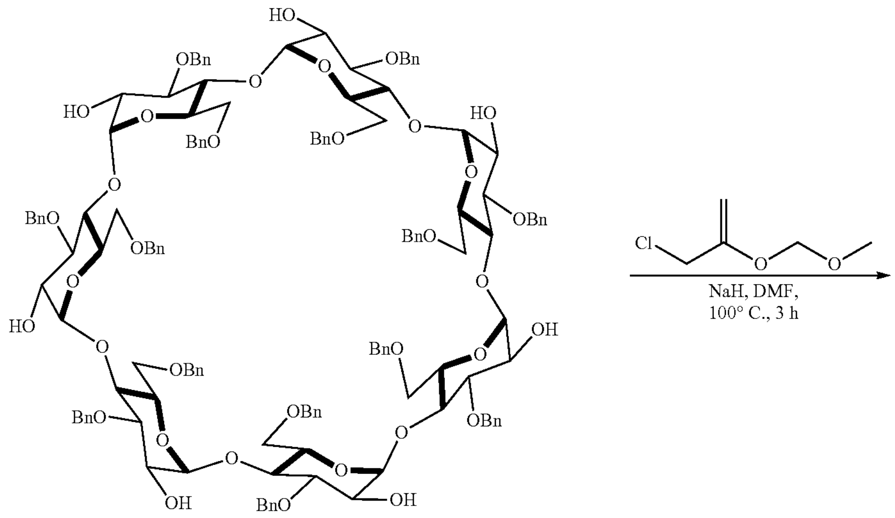

5.5

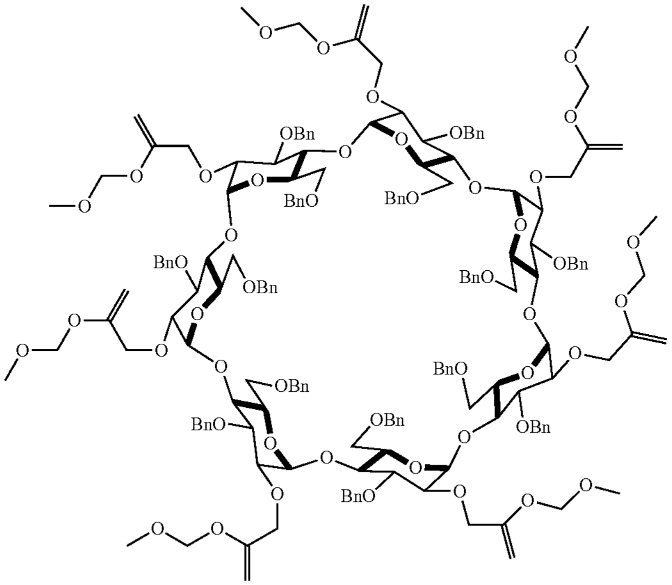

5.6

A solution of (1R,3R,5R,6R,8R,10R,11R,13R,15R,16R,18R,20R,21R,23R,25R,26R,28R,30R,31R,33R,35R,36R,37R,38R,39R,40R,41R,42R,43R,44R,45R,46R,47R,48R,49R)-36,38,40,42,44,46,48-heptakis(benzyloxy)-5,10,15,20,25,30,35-heptakis[(benzyloxy)methyl]-2,4,7,9,12,14,17,19,22,24,27,29,32,34-tetradecaoxaoctacyclo[31.2.2.$2^{3,6}$ $2^{8,11}$.$2^{13,16}$.$2^{18,21}$.$2^{23,26}$.$2^{28,31}$]nonatetracontane-37,39,41,43,45,47,49-heptol (Compound 5.5) (1.05 g, 0.44 mmol, 1 equiv) and 60% NaH (370 mg, 9.20 mmol, 21 equiv) in 10 mL of DMF was stirred for 1 h at RT under a nitrogen atmosphere. Then 3-chloro-2-(methoxymethoxy)prop-1-ene (1.68 g, 12.26 mmol, 28 equiv) was added and the mixture was stirred for additional 3 h at 100° C. The mixture was allowed to cool down to RT and 15 mL of sat. $NH_4Cl$ (aq.) was added. The mixture was extracted with EtOAc (3×50 mL). The combined organic layers were washed with brine (3×50 mL), dried over anhydrous $Na_2SO_4$, filtered, and concentrated under reduced pressure. The residue was purified by prep-TLC (1/1 PE/EA) to afford (1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-36,38,40,42,44,46,48-heptakis(benzyloxy)-5,10,15,20,25,30,35-heptakis[(benzyloxy)methyl]-37,39,41,43,45,47,49-heptakis({[2-(methoxymethoxy)prop-2-en-1-yl]oxy})-2,4,7,9,12,14,17,19,22,24,27,29,32,34-tetradecaoxaoctacyclo[31.2.2.$2^{3,6}$ $2^{8,11}$.$2^{13,16}$.$2^{18,21}$.$2^{23,26}$.$2^{28,31}$]nonatetracontane (Compound 5.6) (750 mg, 55%) as a white solid.

Step 7:

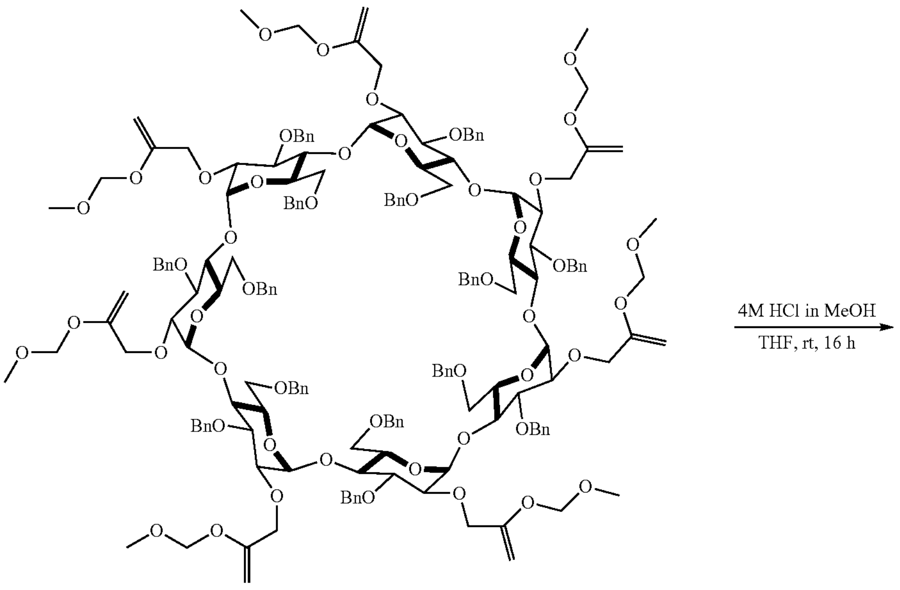

5.6

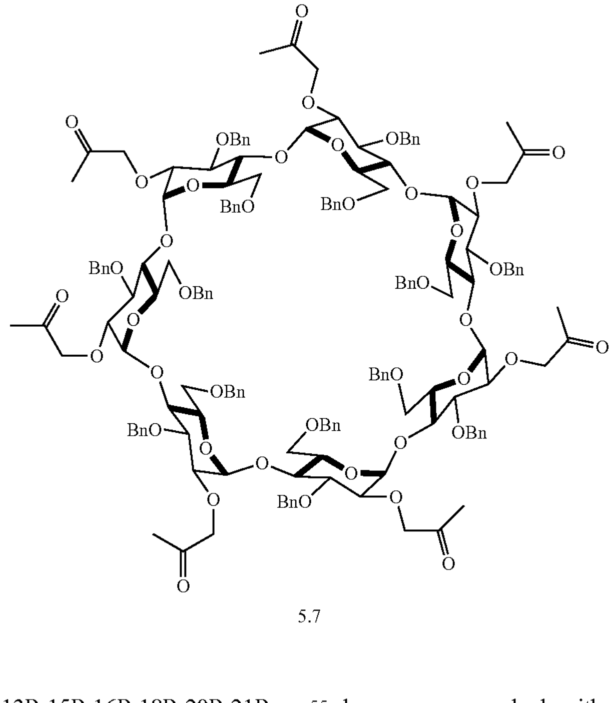

5.7

(1R,3R,5R,6R,8R,10R,1R,13R,15R,16R,18R,20R,21R, 23R,25R,26R,28R,30R,31R,33R,35R,36S,37R,38S,39R, 40S,41R,42S,43R,44S,45R,46S,47R,48S,49R)-36,38,40, 42,44,46,48-heptakis(benzyloxy)-5,10,15,20,25,30,35-heptakis[(benzyloxy)methyl]-37,39,41,43,45,47,49-heptakis({[2-(methoxymethoxy)prop-2-en-1-yl]oxy})-2,4, 7,9,12,14,17,19,22,24,27,29,32,34-tetradecaoxaoctacyclo [31.2.2.$2^{3,6}$.$2^{8,11}$.$2^{13,16}$.$2^{18,21}$.$2^{23,26}$.$2^{28,31}$]nonatetracontane (Compound 5.6) (750 mg, 0.24 mmol, 1 equiv) was added to a mixture of 2 mL of 4 N HCl solution in MeOH and 8 mL of THF. The mixture was stirred for 16 h at RT and then 50 mL of sat. $NaHCO_3$ (aq.) was added. The mixture was extracted with EtOAc (3×30 mL) and the combined organic layers were washed with brine (3×20 mL), dried over anhydrous $Na_2SO_4$, filtered and concentrated under reduced pressure. The residue was purified by prep-TLC (1/1 PE/EA) to afford 1-{[(1R,3R,5R,6R,8R,10R,11R,13R,15R,16R, 18R,20R,21R,23R,25R,26R,28R,30R,31R,33R,35R, 36S, 37R,38S,39R,40S,41R,42S,43R,44S,45R,46S,47R,48S, 49R)-36,38,40,42,44,46,48-heptakis(benzyloxy)-5,10,15, 20,25,30,35-heptakis[(benzyloxy)methyl]-39,41,43,45,47, 49-hexakis(2-oxopropoxy)-2,4,7,9,12,14,17,19,22,24,27, 29,32,34-tetradecaoxaoctacyclo[31.2.2.$2^{3,6}2^{8,11}$.$2^{13,16}$. $2^{18,21}$.$2^{23,26}$.$2^{28,31}$]nonatetracontan-37-yl]oxy}propan-2-one (Compound 5.7) (506 mg, 75%) as a white solid.

Step 8:

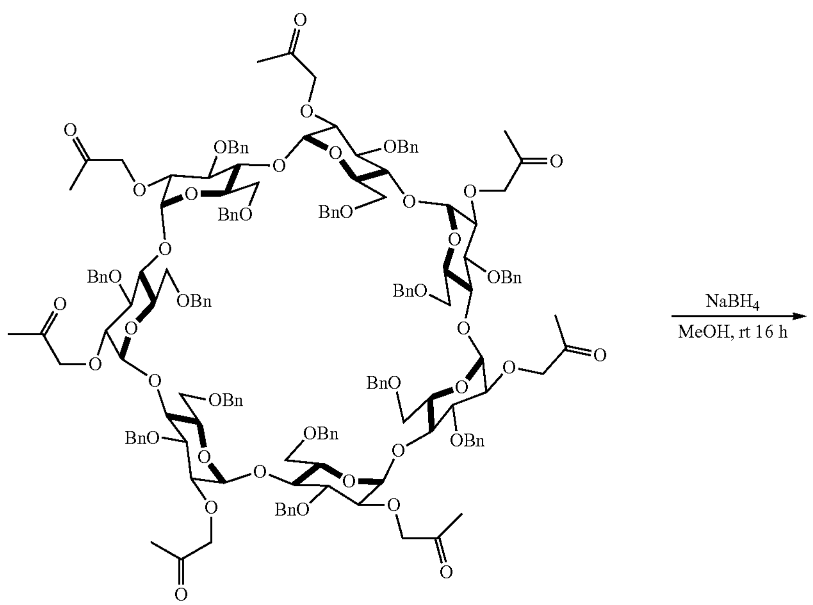

5.7

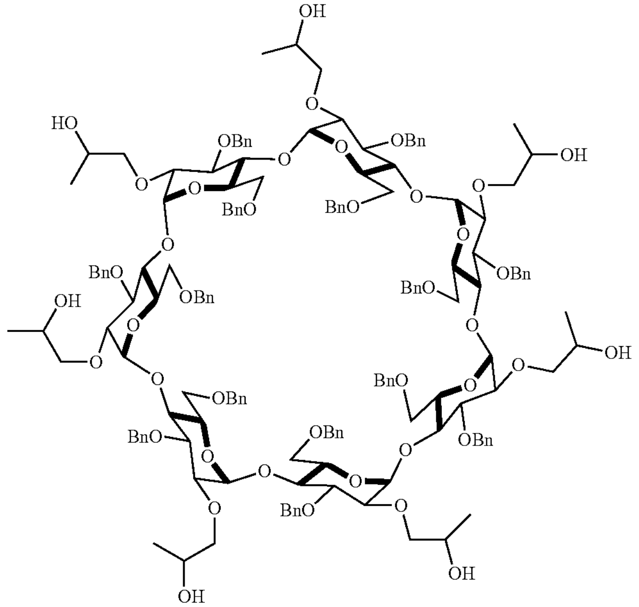

5.8

To a solution of 1-{[(1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-36,38,40,42,44,46,48-heptakis(benzyloxy)-5,10,15,20,25,30,35-heptakis[(benzyloxy)methyl]-39,41,43,45,47,49-hexakis(2-oxopropoxy)-2,4,7,9,12,14,17,19,22,24,27,29,32,34-tetradecaoxaoctacyclo[31.2.2.2$^{3,6}$2$^{8,11}$.2$^{13,16}$.2$^{18,21}$.2$^{23,26}$.2$^{28,31}$]nonatetracontan-37-yl]oxy}propan-2-one (Compound 5.7) (506 mg, 0.18 mmol, 1 equiv) in 5 mL of MeOH was added $NaBH_4$ (144 mg, 3.80 mmol, 21 equiv) and the mixture was stirred for 16 h at RT under a nitrogen atmosphere. Then 5 mL of sat. $NH_4Cl$ (aq.) was added and the resulting mixture was extracted with EtOAc (3×30 mL). The combined organic layers were washed with brine (3×15 mL), dried over anhydrous $Na_2SO_4$, filtered and concentrated under reduced pressure. The residue was purified by prep-TLC (1/1 PE/EA) to afford 1-{[(1R,3R,5R,6R,8R,10R,11R,13R,15R,16R,18R,20R,21R,23R,25R,26R,28R,30R,31R,33R,35R, 36S,37R,38S,39R,40S,41R,42S,43R,44S,45R,46S,47R,48S,49R)-36,38,40,42,44,46,48-heptakis(benzyloxy)-5,10,15,20,25,30,35-heptakis[(benzyloxy)methyl]-39,41,43,45,47,49-hexakis(2-hydroxypropoxy)-2,4,7,9,12,14,17,19,22,24,27,29,32,34-tetradecaoxaoctacyclo[31.2.2.2$^{3,6}$.2$^{8,11}$.2$^{13,16}$.2$^{18,21}$.2$^{23,26}$.2$^{28,31}$]nonatetracontan-37-yl]oxy}propan-2-ol (Compound 5.8) (380 mg, 75%) as a white solid.

Step 9:

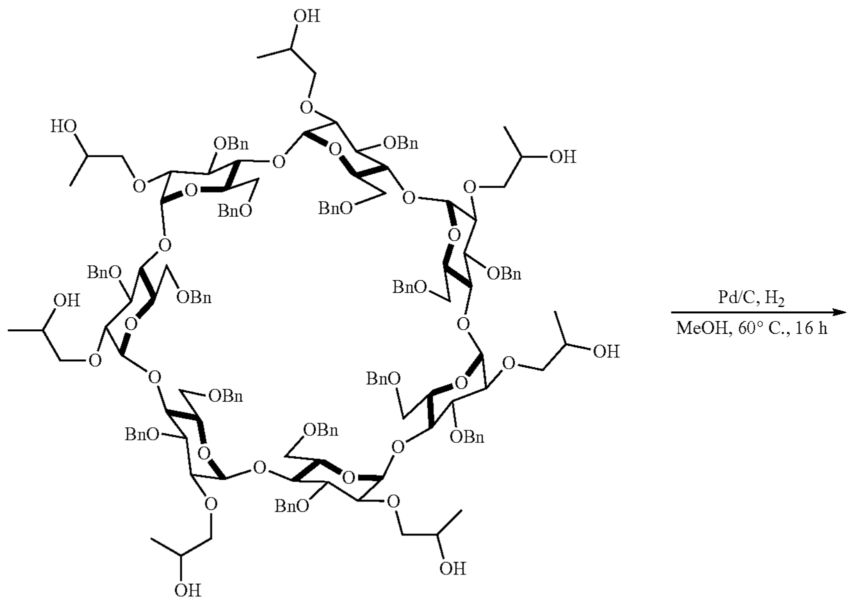

5.8

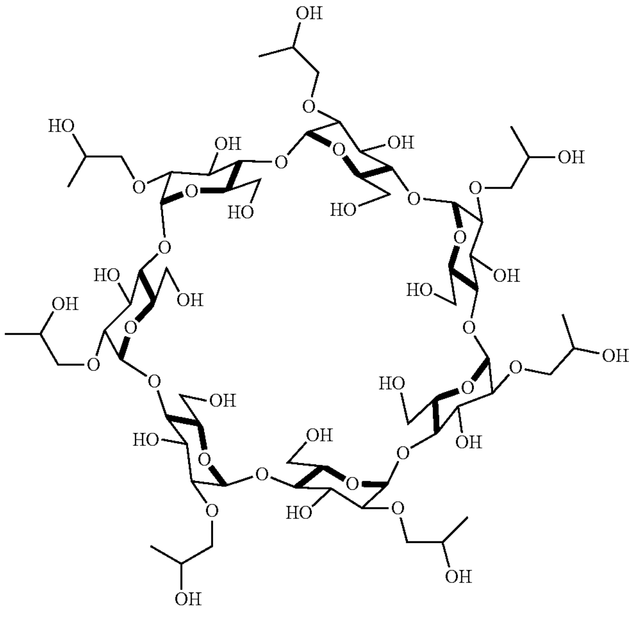

Compound 5

To a solution of 1-{[(1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-36,38,40,42,44,46,48-heptakis(benzyloxy)-5,10,15,20,25,30,35-heptakis[(benzyloxy)methyl]-39,41,43,45,47,49-hexakis(2-hydroxypropoxy)-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontan-37-yl]oxy}propan-2-ol (Compound 5.8) (380 mg, 0.14 mmol, 1 equiv) in 15 mL of MeOH was added Pd/C (202 mg, 10% wet) and the mixture was stirred for 16 h at 60° C. under a hydrogen atmosphere. The resulting mixture was filtered, and the filter cake was washed with MeOH (3×50 mL). The filtrate was concentrated under reduced pressure and the crude product was purified by prep-HPLC with the following conditions (Column: XBridge Prep OBD C18 Column, 19*250 mm, 5 m; Mobile Phase A: 10 mM $NH_4HCO_3$ (aq.)+wt/wt 0.05% $NH_4OH$, Mobile Phase B: MeCN; Flow rate: 20 mL/min; Gradient: 20% B to 50% B in 8 min, 50% B; RT1(min): 7.5; Injection Volume: 500 mL) to afford (1S,3R,5R,6S,8R,10R,11S,13R,15R,16S,18R,20R,21S,23R,25R,26S,28R,30R,31S,33R,35R,36S,37R,38S,39R,40S,41R,42S,43R,44S,45R,46S,47R,48S,49R)-5,10,15,20,25,30,35-heptakis(hydroxymethyl)-37,39,41,43,45,47,49-heptakis(2-hydroxypropoxy)-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontane-36,38,40,42,44,46,48-heptol (Compound 5) (106 mg, 51%) as a white solid. LCMS (ES): $[M-H^+]^-$=1539.80.

The MALDI spectrum of Compound 5 is shown in FIG. 1. The MALDI spectrum of Compound 5 comprises peaks at 1563.916, 1575.839, 1579.896, 1595.851 and/or 1607.950. The MALDI spectrum of Compound 5 is provided in the table below:

| m/z | S/N | Quality Fac. | Res. | Intens. | Area |
|---|---|---|---|---|---|
| 1004.758 | 7 | 690 | 2693 | 569 | 328 |
| 1036.739 | 6 | 592 | 2852 | 508 | 308 |
| 1050.738 | 6 | 171 | 4171 | 510 | 221 |
| 1123.509 | 13 | 1513 | 3176 | 881 | 651 |
| 1343.702 | 19 | 4817 | 3897 | 1124 | 925 |
| 1505.824 | 9 | 1288 | 3895 | 573 | 525 |
| 1561.986 | 7 | 6.69 | 2588 | 534 | 605 |
| 1563.916 | 491 | 233359 | 3339 | 25968 | 35357 |
| 1575.839 | 8 | 299 | 3849 | 604 | 582 |
| 1577.944 | 12 | 122 | 5162 | 780 | 577 |
| 1579.896 | 104 | 31822 | 3901 | 5595 | 6489 |
| 1595.851 | 15 | 1309 | 3713 | 947 | 1040 |
| 1607.950 | 13 | 3631 | 3870 | 851 | 849 |
| 1641.915 | 6 | 859 | 3864 | 479 | 445 |

Figure 3:
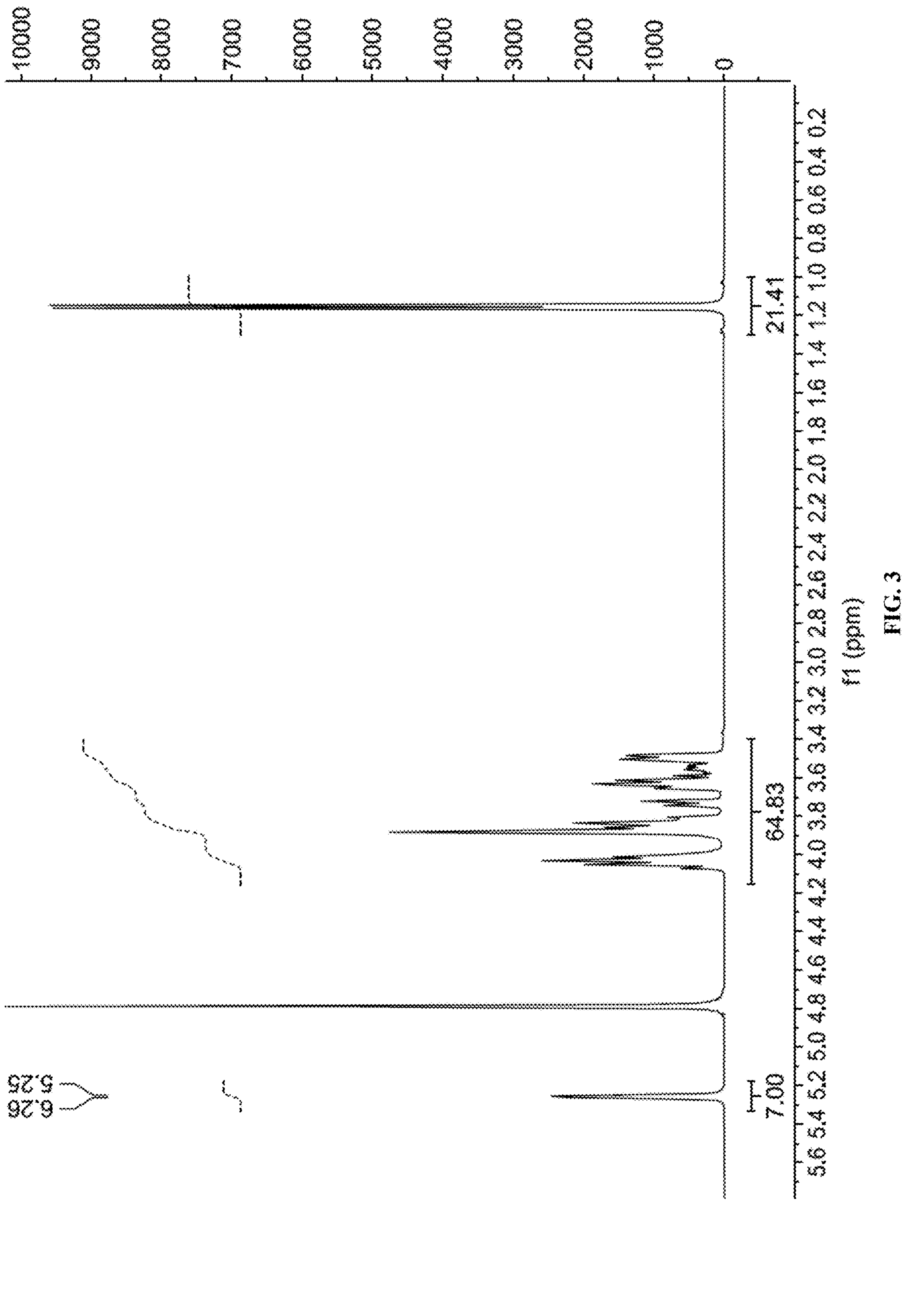
FIG. 3 is a 1D $^1$H-NMR spectrum collected in $D_2O$ of Compound 5, i.e., a 2-HPBCD synthesized as described in Example 1. The calculated average degree of substitution of the sample is 7.
Figure 4:
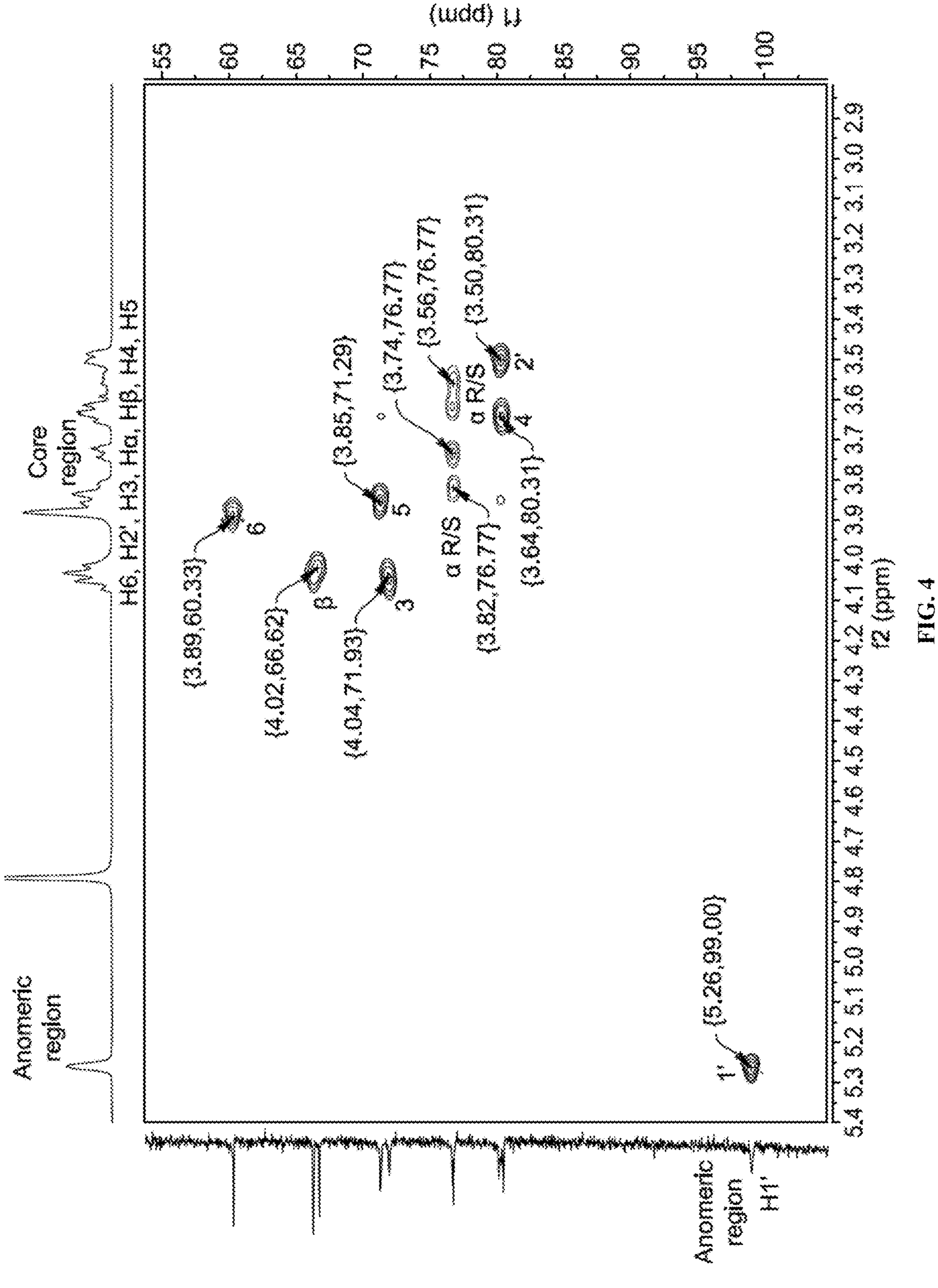
FIG. 4 is a 2D $^1$H-NMR spectrum collected in $D_2O$ of Compound 5, i.e., a 2-HPBCD synthesized as described in Example 1. The calculated average degree of substitution of the sample is 7.
Figure 5:
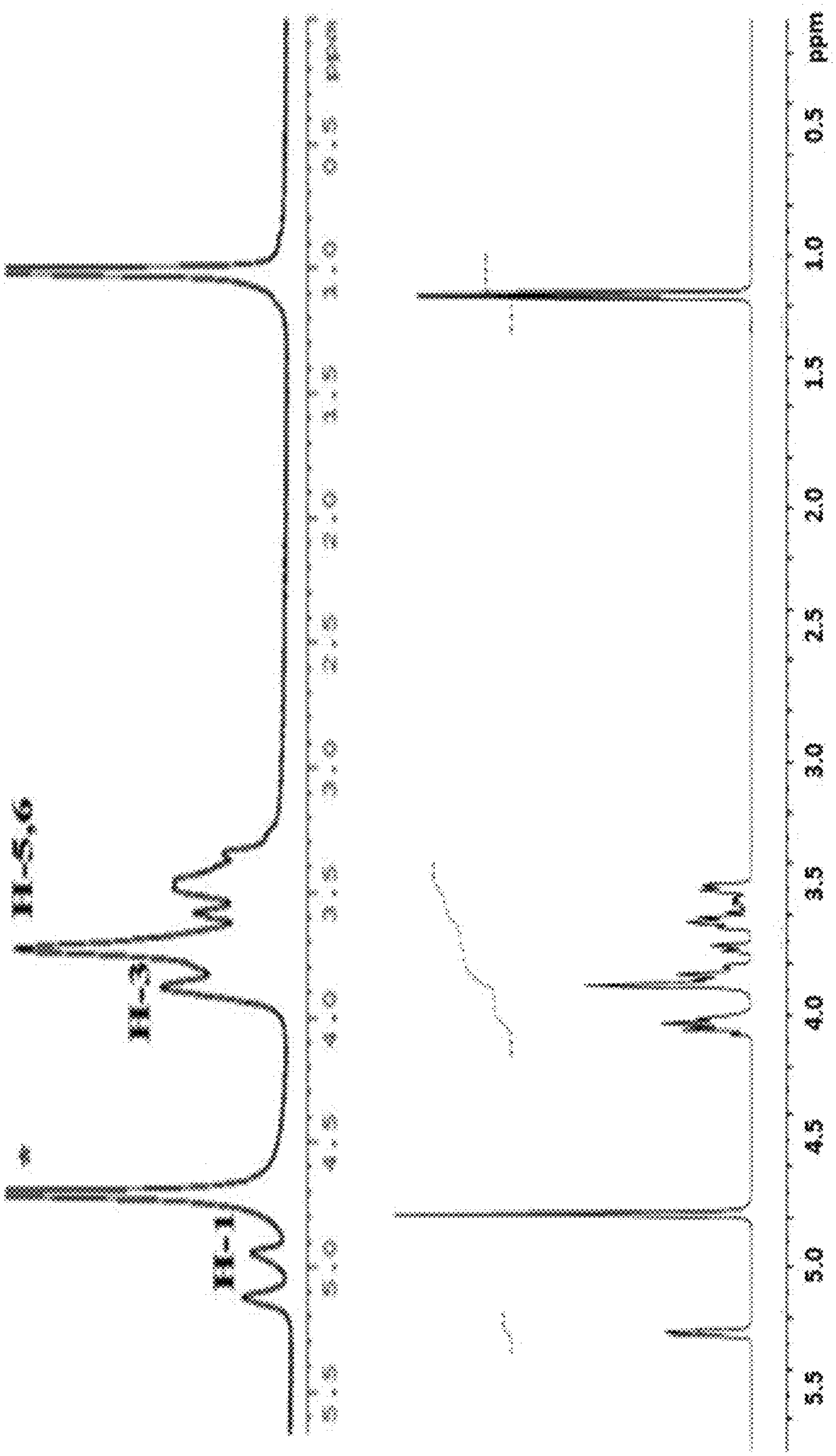
FIG. 5 is a comparison of the 1D $^1$H-NMR spectra of Compound 5 and an exemplary commercially available 2-HPBCD product (namely 2-HPBCD from ABCR GmbH & Co. KG, i.e., the 2-HPBCD starting material shown in FIG. 1(*a*) of CN109675054).

The 1D and 2D 1H-NMR spectra of Compound 5, collected in $D_2O$, are shown in FIGS. 3 and 4, respectively. In the 1H-NMR spectrum, the peak at about 4.8 ppm is due to residual $D_2O$ Structure Elucidation and Characterization of Compound 5 in view of CN109675054

CN109675054 discloses a 2-HPBCD product, commercially purchased from ABCR GmbH & Co. KG. The presence of two separate NMR peaks in the anomeric region of the 1D 1H-NMR spectrum shown in FIG. 1(*a*) of CN109675054 is indicative of the presence of substituted and unsubstituted glucose subunits in the molecule. Specifically, the 1H NMR spectrum of 2-HPBCD molecules of different degrees of substitution was previously found to display two separate peaks in the anomeric region (which contains the peak corresponding to the hydrogen at the C-1 position of the glucose subunit, i.e., the "1H signal"). Beni et al., Carbohydrate Polymers, Volume 338, 15 Aug. 2024. It was found that, as the degree of substitution of the 2-HPBCD increases, the integral value of the anomeric peak at higher chemical shifts also increases. Therefore, the peak at higher chemical shifts is conventionally attributed to the 1H signal of HP-substituted glucose subunits. In fact, the peak at higher resonances has been assigned to the 1H signal when the 2-0 position is substituted. Beni et al., Carbohydrate Polymers, Volume 338, 15 Aug. 2024. Accordingly, the presence of two separate peaks in the anomeric region of the 1H NMR spectrum (including the peak with a higher integral value) shown in FIG. 1(*a*) of CN109675054 confirms the understanding that the 2-HPBCD exemplified in this reference could not have been a molecule in which all seven glucose subunits are identically substituted (such as, e.g., an exclusively 2-0 substituted 2-HPBCD of DS=7). Moreover, the spectrum shown in FIG. 1(*a*) of CN109675054 shows broad and poorly separated peaks in the core region (between 3.0 ppm and 4.5 ppm). This is indicative of the presence of mixture of various different molecular structures rather than a composition comprising compounds sharing a single molecular structure. This is consistent with the commercially available starting material being a mixture of complex 2-HPBCD molecules comprising different regioisomers as well as molecules of different degrees of substitution. In contrast, the present disclosure shows possession and the enabled disclosure of this unique isomer of 2-HPBCD (i.e., Compound 5).

Preparation of Compound 6 (1R,3R,5R,6R,8R,10R,11R,13R,15R,16R,18R,20R,21R,23R,25R,26R,28R,30R,31R,33R,35R,36R,37R,38R,39R,40R,41R,42R,43R,44R,45R,46R,47R,48R,49R)-36,38,40,42,44,46,48-heptakis(2-hydroxy-2-methylpropoxy)-5,10,15,20,25,30,35-heptakis(hydroxymethyl)-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontane-37,39,41,43,45,47,49-heptol Compound 6

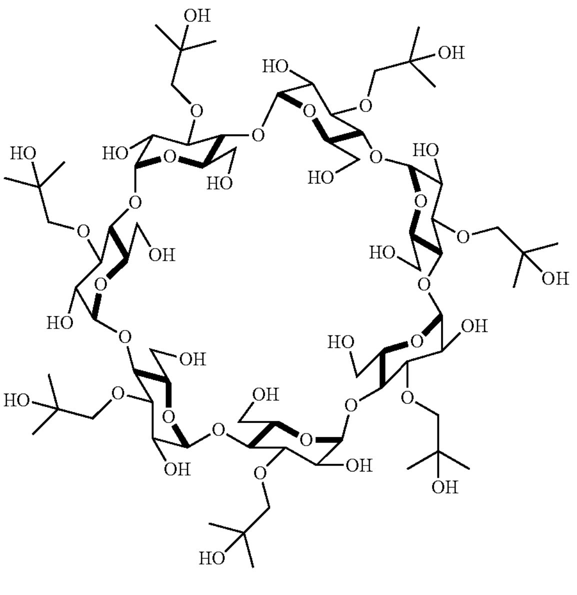

Step 1:

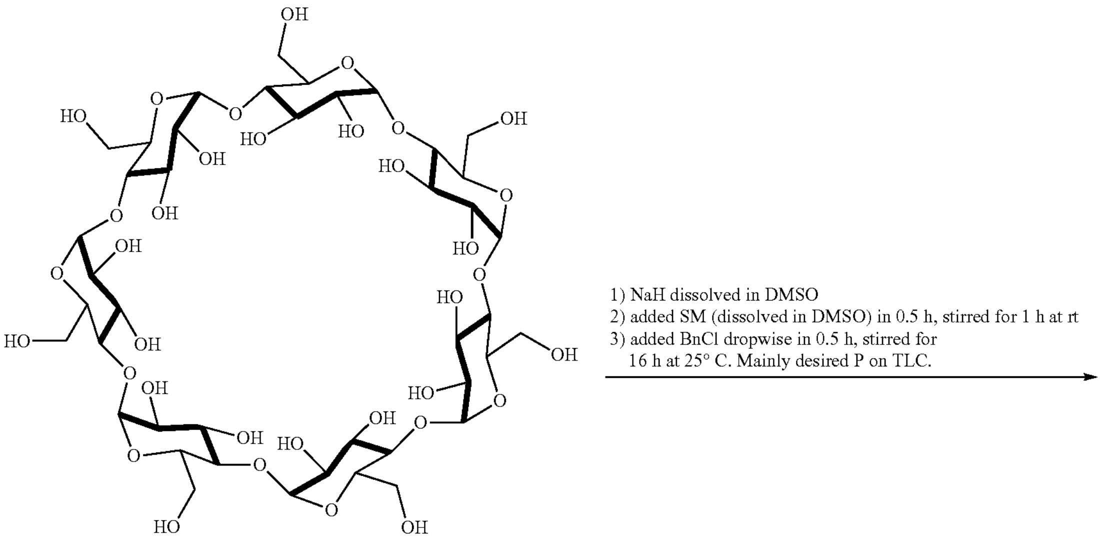

beta-CD

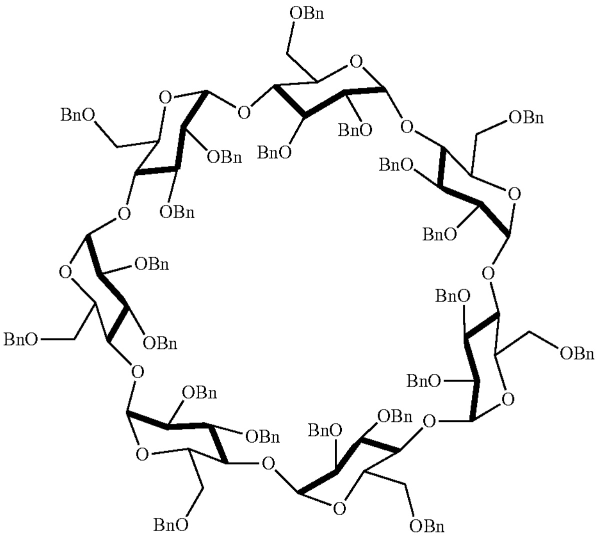

6.1

To a mixture of NaH (44 g, 1111 mmol, 63 equiv, 60% in mineral oil) in DMSO (100 mL) was added (1 S,3R,6S,8R, 11S,13R,16S,18R,21 S,23R,26S,28R,31 S,33R,36R,38R, 40R,42R,44R,46R,48R)-5,10,15,20,25,30,35-heptakis(hydroxymethyl)-2,4,7,9,12,14,17,19,22,24,27,29,32,34-tetradecaoxaoctacyclo[31.2.2.$2^{3,6}$.$2^{8,11}$.$2^{13,16}$$2^{18,21}$.$2^{23,36}$.$2^{28,31}$]nonatetracontane-36,37,38,39,40,41,42,43,44,45,46,47,48,49-tetradecol beta-CD (20 g, 17.64 mmol, 1 equiv) in batches, and stirred for 1 h at room temperature under an atmosphere of nitrogen. To the resulting mixture was added (chloromethyl)benzene (188.2 g, 1481 mmol, 84 equiv) dropwise at room temperature. The resulting mixture was stirred for 16 h at room temperature. Saturated $NH_4Cl$ (aq.) (800 mL) was added, and the resulting mixture was extracted with EtOAc (3×800 mL). The combined organic layers were washed with brine (3×500 mL), dried over anhydrous $Na_2SO_4$, and filtered. The filtrate was concentrated under reduced pressure and the residue was purified by silica gel column chromatography, eluting with 1/1 PE/EtOAc to afford (1R,3R,5R,6R,8R,10R,11R,13R,15R, 16R,18R,20R,21R,23R,25R,26R,28R,30R,31R,33R, 35R, 36S,37R,38S,39R,40S,41R,42S,43R,44S,45R,46S,47R, 48S,49R)-36,37,38,39,40,41,42,43,44,45,46,47,48,49-tetradecakis(benzyloxy)-5,10,15,20,25,30,35-heptakis[(benzyloxy)methyl]-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontane (Compound 6.1) (40 g, 75%) as an oil. MALDI-TOF: $[M+Na]^+$=3050.98.

Step 2:

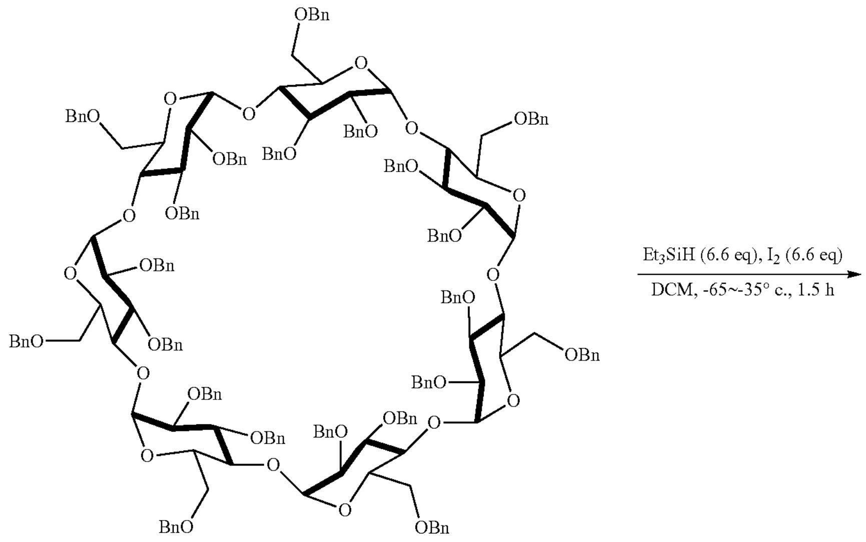

6.1

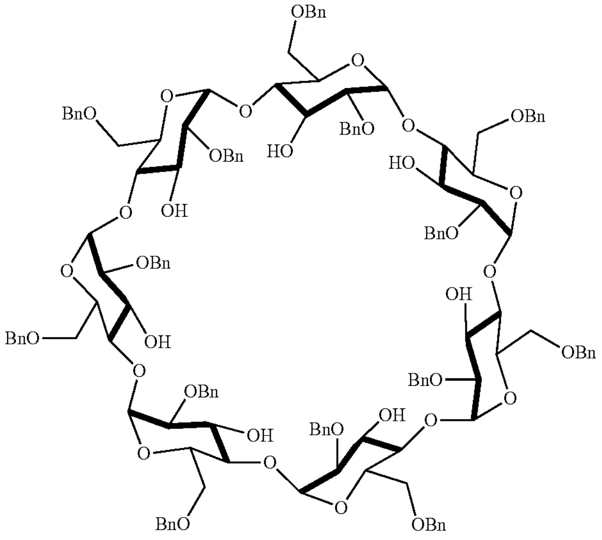

6.2

A solution of (1R,3R,5R,6R,8R,10R,11R,13R,15R,16R, 18R,20R,21R,23R,25R,26R,28R,30R,31R,33R,35R,36S, 37R,38S,39R,40S,41R,42S,43R,44S,45R,46S,47R,48S, 49R)-36,37,38,39,40,41,42,43,44,45,46,47,48,49-tetradecakis(benzyloxy)-5,10,15,20,25,30,35-heptakis [(benzyloxy)methyl]-2,4,7,9,12,14,17,19,22,24,27,29,32, 34-tetradecaoxaoctacyclo[31.2.2.$2^{3,6}$.$2^{8,11}$.$2^{13,16}$.$2^{18,21}$.$2^{23,26}$.$2^{28,31}$]nonatetracontane (Compound 6.1) (10 g, 3.3 mmol, 1 equiv) and $I_2$ (5.6 g, 21.8 mmol, 6.6 equiv) in DCM (100 mL) was stirred for 5 min at RT under a nitrogen atmosphere. To this mixture was added triethylsilane (2.6 g, 21.8 mmol, 6.6 equiv) in portions over 5 min at −65° C. The resulting mixture was stirred for additional 1.5 h between −35° C.~−40° C. The reaction was allowed to cool to RT and 1/1 sat. $Na_2S_2O_3$ (aq.)/sat. $NaHCO_3$ (aq.) was added. The resulting mixture was extracted with DCM (3×500 mL). The combined organic layers were washed with brine (2×300 mL), dried over anhydrous $Na_2SO_4$, filtered and concentrated under reduced pressure. The residue was purified by silica gel column chromatography, eluting with 2/3 PE/EtOAc to afford (1S,3R,5R,6S,8R,10R,11S,13R,15R, 16S,18R,20R,21S,23R,25R,26S,28R,30R,31S,33R,35R, 36S,37R,38S,39R,40S,41R,42S,43R,44S,45R,46S,47R, 48S,49R)-37,39,41,43,45,47,49-heptakis(benzyloxy)-5,10, 15,20,25,30,35-heptakis[(benzyloxy)methyl]-2,4,7,9,12,14, 17,19,22,24,27,29,32,34-tetradecaoxaoctacyclo[31.2.2. $2^{3,6}$.$2^{8,11}$$2^{13,16}$.$2^{18,21}$.$2^{23,26}$.$2^{28,31}$]nonatetracontane-36,38, 40,42,44,46,48-heptol (Compound 6.2) (4.2 g, 52%) as a white solid. QTOF (ES): $[M+Na]^+$=2418.0090.

Step 3:

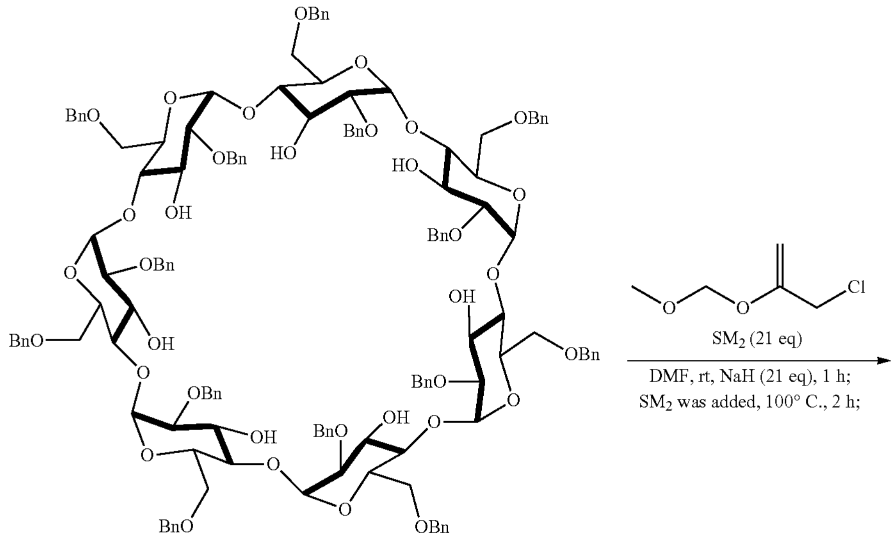

6.2

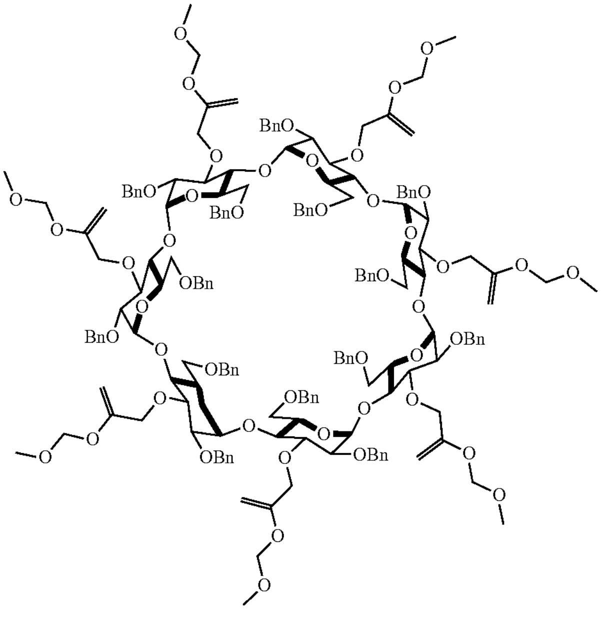

6.3

A solution of (1S,3R,5R,6S,8R,10R,11S,13R,15R,16S,18R,20R,21S,23R,25R,26S,28R,30R,31S,33R,35R,36S,37R,38S,39R,40S,41R,42S,43R,44S,45R,46S,47R,48S,49R)-37,39,41,43,45,47,49-heptakis(benzyloxy)-5,10,15,20,25,30,35-heptakis[(benzyloxy)methyl]-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontane-36,38,40,42,44,46,48-heptol (Compound 6.2) (4.2 g, 1.75 mmol, 1 equiv) and NaH (60%) (1.47 g, 36.83 mmol, 21 equiv) in DMF (45 mL) was stirred for 1 h at RT under a nitrogen atmosphere. To the above mixture was added 3-chloro-2-(methoxymethoxy)prop-1-ene (4.67 g, 34.18 mmol, 21 equiv) and stirred for additional 2 h at 100° C. The reaction was cooled to RT and 150 mL of sat. $NH_4Cl$ was added. The resulting mixture was extracted with EtOAc (2×300 mL). The combined organic layers were washed with brine (2×200 mL), dried over anhydrous $Na_2SO_4$, filtered and concentrated under reduced pressure. The residue was purified by silica gel column chromatography, eluting with 3/2 PE/EA to afford (1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-37,39,41,43,45,47,49-heptakis(benzyloxy)-5,10,15,20,25,30,35-heptakis[(benzyloxy)methyl]-36,38,40,42,44,46,48-heptakis({[2-(methoxymethoxy)prop-2-en-1-yl]oxy})-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontane (Compound 6.3) (3 g, 55%) as a light yellow oil. QTOF (ES): $[M+Na]^+$=3118.3817.

Step 4:

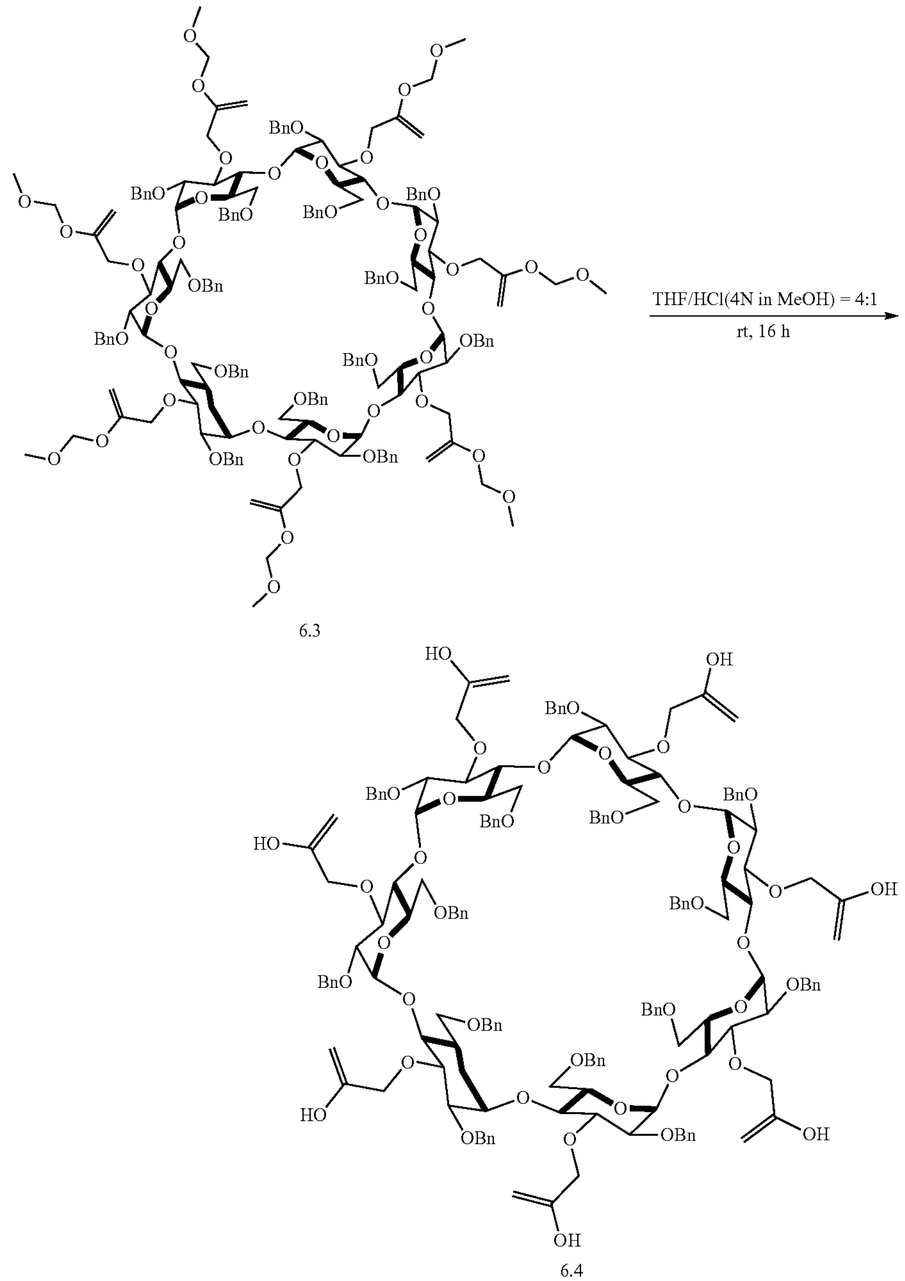

6.3

6.4

A solution of (1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-37,39,41,43,45,47,49-heptakis(benzyloxy)-5,10,15,20,25,30,35-heptakis[(benzyloxy)methyl]-36,38,40,42,44,46,48-heptakis({[2-(methoxymethoxy)prop-2-en-1-yl]oxy})-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontane (Compound 6.3) (3 g, 0.97 mmol, 1 equiv) and 6 mL of HCl (4 N in MeOH) in THF (24 mL) was stirred for 16 h at RT then 150 mL of sat. $NaHCO_3$ (150 mL) was added. The resulting mixture was extracted with EtOAc (3×200 mL). The combined organic layers were washed with brine (2×200 mL), dried over anhydrous $Na_2SO_4$, filtered and concentrated under reduced pressure. The residue was purified by silica gel column chromatography, eluting with 3/2 PE/EtOAc to afford 1-{[(1R,3R,5R,6R,8R,10R,11R,13R,15R,16R,18R,20R,21R,23R,25R,26R,28R,30R,31R,33R,35R, 36S,37R,38S,39R,40S,41R,42S,43R,44S,45R,46S,47R,48S,49R)-37,39,41,43,45,47,49-heptakis(benzyloxy)-5,10,15,20,25,30,35-heptakis[(benzyloxy)methyl]-38,40,42,44,46,48-hexakis(2-oxopropoxy)-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontan-36-yl]oxy}propan-2-one (Compound 6.4) (1.97 g, 73%) as a light yellow oil. QTOF (ES): $[M+Na]^+$=2810.2005.

Step 5:

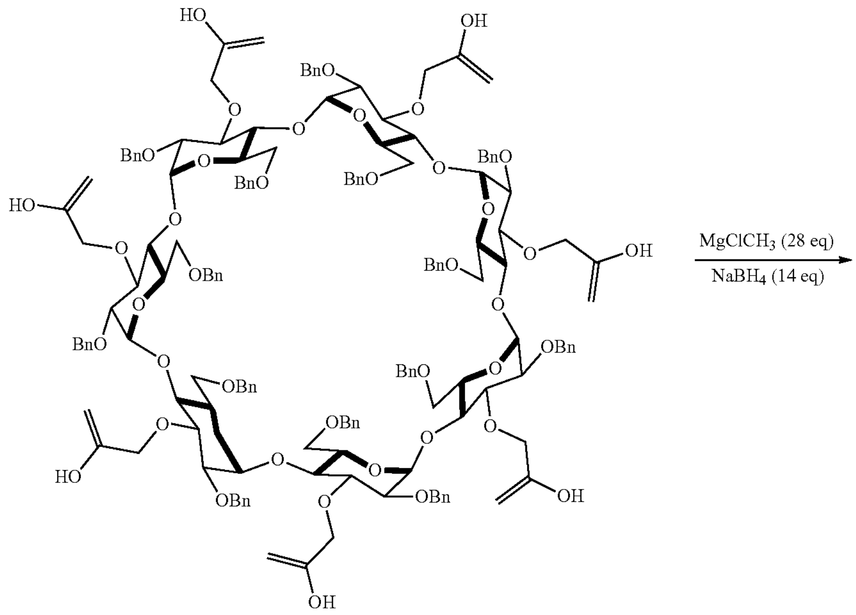

6.4

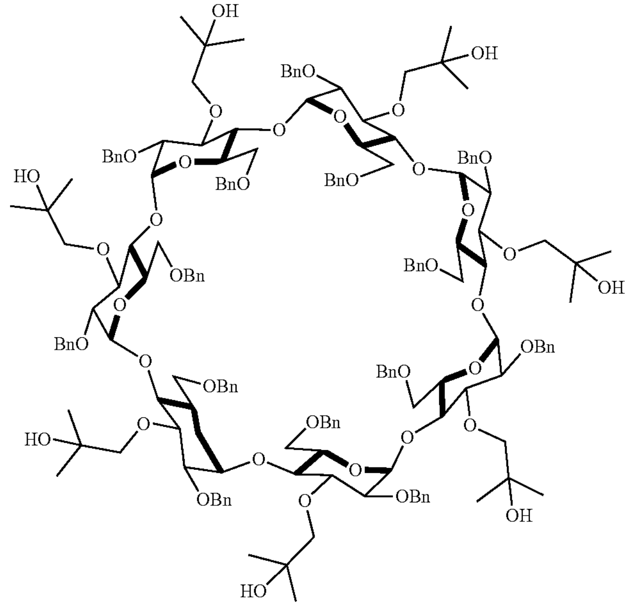

6.5

A solution of 1-{[(1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-37,39,41,43,45,47,49-heptakis(benzyloxy)-5,10,15,20,25,30,35-heptakis[(benzyloxy)methyl]-38,40,42,44,46,48-hexakis(2-oxopropoxy)-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontan-36-yl]oxy}propan-2-one (Compound 6.4) (1.2 g, 0.43 mmol, 1 equiv) and adamantane (1.64 g, 12.04 mmol, 28 equiv) in THF (15 mL) was stirred for 30 min at RT. To this mixture was added bromo(methyl)magnesium (4 mL, 12.04 mmol, 28 equiv). The mixture was stirred for 16 h at 40° C. The reaction was allowed to cool to RT and 150 mL of MeOH (150 mL) was added. The resulting mixture was extracted with EtOAc (3×200 mL). The combined organic layers were washed with brine (2×200 mL), dried over anhydrous $Na_2SO_4$, filtered and concentrated under reduced pressure. The residue was purified by silica gel column chromatography, eluting with 2/3 PE/EtOAc to afford (Compound 6.5) (800 mg, 64%) as a white solid. QTOF (ES): $[M+Na]^+$=2923.4213.

Step 6:

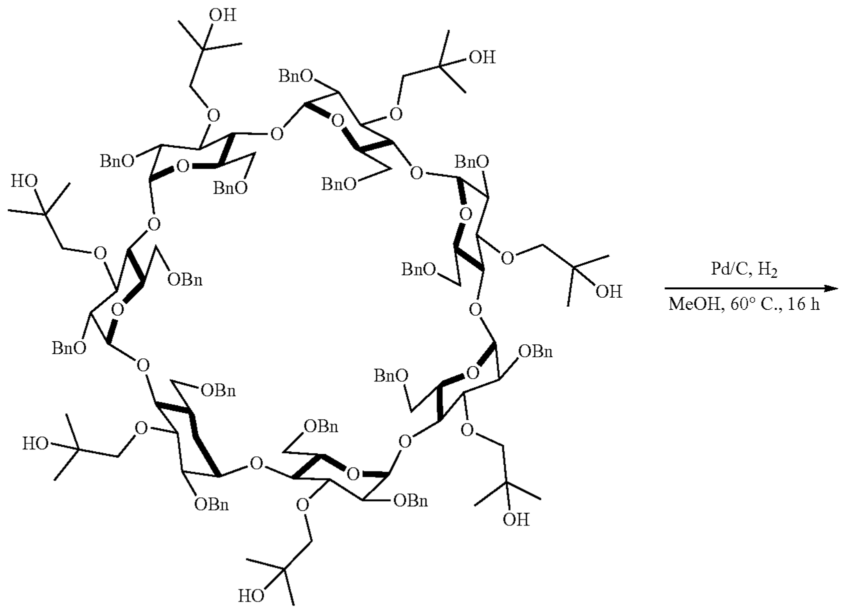

6.5

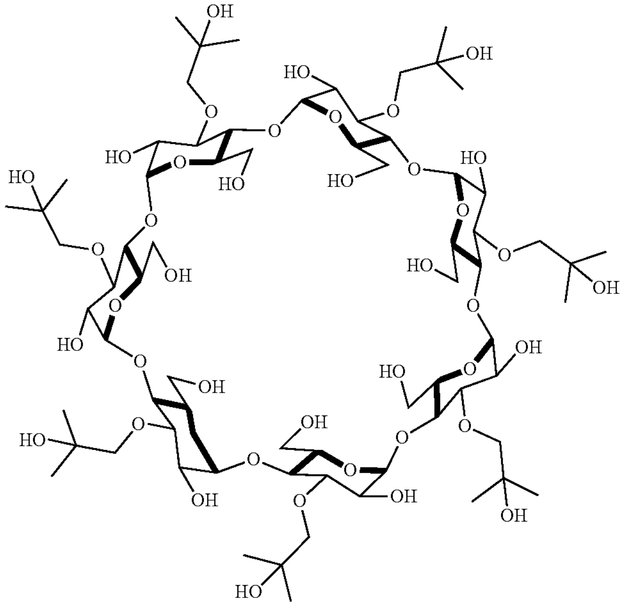

Compound 6

A solution of 1-{[(1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-37,39,41,43,45,47,49-heptakis(benzyloxy)-5,10,15,20,25,30,35-heptakis[(benzyloxy)methyl]-38,40,42,44,46,48-hexakis(2-hydroxy-2-methylpropoxy)-2,4,7,9,12,14,17,19,22,24,27,29,32,34-tetradecaoxaoctacyclo[31.2.2.$2^{3,6}$.$2^{8,11}$.$2^{13,16}$.$2^{18,21}$.$2^{23,26}$.$2^{28,31}$]nonatetracontan-36-yl]oxy}-2-methylpropan-2-ol (Compound 6.5) (470 mg, 0.16 mmol, 1 equiv) and 10% Pd/C (22 mg) in MeOH (8 mL) was stirred for 16 h at 60° C. under a hydrogen atmosphere. The resulting mixture was filtered, and the filter cake was washed with MeOH (3×100 mL). The filtrate was concentrated under reduced pressure and the residue was dissolved in MeOH (4 mL) and filtered with Corp Sep-Pak C18 Plus Short Cartridge (ID: E33062). The filtrate was concentrated under reduced pressure to afford (1R,3R,5R,6R,8R,10R,11R,13R,15R,16R,18R,20R,21R,23R,25R,26R,28R,30R,31R,33R,35R,36R,37R,38R,39R,40R,41R,42R,43R,44R,45R,46R,47R,48R,49R)-36,38,40,42,44,46,48-heptakis(2-hydroxy-2-methylpropoxy)-5,10,15,20,25,30,35-heptakis(hydroxymethyl)-2,4,7,9,12,14,17,19,22,24,27,29,32,34-tetradecaoxaoctacyclo[31.2.2.$2^{3,6}$$2^{8,11}$.$2^{13,16}$.$2^{18,21}$.$2^{23,26}$.$2^{28,31}$]nonatetracontane-37,39,41,43,45,47,49-heptol (Compound 6) (243 mg, 91%) as a white solid. LCMS (ES): $[M+NH_4]^+$=1657.85.

$^1$H NMR (300 MHz, DMSO-$d_6$) δ 5.03 (dd, J=24.4, 4.8 Hz, 14H), 4.78 (s, 7H), 4.58 (s, 7H), 3.80 (d, J=12.5 Hz, 7H), 3.61 (dt, J=20.0, 7.9 Hz, 42H), 3.35 (s, 7H), 1.07 (s, 42H).

$^{13}C$ NMR (101 MHz, DMSO-$d_6$) δ 100.54, 82.55, 81.47, 78.36, 73.24, 72.65, 70.12, 60.59, 27.05, 26.64.
Preparation of Compound 7 (1S,3R,5R,6R,8R,10R,11S,13R,15R,16S,18R,20R,21S,23R,25R,26S,28R,30R,31S,33R,35R,36S,37R,38S,39R,40S,41R,42S,43R,44S,45R,46S,47R,48R,49R)-37,39,41,43,45,47,48-heptakis(2-hydroxy-2-methylpropoxy)-5,10,15,20,25,30,35-heptakis(hydroxymethyl)-2,4,7,9,12,14,17,19,22,24,27,29,32,34-tetradecaoxaoctacyclo[31.2.2.2$^{3,6}$.2$^{8,11}$.2$^{13,16}$.2$^{18,21}$.2$^{23,26}$.2$^{28,31}$]nonatetracontane-36,38,40,42,44,46,49-heptol
Compound 7
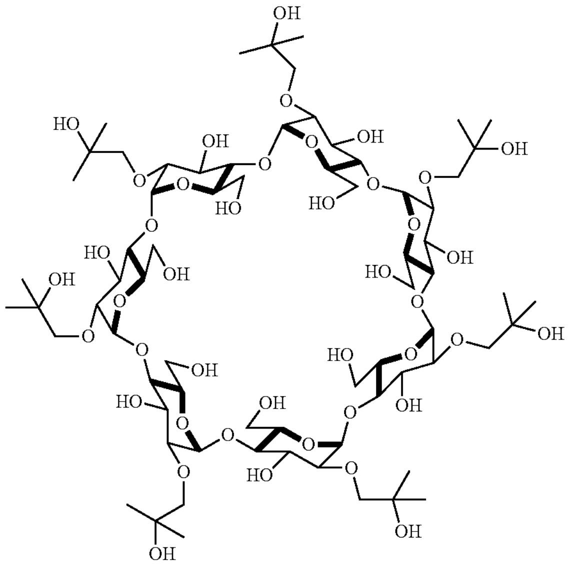
Step 1:
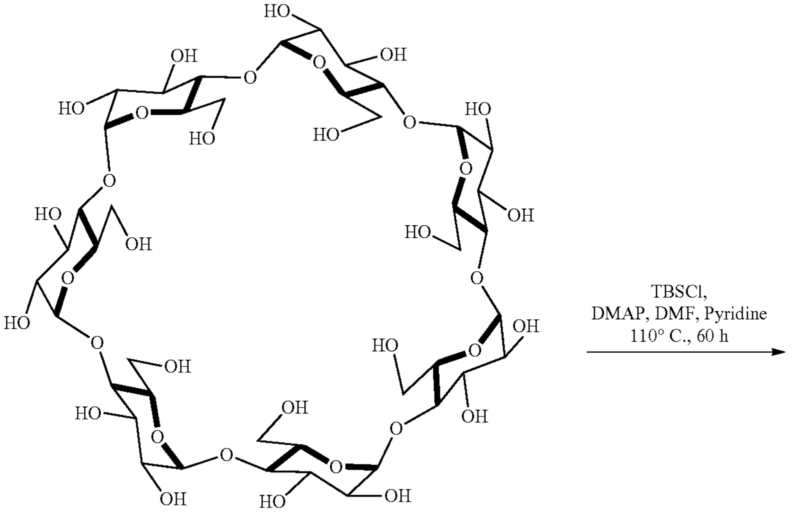
beta-CD -continued

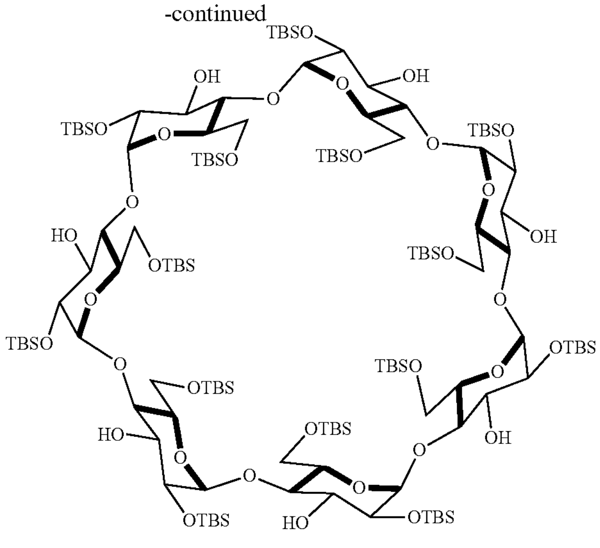

7.1

To a stirred solution of (1S,3R,5R,6S,8R,10R,11S,13R,15R,16S,18R,20R,21S,23R,25R,26S,28R,30R,31S,33R,35R,36R,37R,38R,39R,40R,41R,42R,43R,44R,45R,46R,47R,48R,49R)-5,10,15,20,25,30,35-heptakis (hydroxymethyl)-2,4,7,9,12,14,17,19,22,24,27,29,32,34-tetradecaoxaoctacyclo[31.2.2.$2^{3,6}2^{8,11}.2^{13,16}.2^{18,21}.2^{23,26}.2^{28,31}$]nonatetracontane-36,37,38,39,40,41,42,43,44,45,46,47,48,49-tetradecol beta-CD (20 g, 17.6 mmol, 1 equiv) and DMAP (107 mg, 0.88 mmol, 0.05 equiv) in DMF (200 mL) was added TBSCl (112 g, 741 mmol, 42 equiv) in pyridine (120 mL). The mixture was stirred for 60 h at 110° C. and upon cooling to RT was concentrated under reduced pressure. The residue was dissolved in DCM (500 mL), washed with $KHSO_4$ (0.5 M) (3×150 mL), dried over anhydrous $Na_2SO_4$ and filtered, and concentrated under reduced pressure. The residue was purified by silica gel column chromatography, eluting with 0 to 10% EtOAc in PE to afford (1S,3R,5R,6S,8R,10R,11S,13R,15R,16S,18R,20R,21S,23R,25R,26S,28R,30R,31S,33R,35R,36S,37R,38S,39R,40S,41R,42S,43R,44S,45R,46S,47R,48S,49R)-37,39,41,43,45,47,49-heptakis[(tert-butyldimethylsilyl)oxy]-5,10,15,20,25,30,35-heptakis({[(tert-butyldimethylsilyl)oxy]methyl})-2,4,7,9,12,14,17,19,22,24,27,29,32,34-tetradecaoxaoctacyclo[31.2.2.$2^{3,6}2^{8,11}.2^{13,16}.2^{18,21}.2^{23,26}.2^{28,31}$]nonatetracontane-36,38,40,42,44,46,48-heptol (Compound 7.1) (33 g, 72%) as a white solid.

$^1H$ NMR (400 MHz, Chloroform-d) δ 4.81 (d, J=3.3 Hz, 7H), 4.41 (s, 7H), 3.95-3.78 (m, 14H), 3.65-3.40 (m, 28H), 0.86 (d, J=18.3 Hz, 126H), 0.13 (d, J=4.2 Hz, 42H).

Step 2:

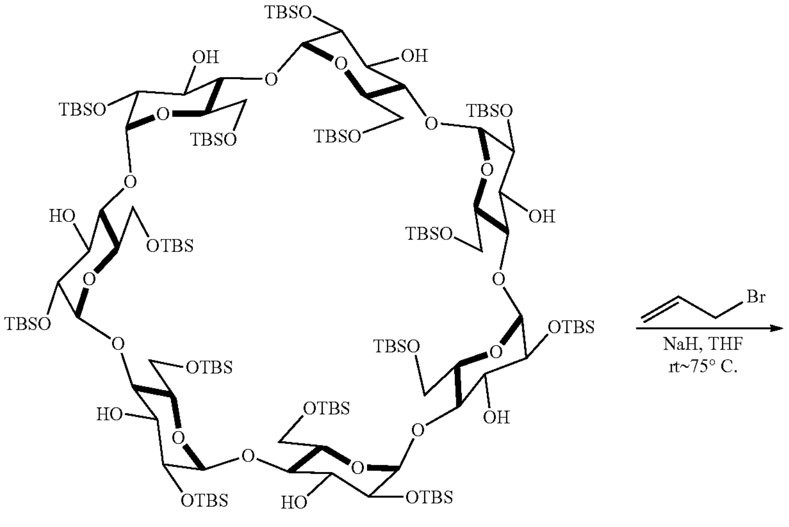

7.1

-continued

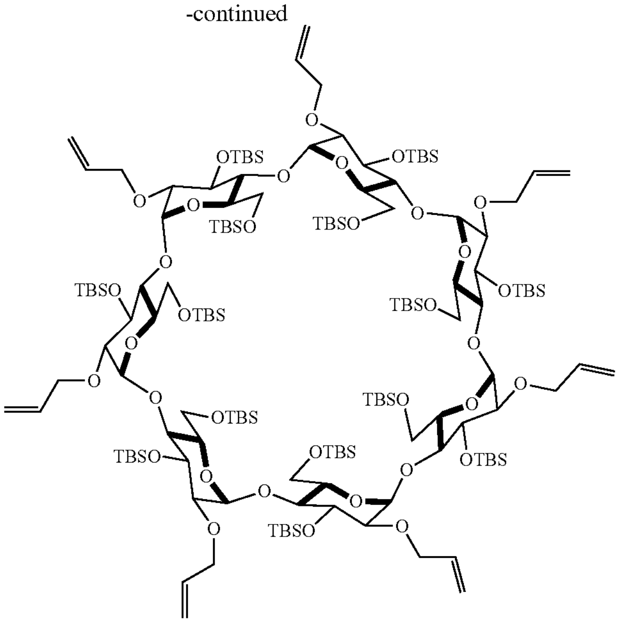

7.2

To a solution of (1S,3R,5R,6S,8R,10R,11S,13R,15R,16S,18R,20R,21S,23R,25R,26S,28R,30R,31S,33R,35R,36S,37R,38S,39R,40S,41R,42S,43R,44S,45R,46S,47R,48S,49R)-37,39,41,43,45,47,49-heptakis[(tert-butyldimethylsilyl)oxy]-5,10,15,20,25,30,35-heptakis({[(tert-butyldimethylsilyl)oxy]methyl})-2,4,7,9,12,14,17,19,22,24,27,29,32,34-tetradecaoxaoctacyclo[31.2.2.2$^{3,6}$2$^{8,11}$.2$^{13,16}$.2$^{18,21}$.2$^{23,26}$.2$^{28,31}$]nonatetracontane-36,38,40,42,44,46,48-heptol (Compound 7.1) (20 g, 7.31 mmol, 1 equiv) in 250 mL of THF was added NaH (60% in mineral oil, 6.14 g, 153.57 mmol, 21 equiv) portion wise and the mixture was allowed to stir for 1 h at room temperature. Allyl bromide (18.58 g, 153.57 mmol, 21 equiv) was added dropwise over 30 min at RT and the mixture was heated to 70° C. for 16 h. The reaction mixture was cooled to room temperature and saturated $NH_4Cl$ (aq., 150 mL) was added. The mixture was extracted with EtOAc (3×500 mL) and the combined organic layers were washed with saturated aqueous sodium chloride solution (3×500 mL), dried over $Na_2SO_4$, filtered and concentrated under reduced pressure. The residue was re-crystallized from 12/1 MeOH/DCM (700 mL) and was then purified by silica gel column chromatography, eluting with 10/1 PE/EtOAc to afford tert-butyl ({[(1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-36,38,40,42,44,46,48-heptakis[(tert-butyldimethylsilyl)oxy]-10,15,20,25,30,35-hexakis({[(tert-butyldimethylsilyl)oxy]methyl})-37,39,41,43,45,47,49-heptakis(prop-2-en-1-yloxy)-2,4,7,9,12,14,17,19,22,24,27,29,32,34-tetradecaoxaoctacyclo[31.2.2.2$^{3,6}$2$^{8,11}$2$^{13,16}$.2$^{18,21}$.2$^{23,26}$.2$^{28,31}$]nonatetracontan-5-yl]methoxy})dimethylsilane] (Compound 7.2) (12.4 g, 4.11 mmol, 56% yield) as a white solid.

Step 3:

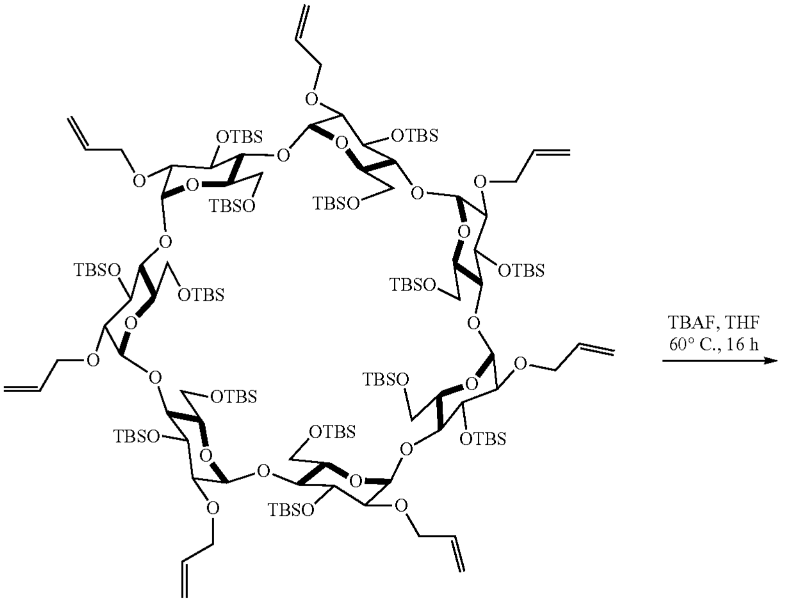

7.2

-continued

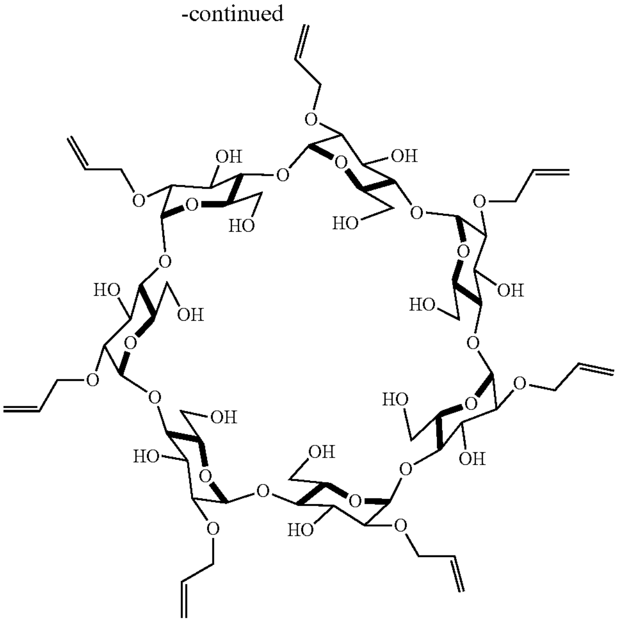

7.3

To a solution of tert-butyl({[(1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-36,38,40,42,44,46,48-heptakis[(tert-butyldimethylsilyl)oxy]-10,15,20,25,30,35-hexakis({[(tert-butyldimethylsilyl)oxy]methyl})-37,39,41,43,45,47,49-heptakis(prop-2-en-1-yloxy)-2,4,7,9,12,14,17,19,22,24,27,29,32,34-tetradecaoxaoctacyclo[31.2.2.$2^{3,6}2^{8,11}.2^{13,16}.2^{18,21}.2^{23,26}.2^{28,31}$]nonatetracontan-5-yl]methoxy})dimethylsilane (Compound 7.2) (12.4 g, 4.11 mmol, 1 equiv) in 60 mL of THF was added tetrabutylammonium fluoride (1 M in THF, 115 mL, 115 mmol, 28 equiv) and stirred for 16 h at 60° C. The mixture was allowed to cool down to RT and concentrated under reduced pressure. The mixture was extracted with EtOAc (3×100 mL) and the combined organic layers were washed with water (5×50 mL), dried over anhydrous $Na_2SO_4$, filtered and concentrated under reduced pressure. The residue was purified by silica gel column chromatography, eluting with 2/1 $CH_2Cl_2$/MeOH to afford (1S,3R,5R,6S,8R,10R,11S,13R,15R,16S,18R,20R,21S,23R,25R,26S,28R,30R,31S,33R,35R,36S,37R,38S,39R,40S,41R,42S,43R,44S,45R,46S,47R,48S,49R)-5,10,15,20,25,30,35-heptakis(hydroxymethyl)-37,39,41,43,45,47,49-heptakis(prop-2-en-1-yloxy)-2,4,7,9,12,14,17,19,22,24,27,29,32,34-tetradecaoxaoctacyclo[31.2.2.$2^{3,6}2^{8,11}.2^{13,16}.2^{18,21}.2^{23,26}.2^{28,31}$]nonatetracontane-36,38,40,42,44,46,48-heptol (Compound 7.3) (3 g, 52%) as a light-yellow solid. QTOF (ES): $[M-H^+]^-$=1413.85.

Step 4:

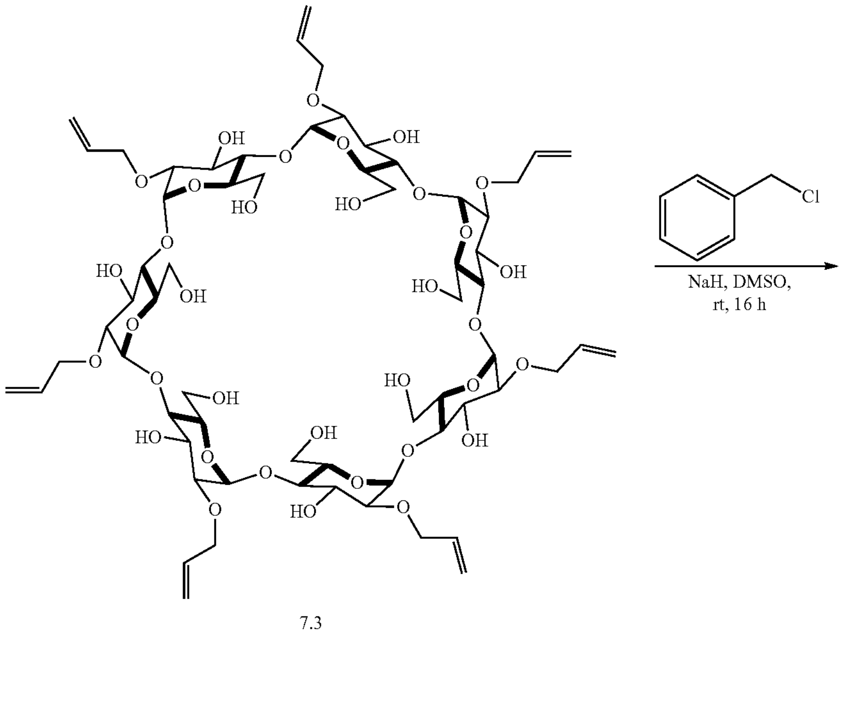

7.3

-continued

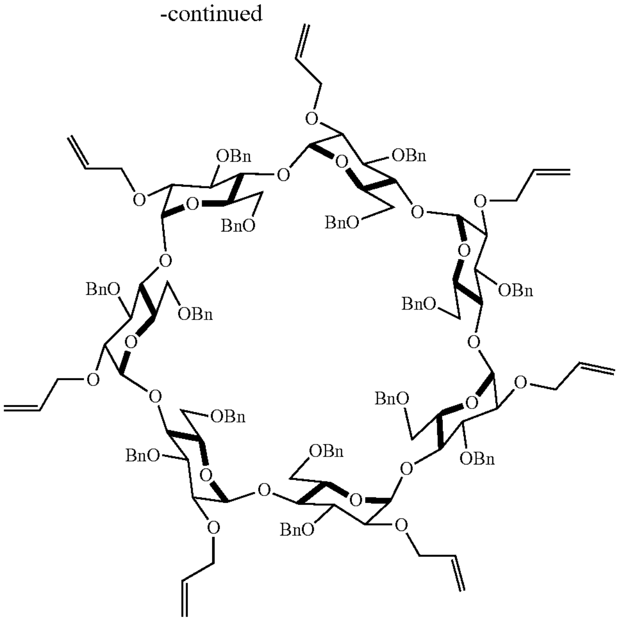

7.4

To a solution of (1S,3R,5R,6S,8R,10R,11S,13R,15R,16S,18R,20R,21S,23R,25R,26S,28R,30R,31S,33R,35R,36S,37R,38S,39R,40S,41R,42S,43R,44S,45R,46S,47R,48S,49R)-5,10,15,20,25,30,35-heptakis(hydroxymethyl)-37,39,41,43,45,47,49-heptakis(prop-2-en-1-yloxy)-2,4,7,9,12,14,17,19,22,24,27,29,32,34-tetradecaoxaoctacyclo[31.2.2.$2^{3,6}2^{8,11}.2^{13,16}.2^{18,21}.2^{23,26}.2^{28,31}$]nonatetracontane-36,38,40,42,44,46,48-heptol (Compound 7.3) (3 g, 2.12 mmol, 1 equiv) in 20 mL of DMSO was added 60% NaH (3.56 g, 89.0 mmol, 42 equiv) in portions over 15 min at 0° C. The mixture was stirred for 1 h at RT and then benzyl chloride (11.27 g, 89.0 mmol, 42 equiv) was added dropwise over 10 min at RT. The mixture was stirred for 16 h at RT and then 200 mL of sat. $NH_4Cl$ (aq.) was added. The mixture was extracted with EtOAc (3x100 mL) and the combined organic layers were washed with brine (3x30 mL), dried over anhydrous $Na_2SO_4$, filtered and concentrated under reduced pressure. The crude product was re-crystallized from MeOH to afford (1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-36,38,40,42,44,46,48-heptakis(benzyloxy)-5,10,15,20,25,30,35-heptakis[(benzyloxy)methyl]-37,39,41,43,45,47,49-heptakis(prop-2-en-1-yloxy)-2,4,7,9,12,14,17,19,22,24,27,29,32,34-tetradecaoxaoctacyclo[31.2.2.$2^{3,6}$.$2^{8,11}.2^{13,16}.2^{18,21}.2^{23,26}.2^{28,31}$]nonatetracontane (Compound 7.4) (2.4 g, 42%) as a light-yellow solid.

Step 5:

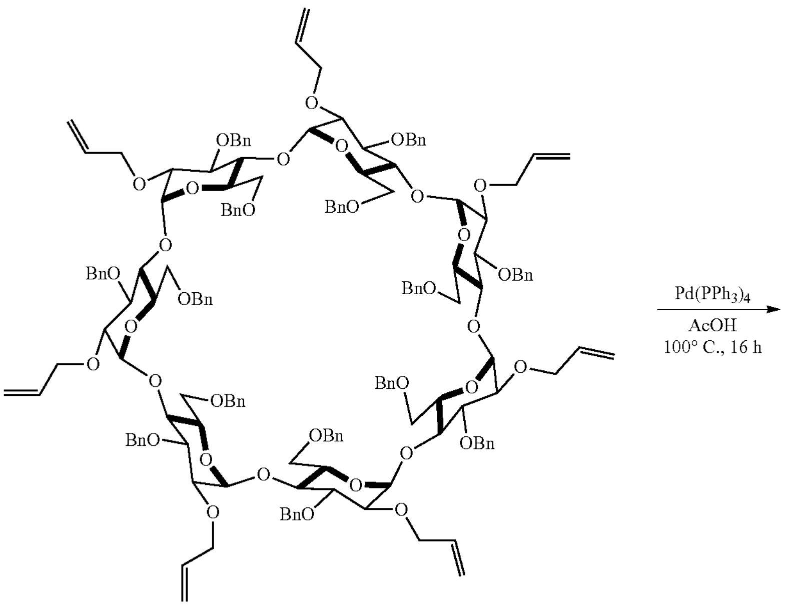

7.4

-continued

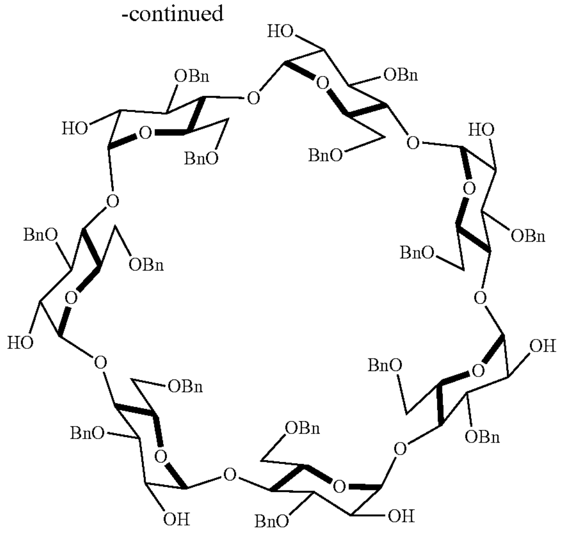

7.5

A solution of (1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-36,38,40,42,44,46,48-heptakis(benzyloxy)-5,10,15,20,25,30,35-heptakis[(benzyloxy)methyl]-37,39,41,43,45,47,49-heptakis(prop-2-en-1-yloxy)-2,4,7,9,12,14,17,19,22,24,27,29,32,34-tetradecaoxaoctacyclo[31.2.2.2$^{3,6}$.2$^{8,11}$.2$^{13,16}$.2$^{18,21}$.2$^{23,26}$.2$^{28,31}$]nonatetracontane (Compound 7.4) (2.4 g, 0.90 mmol, 1 equiv) and tetrakis(triphenylphosphine) palladium(0) (3.63 g, 3.14 mmol, 3.5 equiv) in 30 mL of AcOH was stirred for 16 h at 100° C. under a nitrogen atmosphere. The mixture was allowed to cool down to RT and concentrated under reduced pressure. The residue was dissolved in EtOAc (30 mL) and the organic layer was washed with sat. $NaHCO_3$ (aq.) (3×10 mL), dried over anhydrous $Na_2SO_4$, filtered, and concentrated under reduced pressure. The residue was purified by silica gel column chromatography, eluting with 1/1 PE/EtOAc and then purified by prep-TLC 4/3 PE/EA to afford (1R,3R,5R,6R,8R,10R,11R,13R,15R,16R,18R,20R,21R,23R,25R,26R,28R,30R,31R,33R,35R,36R,37R,38R,39R,40R,41R,42R,43R,44R,45R,46R,47R,48R,49R)-36,38,40,42,44,46,48-heptakis(benzyloxy)-5,10,15,20,25,30,35-heptakis[(benzyloxy)methyl]-2,4,7,9,12,14,17,19,22,24,27,29,32,34-tetradecaoxaoctacyclo[31.2.2.2$^{3,6}$.2$^{8,11}$.2$^{13,16}$.2$^{18,21}$.2$^{23,26}$.2$^{28,31}$]nonatetracontane-37,39,41,43,45,47,49-heptol (Compound 7.5) (1.05 g, 49%) as a light yellow oil.

Step 6:

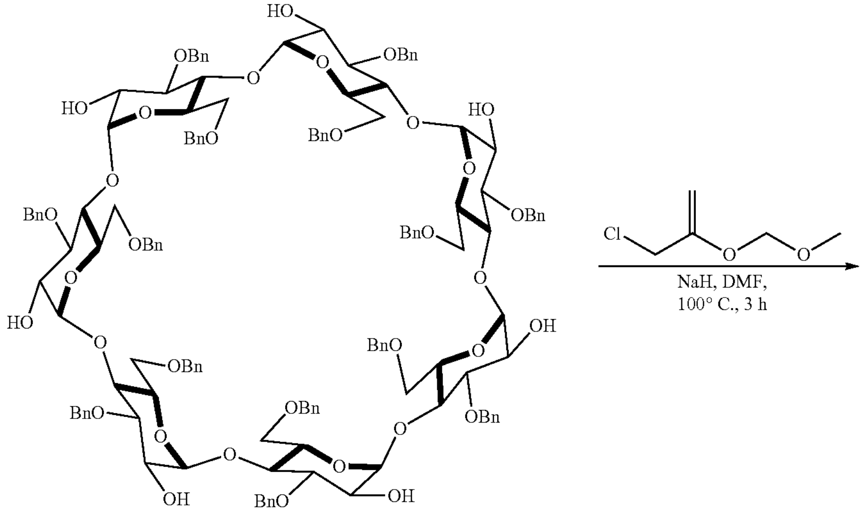

7.5

-continued

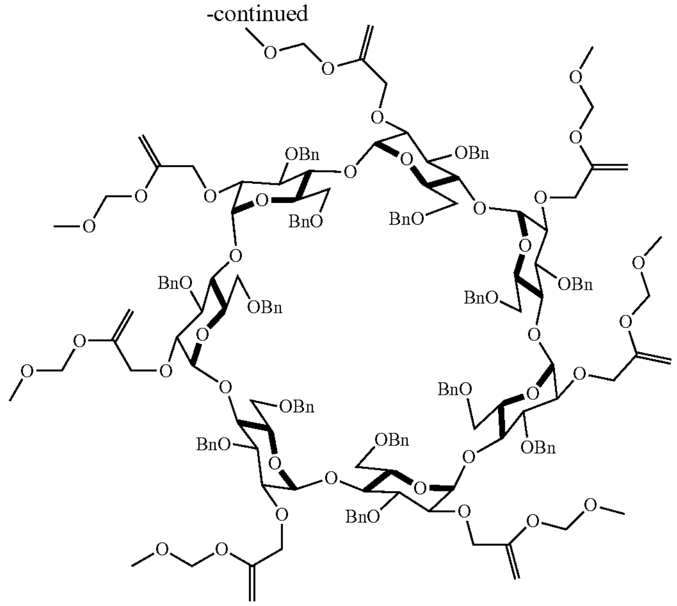

7.6

To a mixture of (1R,3R,5R,6R,8R,10R,1R,13R,15R,16R, 18R,20R,21R,23R,25R,26R,28R,30R,31R,33R,35R,36R, 37R,38R,39R,40R,41R,42R,43R,44R,45R,46R,47R,48R, 49R)-36,38,40,42,44,46,48-heptakis(benzyloxy)-5,10,15, 20,25,30,35-heptakis[(benzyloxy)methyl]-2,4,7,9,12,14,17, 19,22,24,27,29,32,34-tetradecaoxaoctacyclo[31.2.2.2$^{3,6}$.2$^{8,11}$.2$^{13,16}$.2$^{18,21}$.2$^{23,26}$.2$^{28,31}$]nonatetracontane-37,39,41, 43,45,47,49-heptol (Compound 7.5) (1.05 g, 0.44 mmol, 1 equiv) in DMF (15 mL) was added NaH (60% purity in mineral oil, 370 mg, 9.20 mmol, 21 equiv) in batches and stirred for 1 h at RT under nitrogen atmosphere. To the mixture was added 3-chloro-2-(methoxymethoxy) prop-1-ene (1.68 g, 12.26 mmol, 28 equiv) and the mixture was warmed up to 100° C. and stirred for 3 h. The mixture was allowed to cool down to RT and 15 mL of sat. $NH_4Cl$ (aq.) was added. The mixture was extracted with EtOAc (3×50 mL) and the combined organic layers were washed with brine (1×30 mL), dried over anhydrous $Na_2SO_4$, filtered, and concentrated under reduced pressure. The residue was purified by Prep-TLC (2/1 PE/EtOAc) to afford (1R,3R,5R,6R, 8R,10R,11R,13R,15R,16R,18R,20R,21R,23R,25R,26R, 28R,30R,31R,33R,35R,36S,37R,38S,39R,40S,41R,42S, 43R,44S,45R,46S,47R,48S,49R)-36,38,40,42,44,46,49-heptakis(benzyloxy)-5,10,15,20,25,30,35-heptakis [(benzyloxy)methyl]-37,39,41,43,45,47,48-heptakis({[2-(methoxymethoxy)prop-2-en-1-yl]oxy})-2,4,7,9,12,14,17, 19,22,24,27,29,32,34-tetradecaoxaoctacyclo[31.2.2.2$^{3,6}$.2$^{8,11}$.2$^{13,16}$.2$^{18,21}$.2$^{23,26}$.2$^{28,31}$]nonatetracontane (Compound 7.6) (750 mg, 55%) as a white solid. Q-TOF (ES): $[M+Na^+]^+$=3118.4113.

Step 7:

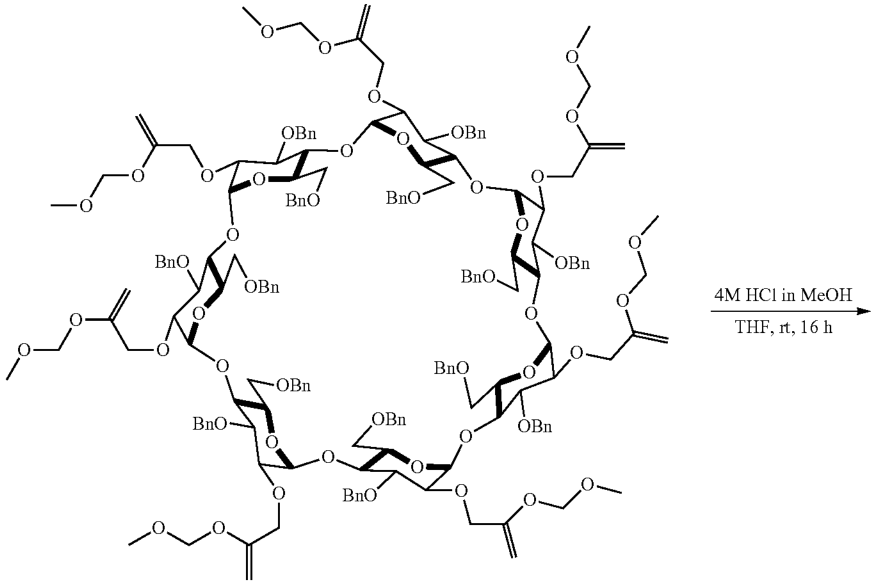

7.6

-continued

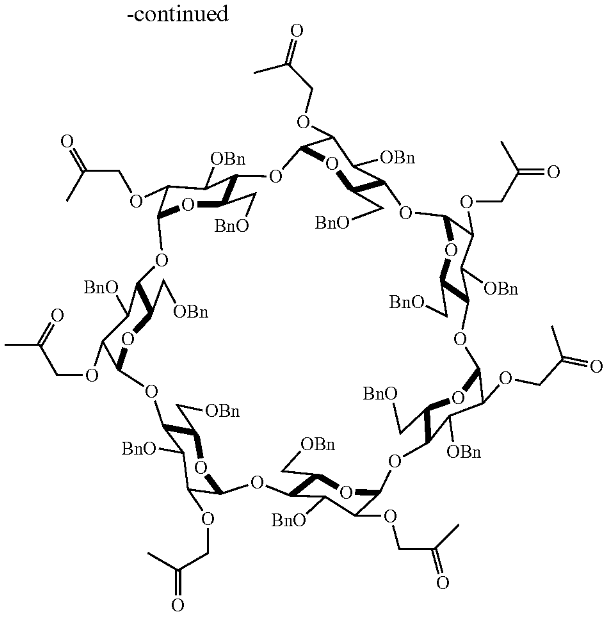

7.7

To a solution of (1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-36,38,40,42,44,46,49-heptakis(benzyloxy)-5,10,15,20,25,30,35-heptakis[(benzyloxy)methyl]-37,39,41,43,45,47,48-heptakis({[2-(methoxymethoxy)prop-2-en-1-yl]oxy})-2,4,7,9,12,14,17,19,22,24,27,29,32,34-tetradecaoxaoctacyclo[31.2.2.2$^{3,6}$2$^{8,11}$.2$^{13,16}$.2$^{18,21}$.2$^{23,26}$.2$^{28,31}$]nonatetracontane (Compound 7.6) (750 mg, 0.24 mmol, 1 equiv) in THF (8 mL) was added 4 N HCl in MeOH (2 mL). The mixture was stirred for 16 h at RT and then 50 mL of sat. $NaHCO_3$ (aq.) was added. The mixture was extracted with EtOAc (3×30 mL) and the combined organic layers were washed with brine (3×20 mL), dried over anhydrous $Na_2SO_4$, filtered and concentrated under reduced pressure. The residue was purified by prep-TLC (3/2 PE/EtOAc) to afford 1-{[(1R,3R,5R,6R,8R,10R,11R,13R,15R,16R,18R,20R,21R,23R,25R,26R,28R,30R,31R,33R,35R, 36S,37R,38S,39R,40S,41R,42S,43R,44S,45R,46S,47R,48S,49R)-37,38,40,42,44,46,48-heptakis(benzyloxy)-5,10,15,20,25,30,35-heptakis[(benzyloxy)methyl]-39,41,43,45,47,49-hexakis(2-oxopropoxy)-2,4,7,9,12,14,17,19,22,24,27,29,32,34-tetradecaoxaoctacyclo[31.2.2.2$^{3,6}$2$^{8,11}$2$^{13,16}$.2$^{18,21}$.2$^{23,26}$.2$^{28,31}$]nonatetracontan-36-yl]oxy}propan-2-one (Compound 7.7) (506 mg, 75%) as a white solid. Q-TOF (ES): [M+Na$^+$]=2811.196.

Step 8:

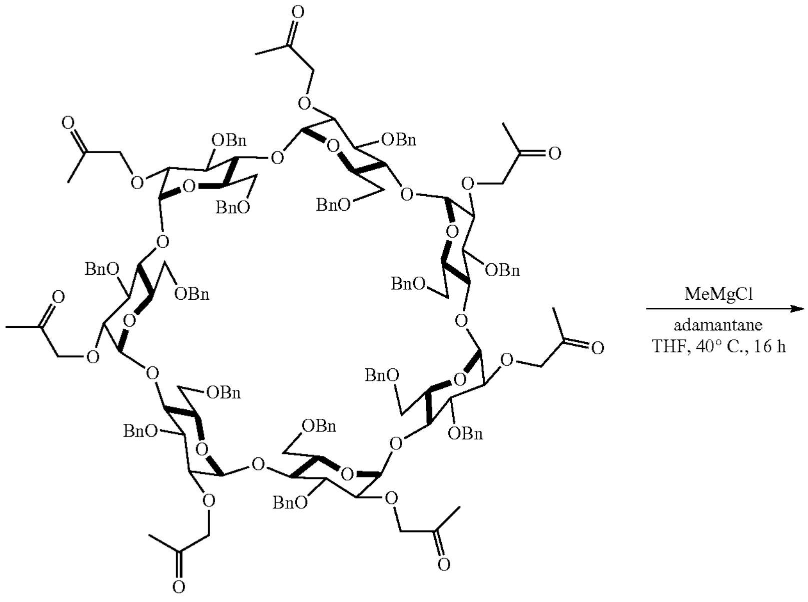

7.7

-continued

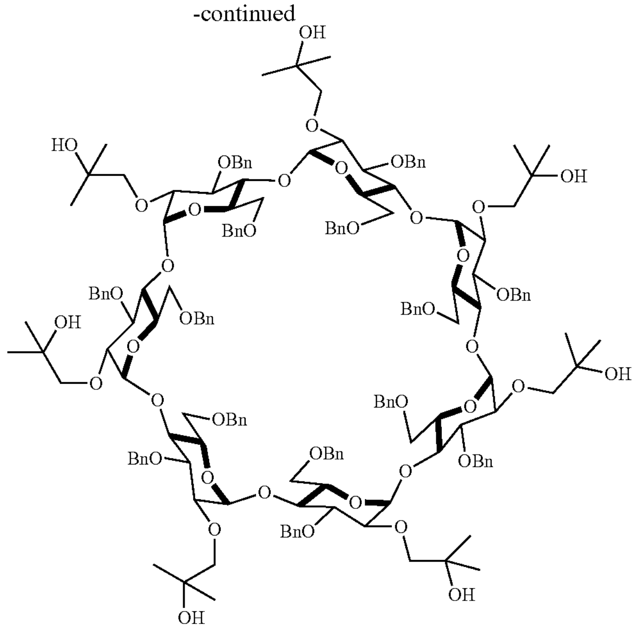

7.8

A solution of {[(1R,3R,5R,6R,8R,10R,11R,13R,15R,16R,18R,20R,21R,23R,25R,26R,28R,30R,31R,33R,35R,36S,37R,38S,39R,40S,41R,42S,43R,44S,45R,46S,47R,48S,49R)-37,38,40,42,44,46,48-heptakis(benzyloxy)-5,10,15,20,25,30,35-heptakis[(benzyloxy)methyl]-39,41,43,45,47,49-hexakis(2-oxopropoxy)-2,4,7,9,12,14,17,19,22,24,27,29,32,34-tetradecaoxaoctacyclo[31.2.2.2$^{3,6}$2$^{8,11}$.2$^{13,16}$.2$^{18,21}$.2$^{23,26}$.2$^{28,31}$]nonatetracontan-36-yl]oxy}propan-2-one (Compound 7.7) (506 mg, 0.18 mmol, 1 equiv) and adamantane (692 mg, 5.08 mmol, 28 equiv) in THF (8 mL) was stirred for 30 min at RT. Then 3 M $CH_3MgCl$ (1.27 mL, 3.80 mmol, 21 equiv) was added at RT and stirred 16 h at RT. Saturated aqueous $NH_4Cl$ (50 mL) was added at RT and the resulting mixture was extracted with EtOAc (3x30 mL). The combined organic layers were washed with brine (3x30 mL), dried over anhydrous $Na_2SO_4$, filtered and concentrated under reduced pressure. The residue was purified by prep-TLC (12/1 DCM/MeOH) to afford 1-{[(1R,3R,5R,6R,8R,10R,11R,13R,15R,16R,18R,20R,21R,23R,25R,26R,28R,30R,31R,33R,35R, 36S,37R,38S,39R,40S,41R,42S,43R,44S,45R,46S,47R,48S,49R)-37,38,40,42,44,46,48-heptakis(benzyloxy)-5,10,15,20,25,30,35-heptakis[(benzyloxy)methyl]-39,41,43,45,47,49-hexakis(2-hydroxy-2-methylpropoxy)-2,4,7,9,12,14,17,19,22,24,27,29,32,34-tetradecaoxaoctacyclo[31.2.2.2$^{3,6}$ 2$^{8,11}$2$^{13,16}$.2$^{18,21}$.2$^{23,26}$.2$^{28,31}$]nonatetracontan-36-yl]oxy}-2-methylpropan-2-ol (Compound 7.8) (346 mg, 66%) as a white solid.

Step 9:

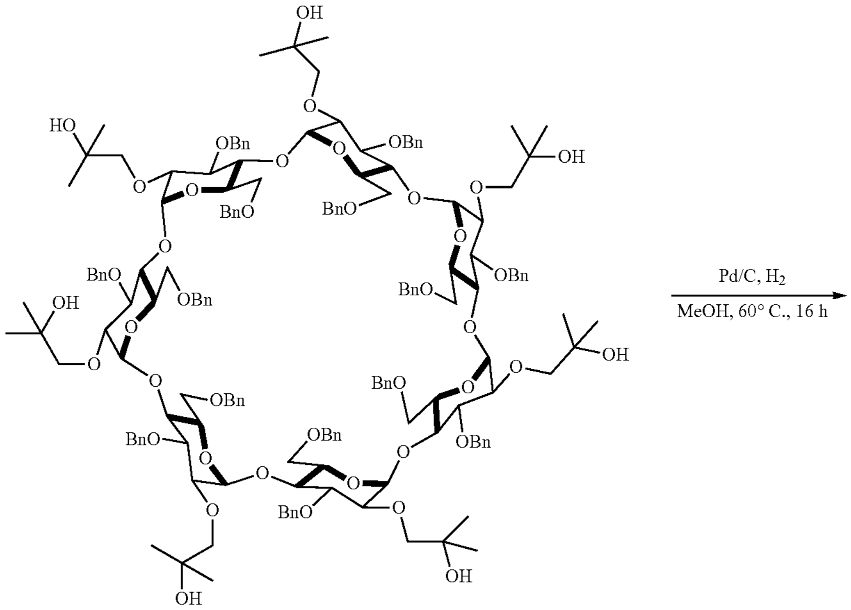

7.8

-continued

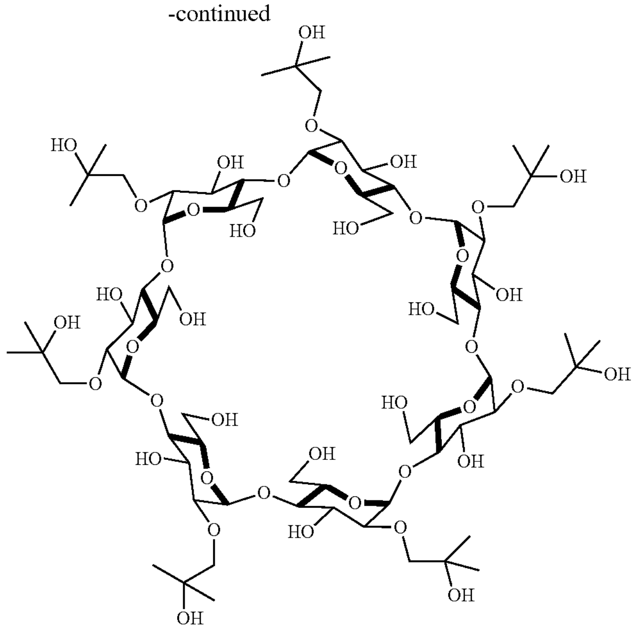

Compound 7

A mixture of 1-{[(1R,3R,5R,6R,8R,10R,11R,13R,15R, 16R,18R,20R,21R,23R,25R,26R,28R,30R,31R,33R,35R, 36S,37R,38S,39R,40S,41R,42S,43R,44S,45R,46S,47R, 48S,49R)-37,38,40,42,44,46,48-heptakis(benzyloxy)-5,10, 15,20,25,30,35-heptakis[(benzyloxy)methyl]-39,41,43,45, 47,49-hexakis(2-hydroxy-2-methylpropoxy)-2,4,7,9,12,14, 17,19,22,24,27,29,32,34-tetradecaoxaoctacyclo[31.2.2. $2^{3,6}2^{8,11}.2^{13,16}.2^{18,21}.2^{23,26}.2^{28,31}$]nonatetracontan-36-yl] oxy}-2-methylpropan-2-ol (Compound 7.8) (346 mg, 0.12 mmol, 1 equiv) and 10% Pd/C (346 mg) in MeOH (20 mL) was stirred for 16 h at 60° C. under hydrogen atmosphere. The resulting mixture was filtered through celite and the filter cake was washed with MeOH (3×50 mL). The filtrate was concentrated under reduced pressure and the crude product was purified by prep-HPLC with the following conditions (Column: XBridge Prep OBD C18 Column, 19*250 mm, 5 m; Mobile Phase A: Water (10 mM $NH_4HCO_3$), Mobile Phase B: MeCN; Flow rate: 20 mL/min; Gradient: 23% B to 53% B in 10 min; RT1(min): 7) to afford (1S,3R,5R,6R,8R,10R,1 S,13R,15R,16S,18R, 20R,21S,23R,25R,26S,28R,30R,31S,33R,35R,36S,37R, 38S,39R,40S,41R,42S,43R,44S,45R,46S,47R,48R,49R)-37,39,41,43,45,47,48-heptakis(2-hydroxy-2-methylpropoxy)-5,20,25,20,350,35-heptakis (hydroxymethyl)-2,4,7,9,12,14,17,19,22,24,27,29,32,34-tetradecaoxaoctacyclo[31.2.2.$2^{3,6}.2^{8,11}.2^{13,16}.2^{18,21}$. $2^{23,26}.2^{28,31}$]nonatetracontane-36,38,40,42,44,46,49-heptol (Compound 7) (67 mg, 34%) as a white solid. LCMS (ES): [M+$NH_4$+]=1657.30. $^1$H NMR (400 MHz, Methanol-$d_4$) δ5.02 (d, J=3.6 Hz, 7H), 3.92 (t, J=9.3 Hz, 7H), 3.75 (tt, J=12.4, 7.1 Hz, 14H), 3.62 (dt, J=10.1, 3.2 Hz, 7H), 3.59-3.49 (m, 14H), 3.45 (t, J=9.3 Hz, 7H), 3.37 (dd, J=9.9, 3.5 Hz, 7H), 1.10 (d, J=11.5 Hz, 42H).

BIOLOGICAL EXAMPLES

Example 1. CEC—Cholesterol Efflux Assay

Cholesterol Efflux from differentiated human THP-1 monocytes was assessed according to the manufacturer's protocol (abcam, ab196985). Briefly, THP-1 monocytes were differentiated for 48 h in presence of 100 nM phorbol 12-myristate-13-acetate (PMA) in RPMI 1640 growth medium (10% FCS, 1% penicillin/streptomycin) in a humidified incubator (37° C., 5% $CO_2$). Differentiated THP-1 macrophage-like cells were harvested, washed with PBS, resuspended in growth medium, seeded at $1\times10^5$ cells into 96-well plates, and allowed to adhere for 6h. Cells were washed with serum-free RPMI media, and labelled with 100 μL of fluorescent cholesterol labelling medium (50 uL Labeling Reagent+50 uL serum-free RPMI) for 1 h protected from light. Labeling medium was removed and replaced with 100 μL, 37° C. pre-warmed equilibration medium (50 uL Equilibration Buffer+2 L/mL Reagent A+10 μL/mL Reagent B+50 uL serum-free RPMI) and incubated for 16±1 h in an incubator (37° C., 5% $CO_2$). Equilibration medium was removed, and cells were washed with RPMI (w/o phenol red, w/o serum). Serum cholesterol acceptor was prepared by mixing 2 parts of Serum Treatment Reagent with 5 parts of human serum, incubated on ice for 20 minutes. The mix was centrifuged at 9,000×g for 10 minutes at 4° C., and supernatants were stored on ice until use. THP-1 cells were incubated for 4 h with 100 uL RPMI media (w/o phenol red, w/o serum), spiked with 10 uL of compound (10× stock in PBS) and 2 uL serum acceptor (2%), or RPMI media spiked with 10 uL PBS and 2 uL serum acceptor (negative control). Following incubation, plates were centrifuged and whole supernatants were transferred to an opaque 96-well plate. Remaining cells were lysed by adding 100 μL of Cell Lysis Buffer and shaking at 500 rpm for 25 minutes protected from light. Cell lysate was resuspended and transferred into an opaque 96-well. Plates containing supernatants or cell lysates were measured in a plate reader at 485 nm (excitation) and 523 nm (emission). Percent (%) cholesterol efflux was measured as RFU supernatant/(RFU supernatant+RFU cell lysate)×100%.

The cholesterol efflux from cells treated with compounds of the disclosure at concentrations of 0.1 mM, 0.3 mM and 1 mM, relative to cholesterol efflux from cells treated with a reference standard, are summarized in Table 1. In the table, A denotes compounds with a CEC of ≥126% of that of the reference standard and B denotes compounds with a CEC of 106% to 125% of that of the reference standard; 0 denotes compounds with a CEC of 96%-105% of that of the reference standard; and - denotes compounds with a CEC of 75%-95% of that of the reference standard. The reference standard is a non-isomerically pure hydroxypropyl beta-cyclodextrin.

TABLE 1

Cholesterol efflux from cells treated with compounds of the disclosure

| | Concentration | | |
|---|---|---|---|
| Compound | 0.1 mM | 0.3 mM | 1 mM |
| 1 | 0 | 0 | 0 |
| 2 | B | A | B |
| 3 | – | – | – |
| 4 | – | – | – |
| 5 | – | – | – |
| 6 | 0 | – | – |
| 7 | A | A | B |

Example 2. Cytotoxicity Assay

Cytotoxicity was measured using a lactate dehydrogenase (LDH) assay, according to the manufacturer's protocol (CytoTox 96® Non-Radioactive Cytotoxicity Assay, Promega, G1780). Supernatants and cell lysates from CEC assay served as samples. Briefly, 50 uL of supernatant and cell lysates were transferred into separate transparent 96-well plates. 50 uL CytoTox 96© Reagent was added to the wells, mixed by pipetting, and incubated for 10 minutes protected from light. 50 μL of Stop Solution was added, mixed by pipetting, and absorbance (OD) was measured at 490 nm in a plate reader. Phenol red-free RPMI with 10% PBS and Cell Lysis Buffer (abcam, ab196985) served as background controls. Percent (%) cytotoxicity was measured as OD supernatant/(OD supernatant+OD cell lysate)x100%.

Lactate dehydrogenase (LDH) released from cells treated with compounds of the disclosure at concentrations of 0.1 mM, 0.3 mM and 1 mM, relative to LDH) released from cells treated with a reference standard, are summarized in Table 2. In the table, A denotes compounds releasing LDH in an amount of ≤70% of that of the reference standard; B denotes compounds releasing LDH in an amount of 71-95% of that of the reference standard; 0 denotes compounds releasing LDH in an amount of 96%-105% of that of the reference standard; + denotes compounds releasing LDH in an amount of 106%-120% of that of the reference standard; and ++ denotes compounds releasing LDH in an amount of ≥120% of that of the reference standard The reference standard is a non-isomerically pure hydroxypropyl beta-cyclodextrin.

TABLE 2

Release of lactate dehydrogenase from cells treated with compounds of the disclosure

| | Concentration | | |
|---|---|---|---|
| Compound | 0.1 mM | 0.3 mM | 1 mM |
| 1 | B | B | B |
| 2 | A | B | 0 |
| 3 | ++ | + | 0 |
| 4 | ++ | ++ | ++ |
| 5 | 0 | 0 | 0 |
| 6 | 0 | + | + |
| 7 | B | + | ++ |

Embodiments

Enumerated Embodiments I

Embodiment 1. A compound of Formula I:

(I)

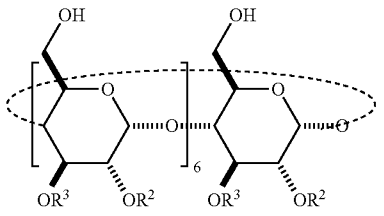

wherein, each $R^2$ and $R^3$ independently, at each occurrence for each of the seven independent monomers, is H or $C_2$-$C_4$ alkyl substituted with one or more groups selected from —O($C_1$-$C_4$ alkyl) and —OH, wherein at least one $R^2$ or at least one $R^3$ is $C_2$-$C_4$ alkyl substituted with one or more groups selected from —O($C_1$-$C_4$ alkyl) and —OH.

Embodiment 2. The compound of embodiment 1, wherein each $R^3$ is H.

Embodiment 3. The compound of any of the preceding embodiments, wherein $R^2$ for each of the seven independent monomers is $C_2$-$C_4$ alkyl substituted with one or more groups selected from —O($C_1$-$C_4$ alkyl) and —OH.

Embodiment 4. The compound of any of the preceding embodiments, wherein each $R^2$ independently is a $C_2$-$C_4$ alkyl substituted with one or two OH.

Embodiment 5. The compound of any of the preceding embodiments, wherein each $R^2$ is 2-hydroxypropyl.

Embodiment 6. The compound of any of the preceding embodiments, wherein each $R^2$ is 2-hydroxybutyl.

Embodiment 7. The compound of any of the preceding embodiments, wherein each $R^2$ independently is $C_2$-$C_4$ alkyl substituted with one or two —O($C_1$-$C_4$ alkyl).

Embodiment 8. The compound of any of the preceding embodiments, wherein each $R^2$ independently is $C_2$-$C_4$ alkyl substituted with one or two —$OCH_3$ or —$OCH_2CH_3$.

Embodiment 9. The compound of any of the preceding embodiments, wherein each $R^2$ independently is $C_2$-$C_4$ alkyl substituted with one —$OCH_3$ or —$OCH_2CH_3$.

Embodiment 10. The compound of any of the preceding embodiments, wherein the $C_2$-$C_4$ alkyl is ethyl.

Embodiment 11. The compound of any of the preceding embodiments, wherein each $R^2$ is H.

Embodiment 12. The compound of any of the preceding embodiments, wherein $R^3$ for each of the seven independent monomers is $C_2$-$C_4$ alkyl substituted with one or more groups selected from —O($C_1$-$C_4$ alkyl) and —OH.

Embodiment 13. The compound of any of the preceding embodiments, wherein each $R^3$ independently is $C_2$-$C_4$ alkyl substituted with one or two OH.

Embodiment 14. The compound of any of the preceding embodiments, wherein each $R^3$ is 2-hydroxypropyl.

Embodiment 15. The compound of any of the preceding embodiments, wherein each $R^3$ is 2-hydroxybutyl.

Embodiment 16. The compound of any of the preceding embodiments, wherein each $R^3$ is 2-hydroxyisobutyl.

Embodiment 17. The compound of any of the preceding embodiments, wherein each $R^3$ independently is $C_2$-$C_4$ alkyl substituted with one or two —O($C_1$-$C_4$ alkyl).

Embodiment 18. The compound of any of the preceding embodiments, wherein each $R^3$ independently is $C_2$-$C_4$ alkyl substituted with one or two —$OCH_3$ or —$OCH_2CH_3$.

Embodiment 19. The compound of any of the preceding embodiments, wherein each $R^3$ independently is $C_2$-$C_4$ alkyl substituted with one $OCH_3$ or —$OCH_2CH_3$.

Embodiment 20. The compound of any of the preceding embodiments, wherein the $C_2$-$C_4$ alkyl is ethyl.

Embodiment 21. The compound of any of the preceding embodiments, wherein each $R^2$ is the same.

Embodiment 22. The compound of any of the preceding embodiments, wherein each $R^3$ is the same.

Embodiment 23. The compound of any of the preceding embodiments, having the Formula Ia:

(Ia)

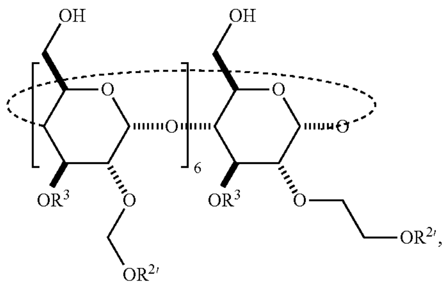

wherein each $R^{2'}$ independently is $C_1$-$C_4$ alkyl.

Embodiment 24. The compound of any of the preceding embodiments, wherein each $R^{2'}$ independently is —$CH_3$ or —$CH_2CH_3$.

Embodiment 25. The compound of any of the preceding embodiments, wherein each $R^{2'}$ is —$CH_3$.

Embodiment 26. The compound of any of the preceding embodiments, wherein each $R^{2'}$ is —$CH_2CH_3$.

Embodiment 27. The compound of any of the preceding embodiments, having the Formula Ib:

(Ib)

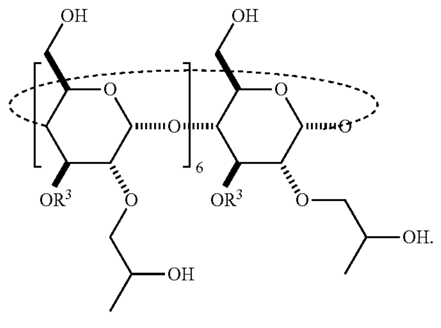

Embodiment 28. The compound of any of the preceding embodiments, having the Formula Ic:

(Ic)

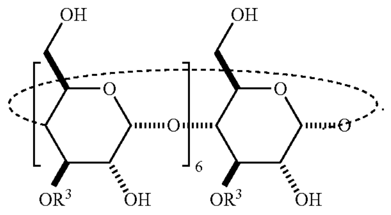

Embodiment 29. The compound of any of the preceding embodiments, having the Formula Id:

(Id)

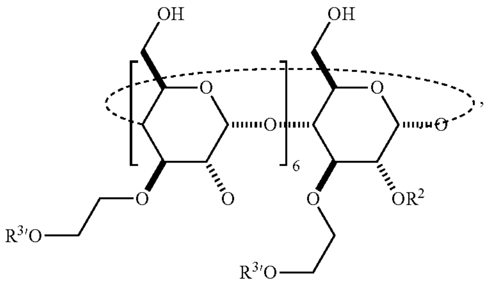

wherein each $R^{3'}$ independently is $C_1$-$C_4$ alkyl.

Embodiment 30. The compound of any of the preceding embodiments, wherein each $R^{3'}$ independently is —$CH_3$ or —$CH_2CH_3$.

Embodiment 31. The compound of any of the preceding embodiments, wherein each $R^{3'}$ is —$CH_3$.

Embodiment 32. The compound of any of the preceding embodiments, wherein each $R^{3'}$ is —$CH_2CH_3$.

Embodiment 33. The compound of any of the preceding embodiments, having the Formula Ie:
(Ie)
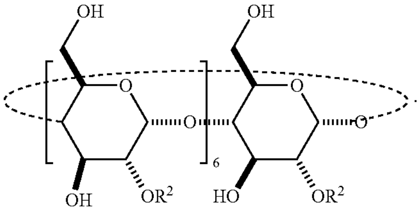
Embodiment 34. The compound of any of the preceding embodiments, having the Formula If:
(If)
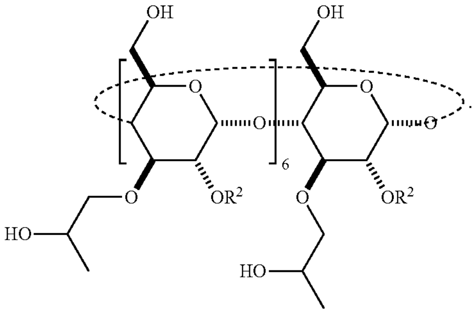
Embodiment 35. The compound of embodiment 1, selected from the group consisting of:
3
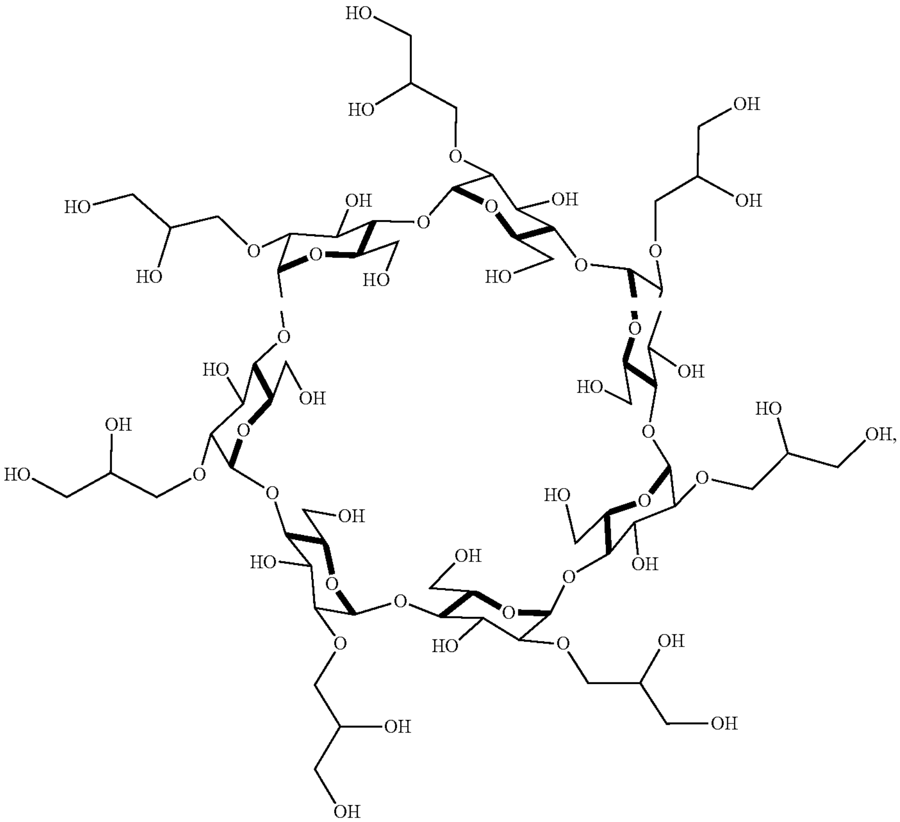
5
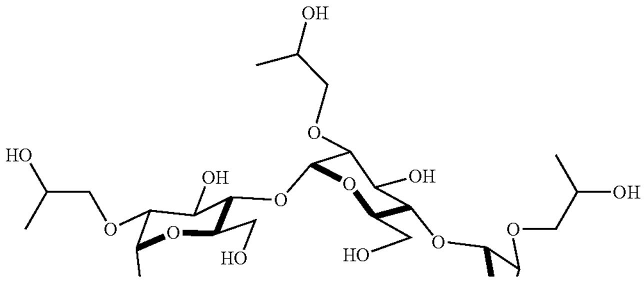

-continued
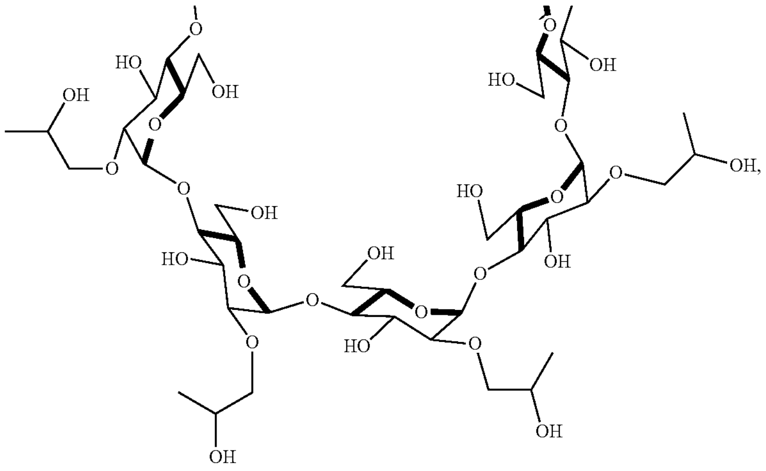
and
7
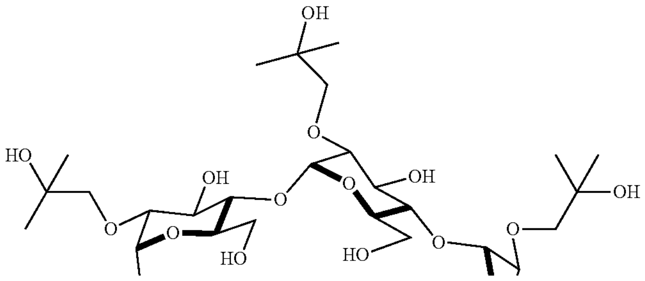
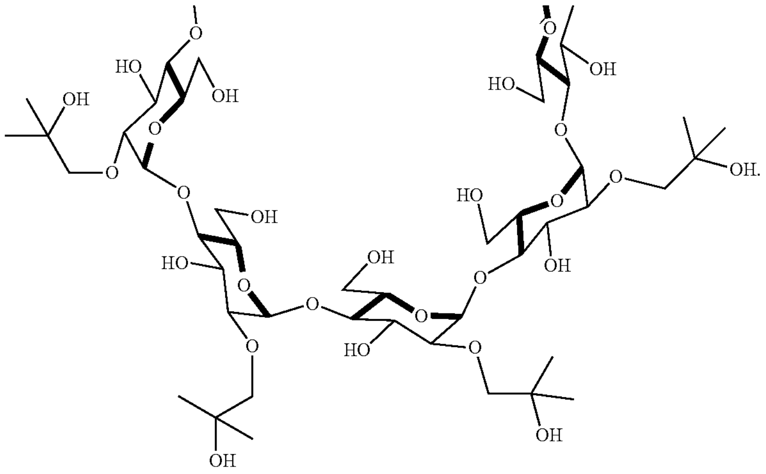

Embodiment 36. The compound of embodiment 1, selected from the group consisting of:
4
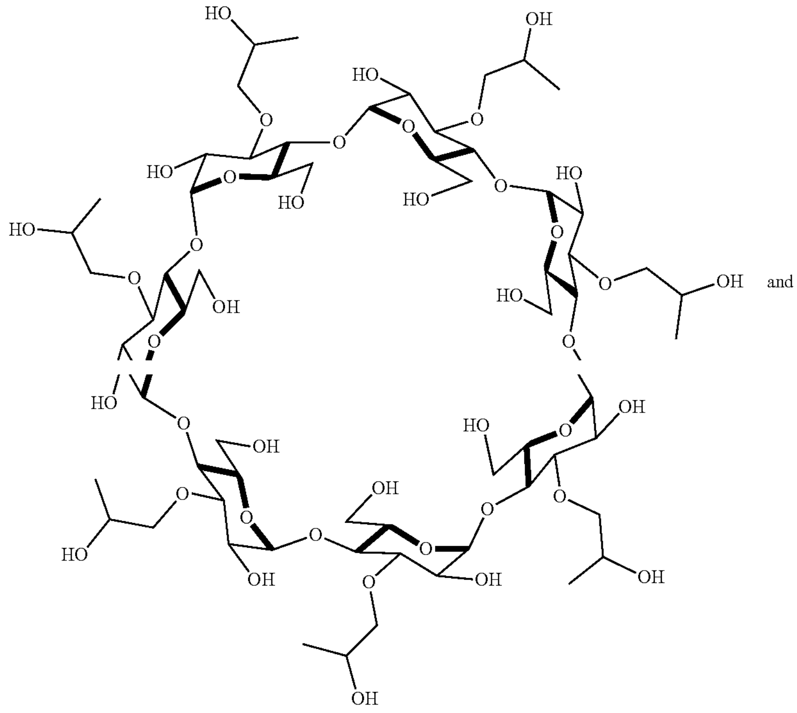
and
6
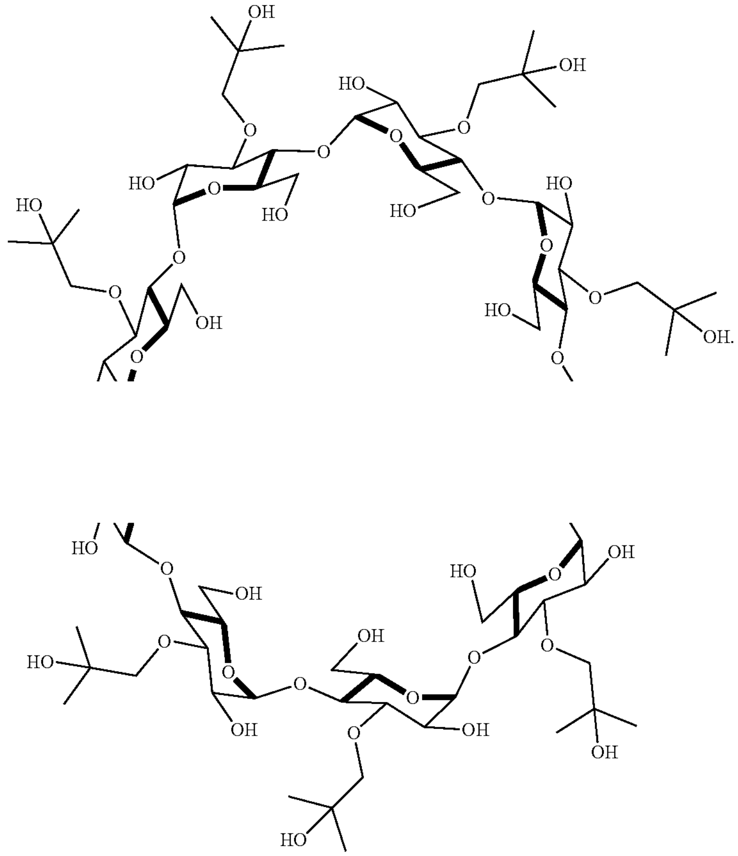

Embodiment 37. The compound of embodiment 1, selected from the group consisting of:
Embodiment 38. The compound of embodiment 1, selected from the group consisting of
1
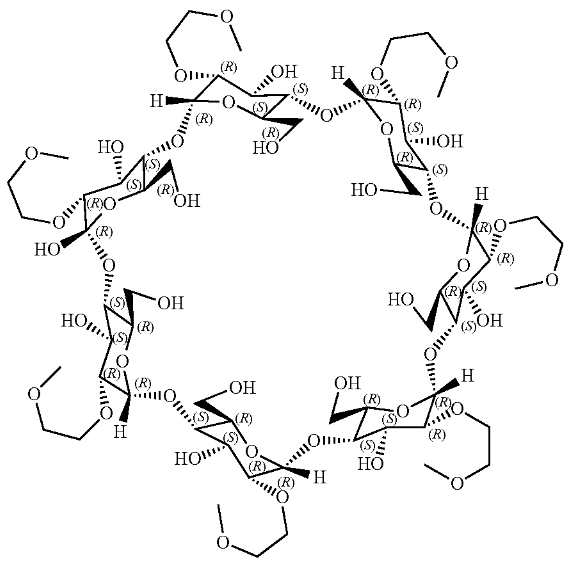
-continued
and
2
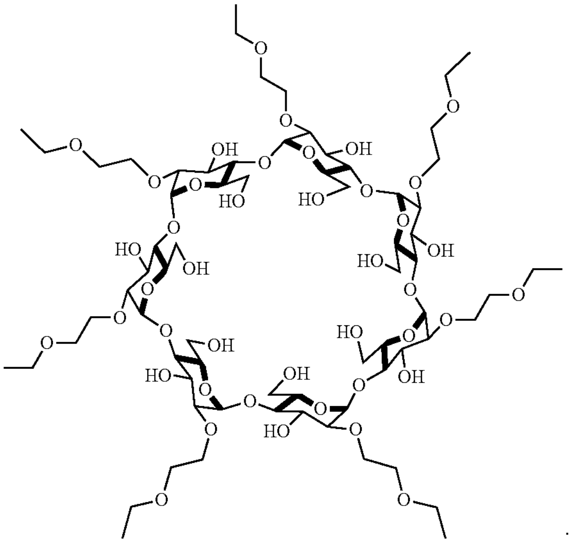
.
2
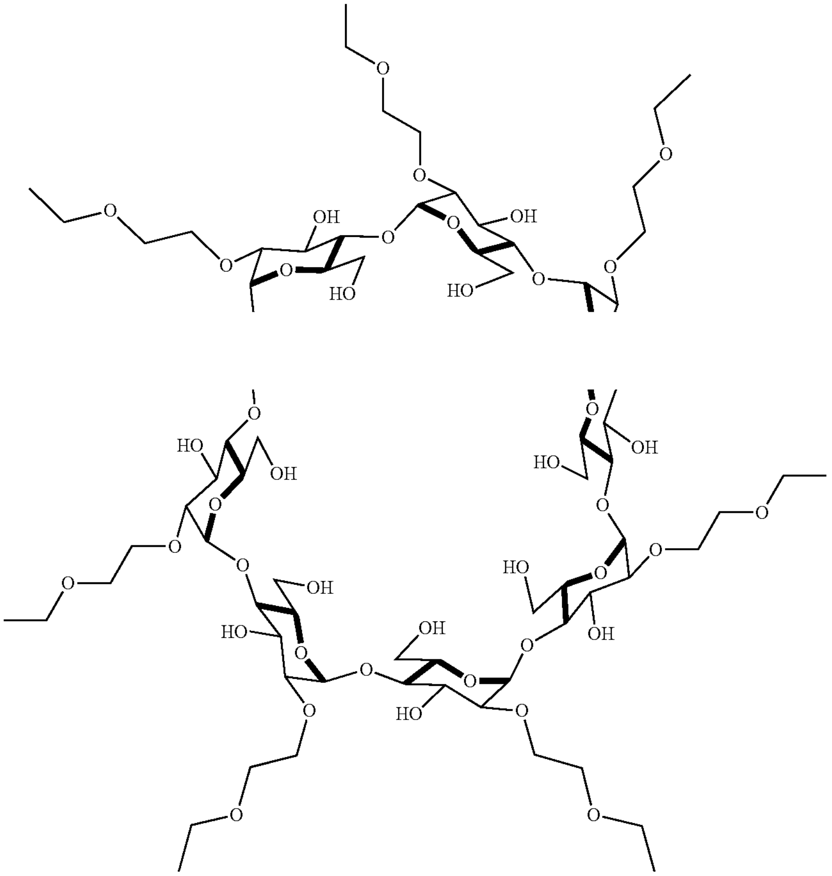
and -continued

7

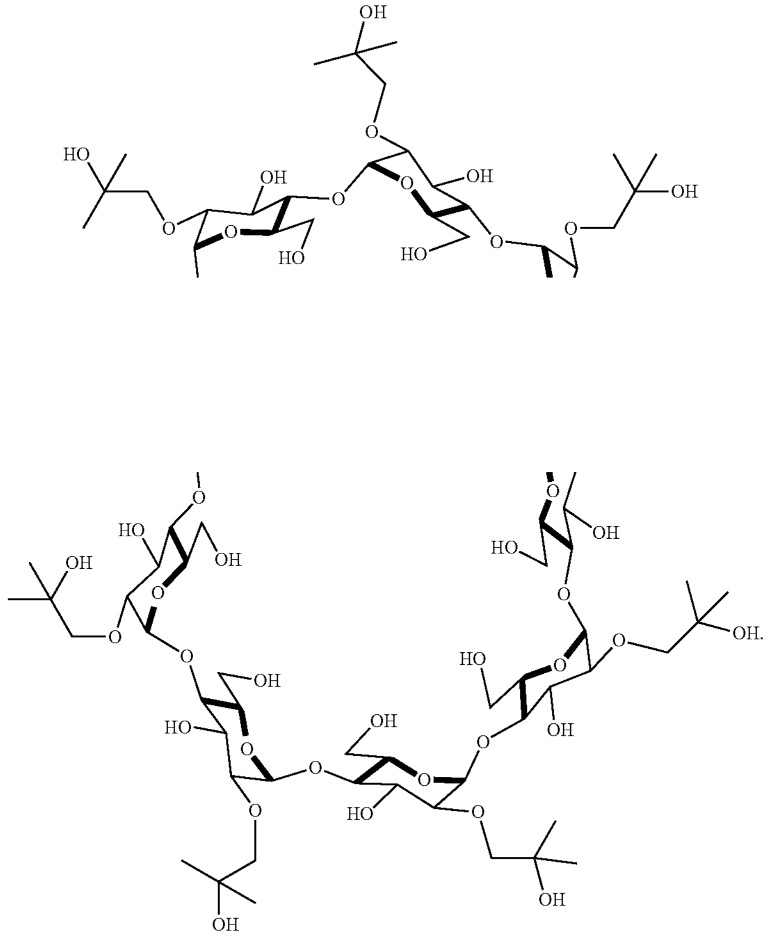

Embodiment 39. A compound of Formula II:

(II)

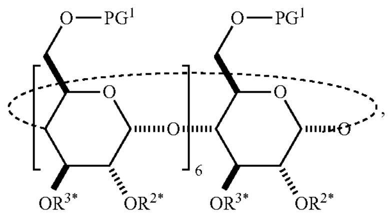

wherein, $PG^1$ is a first alcohol protecting group; and each $R^{2*}$ and $R^{3*}$ independently, at each occurrence for each of the seven independent monomers, is $PG^1$, —$CH_2C(O)CH_3$, or $C_2$-$C_6$ alkenyl optionally substituted with one or more —OH or —$OPG^2$ wherein $PG^2$ is a second alcohol protecting group, and wherein at least one $R^{2*}$ or $R^{3*}$ is —$CH_2C(O)CH_3$ or $C_2$-$C_6$ alkenyl optionally substituted with one or more —OH or —$OPG^2$.

Embodiment 40. The compound of any of the preceding embodiments, wherein $PG^1$ is selected from tert-butyldimethylsilyl, trimethylsilyl, triisopropylsilyloxymethyl, and triisopropylsilyl.

Embodiment 41. The compound of any of the preceding embodiments, wherein $PG^1$ is benzyl, p-methoxybenzyl, dimethoxybenzyl, or p-methoxyphenyl.

Embodiment 42. The compound of any of the preceding embodiments, wherein $PG^2$ is ethoxymethyl or methoxymethyl.

Embodiment 43. The compound of any of the preceding embodiments, wherein each $R^{2*}$ and $R^{3*}$ independently, at each occurrence for each of the seven independent monomers, is $PG^1$ or —$CH_2C(O)CH_3$.

Embodiment 44. The compound of any of the preceding embodiments, wherein each $R^{2*}$ and $R^{3*}$ independently, at each occurrence for each of the seven independent monomers, is $PG^1$ or unsubstituted $C_2$-$C_6$ alkenyl.

Embodiment 45. The compound of any of the preceding embodiments, wherein each $R^{2*}$ and $R^{3*}$ independently, at each occurrence for each of the seven independent monomers, is $PG^1$ or $C_2$-$C_6$ alkenyl substituted with one or more —$OPG^2$.

Embodiment 46. The compound of embodiment 39, selected from the group consisting of:

II-1
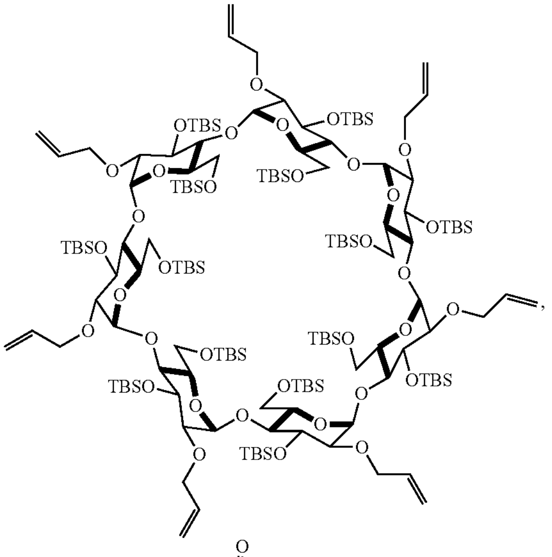
,
II-2
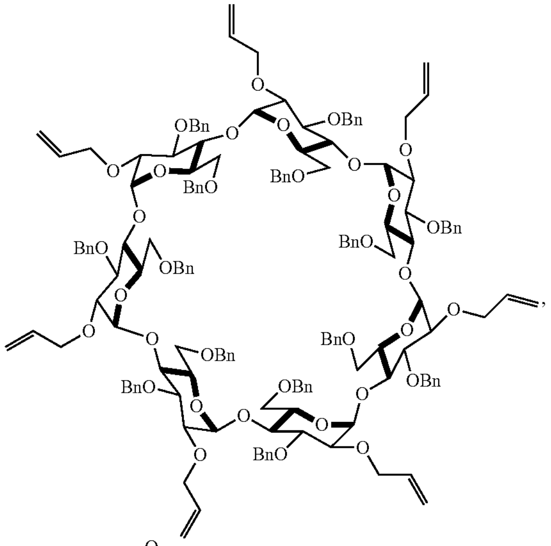
,
II-3
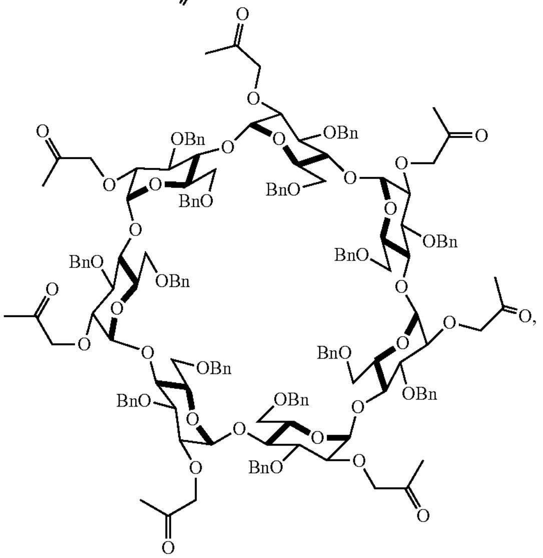
,
II-4
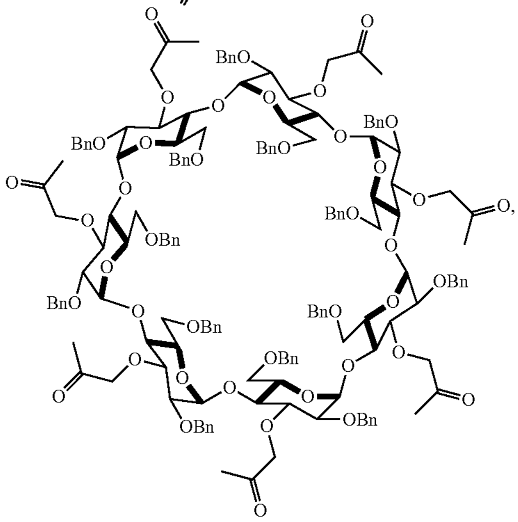
,
II-5
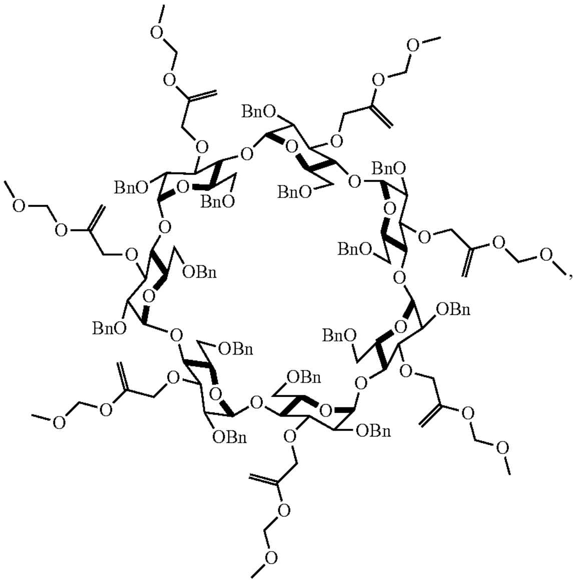
, -continued
II-6
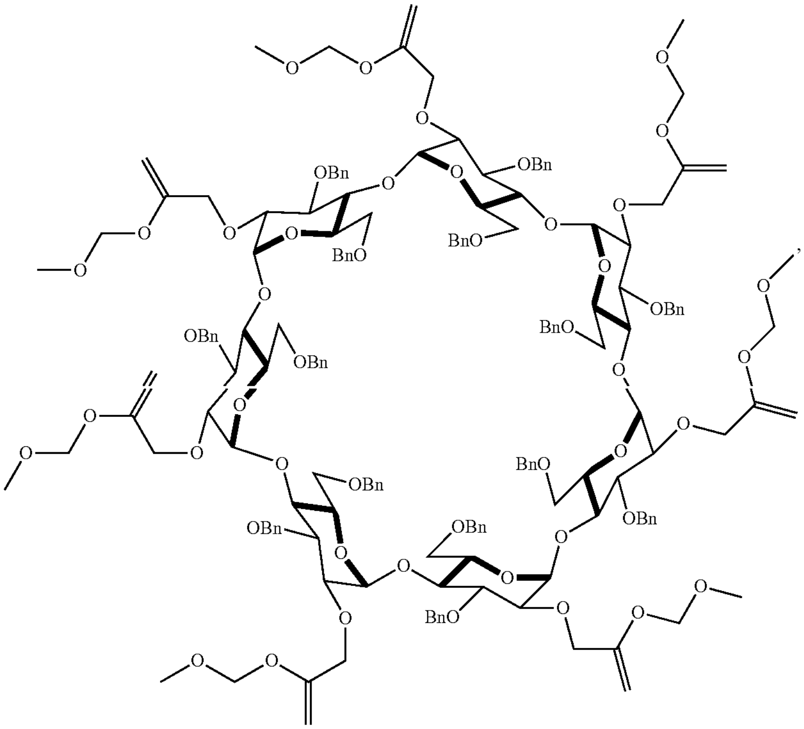
, and
II-7
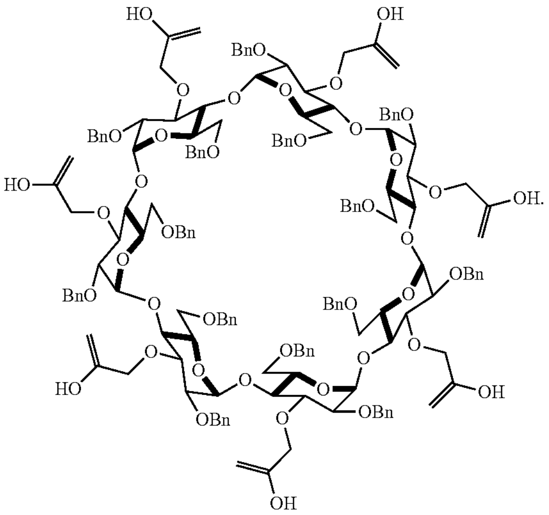
Embodiment 47. A compound of Formula IIa:
(IIa)
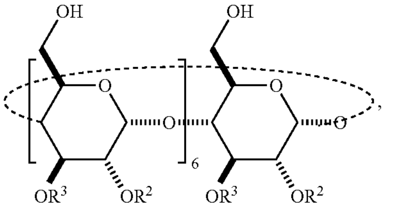
wherein,
each $R^2$ and $R^3$ independently, at each occurrence for each of the seven independent monomers, is H or $C_2$-$C_4$ alkenyl, wherein at least one $R^2$ or at least one $R^3$ is $C_2$-$C_4$ alkenyl.

Embodiment 48. The compound of any one of the preceding embodiments, wherein the compound is:

(II-8)

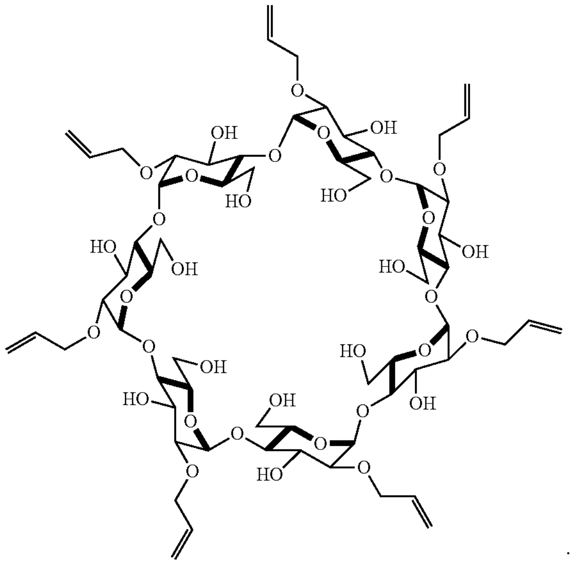

.

Embodiment 49. The compound of any one of the preceding embodiments, wherein the compound has a purity of at least 95%.

Embodiment 50. The compound of any one of the preceding embodiments, wherein the compound has a regioisomeric purity of at least 95%.

Embodiment 51. The compound of any one of the preceding embodiments, wherein the compound has a purity of at least 95%.

Embodiment 52. The compound of any one of the preceding embodiments, wherein the compound has a purity of at least 96%.

Embodiment 53. The compound of any one of the preceding embodiments, wherein the compound has a purity of at least 97%.

Embodiment 54. The compound of any one of the preceding embodiments, wherein the compound has a purity of at least 98%.

Embodiment 55. The compound of any one of the preceding embodiments, wherein the compound has a purity of at least 99%.

Embodiment 56. The compound of any one of the preceding embodiments, wherein the compound has an isomeric purity of at least 95%.

Embodiment 57. The compound of any one of the preceding embodiments, wherein the compound has an isomeric purity of at least 96%.

Embodiment 58. The compound of any one of the preceding embodiments, wherein the compound has an isomeric purity of at least 97%.

Embodiment 59. The compound of any one of the preceding embodiments, wherein the compound has an isomeric purity of at least 98%.

Embodiment 60. The compound of any one of the preceding embodiments, wherein the compound has an isomeric purity of at least 99%.

Embodiment 61. The compound of any one of the preceding embodiments, wherein the compound has a regioisomeric purity of at least 95%.

Embodiment 62. The compound of any one of the preceding embodiments, wherein the compound has a regioisomeric purity of at least 96%.

Embodiment 63. The compound of any one of the preceding embodiments, wherein the compound has a regioisomeric purity of at least 97%.

Embodiment 64. The compound of any one of the preceding embodiments, wherein the compound has a regioisomeric purity of at least 98%.

Embodiment 65. The compound of any one of the preceding embodiments, wherein the compound has a regioisomeric purity of at least 99%.

Embodiment 66. An active pharmaceutical ingredient consisting of a compound of any one of the preceding embodiments.

Embodiment 67. A pharmaceutically active substance consisting of a compound of any one of the preceding embodiments.

Embodiment 68. A pharmaceutical composition comprising an active pharmaceutical ingredient and a pharmaceutically acceptable carrier, wherein the active pharmaceutical ingredient is a compound of any one of the preceding embodiments.

Embodiment 69. A pharmaceutical composition comprising a pharmaceutically active component and a pharmaceutically acceptable carrier, wherein the pharmaceutically active component is a compound of any one of the preceding embodiments.

Embodiment 70. A pharmaceutical composition comprising a compound of any one of the preceding embodiments, and a pharmaceutically acceptable carrier.

Embodiment 71. A method of increasing cholesterol efflux capacity (CEC) of a tissue or a cell in a subject, comprising administering to the subject a therapeutically effective amount of a compound or pharmaceutically active substance of any one of the preceding embodiments, or a pharmaceutical composition of any one of the preceding embodiments.

Embodiment 72. A method of inducing or increasing cholesterol efflux capacity (CEC) out of atheromas of a subject, comprising administering to the subject a therapeutically effective amount of a compound or pharmaceutically active substance of any one of the preceding embodiments, or a pharmaceutical composition of any one of the preceding embodiments.

Embodiment 73. A method of inducing reverse cholesterol transport from macrophages of a subject to the feces or urine of the subject, comprising administering to the subject a therapeutically effective amount of a compound or pharmaceutically active substance of any one of the preceding embodiments, or a pharmaceutical composition of any one of the preceding embodiments.

Embodiment 74. A method of sequestering cholesterol in the blood of a subject, comprising administering to the subject a therapeutically effective amount of a compound or pharmaceutically active substance of any one of the preceding embodiments, or a pharmaceutical composition of any one of the preceding embodiments.

Embodiment 75. A method of reducing intracellular cholesterol in a tissue or cell of a subject in need thereof, the method comprising administering to the subject a compound or pharmaceutically active substance of any one of the preceding embodiments, or a pharmaceutical composition of any one of the preceding embodiments.

Embodiment 76. A method of reducing inflammation and/or oxidative stress induced by oxidized LDL in a subject in need thereof, the method comprising administering to the subject a compound or pharmaceutically active substance of any one of the preceding embodiments, or a pharmaceutical composition of any one of the preceding embodiments.

Embodiment 77. A method of improving the renal and/or hepatogenic clearance of cholesterol in a subject in need thereof, the method comprising administering to the subject a compound or pharmaceutically active substance of any one of the preceding embodiments, or a pharmaceutical composition of any one of the preceding embodiments.

Embodiment 78. A method of increasing circulating and/or systemic levels of one or more oxysterol in a subject in need thereof, the method comprising administering to the subject a compound or pharmaceutically active substance of any one of the preceding embodiments, or a pharmaceutical composition of any one of the preceding embodiments.

Embodiment 79. A method of any one of the preceding embodiments, wherein the oxysterol is 27-hydroxycholesterol, or 24-hydroxycholesterol.

Embodiment 80. A method of any one of the preceding embodiments, wherein the oxysterol is 27-hydroxycholesterol.

Embodiment 81. A method of increasing plasma cholesterol crystal dissolution capacity (CCDC) in a subject in need thereof, the method comprising administering to the subject a compound or pharmaceutically active substance of any one of the preceding embodiments, or a pharmaceutical composition of any one of the preceding embodiments.

Embodiment 82. A method of increasing levels of ABCA1 and/or ABCG1 in a subject in need thereof, the method comprising administering to the subject a compound or pharmaceutically active substance of any one of the preceding embodiments, or a pharmaceutical composition of any one of the preceding embodiments.

Embodiment 83. A method of reducing the risk of or preventing cholesterol crystal embolization (CCE) or a symptom thereof in a subject in need thereof, the method comprising administering to the subject a compound or pharmaceutically active substance of any one of the preceding embodiments, or a pharmaceutical composition of any one of the preceding embodiments.

Embodiment 84. A method of treating a disorder of cholesterol metabolism in a subject in need thereof, comprising administering to the subject a therapeutically effective amount of a compound or pharmaceutically active substance of any one of the preceding embodiments, or a pharmaceutical composition of any one of the preceding embodiments.

Embodiment 85. A method of reducing, inhibiting, or preventing the development of cholesterol rich plaque in a subject in need thereof, the method comprising administering to the subject a compound or pharmaceutically active substance of any one of the preceding embodiments, or a pharmaceutical composition of any one of the preceding embodiments.

Embodiment 86. A method of treating or reducing a risk of a major adverse cardiovascular events (MACE) in a subject in need thereof, the method comprising administering to the subject a compound or pharmaceutically active substance of any one of the preceding embodiments, or a pharmaceutical composition of any one of the preceding embodiments.

Embodiment 87. A method of treating a cardiovascular disease in a subject in need thereof, the method comprising administering to the subject a compound or pharmaceutically active substance of any one of the preceding embodiments, or a pharmaceutical composition of any one of the preceding embodiments.

Embodiment 88. The method of any one of the preceding embodiments, wherein the disorder is a lipid storage disease or disorder.

Embodiment 89. The method of any one of the preceding embodiments, wherein the lipid storage disease or disorder is Niemann-Pick disease Type C (NPC).

Embodiment 90. The method of any one of the preceding embodiments, wherein the disorder is a neurological disease or disorder.

Embodiment 91. The method of any one of the preceding embodiments, wherein the neurological disease or disorder is a neurodegenerative or neurocognitive disorder, cognitive impairment, mild cognitive impairment (MCI), amnestic MCI, nonamnestic MCI, single domain impairment, multiple domain impairment, vascular cognitive impairment, vascular dementia, mixed dementia characterized by at least one A/T biomarker, cerebrovascular ischemia, tauopathy, subcortical dementia, Alzheimer's disease, Huntington's disease, or x-linked adrenoleukodystrophy.

Embodiment 92. The method of any one of the preceding embodiments, wherein the neurological disease or disorder is Alzheimer's disease.

Embodiment 93. The method of any one of the preceding embodiments, wherein the disorder is a cardiovascular disease or disorder.

Embodiment 94. The method of any one of the preceding embodiments, wherein the cardiovascular disease or disorder is atherosclerosis, atherosclerotic cardiovascular disease (ASCVD), peripheral artery disease (PAD), coronary artery disease (CAD), coronary restenosis, peripheral vascular disease (PVD), cerebrovascular artery disease, ischemic cardiomyopathy, ischemic cerebrovascular disease, or homozygous familial hypercholesterolemia (HoFH), or heterozygous familial hypercholesterolemia (HeFH).

Embodiment 95. The method of any one of the preceding embodiments, wherein the cardiovascular disease or disorder is atherosclerosis.

Embodiment 96. The method of any one of the preceding embodiments, wherein the cardiovascular disease or disorder is atherosclerotic cardiovascular disease (ASCVD) Embodiment 97. The method of any one of the preceding embodiments, wherein ASCVD is high-risk ASCVD.

Embodiment 98. The method of any one of the preceding embodiments, wherein the disorder is a liver disease or disorder.

Embodiment 99. The method of any one of the preceding embodiments, wherein the liver disease or disorder is a neonatal liver disease or an acute liver disease.

Embodiment 100. The method of any one of the preceding embodiments, wherein the disorder is hypertriglyceridemia.

Embodiment 101. The method of any one of the preceding embodiments, wherein the disorder is correlated to stroke, chronic kidney disease (CKD) caused by atherosclerosis, end-stage kidney disease (ESKD) caused by atherosclerosis, acute kidney failure caused by atherosclerosis, atherosclerotic renovascular disease (ARVD), renal artery stenosis, aortic aneurysm, idiopathic peripheral atrial hypertension, erectile dysfunction, intermittent claudication, and/or post-surgical or iatrogenic arterial disease.

Embodiment 102. The method of any one of the preceding embodiments, wherein the compound reduces intracellular cholesterol levels in a tissue or a cell in the subject.

Embodiment 103. The method of any one of the preceding embodiments, wherein the compound i) reduces inflammation and/or oxidative stress induced by oxidized LDL;

ii) improves the renal and/or hepatogenic clearance of cholesterol;

iii) increases circulating and/or systemic levels of one or more oxysterol;

iv) increases plasma cholesterol crystal dissolution capacity (CCDC);

v) increases levels of ABCA1 and/or ABCG1; and/or vii) reduces the risk of or prevents cholesterol crystal embolization (CCE) or a symptom thereof.

Embodiment 104. The method of any one of the preceding embodiments, wherein increasing CCDC is measurable by a reduction in an amount of and/or a size of, and/or changing the shape of any one of circulating cholesterol crystals, clots comprising cholesterol crystals, cholesterol-rich plaques, atherosclerotic plaques, low-attenuation plaques, calcified plaques and coronary artery non-calcified plaques.

Embodiment 105. The method of any one of the preceding embodiments, wherein administering the compound, results in a change of at least one of other plaque features described herein (e.g., shape, texture, formation stage, etc.), as an indication of amelioration of plaque symptom in the subject.

Embodiment 106. The method of any one of the preceding embodiments, wherein the compound increases production of at least one cholesterol metabolite in the subject.

Embodiment 107. The method of any one of the preceding embodiments, wherein the cholesterol metabolite is 27-hydroxycholesterol.

Embodiment 108. The method of any one of the preceding embodiments, wherein, the cholesterol metabolite is 24-hydroxycholesterol.

Embodiment 109. The method of any one of the preceding embodiments, wherein the compound does not induce significant cytotoxicity in the tissue or cell in the subject.

Embodiment 110. The method of any one of the preceding embodiments, wherein the compound is capable of:

i) shuttling cholesterol, wherein the compound binds to cholesterol in a 1:1 ratio; and/or ii) sequestering cholesterol, wherein the compound binds to cholesterol in a 2:1 ratio.

Embodiment 111. The method of any one of the preceding embodiments, wherein increasing surface hydrophobicity of the compound facilitates the compound to sequester cholesterol.

Embodiment 112. The method of any one of the preceding embodiments, wherein the amount of cholesterol efflux induced by the compound is greater than the cholesterol efflux induced by a HDL mimetic.

Embodiment 113. The method of any one of the preceding embodiments, wherein the compound or the pharmaceutical composition is administered repeatedly.

Embodiment 114. The method of any one of the preceding embodiments, wherein administering the compound or the pharmaceutical composition does not result in organ toxicity.

Enumerated Embodiments II Embodiment 1. A compound of Formula I:

(I)

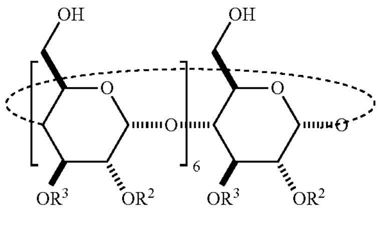

wherein, each $R^2$ and $R^3$ independently, at each occurrence for each of the seven independent monomers, is H or $C_2$-$C_4$ alkyl substituted with one or more groups selected from —O($C_1$-$C_4$ alkyl) and —OH, wherein at least one $R^2$ or at least one $R^3$ is $C_2$-$C_4$ alkyl substituted with one or more groups selected from —O($C_1$-$C_4$ alkyl) and —OH.

Embodiment 2. The compound of Embodiment 1, wherein each $R^3$ is H.

Embodiment 3. The compound of Embodiment 1 or Embodiment 2, wherein $R^2$ for each of the seven independent monomers is $C_2$-$C_4$ alkyl substituted with one or more groups selected from —O($C_1$-$C_4$ alkyl) and —OH.

Embodiment 4. The compound of any one of Embodiment 1-Embodiment 3, wherein each $R^2$ independently is a $C_2$-$C_4$ alkyl substituted with one or two OH.

Embodiment 5. The compound of Embodiment 4, wherein each $R^2$ is 2-hydroxypropyl.

Embodiment 6. The compound of Embodiment 4, wherein each $R^2$ is 2-hydroxybutyl.

Embodiment 7. The compound of any one of Embodiment 1-Embodiment 3, wherein each $R^2$ independently is $C_2$-$C_4$ alkyl substituted with one or two —O($C_1$-$C_4$ alkyl).

Embodiment 8. The compound of any one of Embodiment 1-Embodiment 3, wherein each $R^2$ independently is $C_2$-$C_4$ alkyl substituted with one or two —$OCH_3$ or —$OCH_2CH_3$.

Embodiment 9. The compound of any one of Embodiment 1-Embodiment 3, wherein each $R^2$ independently is $C_2$-$C_4$ alkyl substituted with one —$OCH_3$ or —$OCH_2CH_3$.

Embodiment 10. The compound of any one of Embodiment 3, Embodiment 4 or Embodiment 7-Embodiment 9, wherein the $C_2$-$C_4$ alkyl is ethyl.

Embodiment 11. The compound of Embodiment 1, wherein each $R^2$ is H.

Embodiment 12. The compound of Embodiment 1 or Embodiment 11, wherein $R^3$ for each of the seven independent monomers is $C_2$-$C_4$ alkyl substituted with one or more groups selected from —O($C_1$-$C_4$ alkyl) and —OH.

Embodiment 13. The compound of any one of Embodiment 1, Embodiment 11, or Embodiment 12, wherein each $R^3$ independently is $C_2$-$C_4$ alkyl substituted with one or two OH.

Embodiment 14. The compound of Embodiment 13, wherein each $R^3$ is 2-hydroxypropyl.

Embodiment 15. The compound of Embodiment 13, wherein each $R^3$ is 2-hydroxybutyl.

Embodiment 16. The compound of any one of Embodiments 1, Embodiment 11, or Embodiment 12, wherein each $R^3$ independently is $C_2$-$C_4$ alkyl substituted with one or two —O($C_1$-$C_4$ alkyl).

Embodiment 17. The compound of any one of Embodiment 1, Embodiment 11, or Embodiment 12, wherein each $R^3$ independently is $C_2$-$C_4$ alkyl substituted with one or two —$OCH_3$ or —$OCH_2CH_3$.

Embodiment 18. The compound of any one of Embodiment 1, Embodiment 11, or Embodiment 12, wherein each $R^3$ independently is $C_2$-$C_4$ alkyl substituted with one $OCH_3$ or —$OCH_2CH_3$.

Embodiment 19. The compound of any one of Embodiment 12, Embodiment 13, or Embodiment 16-Embodiment 18, wherein the $C_2$-$C_4$ alkyl is ethyl.

Embodiment 20. The compound of any one of the preceding Embodiments, wherein each $R^2$ is the same.

Embodiment 21. The compound of any one of the preceding Embodiments, wherein each $R^3$ is the same.

Embodiment 22. The compound of Embodiment 1 or Embodiment 2, having the Formula Ia:

(Ia)

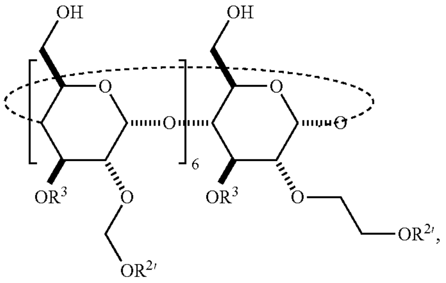

wherein each $R^{2'}$ independently is $C_1$-$C_4$ alkyl.

Embodiment 23. The compound of Embodiment 22, wherein each $R^{2'}$ independently is $-CH_3$ or $-CH_2CH_3$.

Embodiment 24. The compound of Embodiment 22, wherein each $R^{2'}$ is $-CH_3$.

Embodiment 25. The compound of Embodiment 22, wherein each $R^{2'}$ is $-CH_2CH_3$.

Embodiment 26. The compound of Embodiment 1 or Embodiment 2, having the Formula Ib:

(Ib)

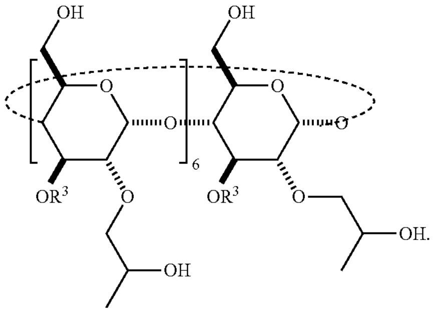

Embodiment 27. The compound of Embodiment 1, having the Formula Ic:

(Ic)

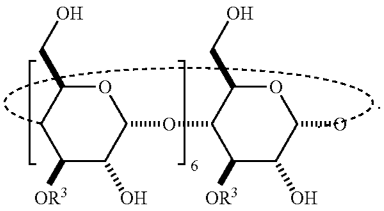

Embodiment 28. The compound of Embodiment 1 or Embodiment 11, having the Formula Id:

(Id)

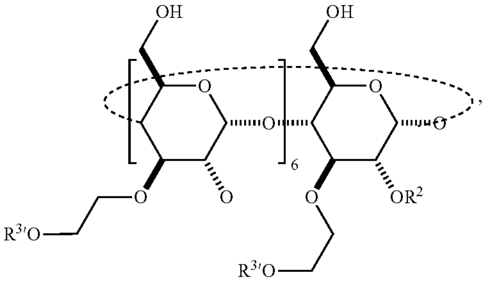

wherein each $R^{3'}$ independently is $C_1$-$C_4$ alkyl.

Embodiment 29. The compound of Embodiment 28, wherein each $R^{3'}$ independently is $-CH_3$ or $-CH_2CH_3$.

Embodiment 30. The compound of Embodiment 28, wherein each $R^{3'}$ is $-CH_3$.

Embodiment 31. The compound of Embodiment 28, wherein each $R^{3'}$ is $-CH_2CH_3$.

Embodiment 32. The compound of any one of Embodiments 1-10, having the Formula Ie:

(Ie)

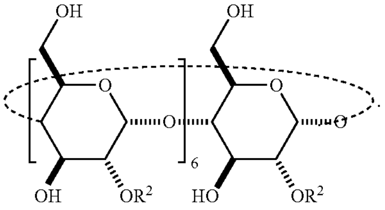

Embodiment 33. The compound of any one of Embodiments 1 or Embodiment 3-Embodiment 11, having the Formula If:

(If)

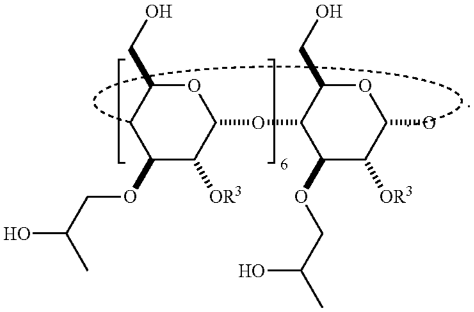

Embodiment 34. The compound of Embodiment 1, selected from the group consisting of:
3
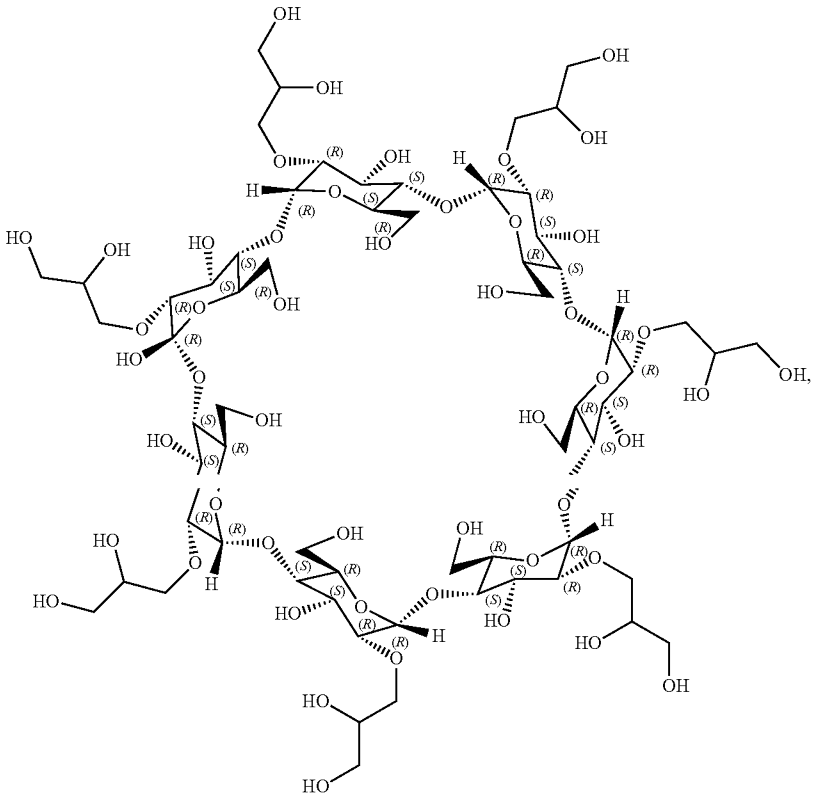
5
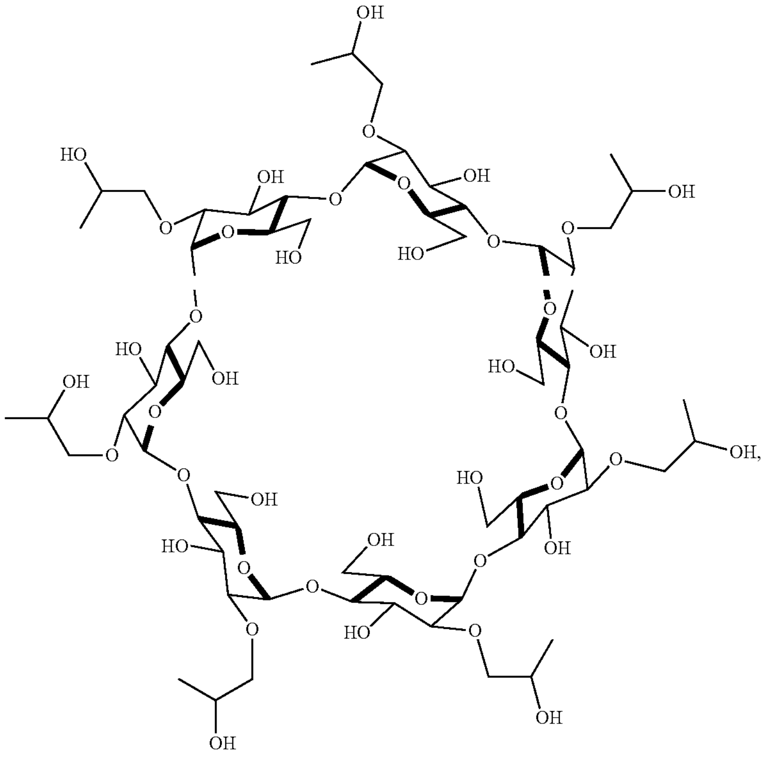
and -continued
7
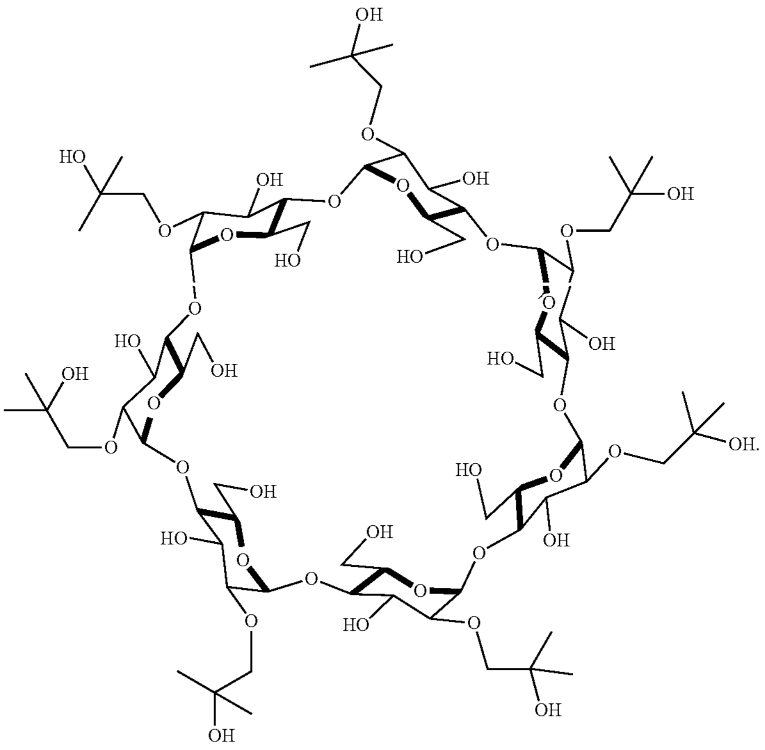
Embodiment 35. The compound of Embodiment 1, selected from the group consisting of.
4
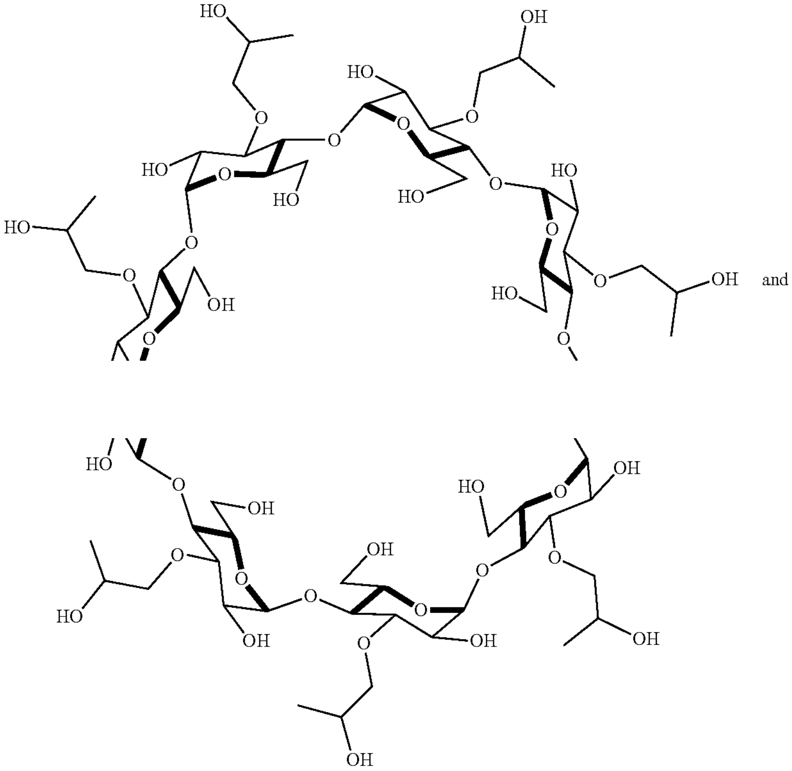
and -continued
6
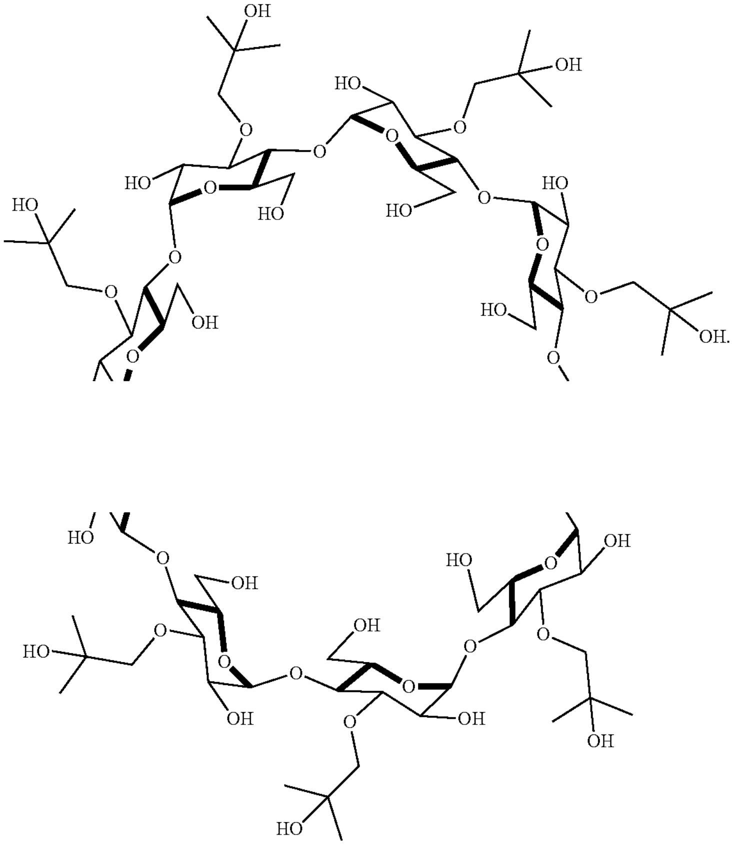
Embodiment 36. The compound of Embodiment 1, selected from the group consisting of:
1
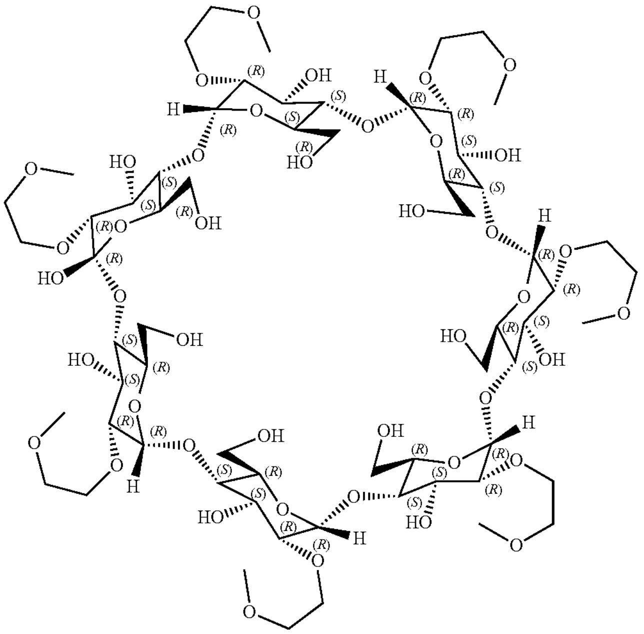
and -continued
2
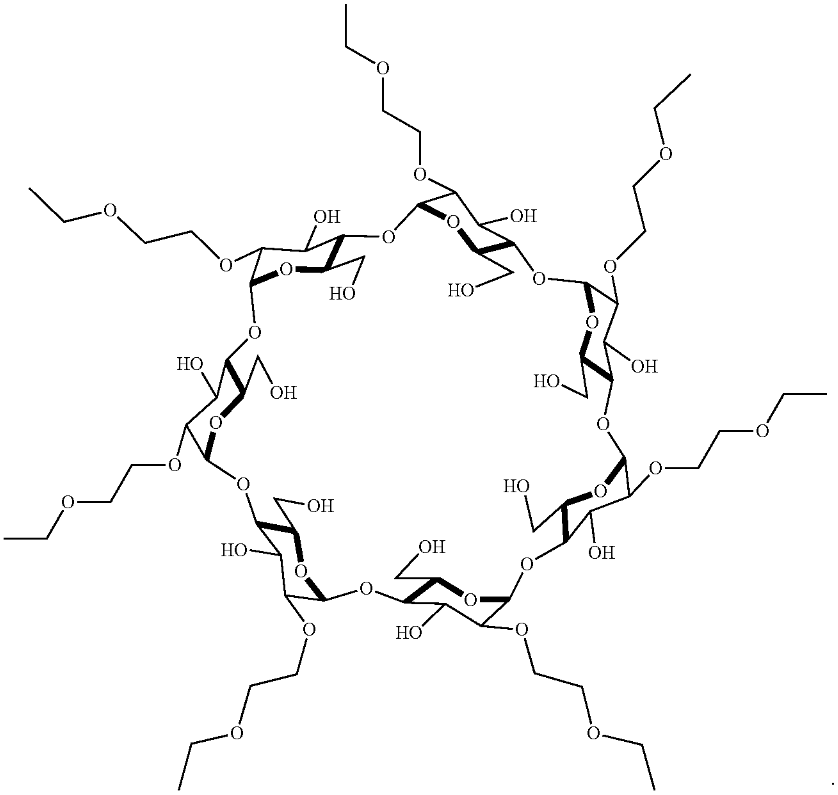
.
Embodiment 37. The compound of Embodiment 1, selected from the group consisting of:
2
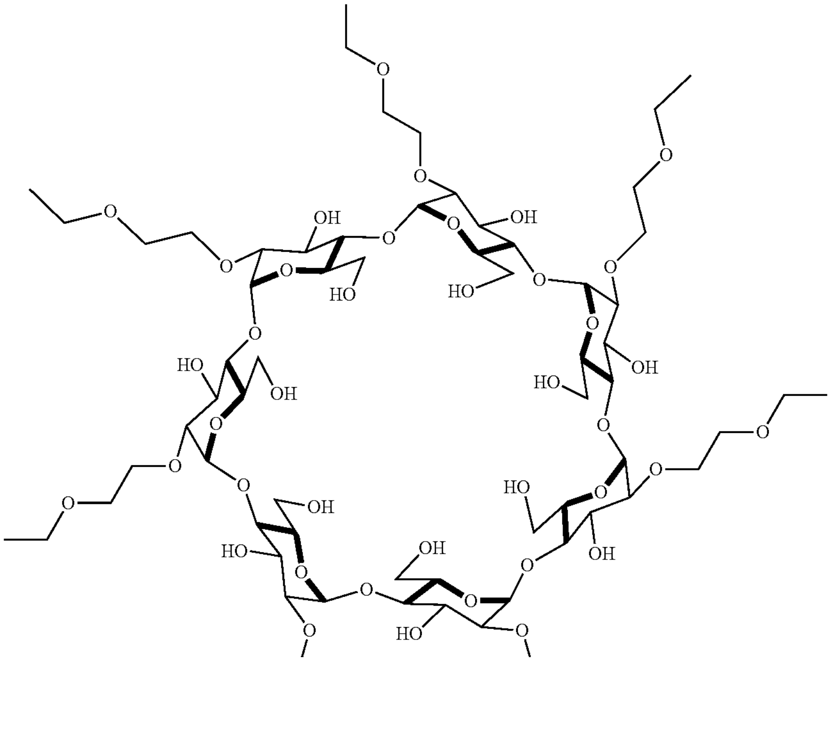

-continued

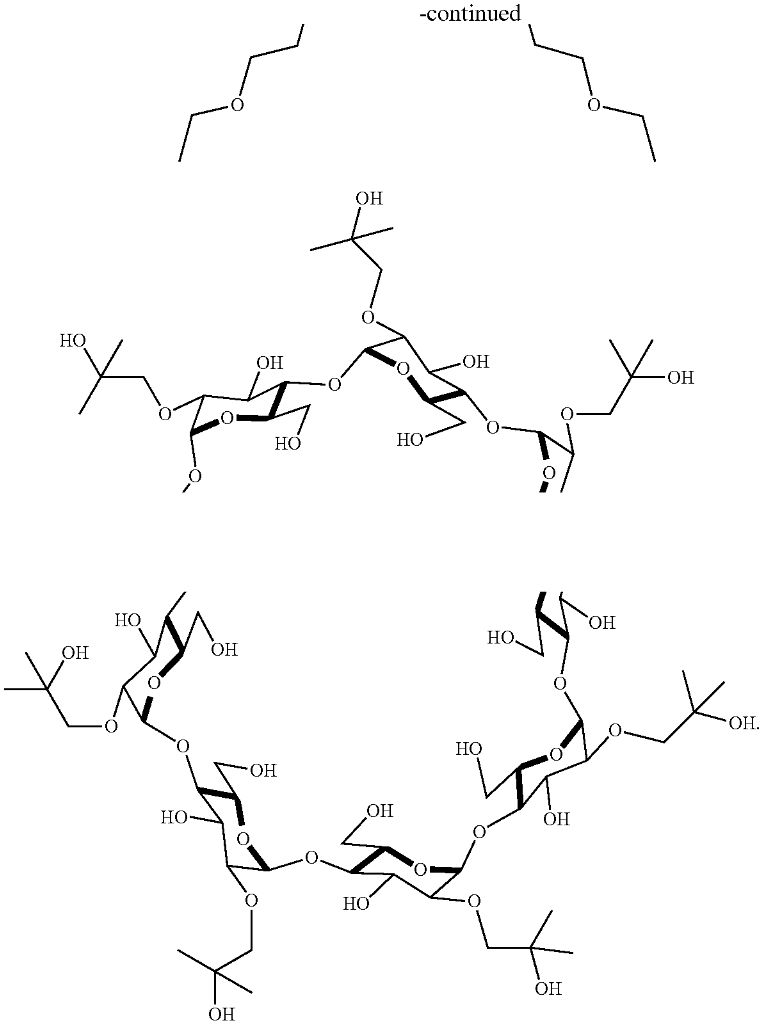

and

7

Embodiment 38. A compound of Formula II:

(II)

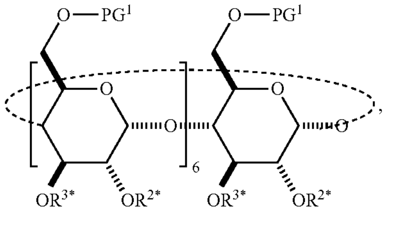

wherein, $PG^1$ is a first alcohol protecting group; and each $R^{2*}$ and $R^{3*}$ independently, at each occurrence for each of the seven independent monomers, is $PG^1$, —$CH_2C(O)CH_3$, or $C_2$-$C_6$ alkenyl optionally substituted with one or more —OH or —$OPG^2$, wherein $PG^2$ is a second alcohol protecting group, and wherein at least one $R^{2*}$ or $R^{3*}$ is —$CH_2C(O)CH_3$ or $C_2$-$C_6$ alkenyl optionally substituted with one or more —OH or —$OPG^2$.

Embodiment 39. The compound of Embodiment 38, wherein $PG^1$ is selected from tert-butyldimethylsilyl, trimethylsilyl, triisopropylsilyloxymethyl, and triisopropylsilyl.

Embodiment 40. The compound of Embodiment 38, wherein $PG^1$ is benzyl, p-methoxybenzyl, dimethoxybenzyl, or p-methoxyphenyl.

Embodiment 41. The compound of any one of Embodiment 38-Embodiment 40, wherein $PG^2$ is ethoxymethyl or methoxymethyl.

Embodiment 42. The compound of any one of Embodiment 38-Embodiment 40, wherein each $R^{2*}$ and $R^{3*}$ independently, at each occurrence for each of the seven independent monomers, is $PG^1$ or —$CH_2C(O)CH_3$.

Embodiment 43. The compound of any one of Embodiment 38-Embodiment 40, wherein each $R^{2*}$ and $R^{3*}$ independently, at each occurrence for each of the seven independent monomers, is $PG^1$ or unsubstituted $C_2$-$C_6$ alkenyl.

Embodiment 44. The compound of any one of Embodiment 38-Embodiment 41, wherein each $R^{2*}$ and $R^{3*}$ independently, at each occurrence for each of the seven independent monomers, is $PG^1$ or $C_2$-$C_6$ alkenyl substituted with one or more —$OPG^2$.

Embodiment 45. The compound of Embodiment 38, selected from the group consisting of:
II-1
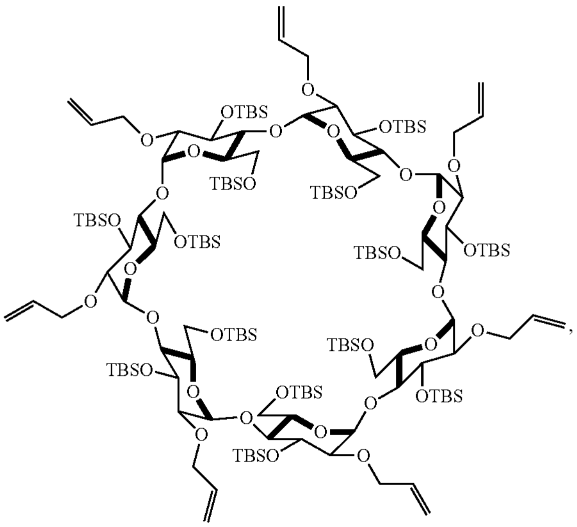
II-2
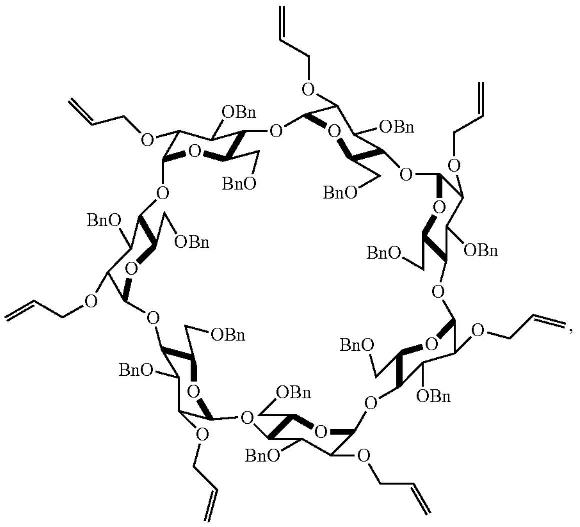
,
II-3
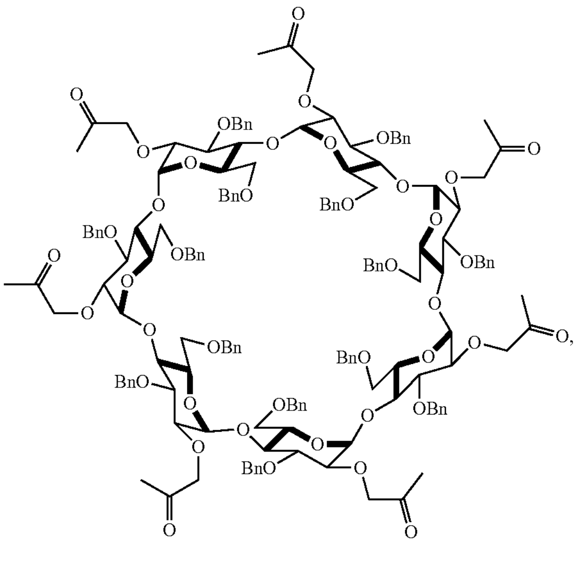
II-4
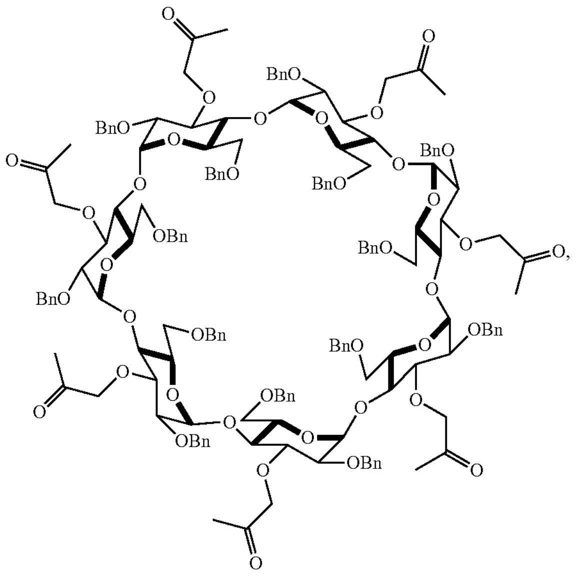
, -continued
II-5
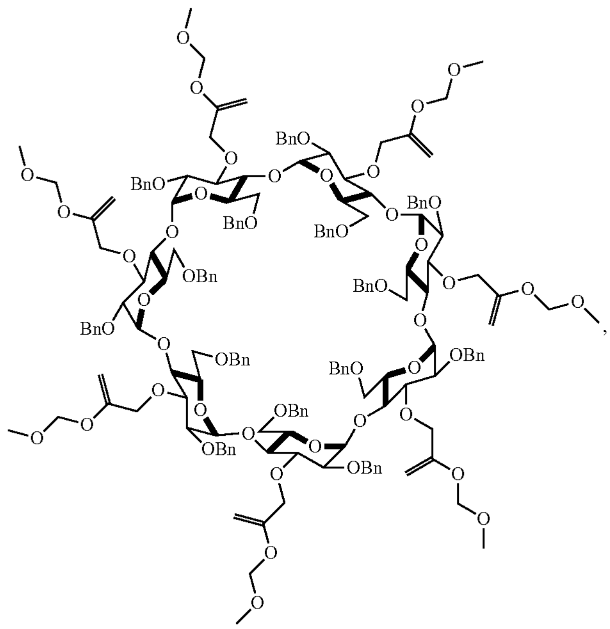
, and
II-6
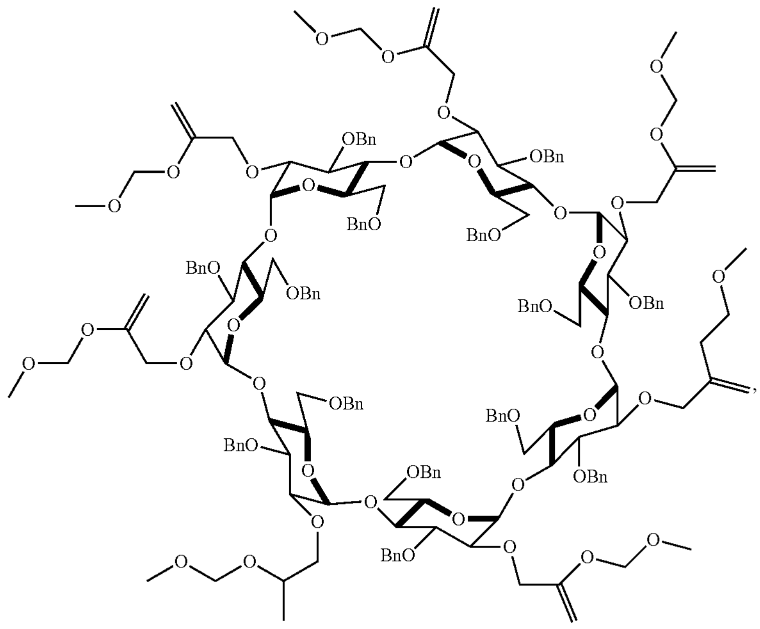
, -continued

II-7

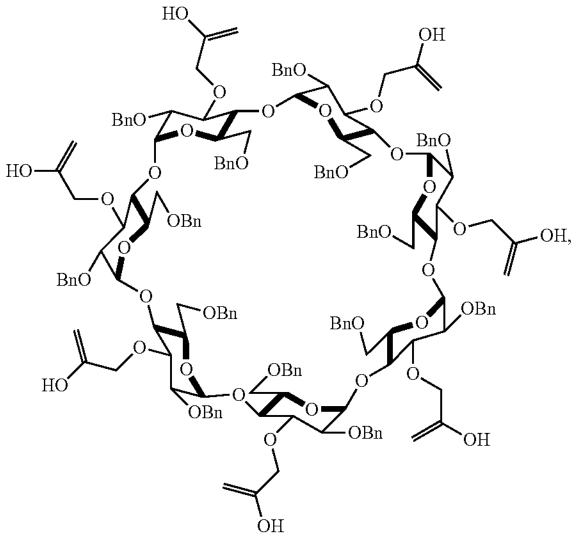

Embodiment 46. A compound of Formula IIa:

(IIa)

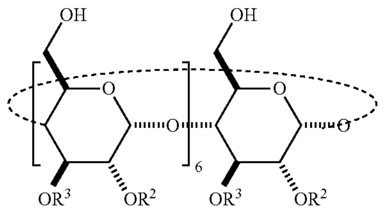

wherein, each $R^2$ and $R^3$ independently, at each occurrence for each of the seven independent monomers, is H or $C_2$-$C_4$ alkenyl, wherein at least one $R^2$ or at least one $R^3$ is $C_2$-$C_4$ alkenyl.

Embodiment 47. The compound of Embodiment 46, wherein the compound is:

(II-8)

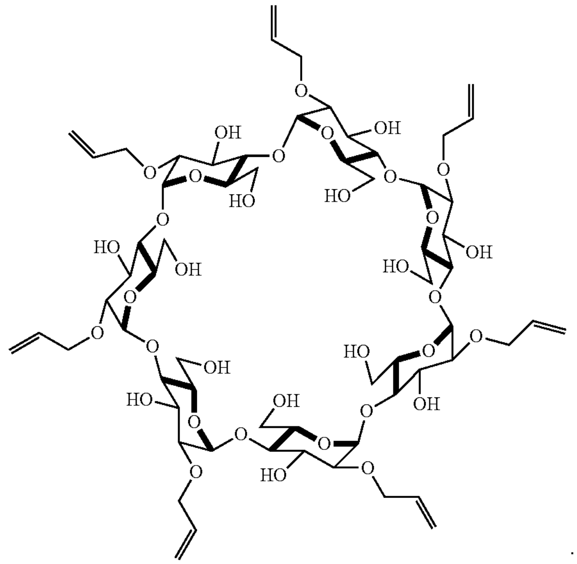

Embodiment 48. The compound of any one of the preceding Embodiments, wherein the compound has a purity of at least 9500.

Embodiment 49. The compound of any one of the preceding Embodiments, wherein the compound has a regioisomeric purity of at least 95%.

Embodiment 50. A pharmaceutically active substance consisting of a compound of any one of Embodiment 1-Embodiment 37.

Embodiment 51. A pharmaceutical composition comprising a pharmaceutically active component and a pharmaceutically acceptable carrier, wherein the pharmaceutically active component is a compound or pharmaceutically active substance of any one of Embodiment 1-Embodiment 37 or Embodiment 50.

Embodiment 52. A method of increasing cholesterol efflux capacity (CEC) of a tissue or a cell in a subject, comprising administering to the subject a therapeutically effective amount of a compound or pharmaceutically active substance ofany one of Embodiment 1-Embodiment 37 or Embodiment 50, or a pharmaceutical composition of Embodiment 51.

Embodiment 53. A method of inducing or increasing cholesterol efflux capacity (CEC) out of atheromas of a subject, comprising administering to the subject a therapeutically effective amount of a compound or pharmaceutically active substance of any one of Embodiment 1-Embodiment 37 or Embodiment 50, or a pharmaceutical composition of Embodiment 51.

Embodiment 54. A method of inducing reverse cholesterol transport from macrophages of a subject to the feces or urine of the subject, comprising administering to the subject a therapeutically effective amount of a compound or pharmaceutically active substance of any one of Embodiment 1-Embodiment 37 or Embodiment 50, or a pharmaceutical composition of Embodiment 51.

Embodiment 55. A method of sequestering cholesterol in the blood of a subject, comprising administering to the subject a therapeutically effective amount of a compound or pharmaceutically active substance of any one of Embodiment 1-Embodiment 37 or Embodiment 50, or a pharmaceutical composition of Embodiment 51.

Embodiment 56. A method of reducing intracellular cholesterol in a tissue or cell of a subject in need thereof, the method comprising administering to the subject a compound or pharmaceutically active substance of any one of Embodiment 1-Embodiment 37 or Embodiment 50, or a pharmaceutical composition of Embodiment 51.

Embodiment 57. A method of reducing inflammation and/or oxidative stress induced by oxidized LDL in a subject in need thereof, the method comprising administering to the subject a compound or pharmaceutically active substance of any one of Embodiment 1-Embodiment 37 or Embodiment 50, or a pharmaceutical composition of Embodiment 51.

Embodiment 58. A method of improving the renal and/or hepatogenic clearance of cholesterol in a subject in need thereof, the method comprising administering to the subject a compound or pharmaceutically active substance of any one of Embodiment 1-Embodiment 37 or Embodiment 50, or a pharmaceutical composition of Embodiment 51.

Embodiment 59. A method of increasing circulating and/or systemic levels of one or more oxysterol in a subject in need thereof, the method comprising administering to the subject a compound or pharmaceutically active substance of any one of Embodiment 1-Embodiment 37 or Embodiment 50, or a pharmaceutical composition of Embodiment 51.

Embodiment 60. A method of increasing plasma cholesterol crystal dissolution capacity (CCDC) in a subject in need thereof, the method comprising administering to the subject a compound or pharmaceutically active substance of any one of Embodiment 1-Embodiment 37 or Embodiment 50, or a pharmaceutical composition of Embodiment 51.

Embodiment 61. A method of increasing levels of ABCA1 and/or ABCG1 in a subject in need thereof, the method comprising administering to the subject a compound or pharmaceutically active substance of any one of Embodiment 1-Embodiment 37 or Embodiment 50, or a pharmaceutical composition of Embodiment 51.

Embodiment 62. A method of reducing the risk of or preventing cholesterol crystal embolization (CCE) or a symptom thereof in a subject in need thereof, the method comprising administering to the subject a compound or pharmaceutically active substance of any one of Embodiment 1-Embodiment 37 or Embodiment 50, or a pharmaceutical composition of Embodiment 51.

Embodiment 63. A method of reducing, inhibiting, or preventing the development of cholesterol rich plaque in a subject in need thereof, the method comprising administering to the subject a compound or pharmaceutically active substance of any one of Embodiment 1-Embodiment 37 or Embodiment 50, or a pharmaceutical composition of Embodiment 51.

Embodiment 64. A method of treating or reducing a risk of a major adverse cardiovascular events (MACE) in a subject in need thereof, the method comprising administering to the subject a compound or pharmaceutically active substance of any one of Embodiment 1-Embodiment 37 or Embodiment 50, or a pharmaceutical composition of Embodiment 51.

Embodiment 65. A method of treating a cardiovascular disease in a subject in need thereof, the method comprising administering to the subject a compound or pharmaceutically active substance of any one of Embodiment 1-Embodiment 37 or Embodiment 50, or a pharmaceutical composition of Embodiment 51.

Embodiment 66. A method of treating a disorder of cholesterol metabolism in a subject in need thereof, comprising administering to the subject a therapeutically effective amount of a compound or pharmaceutically active substance of any one of Embodiment 1-Embodiment 37 or Embodiment 50, or a pharmaceutical composition of Embodiment 51.

Embodiment 67. The method of Embodiment 66, wherein the disorder is a lipid storage disease or disorder.

Embodiment 68. The method of Embodiment 66, wherein the lipid storage disease or disorder is Niemann-Pick disease Type C (NPC).

Embodiment 69. The method of Embodiment 66, wherein the disorder is a neurological disease or disorder.

Embodiment 70. The method of Embodiment 69, wherein the neurological disease or disorder is a neurodegenerative or neurocognitive disorder, cognitive impairment, mild cognitive impairment (MCI), amnestic MCI, nonamnestic MCI, single domain impairment, multiple domain impairment, vascular cognitive impairment, vascular dementia, mixed dementia characterized by at least one A/T biomarker, cerebrovascular ischemia, tauopathy, subcortical dementia, Alzheimer's disease, Huntington's disease, or x-linked adrenoleukodystrophy; Embodiment 71. The method of Embodiment 69, wherein the neurological disease or disorder is Alzheimer's disease.

Embodiment 72. The method of Embodiment 66, wherein the disorder is a cardiovascular disease or disorder.

Embodiment 73. The method of Embodiment 72, wherein the cardiovascular disease or disorder is atherosclerosis, atherosclerotic cardiovascular disease (ASCVD), peripheral artery disease (PAD), coronary artery disease (CAD), coronary restenosis, peripheral vascular disease (PVD), cerebrovascular artery disease, ischemic cardiomyopathy, ischemic cerebrovascular disease, or homozygous familial hypercholesterolemia (HoFH), or heterozygous familial hypercholesterolemia (HeFH).

Embodiment 74. The method of Embodiment 72, wherein the cardiovascular disease or disorder is atherosclerosis.

Embodiment 75. The method of Embodiment 72, wherein the cardiovascular disease or disorder is atherosclerotic cardiovascular disease (ASCVD).

Embodiment 76. The method of Embodiment 75, wherein ASCVD is high-risk ASCVD.

Embodiment 77. The method of Embodiment 66 wherein the disorder is a liver disease or disorder.

Embodiment 78. The method of Embodiment 77, wherein the liver disease or disorder is a neonatal liver disease or an acute liver disease.

Embodiment 79. The method of Embodiment 66, wherein the disorder is hypertriglyceridemia.

Embodiment 80. The method of Embodiment 66, wherein the disorder is correlated to stroke, chronic kidney disease (CKD) caused by atherosclerosis, end-stage kidney disease (ESKD) caused by atherosclerosis, acute kidney failure caused by atherosclerosis, atherosclerotic renovascular disease (ARVD), renal artery stenosis, aortic aneurysm, idiopathic peripheral atrial hypertension, erectile dysfunction, intermittent claudication, and/or post-surgical or iatrogenic arterial disease.

Embodiment 81. The method of any one of Embodiment 66-Embodiment 80, wherein the compound reduces intracellular cholesterol levels in a tissue or a cell in the subject.

Embodiment 82. The method of any one of Embodiment 66-Embodiment 80, wherein the compound i) reduces inflammation and/or oxidative stress induced by oxidized LDL;

ii) improves the renal and/or hepatogenic clearance of cholesterol;

iii) increases circulating and/or systemic levels of one or more oxysterol;

iv) increases plasma cholesterol crystal dissolution capacity (CCDC);

v) increases levels of ABCA1 and/or ABCG1; and/or vi) reduces the risk of or prevents cholesterol crystal embolization (CCE) or a symptom thereof.

Embodiment 83. The method of Embodiment 82, wherein increasing CCDC is measurable by a reduction in an amount of and/or a size of, and/or changing the shape of any one of circulating cholesterol crystals, clots comprising cholesterol crystals, cholesterol-rich plaques, atherosclerotic plaques, low-attenuation plaques, calcified plaques and coronary artery non-calcified plaques.

Embodiment 84. The method of any one of Embodiment 66-Embodiment 83, wherein the compound does not induce significant cytotoxicity in the tissue or cell in the subject.

Embodiment 85. The method of any one of Embodiment 66-Embodiment 83, wherein the compound is capable of:

i) shuttling cholesterol, wherein the compound binds to cholesterol in a 1:1 ratio; and/or ii) sequestering cholesterol, wherein the compound binds to cholesterol in a 2:1 ratio.

Embodiment 86. The method of Embodiment 85, wherein sequestering cholesterol comprises increasing surface hydrophobicity of the compound.

Enumerated Embodiments III

Embodiment 1. A process for the preparation of a compound of Formula A:

(A)

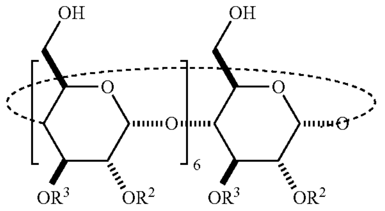

wherein, $R^2$ and $R^3$ are independently, at each occurrence for each independent monomer, H, or $C_2$-$C_4$ alkyl substituted with one or more groups selected from —O($C_1$-$C_4$ alkyl) and —OH, wherein at least one $R^2$ or at least one $R^3$ is $C_2$-$C_4$ alkyl substituted with one or more groups selected from —O($C_1$-$C_4$ alkyl) and —OH; and said process comprising:

Step 1: treating a compound of formula (i1):

(i1)

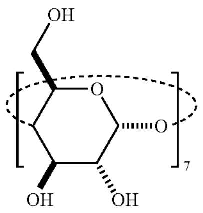

with a first reagent ($XPG^1$) to yield a compound of formula (i1a'):

(i1a')

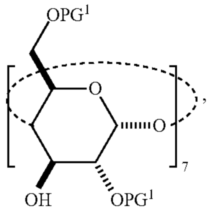

wherein $PG^1$ is a first alcohol protecting group and $XPG^1$ is a compound comprising $PG^1$.

Embodiment 2. The process of Embodiment 1, further comprising after Step 1: Step 1-1a: reacting the compound of formula (i1a') with a $C_1$-$C_4$ alkylene-O—$C_1$-$C_4$ alkyl halide, to yield a compound of formula (A-i4-1):

(A-i4-1)

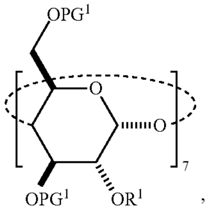

wherein each $R^1$ is $C_1$-$C_4$ alkylene-O—$C_1$-$C_4$ alkyl.

Embodiment 3. The process of Embodiment 1, further comprising:

after Step 1: Step 1-2a: reacting a compound of formula (i1a') with a compound X4:

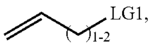

wherein LG1 is a leaving group to yield a compound of formula (A-i1b):

(A-i1b)

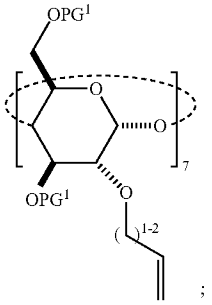

after Step 1-2a: Step 1-2b: treating a compound of formula (A-i1b) with a deprotecting agent to remove $PG^1$ and to yield a compound of formula (A-i1c): (A-i1c);

(A-i1c)

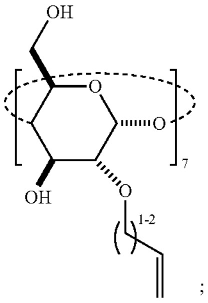

after Step 1-2b: Step 1-2c: treating a compound of formula (A-i1c) with a reagent ($XPG^2$) to yield a compound of formula (A-i1d):

(A-i1d)

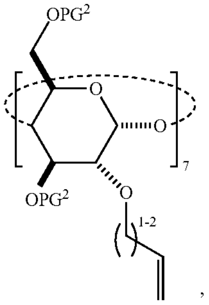

wherein $PG^2$ is an alcohol protecting group and $XPG^2$ is a compound comprising $PG^2$.

Embodiment 4. The process of Embodiment 3, further comprising after Step 1-2c: Step 1-2d: dihydroxylating a compound of formula (A-i1d) to yield a compound of formula (A-i4-2):

(A-i4-2)

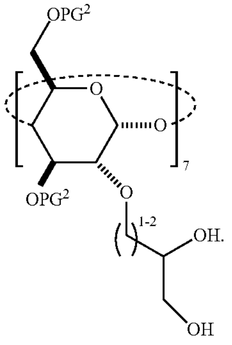

Embodiment 5. The process of Embodiment 3, further comprising after Step 1-2c: Step 2: deprotecting the compound of formula (A-i1d) to yield a compound of formula (A-i2):

(A-i2)

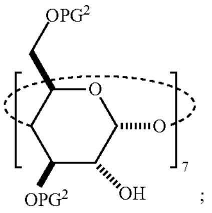

after Step 2: Step 3-1: reacting the compound of formula (A-i2) with a compound of formula X1:

(X1)

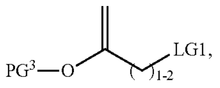

wherein $PG^3$ is an alcohol protecting group and LG1 is a leaving group, to yield a compound of formula (A-i3-1a):

(A-i3-1a)

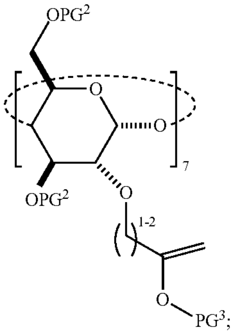

after Step 3-1: Step 3-2: treating a compound of formula (A-i3-1a) with a deprotecting agent to remove $PG^3$ and provide a compound of formula (A-i3-1b):

(A-i3-1b)

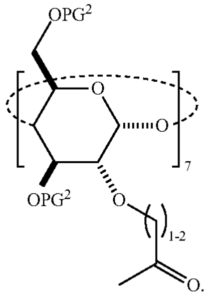

Embodiment 6. The process of Embodiment 5, further comprising after Step 3-2: Step 3-3a: treating a compound of formula (A-i3-1b) with a reducing agent to provide a compound of formula (A-i4-3):

(A-i4-3)

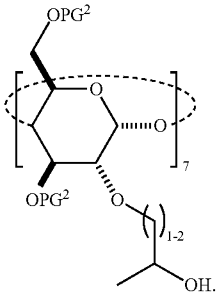

Embodiment 7. The process of Embodiment 5, further comprising after Step 3-2: Step 3-3b: reacting a compound of formula (A-i3-1b), with MeMgHal, where Hal is halogen, to provide a compound of formula (A-i4-4):

(A-i4-4)

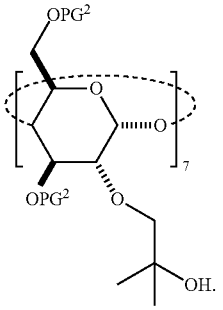

Embodiment 8. A process for the preparation of a compound of Formula A:

(A)

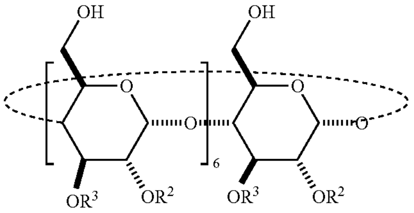

wherein, $R^2$ and $R^3$ are independently, at each occurrence for each independent monomer, H, $C_2$-$C_4$ alkyl substituted with one or more groups selected from —O($C_1$-$C_4$ alkyl) and —OH, wherein at least one $R^2$ or least one $R^3$ is $C_2$-$C_4$ alkyl substituted with one or more groups selected from —O($C_1$-$C_4$ alkyl) and —OH; and said process comprising:

Step 1': treating a compound of formula (i1):

(i1)

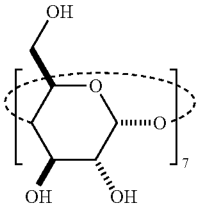

with a reagent ($XPG^2$) to yield a compound of formula (i2'):

(i2')

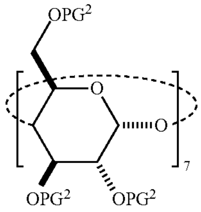

, wherein $PG^2$ is an alcohol protecting group and $XPG^2$ is a compound comprising $PG^2$; and after Step 1': Step 2': treating the compound of formula (i2') with a deprotecting agent to yield a compound of formula (A-i3):

(A-i3)

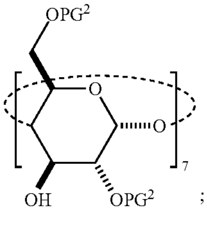

;

after Step 2': Step 3'-1: reacting the compound of formula (A-i3) with a compound of formula X1:

(X1)

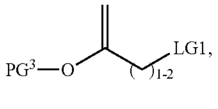

wherein $PG^3$ is an alcohol protecting group and LG1 is a leaving group, to yield a compound of formula (A-i3-1):

(A-i3-1)

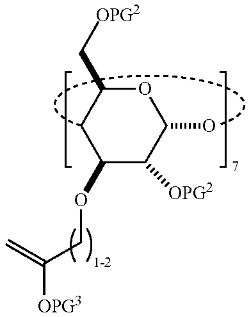

;

after Step 3'-1: Step 3'-2: treating a compound of formula (A-i3-1) with a deprotecting agent to remove $PG^3$ provide a compound of formula (A-i3-2):

(A-i3-2)

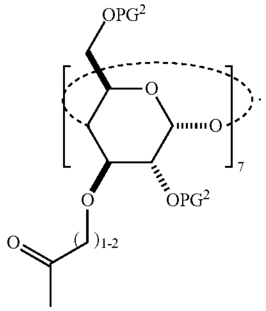

Embodiment 9. The process of Embodiment 8, further comprising after Step 3'-2: Step 3'-3a: treating a compound of formula (A-i3-2) with a reducing agent to provide a compound of formula (A-i4-5):

(A-i4-5)

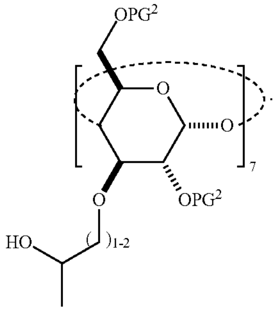

Embodiment 10. The process of Embodiment 8, further comprising after Step 3'-2: Step 3'-3b: treating a compound of formula (A-i3-2), wherein the compound of formula (A-i3-2) has the following structure:

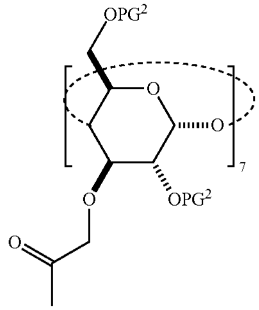

with MeMgHal, wherein Hal is halogen, to provide a compound of formula (A-i4-6):

(A-i4-6)

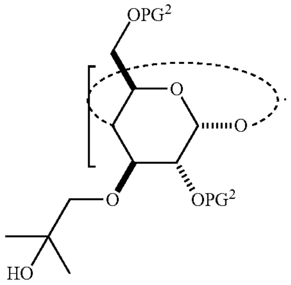

Embodiment 11. The process of any one of Embodiment 4, Embodiment 6, Embodiment 7, and Embodiment 9-Embodiment 10, further comprising after Step 1-2d, Step 3-3a, Step 3-3b, Step 3'-3a, or Step 3'-3b:

Step 4: removing $PG^2$ from the compound of formula (A-i4-2), (A-i4-3), (A-i4-4), (A-i4-5), or (A-i4-6) to yield a compound of Formula (A).

Embodiment 12. The process of Embodiment 2, further comprising after Step 1-1a:

Step 4: treating the compound of formula (A-i4-1) with a deprotecting agent to remove $PG^1$ and yield a compound of Formula (A).

Embodiment 13. The process of Embodiment 11, wherein removing $PG^2$ comprises palladium catalyzed dehydrogenation.

Embodiment 14. The process of Embodiment 13, wherein the palladium catalyst used comprises Pd(I) or Pd(II).

Embodiment 15. The process of Embodiment 13, wherein the palladium catalyst used is Pd/C.

Embodiment 16. The process of Embodiment 12, wherein the deprotecting agent for removing $PG^1$ provides a fluoride ion.

Embodiment 17. The process of Embodiment 12, wherein the deprotecting agent for removing $PG^1$ comprises tetra-n-butylammonium fluoride (TBAF), HF, $NH_4F$, or a mixture of same.

Embodiment 18. The process of Embodiment 5, wherein the deprotecting the compound of formula (A-i1 d) comprises treating the compound of formula (A-i1 d) with $Pd(PPh_3)_4$.

Embodiment 19. The process of Embodiment 1 or Embodiment 8, further comprising converting the compound of formula (i1a') or (A-i3) to a compound of Formula (A).

Embodiment 20. The process of Embodiment 1, wherein $XPG^1$ is selected from tert-butyldimethylsilyl chloride, trimethylsilyl chloride, tri-iso-propylsilyloxymethyl chloride, and tri-iso-propylsilylchloride.

Embodiment 21. The process of Embodiment 3 or Embodiment 8, wherein $XPG^2$ is selected from benzyl bromide, benzyl chloride, p-methoxybenzyl chloride, p-methoxybenzyl bromide, dimethoxybenzyl chloride, and dimethoxybenzyl bromide.

Embodiment 22. The process of any one of Embodiment 1-Embodiment 3, wherein $PG^1$ is selected from tert-butyldimethylsilyl, trimethylsilyl, tri-iso-propylsilyloxymethyl, and tri-iso-propylsilyl.

Embodiment 23. The process of any one of Embodiment 3-Embodiment 10, wherein $PG^2$ is selected from benzyl, p-methoxybenzyl, and dimethoxybenzyl.

Embodiment 24. The process of Embodiment 8, wherein the deprotecting agent in Step 2' is triethylsilane.

Embodiment 25. The process of Embodiment 8 or Embodiment 24, wherein Step 2' is carried out at a temperature of from about −80° C. to about −50° C.

Embodiment 26. The process of Embodiment 8 or Embodiment 24, wherein Step 2' is carried out at a temperature of from about −70° C. to about −60° C.

Embodiment 27. The process of Embodiment 8 or Embodiment 24, wherein Step 2' is carried out at a temperature of about −65° C.

Embodiment 28. The process of Embodiment 7 or Embodiment 10, wherein Hal is selected from fluoride, chloride, bromide, and iodide.

Embodiment 29. The process of Embodiment 2, wherein the $C_1$-$C_4$ alkylene-O—$C_1$-$C_4$ alkyl halide is $CH_3O(CH_2)_2Br$, $CH_3O(CH_2)_2C_1$, $CH_3O(CH_2)_2I$, $CH_3CH_2O(CH_2)_2C_1$, $CH_3CH_2O(CH_2)_2Br$, or $CH_3CH_2O(CH_2)_2I$.

Embodiment 30. The process of Embodiment 2, wherein the $C_1$-$C_4$ alkylene-O—$C_1$-$C_4$ alkyl halide is $CH_3O(CH_2)_2Br$ or $CH_3CH_2O(CH_2)_2Br$.

Embodiment 31. The process of Embodiment 6 or Embodiment 9, wherein the reducing agent is selected from $LiBH(Et)_3$, $LiAlH_4$, $LiBH_4$, $NaBH_4$, $Mg(BH_4)_2$, $Al(BH_4)_3$, $Ca(BH_4)_2$, $Zn(BH_4)_2$, $Ce(BH_4)_2$, and $NaBH_3CN$.

Embodiment 32. The process of any of Embodiment 6 or Embodiment 9, wherein the reducing agent is $NaBH_4$.

Embodiment 33. The process of Embodiment 1, wherein Step 1 is carried out at a temperature of from about 10° C. to about 40° C.

Embodiment 34. The process of Embodiment 1, wherein Step 1 is carried out at a temperature of from about 20° C. to about 30° C.

Embodiment 35. The process of Embodiment 1, wherein Step 1 is carried out at a temperature of about 25° C.

Embodiment 36. The process of Embodiment 1, wherein Step 1 is carried out at a temperature of from about 50° C. to about 200° C.

Embodiment 37. The process of Embodiment 1, wherein Step 1 is carried out at a temperature of from about 80° C. to about 150° C.

Embodiment 38. The process of Embodiment 1, wherein Step 1 is carried out at a temperature of from about 90° C. to about 130° C.

Embodiment 39. The process of Embodiment 1, wherein Step 1 is carried out at a temperature of about 110° C.

Embodiment 40. The process of Embodiment 3 or Embodiment 8, wherein the treating with $XPG^2$ comprises adding $XPG^2$ to the compound of formula (i1) or (i1a) at a temperature of from about 10° C. to about 40° C.

Embodiment 41. The process of Embodiment 3 or Embodiment 8, wherein the treating with $XPG^2$ comprises adding $XPG^2$ to the compound of formula (i1) or (i1a) at a temperature of from about 20° C. to about 30° C.

Embodiment 42. The process of Embodiment 3 or Embodiment 8, wherein the treating with $XPG^2$ comprises adding $XPG^2$ to the compound of formula (i1) or (i1a) at a temperature of about 25° C.

Embodiment 43. The process of Embodiment 5 or Embodiment 8, wherein the reacting with compound X1 comprises adding the compound of formula X1 to the compound of formula (A-i2) or (A-i3), and heating the resulting mixture to a temperature of from about 80° C. to about 120° C.

Embodiment 44. The process of Embodiment 5 or Embodiment 8, wherein the reacting with compound X1 comprises adding the compound of formula X1 to the compound of formula (A-i2) or (A-i3), and heating the resulting mixture to a temperature of from about 90° C. to about 110° C.

Embodiment 45. The process of Embodiment 5 or Embodiment 8, wherein the reacting with compound X1 comprises adding the compound of formula X1 to the compound of formula (A-i2) or (A-i3), and heating the resulting mixture to a temperature of about 100° C.

Embodiment 46. The process of Embodiment 3, wherein the reacting with X4 comprises adding the compound of formula X4 to the compound of formula (i1a') and heating the resulting mixture to a temperature of 60° C. to about 100° C.

Embodiment 47. The process of Embodiment 3, wherein the reacting with X4 comprises adding the compound of formula X4 to the compound of formula (i1a') and heating the resulting mixture to a temperature of from about 70° C. to about 90° C.

Embodiment 48. The process of Embodiment 3, wherein the reacting with X4 comprises adding the compound of formula X4 to the compound of formula (i1a') and heating the resulting mixture to a temperature of about 75° C.

Embodiment 49. The process of Embodiment 3, wherein the reacting with X4 comprises adding the compound of formula X4 to the compound of formula (i1a') at a temperature of from about −20° C. to about 20° C.

Embodiment 50. The process of Embodiment 3, wherein the reacting with X4 comprises adding the compound of formula X4 to the compound of formula (i1a') at a temperature of from about −10° C. to about 10° C.

Embodiment 51. The process of Embodiment 3, wherein the reacting with X4 comprises adding the compound of formula X4 to the compound of formula (i1a') at a temperature of about 0° C.

Embodiment 52. The process of Embodiment 5 or Embodiment 8, wherein the treating with a deprotecting agent to remove $PG^3$ is carried out at a temperature of from about 10° C. to about 40° C.

Embodiment 53. The process of any one of Embodiment 5 or Embodiment 8, wherein the treating with a deprotecting agent to remove $PG^3$ is carried out at a temperature of from about 20° C. to about 30° C.

Embodiment 54. The process of any one of Embodiment 5 or Embodiment 8, wherein the treating with a deprotecting agent to remove $PG^3$ is carried out at a temperature of about 25° C.

Embodiment 55. The process of Embodiment 16 or Embodiment 17, wherein the treating with a deprotecting agent to remove $PG^1$ comprises adding the deprotection agent to the compound of formula (i2) or (A-i1b) at a temperature of from about 10° C. to about 40° C.

Embodiment 56. The process of Embodiment 16 or Embodiment 17, wherein the treating with a deprotecting agent to remove $PG^1$ comprises adding the deprotection agent to the compound of formula (i2) or (A-i1b) at a temperature of from about 20° C. to about 30° C.

Embodiment 57. The process of Embodiment 16 or Embodiment 17, wherein the treating with a deprotecting agent to remove $PG^1$ comprises adding the deprotection agent to the compound of formula (i2) or (A-i1b) at a temperature of about 25° C.

Embodiment 58. The process of Embodiment 16 or Embodiment 17, wherein the treating with a deprotecting agent to remove $PG^1$ comprises heating a mixture of the compound of formula (i2) or (A-i1b) and the deprotecting agent to a temperature of from about 40° C. to about 80° C.

Embodiment 59. The process of Embodiment 16 or Embodiment 17, wherein the treating with a deprotecting agent to remove $PG^1$ comprises heating a mixture of the compound of formula (i2) or (A-i1b) and the deprotecting agent to a temperature of from about 50° C. to about 70° C.

Embodiment 60. The process of Embodiment 16 or Embodiment 17, wherein the treating with a deprotecting agent to remove $PG^1$ comprises heating a mixture of the compound of formula (i2) or (A-i1b) and the deprotecting agent a mixture of to a temperature of about 60° C.

Embodiment 61. The process of Embodiment 13 or Embodiment 14, wherein the palladium catalyzed dehydrogenation is carried out at a temperature of from about 10° C. to about 40° C.

Embodiment 62. The process of Embodiment 13 or Embodiment 14, wherein the palladium catalyzed dehydrogenation is carried out at a temperature of from about 20° C. to about 30° C.

Embodiment 63. The process of Embodiment 13 or Embodiment 14, wherein the palladium catalyzed dehydrogenation is carried out at a temperature of about 25° C.

Embodiment 64. The process of Embodiment 13 or Embodiment 14, wherein the palladium catalyzed dehydrogenation is carried out at a temperature of from about 40° C. to about 80° C.

Embodiment 65. The process of Embodiment 13 or Embodiment 14, wherein the palladium catalyzed dehydrogenation is carried out at a temperature of from about 50° C. to about 70° C.

Embodiment 66. The process of Embodiment 13 or Embodiment 14, wherein the palladium catalyzed dehydrogenation is carried out at a temperature of about 60° C.

Embodiment 67. The process of any one of Embodiment 1-Embodiment 66, wherein after each step, the resulting compound is isolated from the reaction mixture and purified.

Embodiment 68. The process of Embodiment 67, wherein the resulting compound is purified by column chromatography.

Embodiment 69. A compound made by the process of any one of Embodiment 1-Embodiment 68.

Embodiment 70. A process for the preparation of Compound 3:

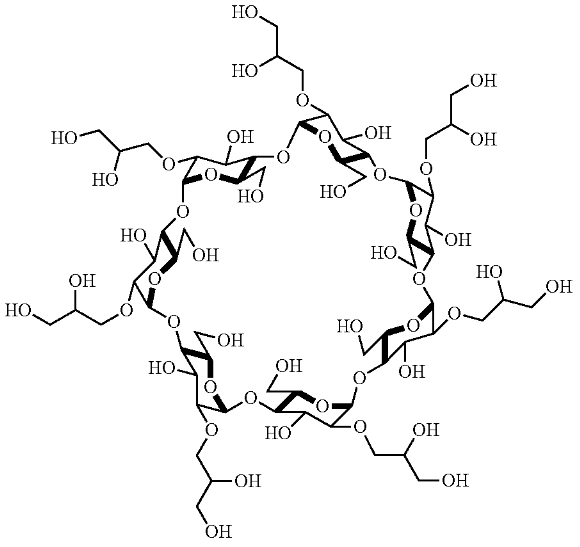

said process comprising:

Step 1: treating a compound of formula (i1):

(i1)

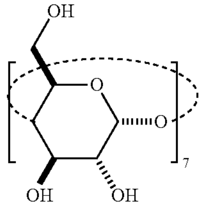

with a first reagent ($XPG^1$) to yield a compound of formula (i1a'):

(i1a')

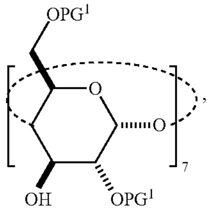

wherein $PG^1$ is a first alcohol protecting group and $XPG^1$ is a compound comprising $PG^1$;

after Step 1: Step 1-2a: reacting a compound of formula (i1a') with a compound X4:

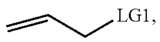

wherein LG1 is a leaving group to yield a compound of formula (A-i1b):

(A-i1b)

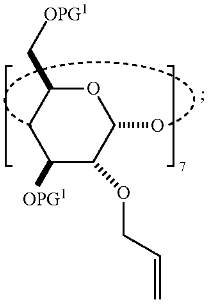

;

after Step 1-2a: Step 1-2b: treating a compound of formula (A-i1b) with a deprotecting agent to remove $PG^1$ and to yield a compound of formula (A-i1c):

(A-i1c)

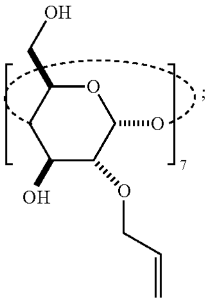

;

after Step 1-2b: Step 1-2c: treating a compound of formula (A-i1c) with a reagent ($XPG^2$) to yield a compound of formula (A-i1d):

(A-i1d)

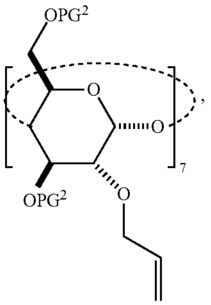

, wherein $PG^2$ is an alcohol protecting group and $XPG^2$ is a compound comprising $PG^2$;

after Step 1-2c: step 1-2d: dihydroxylating a compound of formula (A-i1d) to yield a compound of formula (A-i4-2):

(A-i4-2)

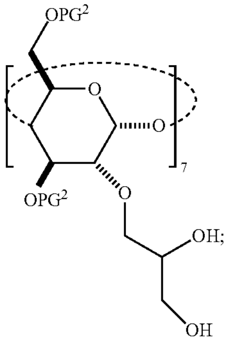

and after Step 1-2d:

Step 4: removing $PG^2$ from the compound of formula (A-i4-2) to yield Compound 3.

Embodiment 71. A process for the preparation of Compound 5:

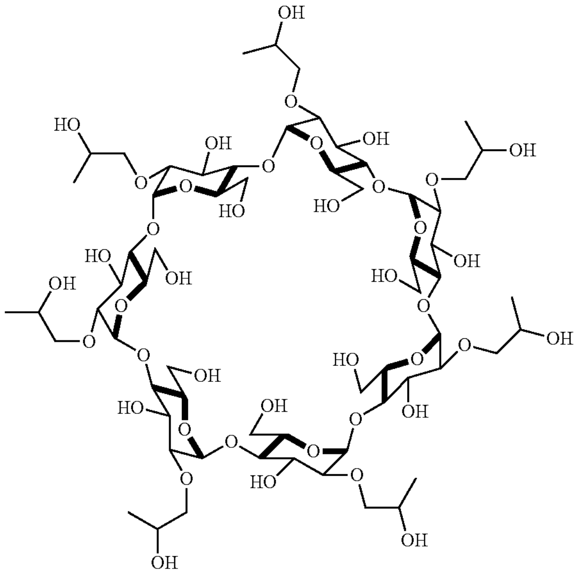

said process comprising:

Step 1: treating a compound of formula (i1):

(i1)

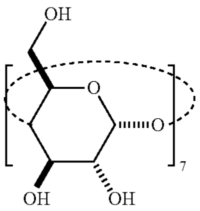

with a first reagent ($XPG^1$) to yield a compound of formula (i1a'):

(i1a')

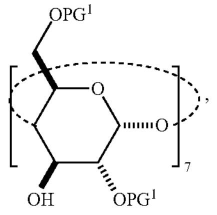

wherein $PG^1$ is a first alcohol protecting group and $XPG^1$ is a compound comprising $PG^1$;

after Step 1: Step 1-2a: reacting a compound of formula (i1a') with a compound X4:

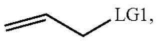

wherein LG1 is a leaving group to yield a compound of formula (A-i1b):

(A-i1b)

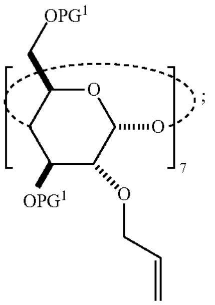

after Step 1-2a: Step 1-2b: treating a compound of formula (A-i1b) with a deprotecting agent to remove $PG^1$ and to yield a compound of formula (A-i1c):

(A-i1c)

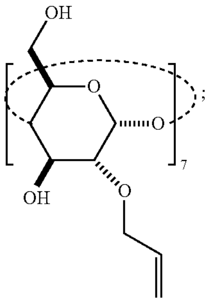

after Step 1-2b: Step 1-2c: treating a compound of formula (A-i1c) with a reagent ($XPG^2$) to yield a compound of formula (A-i1d):

(A-i1d)

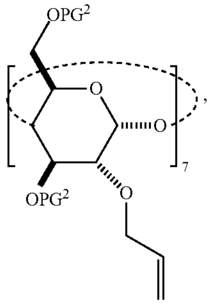

wherein $PG^2$ is an alcohol protecting group and $XPG^2$ is a compound comprising $PG^2$;

after Step 1-2c: Step 2: deprotecting the compound of formula (A-i1d) to yield a compound of formula (A-i2):

(A-i2)

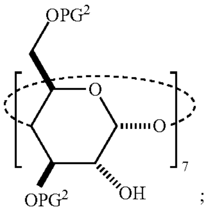

;

after Step 2: Step 3-1: reacting the compound of formula (A-i2) with a compound of formula X1:

(X1)

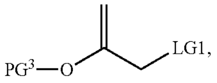

wherein $PG^3$ is an alcohol protecting group and LG1 is a leaving group, to yield a compound of formula (A-i3-1a):

(A-i3-1a)

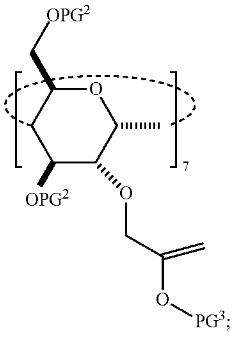

after Step 3-1: Step 3-2: treating a compound of formula (A-i3-1a) with a deprotecting agent to remove $PG^3$ and provide a compound of formula (A-i3-1b):

(A-i3-1b)

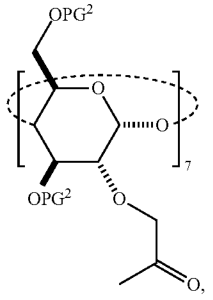

after Step 3-2: Step 3-3a: treating a compound of formula (A-i3-1b) with a reducing agent to provide a compound of formula (A-i4-3):

(A-i4-3)

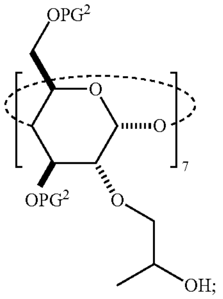

and after Step 3-3a:

Step 4: removing $PG^2$ from the compound of formula (A-i4-3) to yield Compound 5.

Embodiment 72. A process for the preparation of Compound 7:

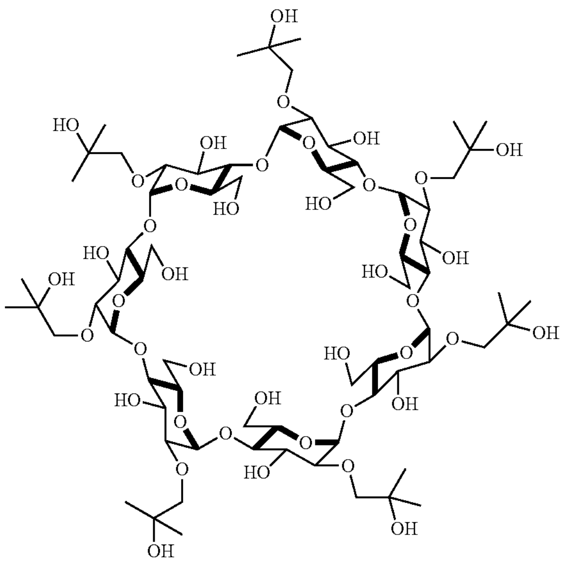

said process comprising:

Step 1: treating a compound of formula (i1):

(i1)

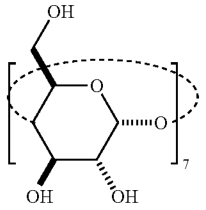

with a first reagent ($XPG^1$) to yield a compound of formula (i1a'):

(i1a')

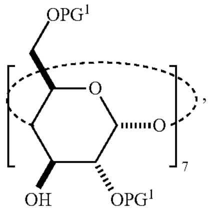

wherein $PG^1$ is a first alcohol protecting group and $XPG^1$ is a compound comprising $PG^1$;

after Step 1: Step 1-2a: reacting a compound of formula (i1a') with a compound X4:

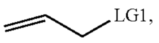

wherein LG1 is a leaving group to yield a compound of formula (A-i1b):

(A-i1b)

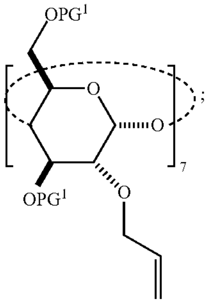

after Step 1-2a: Step 1-2b: treating a compound of formula (A-i1b) with a deprotecting agent to remove $PG^1$ and to yield a compound of formula (A-i1c):

(A-i1c)

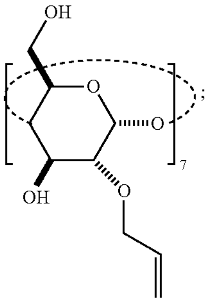

after Step 1-2b: Step 1-2c: treating a compound of formula (A-i1c) with a reagent ($XPG^2$) to yield a compound of formula (A-i1d):

(A-i1d)

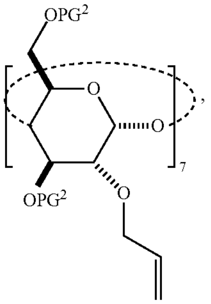

wherein $PG^2$ is an alcohol protecting group and $XPG^2$ is a compound comprising $PG^2$;

after Step 1-2c: Step 2: deprotecting the compound of formula (A-i1d) to yield a compound of formula (A-i2):

(A-i2)

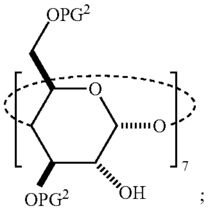

after Step 2: Step 3-1: reacting the compound of formula (A-i2) with a compound of formula X1:

(X1)

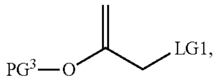

wherein $PG^3$ is an alcohol protecting group and LG1 is a leaving group, to yield a compound of formula (A-i3-1a):

(A-i3-1a)

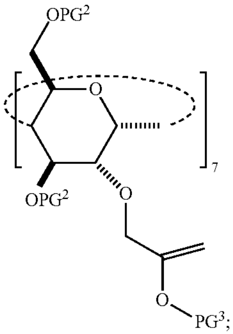

after Step 3-1: Step 3-2: treating a compound of formula (A-i3-1a) with a deprotecting agent to remove $PG^3$ and provide a compound of formula (A-i3-1b):

(A-i3-1b)

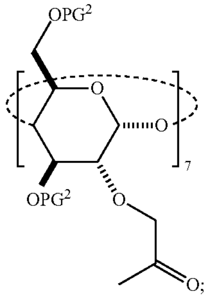

after Step 3-2:

Step 3-3b: reacting a compound of formula (A-i3-1b), with MeMgHal, where Hal is halogen, to provide a compound of formula (A-i4-4):

(A-i4-4)

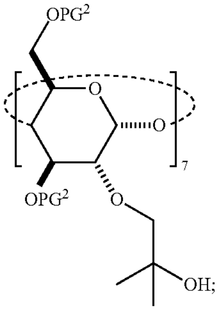

and after Step 3-3b:

Step 4: removing $PG^2$ from the compound of formula (A-i4-4) to yield Compound 7.

Embodiment 73. The process of any one of Embodiment 70-Embodiment 72, wherein removing $PG^2$ comprises palladium catalyzed dehydrogenation.

Embodiment 74. The process of Embodiment 73, wherein the palladium catalyst used comprises Pd(I) or Pd(II).

Embodiment 75. The process of Embodiment 73, wherein the palladium catalyst used is Pd/C.

Embodiment 76. The process of any one of Embodiment 70-Embodiment 72, wherein the deprotecting the compound of formula (A-i1 d) comprises treating the compound of formula (A-i1 d) with $Pd(PPh_3)_4$.

Embodiment 77. The process of any one of Embodiment 70-Embodiment 72, wherein $XPG^1$ is selected from tert-butyldimethylsilyl chloride, trimethylsilyl chloride, tri-iso-propylsilyloxymethyl chloride, and tri-iso-propylsilylchloride.

Embodiment 78. The process of any one of Embodiment 70-Embodiment 72, wherein $XPG^1$ is tert-butyldimethylsilyl chloride.

Embodiment 79. The process of any one of Embodiment 70-Embodiment 72, wherein $XPG^2$ is selected from benzyl bromide, benzyl chloride, p-methoxybenzyl chloride, p-methoxybenzyl bromide, dimethoxybenzyl chloride, and dimethoxybenzyl bromide.

Embodiment 80. The process of any one of Embodiment 70-Embodiment 72, wherein $XPG^2$ is benzyl chloride.

Embodiment 81. The process of any one of Embodiment 70-Embodiment 72, wherein $PG^1$ is selected from tert-butyldimethylsilyl, trimethylsilyl, tri-iso-propylsilyloxymethyl, and tri-iso-propylsilyl.

Embodiment 82. The process of any one of Embodiment 70-Embodiment 72, wherein $PG^1$ is tert-butyldimethylsilyl.

Embodiment 83. The process of any one of Embodiment 70-Embodiment 72, wherein $PG^2$ is benzyl.

Embodiment 84. The process of any one of Embodiment 70-Embodiment 72, wherein $PG^2$ is selected from benzyl, p-methoxybenzyl, and dimethoxybenzyl.

Embodiment 85. The process of any one of Embodiment 70-Embodiment 72, wherein the deprotecting agent for removing $PG^1$ provides a fluoride ion.

Embodiment 86. The process of any one of Embodiment 70-Embodiment 72 wherein the deprotecting agent for removing $PG^1$ comprises tetra-n-butylammonium fluoride (TBAF), HF, $NH_4F$, or a mixture of same.

Embodiment 87. The process of any one of Embodiment 70-Embodiment 72, wherein the deprotecting agent for removing $PG^1$ comprises tetra-n-butylammonium fluoride (TBAF).

Embodiment 88. The process of any one of Embodiment 70-Embodiment 72, wherein Step 1 is carried out at a temperature of from about 90° C. to about 130° C.

Embodiment 89. The process of any one of Embodiment 70-Embodiment 72, wherein Step 1 is carried out at a temperature of about 110° C.

Embodiment 90. The process of any one of Embodiment 70-Embodiment 72, wherein the treating with $XPG^2$ comprises adding $XPG^2$ to the compound of formula (i1) or (i1a) at a temperature of from about 10° C. to about 40° C.

Embodiment 91. The process of any one of Embodiment 70-Embodiment 72, wherein the treating with $XPG^2$ comprises adding $XPG^2$ to the compound of formula (i1) or (i1a) at a temperature of from about 20° C. to about 30° C.

Embodiment 92. The process of any one of Embodiment 70-Embodiment 72, wherein the treating with $XPG^2$ comprises adding $XPG^2$ to the compound of formula (i1) or (i1a) at a temperature of about 25° C.

Embodiment 93. The process of any one of Embodiment 70-Embodiment 72, wherein the reacting with compound X1 comprises adding the compound of formula X1 to the compound of formula (A-i2) or (A-i3), and heating the resulting mixture to a temperature of from about 80° C. to about 120° C.

Embodiment 94. The process of any one of Embodiment 70-Embodiment 72, wherein the reacting with compound X1 comprises adding the compound of formula X1 to the compound of formula (A-i2) or (A-i3), and heating the resulting mixture to a temperature of from about 90° C. to about 110° C.

Embodiment 95. The process of any one of Embodiment 70-Embodiment 72, wherein the reacting with compound X1 comprises adding the compound of formula X1 to the compound of formula (A-i2) or (A-i3), and heating the resulting mixture to a temperature of about 100° C.

Embodiment 96. The process of any one of Embodiment 70-Embodiment 72, wherein the treating with a deprotecting agent to remove $PG^3$ is carried out at a temperature of from about 10° C. to about 40° C.

Embodiment 97. The process of any one of Embodiment 70-Embodiment 72, wherein the treating with a deprotecting agent to remove $PG^3$ is carried out at a temperature of from about 20° C. to about 30° C.

Embodiment 98. The process of any one of Embodiment 70-Embodiment 72, wherein the treating with a deprotecting agent to remove $PG^3$ is carried out at a temperature of about 25° C.

Embodiment 99. The process of any one of Embodiment 70-Embodiment 72, wherein the treating with a deprotecting agent to remove $PG^1$ comprises adding the deprotection agent to the compound of formula (i2) or (A-i1b) at a temperature of from about 10° C. to about 40° C.

Embodiment 100. The process of any one of Embodiment 70-Embodiment 72, wherein the treating with a deprotecting agent to remove $PG^1$ comprises adding the deprotection agent to the compound of formula (i2) or (A-i1b) at a temperature of from about 20° C. to about 30° C.

Embodiment 101. The process of any one of Embodiment 70-Embodiment 72, wherein the treating with a deprotecting agent to remove $PG^1$ comprises adding the deprotection agent to the compound of formula (i2) or (A-i1b) at a temperature of about 25° C.

Embodiment 102. The process of any one of Embodiment 70-Embodiment 72, wherein the treating with a deprotecting agent to remove $PG^1$ comprises heating a mixture of the compound of formula (i2) or (A-i1b) and the deprotecting agent to a temperature of from about 40° C. to about 80° C.

Embodiment 103. Compound 3, made by the process of any one of Embodiment 70 and Embodiment 73-Embodiment 102.

Embodiment 104. Compound 5, made by the process of any one of Embodiment 71 and Embodiment 73-Embodiment 102.

Embodiment 105. Compound 7, made by the process of any one of Embodiment 72-Embodiment 102.

Embodiment 106. A compound having the following structure:

(Compound 1)

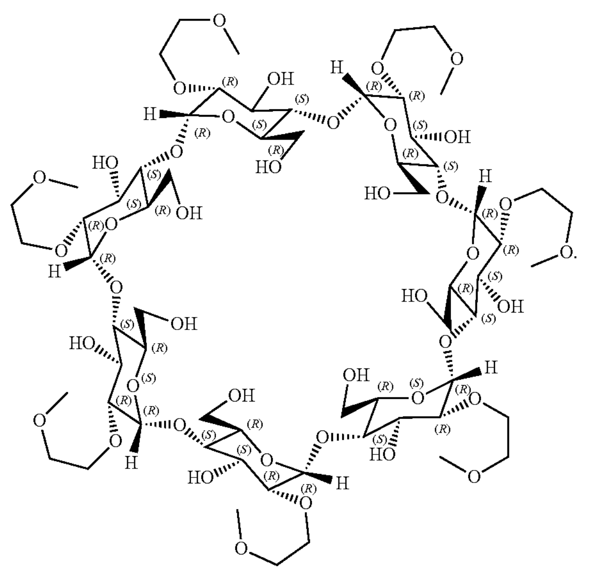

Embodiment 107. The compound of Embodiment 106, characterized by a 1D H-NMR spectrum having only a single peak attributable to the hydrogen at the anomeric center.

Embodiment 108. The compound of Embodiment 106, characterized by a 1D H-NMR spectrum collected in $D_2O$ having only a single peak in the anomeric region.

Embodiment 109. The compound of Embodiment 106, characterized by a 1D H-NMR spectrum collected in $D_2O$ having only a single peak attributable to the compound in the region located between 4.4 ppm and 5.6 ppm, including the endpoints.

Embodiment 110. The compound of Embodiment 106, characterized by a 1D H-NMR spectrum collected in $D_2O$ having only a single peak attributable to the compound in the region located between 5.0 ppm and 5.6 ppm, including the endpoints.

Embodiment 111. The compound of Embodiment 106, characterized by a 1D H-NMR spectrum collected in $D_2O$ having only a single peak attributable to the compound in the region located between 5.2 ppm and 5.6 ppm, including the endpoints.

Embodiment 112. The compound of Embodiment 106, wherein the single peak occurs at a chemical shift of 5.0 ppm or higher.

Embodiment 113. The compound of Embodiment 107-Embodiment 109, wherein the single peak occurs at a chemical shift of 5.2 ppm or higher.

Embodiment 114. The compound of any one of Embodiment 107-Embodiment 109, wherein the single peak occurs at a chemical shift of between about 5.0 ppm and about 5.5 ppm, including the endpoints.

Embodiment 115. The compound of Embodiment 107-Embodiment 109, wherein the single peak occurs at a chemical shift of between about 5.2 ppm and about 5.5 ppm, including the endpoints.

Embodiment 116. A compound having the following structure:

(Compound 2)

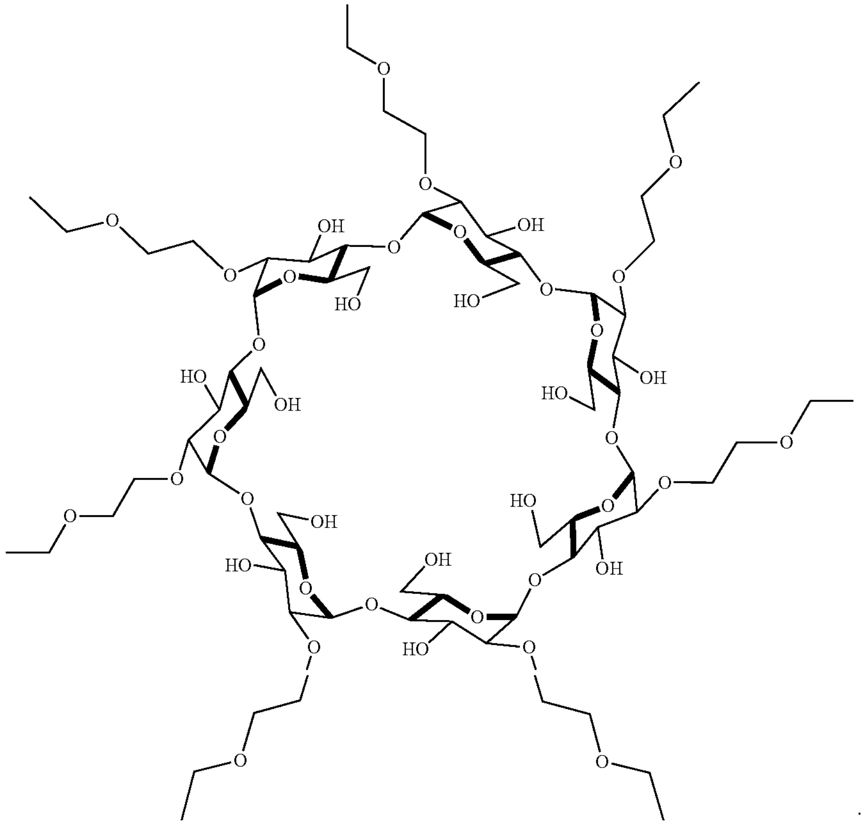

Embodiment 117. The compound of Embodiment 116, characterized by a 1D H-NMR spectrum having only a single peak attributable to the hydrogen at the anomeric center.

Embodiment 118. The compound of Embodiment 116, characterized by a 1D H-NMR spectrum collected in $D_2O$ having only a single peak in the anomeric region.

Embodiment 119. The compound of Embodiment 116, characterized by a 1D H-NMR spectrum collected in $D_2O$ having only a single peak attributable to the compound in the region located between 4.4 ppm and 5.6 ppm, including the endpoints.

Embodiment 120. The compound of Embodiment 116, characterized by a 1D H-NMR spectrum collected in $D_2O$ having only a single peak attributable to the compound in the region located between 5.0 ppm and 5.6 ppm, including the endpoints.

Embodiment 121. The compound of Embodiment 116, characterized by a 1D H-NMR spectrum collected in $D_2O$ having only a single peak attributable to the compound in the region located between 5.2 ppm and 5.6 ppm, including the endpoints.

Embodiment 122. The compound of any one of Embodiment 117-Embodiment 119, wherein the single peak occurs at a chemical shift of 5.0 ppm or higher.

Embodiment 123. The compound of any one of Embodiment 117-Embodiment 119, wherein the single peak occurs at a chemical shift of 5.2 ppm or higher.

Embodiment 124. The compound of any one of Embodiment 117-Embodiment 119, wherein the single peak occurs at a chemical shift of between about 5.0 ppm and about 5.5 ppm, including the endpoints.

Embodiment 125. The compound of any one of Embodiment 117-Embodiment 119, wherein the single peak occurs at a chemical shift of between about 5.2 ppm and about 5.5 ppm, including the endpoints.

Embodiment 126. A compound having the following structure:

(Compound 3)

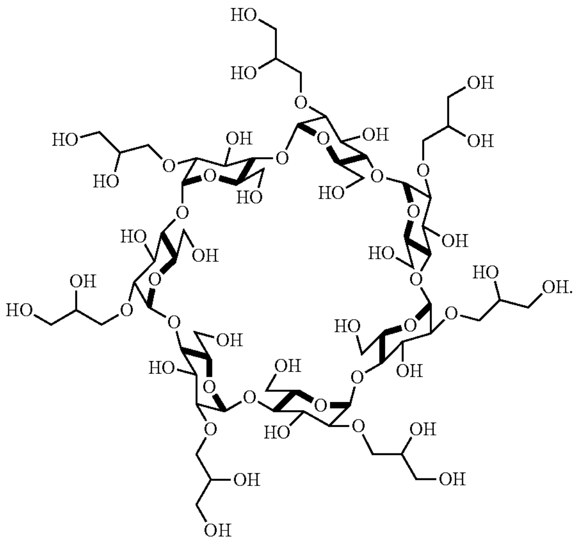

Embodiment 127. The compound of Embodiment 126, characterized by a 1D H-NMR spectrum having only a single peak attributable to the hydrogen at the anomeric center.

Embodiment 128. The compound of Embodiment 126, characterized by a 1D H-NMR spectrum collected in $D_2O$ having only a single peak in the anomeric region.

Embodiment 129. The compound of Embodiment 126, characterized by a 1D H-NMR spectrum collected in $D_2O$ having only a single peak attributable to the compound in the region located between 4.4 ppm and 5.6 ppm, including the endpoints.

Embodiment 130. The compound of Embodiment 126, characterized by a 1D H-NMR spectrum collected in $D_2O$ having only a single peak attributable to the compound in the region located between 5.0 ppm and 5.6 ppm, including the endpoints.

Embodiment 131. The compound of Embodiment 126, characterized by a 1D H-NMR spectrum collected in $D_2O$ having only a single peak attributable to the compound in the region located between 5.2 ppm and 5.6 ppm, including the endpoints.

Embodiment 132. The compound of Embodiment 127-Embodiment 129, wherein the single peak occurs at a chemical shift of 5.0 ppm or higher.

Embodiment 133. The compound of any one of Embodiment 127-Embodiment 129, wherein the single peak occurs at a chemical shift of 5.2 ppm or higher.

Embodiment 134. The compound of any one of Embodiment 127-Embodiment 129, wherein the single peak occurs at a chemical shift of between about 5.0 ppm and about 5.5 ppm, including the endpoints.

Embodiment 135. The compound of any one of Embodiment 127-Embodiment 129, wherein the single peak occurs at a chemical shift of between about 5.2 ppm and about 5.5 ppm, including the endpoints.

Embodiment 136. A compound having the following structure:

(Compound 5)

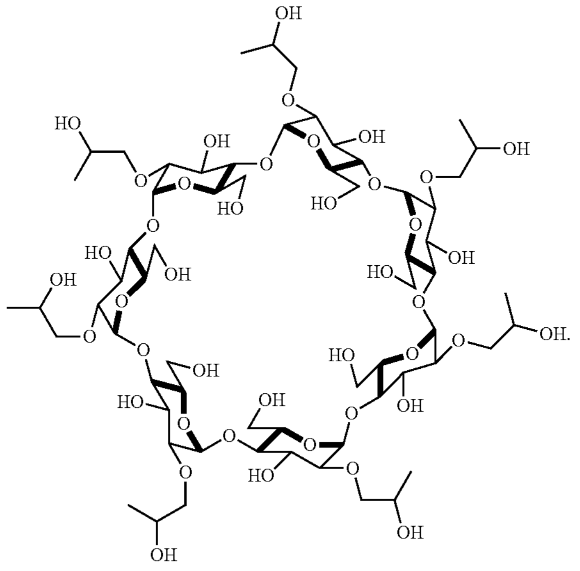

Embodiment 137. The compound of Embodiment 136, characterized by a 1D H-NMR spectrum having only a single peak attributable to the hydrogen at the anomeric center.

Embodiment 138. The compound of Embodiment 136, characterized by a 1D H-NMR spectrum collected in $D_2O$ having only a single peak in the anomeric region.

Embodiment 139. The compound of Embodiment 136, characterized by a 1D H-NMR spectrum collected in $D_2O$ having only a single peak attributable to the compound in the region located between 4.4 ppm and 5.6 ppm, including the endpoints.

Embodiment 140. The compound of Embodiment 136, characterized by a 1D H-NMR spectrum collected in $D_2O$ having only a single peak attributable to the compound in the region located between 5.0 ppm and 5.6 ppm, including the endpoints.

Embodiment 141. The compound of Embodiment 136, characterized by a 1D H-NMR spectrum collected in $D_2O$ having only a single peak attributable to the compound in the region located between 5.2 ppm and 5.6 ppm, including the endpoints.

Embodiment 142. The compound of any one of Embodiment 137-Embodiment 139, wherein the single peak occurs at a chemical shift of 5.0 ppm or higher.

Embodiment 143. The compound of any one of Embodiment 137-Embodiment 139, wherein the single peak occurs at a chemical shift of 5.2 ppm or higher.

Embodiment 144. The compound of any one of Embodiment 137-Embodiment 139, wherein the single peak occurs a chemical shift of between about 5.0 ppm and about 5.5 ppm, including the endpoints.

Embodiment 145. The compound of any one of Embodiment 137-Embodiment 139, wherein the single peak occurs at a chemical shift of between about 5.2 ppm and about 5.5 ppm, including the endpoints.

Embodiment 146. The compound of any one of Embodiment 137-Embodiment 139, wherein the single peak occurs at a chemical shift of about 5.3 ppm.

Embodiment 147. The compound of Embodiment 136, characterized by a 1D H-NMR spectrum collected in $D_2O$ that is substantially the same as the spectrum of FIG. 3.

Embodiment 148. The compound of Embodiment 136, characterized by a 1D H-NMR spectrum collected in $D_2O$ that is substantially as the spectrum of FIG. 3 in the region located between 3.0 ppm and 4.0 ppm, including the endpoints.

Embodiment 149. A compound having the following structure:

(Compound 7)

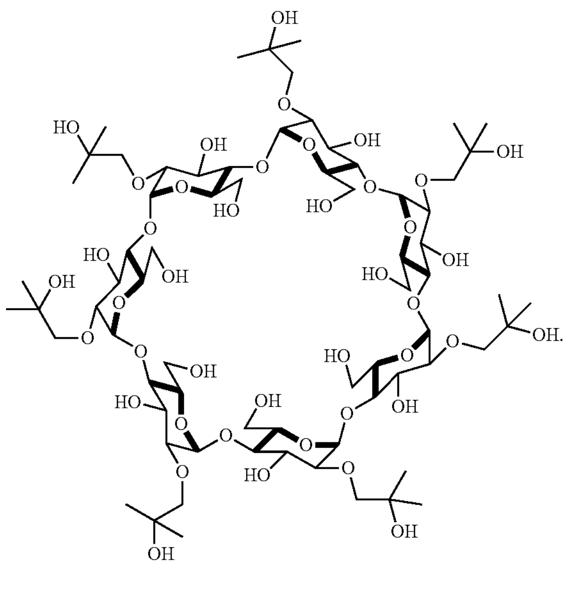

Embodiment 150. The compound of Embodiment 149, characterized by a 1D H-NMR spectrum having only a single peak attributable to the hydrogen at the anomeric center.

Embodiment 151. The compound of Embodiment 149, characterized by a 1D H-NMR spectrum collected in $D_2O$ having only a single peak in the anomeric region.

Embodiment 152. The compound of Embodiment 149, characterized by a 1D H-NMR spectrum collected in $D_2O$ having only a single peak attributable to the compound in the region located between 4.4 ppm and 5.6 ppm, including the endpoints.

Embodiment 153. The compound of Embodiment 149, characterized by a 1D H-NMR spectrum collected in $D_2O$ having only a single peak attributable to the compound in the region located between 5.0 ppm and 5.6 ppm, including the endpoints.

Embodiment 154. The compound of any one of Embodiment 150-Embodiment 153, wherein the single peak occurs at a chemical shift of 5.0 ppm or higher.

Embodiment 155. The compound of any one of Embodiment 150-Embodiment 153, wherein the single peak occurs at a chemical shift of between about 5.0 ppm and about 5.5 ppm, including the endpoints.

Embodiment 156. The compound of any one of Embodiment 106-Embodiment 155, wherein the compound has a regioisomeric purity of at least 95%.

Embodiment 157. The compound of any one of Embodiment 106-Embodiment 155, wherein the compound has a regioisomeric purity of at least 96%.

Embodiment 158. The compound of any one of Embodiment 106-Embodiment 155, wherein the compound has a regioisomeric purity of at least 97%.

Embodiment 159. The compound of any one of Embodiment 106-Embodiment 155, wherein the compound has a regioisomeric purity of at least 98%.

Embodiment 160. The compound of any one of Embodiment 106-Embodiment 155, wherein the compound has a regioisomeric purity of at least 99%.

Embodiment 161. An active pharmaceutical ingredient consisting of a compound of any one of Embodiment 106-Embodiment 160.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

All publications and patent applications cited in this specification are herein incorporated by reference as if each individual publication or patent application were specifically and individually indicated to be incorporated by reference.

What is claimed is:

1. A compound having the following structure:

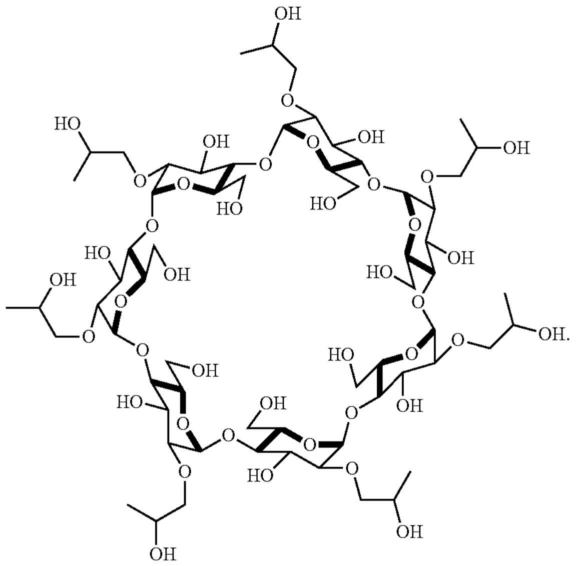

2. The compound of claim 1, characterized by a 1D H-NMR spectrum having only a single peak attributable to the hydrogen at the anomeric center.

3. The compound of claim 1, characterized by a 1D H-NMR spectrum collected in $D_2O$ having only a single peak attributable to the compound in the region located between 4.4 ppm and 5.6 ppm, including the endpoints.

4. The compound of claim 1, characterized by a 1D H-NMR spectrum collected in $D_2O$ having only a single peak attributable to the compound in the region located between 5.0 ppm and 5.6 ppm, including the endpoints.

5. The compound of claim 1, characterized by a 1D H-NMR spectrum collected in $D_2O$ that is substantially the same as the spectrum of FIG. 3.

6. The compound of claim 1, wherein the compound has a purity of at least 95%.

7. A pharmaceutical composition comprising a pharmaceutically active component and a pharmaceutically acceptable carrier, wherein the pharmaceutically active component is a compound of claim 1.

8. The compound of claim 4, wherein the single peak occurs at a chemical shift of between about 5.0 ppm and about 5.5 ppm, including the endpoints.

9. The compound of claim 4, wherein the single peak occurs at a chemical shift of between about 5.2 ppm and about 5.5 ppm, including the endpoints.

10. The compound of claim 4, wherein the single peak occurs at a chemical shift of about 5.3 ppm.

11. The pharmaceutical composition of claim 7, wherein the compound is characterized by a 1D H-NMR spectrum collected in $D_2O$ having only a single peak attributable to the hydrogen at the anomeric center.

12. The pharmaceutical composition of claim 7, wherein the compound is characterized by a 1D H-NMR spectrum collected in $D_2O$ having only a single peak attributable to the compound in the region located between 4.4 ppm and 5.6 ppm, including the endpoints.

13. The pharmaceutical composition of claim 7, wherein the compound is characterized by a 1D H-NMR spectrum collected in $D_2O$ having only a single peak attributable to the compound in the region located between 5.0 ppm and 5.6 ppm, including the endpoints.

14. The pharmaceutical composition of claim 13, wherein the single peak occurs a chemical shift of between about 5.0 ppm and about 5.5 ppm, including the endpoints.

15. The pharmaceutical composition of claim 13, wherein the single peak occurs at a chemical shift of between about 5.2 ppm and about 5.5 ppm, including the endpoints.

16. The pharmaceutical composition of claim 13, wherein the single peak occurs at a chemical shift of about 5.3 ppm.

17. The compound of claim 2, wherein the compound has a purity of at least 95%.

18. The compound of claim 3, wherein the compound has a purity of at least 95%.

19. The compound of claim 4, wherein the compound has a purity of at least 95%.

20. The compound of claim 5, wherein the compound has a purity of at least 95%.

* * * * *